US012011486B2

(12) United States Patent
Coleman et al.

(10) Patent No.: US 12,011,486 B2
(45) Date of Patent: *Jun. 18, 2024

(54) MOMP TELONANOPARTICLES, AND RELATED COMPOSITIONS, METHODS AND SYSTEMS

(71) Applicant: LAWRENCE LIVERMORE NATIONAL SECURITY, LLC, Livermore, CA (US)

(72) Inventors: Matthew A. Coleman, Oakland, CA (US); Nicholas O. Fischer, Livermore, CA (US); Amy Rasley, Livermore, CA (US); Craig D. Blanchette, San Leandro, CA (US); Todd Peterson, Coronado, CA (US)

(73) Assignee: LAWRENCE LIVERMORE NATIONAL SECURITY, LLC, Livermore, CA (US)

( * ) Notice: Subject to any disclaimer, the term of this patent is extended or adjusted under 35 U.S.C. 154(b) by 205 days.

This patent is subject to a terminal disclaimer.

(21) Appl. No.: 17/561,625

(22) Filed: Dec. 23, 2021

(65) Prior Publication Data
US 2022/0211866 A1 Jul. 7, 2022

Related U.S. Application Data

(63) Continuation of application No. 16/609,420, filed as application No. PCT/US2018/030537 on May 1, 2018, now Pat. No. 11,207,422.

(60) Provisional application No. 62/500,435, filed on May 2, 2017.

(51) Int. Cl.
A61K 39/00 (2006.01)
A61K 9/00 (2006.01)
A61K 9/127 (2006.01)
A61K 39/02 (2006.01)
A61K 39/39 (2006.01)
A61K 47/69 (2017.01)
A61P 31/04 (2006.01)
B82Y 5/00 (2011.01)

(52) U.S. Cl.
CPC ........ A61K 47/6915 (2017.08); A61K 9/0019 (2013.01); A61K 9/0043 (2013.01); A61K 9/1273 (2013.01); A61K 9/1277 (2013.01); A61K 39/0208 (2013.01); A61K 39/39 (2013.01); A61P 31/04 (2018.01); B82Y 5/00 (2013.01); A61K 2039/54 (2013.01); A61K 2039/543 (2013.01); A61K 2039/545 (2013.01); A61K 2039/6018 (2013.01); A61K 2039/6093 (2013.01)

(58) Field of Classification Search
CPC ................................................ A61K 47/6915
See application file for complete search history.

(56) References Cited

U.S. PATENT DOCUMENTS

| 5,679,559 A | 10/1997 | Kim et al. |
| 10,934,628 B2 | 3/2021 | Hoeprich, Jr. et al. |
| 11,207,422 B2 | 12/2021 | Coleman et al. |
| 11,279,749 B2 | 3/2022 | Hoeprich, Jr. et al. |
| 11,300,572 B2 | 4/2022 | Coleman et al. |
| 11,713,359 B2 | 8/2023 | Luo et al. |
| 2004/0053384 A1 | 3/2004 | Sligar et al. |
| 2004/0204354 A1 | 10/2004 | Nelson et al. |
| 2006/0088524 A1 | 4/2006 | Morrissey et al. |
| 2021/0317234 A1 | 10/2021 | Luo et al. |
| 2022/0283171 A1 | 9/2022 | Coleman et al. |
| 2023/0416414 A1 | 12/2023 | Luo et al. |

FOREIGN PATENT DOCUMENTS

WO    2004/090165 A1    10/2004

OTHER PUBLICATIONS

Final Office Action for U.S. Appl. No. 15/755,018, filed Feb. 23, 2018 on behalf of Lawrence Livermore National Security, LLC dated Dec. 27, 2021 18 pages.
Final Office Action for U.S. Appl. No. 16/082,924, filed Sep. 6, 2018 on behalf of Lawrence Livermore National Security, LLC dated Jan. 25, 2022 21 pages.
Notice of Allowability for U.S. Appl. No. 16/159,189, filed Oct. 12, 2018, on behalf of Lawrence Livermore National Security, LLC, dated Dec. 21, 2021. 4 Pages.
Notice of Allowance for U.S. Appl. No. 15/744,754, filed Jan. 12, 2018 on behalf of Lawrence Livermore National Security, LLC, dated Nov. 22, 2021 11 pages.
Notice of Allowance for U.S. Appl. No. 16/159,189, filed Oct. 12, 2018 on behalf of Lawrence Livermore National Security, LLC, dated Dec. 9, 2021. 10 Pages.
Restriction Requirement for U.S. Appl. No. 15/969,311, filed May 2, 2018 on behalf of Lawrence Livermore National Security, LLC., dated Dec. 20, 2021. 9 Pages.
Schuler M et al., "Nanodiscs as a new tool to examine lipid-protein interactions" Methods Mol Biol., 2013; 974, pp. 415-433.
Advisory Action for U.S. Appl. No. 16/082,924, filed Sep. 6, 2018 on behalf of Lawrence Livermore National Security, LLC, dated Jan. 12, 2024. 4 pages.
Alasiri, H. Determining Critical Micelle Concentrations of Surfactants Based on Viscosity Calculations from Coarse-Grained Molecular Dynamics Simulations. Energy Fuels, Jan. 2019, 33, 3, 2408-2412. 7 pages. Website: pubs.acs.org/doi/full/10.1021/acs.energyfuels.8b04228.
Cai L. et al., "A facile surfactant critical micelle concentration determination" Chem Commun, vol. 47 No. 19, May 21, 2011, pp. 5527-5529.

(Continued)

Primary Examiner — Albert M Navarro
(74) Attorney, Agent, or Firm — Steinfl + Bruno LLP

(57) ABSTRACT

A telodendrimer-nanolipoprotein particle (t-NLP), comprising one or more membrane forming lipids, one or more telodendrimers, and a scaffold protein and a Chlamydia major outer membrane protein (MOMP) comprising a MOMP hydrophobic region, and related compositions methods and systems.

31 Claims, 35 Drawing Sheets
Specification includes a Sequence Listing.

(56) References Cited

OTHER PUBLICATIONS

Castro M. J. L. et al., "A Simplified Method for the Determination of Critical Micelle Concentration" *Journal of Chemical Education*, vol. 78 No. 3, Mar. 2001, pp. 347-348.
Dai, S. et al. Isothermal titration calorimetric studies of alkyl phenol ethoxylate surfactants in aqueous solutions. Colloids and Surfaces A. Physiochem. Eng. Aspects, 229, (2003) 157-168.
European Examination Report for EP Application No. 17763807.9 filed on Mar. 3, 2017 on behalf of Lawrence Livermore National Security, LLC dated Aug. 17, 2022 6 pages.
Examiner's Answer for U.S. Appl. No. 15/755,018, filed Feb. 23, 2018 on behalf of Lawrence Livermore National Security, LLC dated Nov. 1, 2023 26 pages.
Final Office Action for U.S. Appl. No. 15/755,018, filed Feb. 23, 2018 on behalf of Lawrence Livermore National Security, LLC dated Nov. 17, 2022 20 pages.
Final Office Action for U.S. Appl. No. 15/969,311, filed May 2, 2018 on behalf of Lawrence Livermore National Security, LLC dated Nov. 18, 2022, 9 pages.
Final Office Action for U.S. Appl. No. 16/082,924, filed Sep. 6, 2018 on behalf of Lawrence Livermore National Security, LLC dated Sep. 25, 2023 25 pages.
Frankel D. et al., "Photoinduced destabilization of bilayer vesicles" *J. Am. Chem. Soc.* vol. 111 No. 26, 1989, pp. 9262-9263.
Geall A. J. et al., "Nonviral delivery of self-amplifying RNA vaccines" *PNAS*, vol. 109 No. 36, Sep. 2012, pp. 14604-14609.
He, W. et al. "Cationic HDL mimetics enhance in vivo delivery of self-replicating mRNA", Nanomedicine, Feb. 2020; 24: 102154. 20 pages. Doi:10.1016/j.nano.2020.102154.
Heerklotz, Heiko et al., The Enthalpy of Acyl Chain Packing and the Apparent Water-Accessible Apolar Surface Area of Phosphlipids. Biophysical Journal, vol. 80, Jan. 2001, pp. 271-279.
Held, P. et al. Rapid Critical Micelle Concentration (CMC) Determination Using Fluorescence Polarization, Agilent Application Note, Sep. 1, 2021, 9 pages.
Hossain, M.S. et al. Aggregation Behavior of Medium Chain Fatty Acids Studied by Coarse-Grained Molecular Dynamics Simulation. AAPS PharmSCiTech, Jan. 2019, 20:61. DOI: 10/1208/s12249-018-1289-4. 8 pages. Website: uu.diva-portal.org/smash/get/diva2:1283672/FULLTEXT01.pdf.
Houseley J. et al., "The Many Pathways of RNA Degradation" *Cell*, vol. 136, Feb. 2009, pp. 763-776.
Huibers, Paul D.T. et al. Prediction of Critical Micelle Concentration Using a Quantitative Structure-Property Relationship Approach. 1. Nonionic Surfactants. *Langmuir* 1996, vol. 12 No. 6, 1462-1470.
Janke, J.J. et al., "Oleic Acid Phase Behavior from Molecular Dynamics Simulations", Langmuir, 2014, 30, 35, 10661-10667, Aug. 18, 2014. Website: doi.org/10.1021/la501962n.
Jarin, Z. et al. Finite-Size Effects in Simulations of Peptide/Lipid Assembly. The Journal of Membrane Biology, 2022, 255: 437-449. Website: www.ncbi.nlm.nih.gov/pmc/articles/PMC9581812/.
Kauffman K. J. et al., "Materials for non-viral intracellular delivery of messenger RNA therapeutics" *Journal of Controlled Release*, vol. 240, 2016, pp. 227-234.
Lamparski H. et al., "Photoinduced destabilization of liposomes" *Biochemistry*, vol. 31 No. 3, 1992, pp. 685-694.
"Technical Bulletin: pSV-β Galactosidase Control Vector: Instructions for Use of Product E1081", Promega , Revised Sep. 2006. 9 pages. Website: www.promega.com.
Li, et al. The critical micelle concentrations of lysophosphatidic acid and sphingosylphosphorycholine. Chemistry and Physics of Lipids, 130 (2004) 197-201.

Martini website: General Purpose Coarse-Grained Force Field. Surfactant Micelles. Last updated: Feb. 18, 2021. 2 pages. Website: cgmartini.nl/index.php/martini-projects/sm.
Midoux P. et al. "Lipid-based mRNA vaccine delivery systems" *Expert Rev. Vaccines*, 2014, pp. 1-14.
Mueller A. et al., "Supramolecular materials via polymerization of mesophases of hydrated amphiphiles" *Chem. Rev.* 102(3), Mar. 2002, pp. 727-757. 64 pages.
Non-Final Office Action for U.S. Appl. No. 15/969,311, filed May 2, 2018, on behalf of Synthetic Genomics, Inc, dated Jun. 10, 2022. 55 Pages.
Non-Final Office Action for U.S. Appl. No. 15/969,311, filed May 2, 2018 on behalf of Synthetic Genomics, Inc, dated May 12, 2023 8 pages.
Non-Final Office Action for U.S. Appl. No. 16/082,924, filed Sep. 6, 2018 on behalf of Lawrence Livermore National Security, LLC dated Dec. 2, 2022 25 pages.
Non-Final Office Action for U.S. Appl. No. 15/969,311, filed May 2, 2018 in the name of Lawrence Livermore National Security, LLC, dated Nov. 10, 2022. 12 pages.
Notice of Allowance for U.S. Appl. No. 15/969,311, filed May 2, 2018 in the name of Lawrence Livermore National Security, LLC, dated Oct. 25, 2023. 8 pages.
Notice of Allowance for U.S. Appl. No. 17/308,921, filed May 5, 2021 in the name of Lawrence Livermore National Security, LLC, dated Mar. 9, 2023. 10 pages.
Pardi N. et al., "Expression kinetics of nucleoside-modified mRNA delivered in lipid nanoparticles to mice by various routes." *J. Control Release*, Nov. 2015, pp. 1-18.
Pardi N. et al., "mRNA vaccines—a new era in vaccinology" *Nature Reviews*, vol. 17, Apr. 2018, pp. 261-279.
Qin S. et al., "Predicting Critical Micelle Concentrations for Surfactants Using Graph Convolutional Neural Networks" *J. Phys. Chem. B*, Sep. 9, 2021, 125, 37, pp. 10610-10620.
Ramachandran S. et al., "Delivery Strategies for mRNA Vaccines" *Pharmaceutical Medicine*, vol. 36, Jan. 2022, pp. 11-20.
Reichmuth A. M. et al., "mRNA vaccine delivery using lipid nanoparticles" *Ther. Deliv.*, vol. 7 No. 5, Apr. 2016, pp. 319-334.
Roberts, David W. Application of Octanol/Water Partition Coefficients in Surfactant Science: A Quantitative Structure-Property Relationship for Micellization of Anionic Surfactants. Langmuir (2002), 18, 345-352.
Sapay, N. et al. "Thermodynamics of flip-flop and desorption for a systemic series of phosphatidylcholine lipids", Soft Matter, Issue 17, 5, 3295-3302, (May 21, 2009). Website: doi.org/10.1039/B902376C.
Schmidt S. T. et al., "Liposome-Based Adjuvants for Subunit Vaccines: Formulation Strategies for Subunit Antigens and Immunostimulators" *Pharmaceutics*, Mar. 2016, vol. 8 No. 7, pp. 1-22.
Tifrea, D.F., et al., Induction of Protection in Mice against a *Chlamydia muridarum* Respiratory Challenge by a Vaccine Formulated with the Major Outer Membrane Protein in Nanolipoprotein Particles. Vaccines, 2021, 9, 755. https://doi.org/10.3390 /vaccines9070755, pp. 1-19 (19 pages).
Tyminski P. N. et al., "Rhodopsin in polymerized bilayer membranes" *J. Am. Chem. Soc.* vol. 107 No. 25, 1985, pp. 7769-7770.
Tyminski P.N. et al., "Reconstitution of Rhodopsin and the cGMP cascade in polymerized bilayer membranes" *Biochemistry*, vol. 27 No. 8, 1988, pp. 2696-2705.
Weissman D. et al., "mRNA transcript therapy" *Expert Rev. Vaccines*, 2014, pp. 1-17.
Wielandt A. G. et al., "Specific Activation of the Plant P-type Plasma Membrane H+-ATPase by Lysophospholipids Depends on the Autoinhibitory N- and C-terminal Domains" *Journal of Biological Chemistry*, vol. 290 No. 26, Jun. 26, 2015, pp. 16281-16291.
Yu. D et al., "Determination of Critical Concentrations by Synchronous Fluorescence Spectrometry" Electronic Supplementary Information, *The Royal Society of Chemistry*,2011, pp. S1-S18.

D  GDNENQKTVKAESVPNMSFDQSVVELYT    EWQASLALSYRLNMFTPYIGV
E  GDNENQSTVKTNSVPNMSLDQSVVELYT    EWQASLALSYRLNMFTPYIGV

*FIG. 1D*

```
Nat_mdel49A1    CTGAATCTCCTGGAAAACTGGGACACTCTGGGTTCAACCGTTAGTCAGCTGCAGGAACGG
Opt_mdel49A1    CTGAATCTGCTGGAAAACTGGGACACCCTGGGCTCCACGGTGTCACAGCTGCAAGAACGC
                ******* ****************** ***** ** ** **       ******* ****

Nat_mdel49A1    CTGGGCCCATTGACTCGGGACTTCTGGGATAACCTGGAGAAAGAAACAGATTGGGTGAGA
Opt_mdel49A1    CTGGGTCCGCTGACGCGTGATTTTTGGGACAACCTGGAAAAAGAAACCGATTGGGTTCGC
                ***** **  **** ** ** ** ***** ******** ******* ********  *

Nat_mdel49A1    CAGGAGATGAACAAGGACCTAGAGGAAGTGAAACAGAAGGTGCAGCCCTACCTGGACGAA
Opt_mdel49A1    CAGGAAATGAATAAGGACCTGGAAGAAGTGAAACAGAAGGTTCAACCGTATCTGGATGAA
                ***** ***** ******** ** ***************** ** ** ** ***** ***

Nat_mdel49A1    TTCCAGAAGAAATGGAAAGAGGATGTGGAGCTCTACCGCCAGAAGGTGGCGCCTCTGGGC
Opt_mdel49A1    TTTCAGAAAAAGTGGAAAGAAGACGTCGAACTGTACCGTCAGAAGGTGGCACCGCTGGGC
                ** ***** ** ******** ** ** ** ** ****** ********** ** ******

Nat_mdel49A1    GCCGAGCTGCAGGAGAGCGCGCGCCAGAAGCTGCAGGAGCTGCAAGGGAGACTGTCCCCT
Opt_mdel49A1    GCTGAACTGCAAGAATCCGCACGCCAGAAACTGCAAGAACTGCAAGGTCGTCTGTCACCG
                ** ** ***** **    *** ******* ***** ** ****** **     **** ***

Nat_mdel49A1    GTGGCTGAGGAATTTCGCGACCGCATGCGCACACACGTAGACTCTCTGCGCACACAGCTA
Opt_mdel49A1    GTTGCTGAAGAATTTCGTGATCGCATGCGTACGCATGTGGATTCGCTGCGCACCCAACTG
                ** ***** ******** ** ******** ** ** ** ** ** ******** ** **

Nat_mdel49A1    GCGCCCACAGCGAACAGATGCGCGAGAGCCTGGCCCAGCGCCTGGCTGAGCTCAAGAGC
Opt_mdel49A1    GCACCGCACTCTGAACAGATGCGCGAAAGTCTGGCGCAACGTCTGGCCGAACTGAAAAGT
                ** **  ***    ************ ** ***** ** ** ***** ** ** ** **

Nat_mdel49A1    AACCCTACCTTGAACGAGTACCACACCAGGGCCAAAACCCACCTGAAGACACTTGGCGAG
Opt_mdel49A1    AACCCGACCCTGAATGAATACCATACCCGTGCCAAAACGCACCTGAAGACCCTGGGTGAA
                ***** *** **** ** ***** *** * ******** ***********  ** ** **

Nat_mdel49A1    AAAGCCAGACCTGCGCTGGAGGACCTGCGCCATAGTCTGATGCCCATGCTGGAGACGCTT
Opt_mdel49A1    AAAGCACGTCCGGCGCTGGAAGACCTGCGTCATTCTCTGATGCCGGATGCTGGAAACCCTG
                *****  * **  ******* ******** ***   ******** ** ******  ** **

Nat_mdel49A1    AAGACCCAAGTCCAGAGTGTGATCGACAAGGCCAGCGAGACTCTGACTGCCCAG
Opt_mdel49A1    AAAACCCAAGTCCAGTCGGTGATTGACAAAGCAAGCGAAACCCTGACGGCACAG
                ** *********** *  ***** ***** ** ***** ** ***** ** ***
```

FIG. 3A

```
Nat_MOMP1  CTGCCTGTGGGGAATCCTGCTGAACCAAGCCTTATGATTGACGGGATTCTTTGGGAAGGT
Opt_MOMP1  CTGCCGGTTGGTAACCCGGCTGAACCGTCTCTGATGATCGATGGTATCCTGTGGGAAGGT
           *****  ** **  ** ** *******   ** *****  ** ** ** ** *********

Nat_MOMP1  TTCGGTGGAGATCCTTGCGATCCTTGCACAACTTGGTGTGATGCCATCAGCCTACGTCTC
Opt_MOMP1  TTCGGTGGTGATCCGTGTGATCCGTGTACTACTTGGTGTGATGCTATCTCTCTGCGTCTG
           ********  ***** ** ***** ** ** ************* *** ** *  *****

Nat_MOMP1  GGCTACTATGGGGACTTCGTTTTTGATCGTGTTTTGAAAACAGACGTGAACAAACAGTTC
Opt_MOMP1  GGTTACTACGGTGATTTCGTTTTCGATCGTGTTCTGAAAACTGACGTTAACAAACAGTTC
           ** ***** ** ** ******** ********* ******* *****  ***********

Nat_MOMP1  GAAATGGGAGCAGCTCCTACAGGAGATGCAGACCTTACTACAGCACCTACTCCTGCATCA
Opt_MOMP1  GAAATGGGTGCTGCTCCGACTGGTGACGCTGACCTGACCACTGCTCCGACTCCGGCTTCT
           ******** ** ***** ** ** ** ** ***** ** ** ** ** ***** **

Nat_MOMP1  AGAGAGAATCCCGCTTATGGCAAGCATATGCAAGATGCAGAAATGTTCACTAATGCTGCG
Opt_MOMP1  CGTGAAAACCCGGCTTACGGTAAACACATGCAGGACGCTGAAATGTTCACTAACGCTGCT
           * ** ** ** *******  ** ** ** ** ** ** ** ************** *****

Nat_MOMP1  TACATGGCTTTAAACATTTGGGACCGTTTCGATGTATTTTGTACATTGGGAGCAACTAGC
Opt_MOMP1  TACATGGCTCTGAACATCTGGGACCGTTTCGACGTTTTCTGCACTCTGGGTGCTACTTCT
           ********* * ***** **************  ** ** ** ** *****  ** ** ***

Nat_MOMP1  GGATATCTTAAAGGTAATTCTGCCGCCTTTAACTTAGTTGGTCTGTTTGGAAGAGATGAA
Opt_MOMP1  GGTTACCTGAAAGGTAACTCTGCTGCTTTCAACCTGGTTGGTCTGTTCGGTCGTGACGAA
           ** **  ** ******** ***** ** ***  *  ***********  **  * ** ***

Nat_MOMP1  ACTGCAGTTGCAGCTGACGACATACCTAACGTCAGCTTGTCTCAAGCTGTTGTCGAACTC
Opt_MOMP1  ACTGCTGTTGCTGCTGACGACATCCCGAACGTTTCTCTGTCTCAGGCTGTTGTTGAACTG
           ***** ***** ***********  ** *****    * ****** ******* *****

Nat_MOMP1  TACACAGACACAGCTTTCGCTTGGAGCGTCGGTGCTAGAGCAGCTTTATGGGAGTGCGGA
Opt_MOMP1  TACACTGACACTGCTTTCGCTTGGTCTGTTGGTGCTCGTGCTGCTCTGTGGGAATGTGGT
           ***** ***** ************    ** ******  ** *** * *****  ** **

Nat_MOMP1  TGTGCAACTTTAGGAGCTTCCTTCCAATATGCTCAATCTAAGCCAAAAGTAGAGGAATTA
Opt_MOMP1  TGCGCTACTCTGGGTGCTTCTTTCCAGTACGCTCAGTCTAAACCGAAAGTTGAAGAACTG
           ** **  ***  * ** ***** ******** ***** ***** ** ***** ** *** *

Nat_MOMP1  AACGTTCTCTGTAATGCGGCAGAATTCACTATTAACAAGCCTAAAGGATACGTTGGACAA
Opt_MOMP1  AACGTTCTGTGTAACGCTGCTGAATTCACCATCAACAAACCGAAAGGCTACGTTGGCCAG
           ******** ***** **  ** ********* ** *****  ** ***** ********  **

Nat_MOMP1  GAGTTTCCTCTTAACATTAAAGCTGGAACAGTTAGCGCTACAGATACTAAAGATGCTTCC
Opt_MOMP1  GAATTCCCGCTGAACATCAAAGCTGGTACCGTTTCTGCTACTGACACCAAAGACGCTTCC
           ** ** ** ** ** ***** ********  ** ***   ***** **  ***** ******
```

```
Nat_MOMP1    ATCGATTACCATGAGTGGCAAGCAAGCTTGGCTTTGTCTTACAGACTGAATATGTTCACT
Opt_MOMP1    ATCGACTACCACGAATGGCAGGCTTCCCTGGCTCTGTCCTACCGTCTGAACATGTTCACT
             ***** ***** ** ***** **  * ***** **** *** * ***** *********

Nat_MOMP1    CCTTACATTGGAGTTAAGTGGTCTAGAGCAAGCTTTGATGCCGACACTATCCGCATTGCG
Opt_MOMP1    CCGTACATCGGTGTTAAATGGTCTCGTGCTTCTTTCGACGCTGACACTATCCGTATCGCT
             ** ***** ** ***** ****** ** **  ** ** ** *********** ** **

Nat_MOMP1    CAGCCTAAGCTTGAGACCTCTATCTTAAAAATGACCACTTGGAACCCAACGATCTCTGGA
Opt_MOMP1    CAGCCGAAACTGGAAACTTCTATCCTGAAAATGACTACCTGGAACCCGACTATCTCTGGT
             ***** ** ** ** ** ****** * ******** ** ******* ** ********

Nat_MOMP1    TCTGGTATAGACGTTGATACAAAAATCACGGATACATTACAAATTGTTTCCTTGCAGCTC
Opt_MOMP1    TCTGGTATCGACGTTGACACCAAAATCACCGACACCCTGCAGATCGTTTCCCTGCAGCTG
             ******** ******** ** ******** ** **   * ** ** ****** *******

Nat_MOMP1    AACAAGATGAAATCCAGAAAATCTTGCGGTCTTGCAATTGGAACAACAATTGTAGATGCT
Opt_MOMP1    AACAAAATGAAATCCCGTAAATCCTGCGGCCTGGCTATCGGTACCACCATCGTTGACGCT
             ***** ********* * ***** ***** ** ** ** ** ** ** ** ** ** ***

Nat_MOMP1    GATAAATATGCAGTTACTGTTGAGACACGCTTGATCGATGAAAGAGCAGCTCACGTAAAT
Opt_MOMP1    GACAAATACGCTGTTACCGTTGAAACCGTCTGATCGACGAACGTGCTGCTCACGTTAAC
             ** ***** ** ***** ***** **  *******  ** *** ** ******** **

Nat_MOMP1    GCTCAGTTCCGTTTC
Opt_MOMP1    GCTCAGTTCCGTTTC
             ***************
```

FIG. 3B (Continued)

FIG. 5A
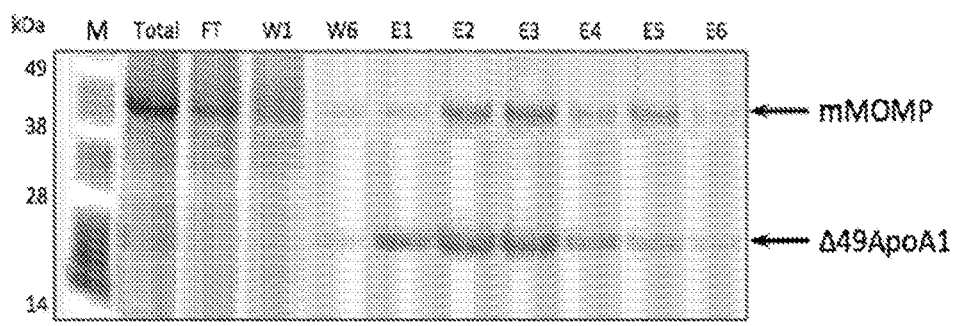
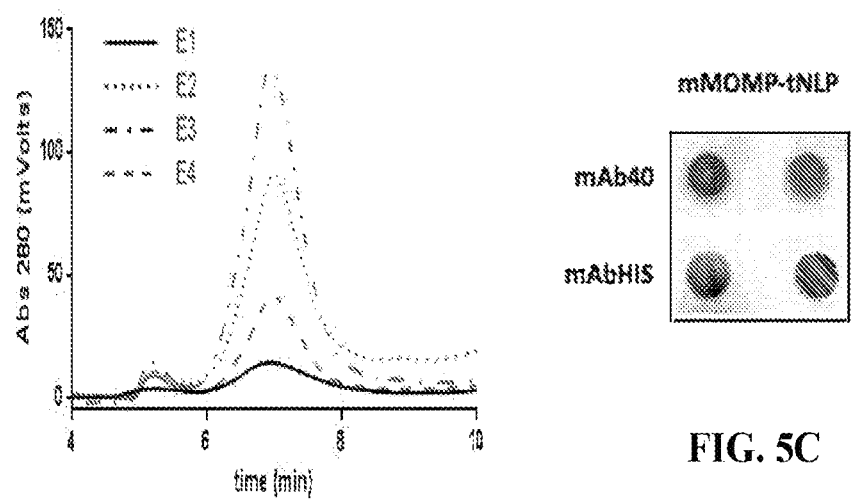
FIG. 5B
FIG. 5C

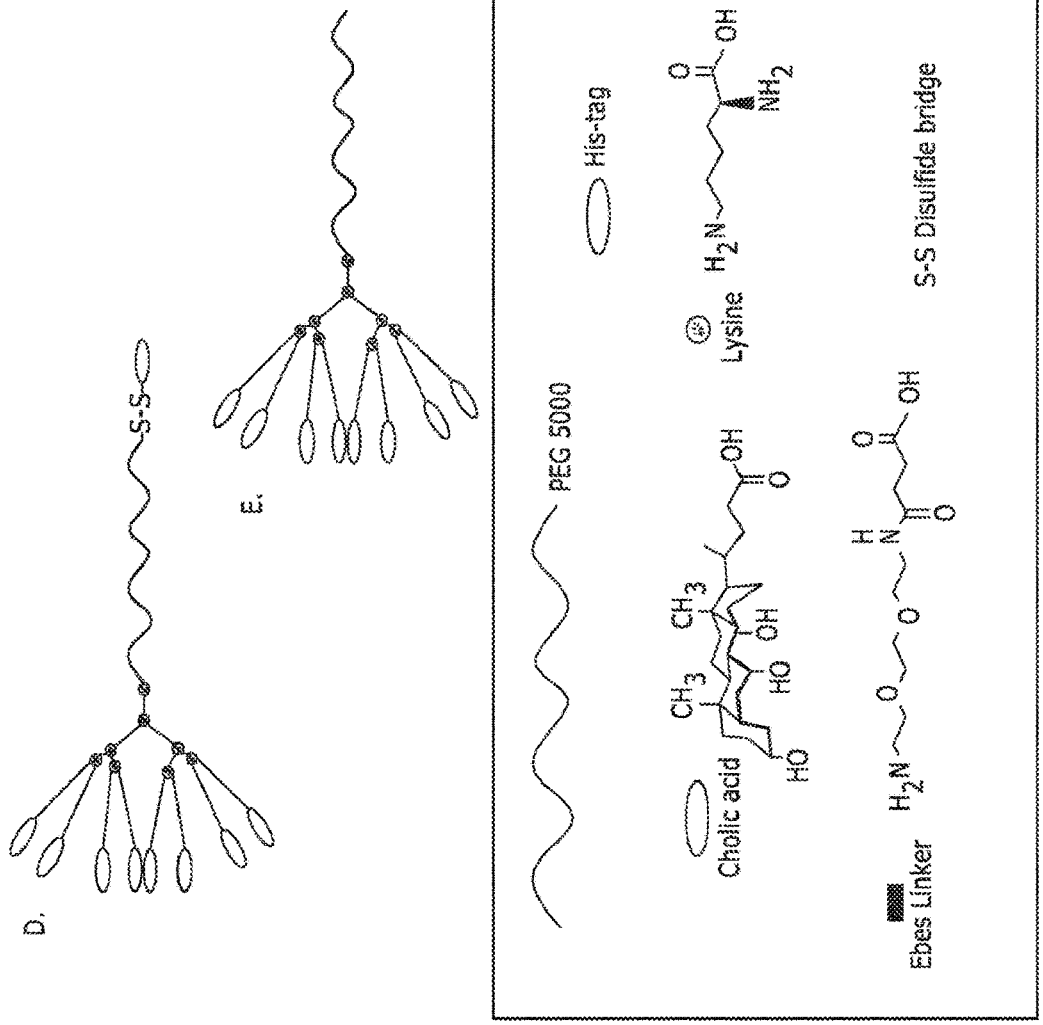
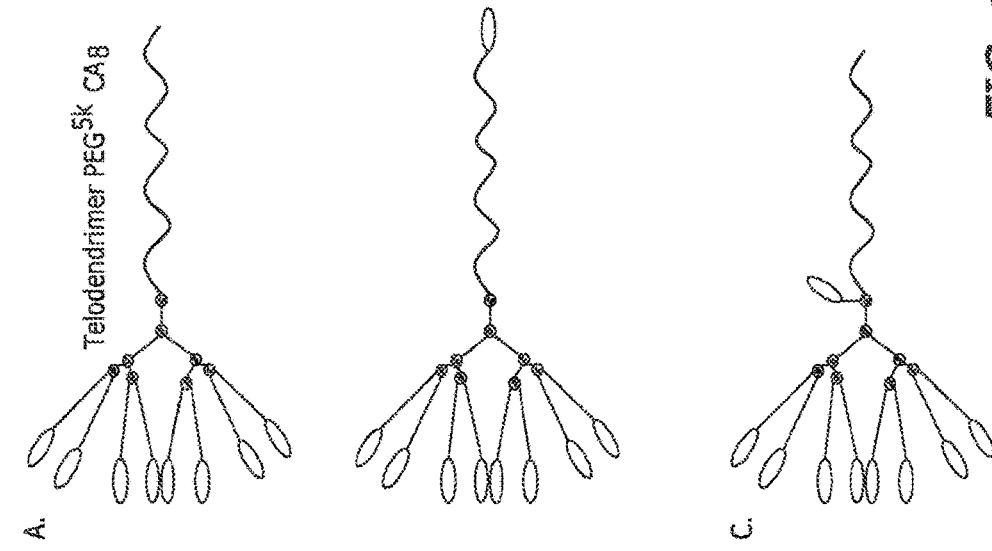
FIG. 11B

LLNL Mouse Δ49ApoA1

Codon optimized –Genscript optimization

___ restriction sites NdeI

_ _ _ _ restriction sites BamHI catatgCTGAATCTGCTGGAAAACTGGGACACCCTGGGCTCCACGGTGTCACAGCTGCAAGAACG
CCTGGGTCCGCTGACGCGTGATTTTTGGGACAACCTGGAAAAAGAAACCGATTGGGTTCGCCAGG
AAATGAATAAGGACCTGGAAGAAGTGAAACAGAAGGTTCAACCGTATCTGGATGAATTTCAGAAA
AAGTGGAAAGAAGACGTCGAACTGTACCGTCAGAAGGTGGCACCGCTGGGCGCTGAACTGCAAGA
ATCCGCACGCCAGAAACTGCAAGAACTGCAAGGTCGTCTGTCACCGGTTGCTGAAGAATTTCGTG
ATCGCATGCGTACGCATGTGGATTCGCTGCGCACCCAACTGGCACCGCACTCTGAACAGATGCGC
GAAAGTCTGGCGCAACGTCTGGCCGAACTGAAAAGTAACCCGACCCTGAATGAATACCATACCCG
TGCCAAAACGCACCTGAAGACCCTGGGTGAAAAGCACGTCCGGCGCTGGAAGACCTGCGTCATT
CTCTGATGCCGATGCTGGAAACCCTGAAAACCCAAGTCCAGTCGGTGATTGACAAAGCAAGCGAA
ACCCTGACGGCACAGggatcc Amino acid Sequence LNLLENWDTLGSTVSQLQERLGPLTRDFWDNLEKETDWVRQEMNKDLEEVKQKVQPYLDEFQKKW
KEDVELYRQKVAPLGAELQESARQKLQELQGRLSPVAEEFRDRMRTHVDSLRTQLAPHSEQMRES
LAQRLAELKSNPTLNEYHTRAKTHLKTLGEKARPALEDLRHSLMPMLETLKTQVQSVIDKASETL
TAQ

FIG. 12A

LLNL Mouse ApoE4, 22k

Codon Optimized – Genscript optimization

— restriction sites NdeI

- - - - restriction sites BamHI

<u>catatg</u>GGTGAACCGGAAGTGACCGATCAACTGGAATGGCAATCTAATCAACCGTGGGAACAAGC
CCTGAACCGTTTTTGGGACTATCTGCGCTGGGTGCAAACCCTGAGCGATCAGGTTCAAGAAGAAC
TGCAGAGCTCTCAAGTTACCCAGGAACTGACGGCACTGATGGAAGACACCATGACGGAAGTCAAA
GCTTATAAAAAGGAACTGGAAGAACAGCTGGGCCCGGTCGCAGAAGAAACGCGTGCTCGCCTGGG
TAAAGAAGTGCAAGCAGCACAGGCACGTCTGGGTGCAGATATGGAAGACCTGCGTAACCGCCTGG
GTCAATACCGTAATGAAGTGCATACCATGCTGGGCCAGAGTACGGAAGAAATTCGTGCGCGCCTG
TCCACCCACCTGCGTAAAATGCGTAAGCGCCTGATGCGCGATGCGGAAGACCTGCAGAAACGTCT
GGCCGTTTATAAGGCAGGCGCTCGCGAAGGTGCCGAACGTGGTGTGTCGGCAATCCGTGAACGCC
TGGGTCCGCTGGTTAACAAGGTCGTCAG<u>ggatcc</u>

Amino Acid sequence Mouse_E422k

HMGEPEVTDQLEWQSNQPWEQALNRFWDYLRWVQTLSDQVQEELQSSQVTQEL
TALMEDTMTEVKAYKKELEEQLGPVAEETRARLGKEVQAAQARLGADMEDLRN
RLGQYRNEVHTMLGQSTEEIRARLSTHLRKMRKRLMRDAEDLQKRLAVYKAGAR
EGAERGVSAIRERLGPLVEQGRQGS

FIG. 12B

LLNL MoPn MOMP

Based on (NP_296436) WP_010232357 and codon optimized

ATATTTTGTTTACTTTAAGAAGGAGATATACCATGGCACATATGCTGCCGGTTG
GTAACCCGGCTGAACCGTCTCTGATGATCGATGGTATCCTGTGGGAAGGTTTC
GGTGGTGATCCGTGTGATCCGTGTACTACTTGGTGTGATGCTATCTCTCTGCGT
CTGGGTTACTACGGTGATTTCGTTTTCGATCGTGTTCTGAAAACTGACGTTAAC
AAACAGTTCGAAATGGGTGCTGCTCCGACTGGTGACGCTGACCTGACCACTGC
TCCGACTCCGGCTTCTCGTGAAAACCCGGCTTACGGTAAACACATGCAGGACG
CTGAAATGTTCACTAACGCTGCTTACATGGCTCTGAACATCTGGGACCGTTTCG
ACGTTTTCTGCACTCTGGGTGCTACTTCTGGTTACCTGAAAGGTAACTCTGCTG
CTTTCAACCTGGTTGGTCTGTTCGGTCGTGACGAAACTGCTGTTGCTGCTGACG
ACATCCCGAACGTTTCTCTGTCTCAGGCTGTTGTTGAACTGTACACTGACACTG
CTTTCGCTTGGTCTGTTGGTGCTCGTGCTGCTCTGTGGGAATGTGGTTGCGCTA
CTCTGGGTGCTTCTTTCCAGTACGCTCAGTCTAAACCGAAAGTTGAAGAACTGA
ACGTTCTGTGTAACGCTGCTGAATTCACCATCAACAAACCGAAAGGCTACGTTG
GCCAGGAATTCCCGCTGAACATCAAAGCTGGTACCGTTTCTGCTACTGACACCA
AAGACGCTTCCATCGACTACCACGAATGGCAGGCTTCCCTGGCTCTGTCCTACC
GTCTGAACATGTTCACTCCGTACATCGGTGTTAAATGGTCTCGTGCTTCTTTCG
ACGCTGACACTATCCGTATCGCTCAGCCGAAACTGGAAACTTCTATCCTGAAAA
TGACTACCTGGAACCCGACTATCTCTGGTTCTGGTATCGACGTTGACACCAAAA
TCACCGACACCCTGCAGATCGTTTCCCTGCAGCTGAACAAAATGAAATCCCGTA
AATCCTGCGGCCTGGCTATCGGTACCACCATCGTTGACGCTGACAAATACGCT
GTTACCGTTGAAACCCGTCTGATCGACGAACGTGCTGCTCACGTTAACGCTCA
GTTCCGTTTCGGATCCGGCTGCTAACAAAGCCCGAA

Amino acid Sequence

MLPVGNPAEPSLMIDGILWEGFGGDPCDPCTTWCDAISLRLGYYGDFVFDRVLKTDVNKQFEMGA
APTGDADLTTAPTPASRENPAYGKHMQDAEMFTNAAYMALNIWDRFDVFCTLGATSGYLKGNSAA
FNLVGLFGRDETAVAADDIPNVSLSQAVVELYTDTAFAWSVGARAALWECGCATLGASFQYAQSK
PKVEELNVLCNAAEFTINKPKGYVGQEFPLNIKAGTVSATDTKDASIDYHEWQASLALSYRLNMF
TPYIGVKWSRASFDADTIRIAQPKLETSILKMTTWNPTISGSGIDVDTKITDTLQIVSLQLNKMK
SRKSCGLAIGTTIVDADKYAVTVETRLIDERAAHVNAQFRF

FIG. 12C

Wild type mouse nucleic acid sequence for the encoded Δ49ApoA1 gene

CTGAATCTCCTGGAAAACTGGGACACTCTGGGTTCAACCGTTAGTCAGCTGCAGGAACGGCTGGG
CCCATTGACTCGGGACTTCTGGGATAACCTGGAGAAAGAAACAGATTGGGTGAGACAGGAGATGA
ACAAGGACCTAGAGGAAGTGAAACAGAAGGTGCAGCCCTACCTGGACGAATTCCAGAAGAAATGG
AAAGAGGATGTGGAGCTCTACCGCCAGAAGGTGGCGCCTCTGGGCGCCGAGCTGCAGGAGAGCGC
GCGCCAGAAGCTGCAGGAGCTGCAAGGGAGACTGTCCCTGTGGCTGAGGAATTTCGCGACCGCA
TGCGCACACACGTAGACTCTCTGCGCACACAGCTAGCGCCCCACAGCGAACAGATGCGCGAGAGC
CTGGCCCAGCGCCTGGCTGAGCTCAAGAGCAACCCTACCTTGAACGAGTACCACACCAGGGCCAA
AACCCACCTGAAGACACTTGGCGAGAAAGCCAGACCTGCGCTGGAGGACCTGCGCCATAGTCTGA
TGCCCATGCTGGAGACGCTTAAGACCCAAGTCCAGAGTGTGATCGACAAGGCCAGCGAGACTCTG
ACTGCCCAG

FIG. 13

LLNL codon optimized mouse nucleic acid sequence for the encoded Δ49ApoA1 gene

CTGAATCTGCTGGAAAACTGGGACACCCTGGGCTCCACGGTGTCACAGCTGCAAGAACGCCTGGG
TCCGCTGACGCGTGATTTTTGGGACAACCTGGAAAAAGAAACCGATTGGGTTCGCCAGGAAATGA
ATAAGGACCTGGAAGAAGTGAAACAGAAGGTTCAACCGTATCTGGATGAATTTCAGAAAAAGTGG
AAAGAAGACGTCGAACTGTACCGTCAGAAGGTGGCACCGCTGGGCGCTGAACTGCAAGAATCCGC
ACGCCAGAAACTGCAAGAACTGCAAGGTCGTCTGTCACCGGTTGCTGAAGAATTTCGTGATCGCA
TGCGTACGCATGTGGATTCGCTGCGCACCCAACTGGCACCGCACTCTGAACAGATGCGCGAAAGT
CTGGCGCAACGTCTGGCCGAACTGAAAAGTAACCCGACCCTGAATGAATACCATACCCGTGCCAA
AACGCACCTGAAGACCCTGGGTGAAAAGCACGTCCGGCGCTGGAAGACCTGCGTCATTCTCTGA
TGCCGATGCTGGAAACCCTGAAAACCCAAGTCCAGTCGGTGATTGACAAAGCAAGCGAAACCCTG
ACGGCACAG

FIG. 14

LLNL codon optimized BALBC mouse nucleic acid sequence for the encoded Δ49ApoA1 gene CTGAACCTGCTGGAAAACTGGGACACCCTGGGTTCTACCGTTTCTCAGCTGCAGGAACGTCTGGGTCCGC
TGACCCGTGACTTCTGGGACAACCTGGAAAAAGAAACCGACTGGGTTCGTCAGGAAATGAACAAAGACCT
GGAAGAAGTTAAACAGAAAGTTCAGCCGTACCTGGACGAATTCCAGAAAAAATGGAAAGAAGACGTTGAA
CTGTACCGTCAGAAAGTTGCGCCGCTGGGTGCGGAACTGCAGGAATCTGCGCGTCAGAAACTGCAGGAAC
TGCAGGGTCGTCTGTCTCCGGTTGCGGAAGAATTCCGTGACCGTATGCGTACCCACGTTGACTCTCTGCG
TACCCAGCTGGCGCCGCACTCTGAACAGATGCGTGAATCTCTGGCGCAGCGTCTGGCGGAACTGAAATCT
AACCCGACCCTGAACGAATACCACACCCGTGCGAAAACCCACCTGAAAACCCTGGGTGAAAAAGCGCGTC
CGGCGCTGGAAGACCTGCGTCACTCTCTGATGCCGATGCTGGAAACCCTGAAAACCAAAGCGCAGTCTGT
TATCGACAAAGCGTCTGAAACCCTGACCGCGCAG

FIG. 15

Wild type *Chlamydia muridarum* MOMP nucleic acid sequence

CTGCCTGTGGGGAATCCTGCTGAACCAAGCCTTATGATTGACGGGATTCTTTGGGAAGGTTTCGGTGGAG
ATCCTTGCGATCCTTGCACAACTTGGTGTGATGCCATCAGCCTACGTCTCGGCTACTATGGGGACTTCGT
TTTTGATCGTGTTTTGAAAACAGACGTGAACAAACAGTTCGAAATGGGAGCAGCTCCTACAGGAGATGCA
GACCTTACTACAGCACCTACTCCTGCATCAAGAGAGAATCCCGCTTATGGCAAGCATATGCAAGATGCAG
AAATGTTCACTAATGCTGCGTACATGGCTTTAAACATTTGGGACCGTTTCGATGTATTTTGTACATTGGG
AGCAACTAGCGGATATCTTAAAGGTAATTCTGCCGCCTTTAACTTAGTTGGTCTGTTTGGAAGAGATGAA
ACTGCAGTTGCAGCTGACGACATACCTAACGTCAGCTTGTCTCAAGCTGTTGTCGAACTCTACACAGACA
CAGCTTTCGCTTGGAGCGTCGGTGCTAGAGCAGCTTTATGGGAGTGCGGATGTGCAACTTTAGGAGCTTC
CTTCCAATATGCTCAATCTAAGCCAAAAGTAGAGGAATTAAACGTTCTCTGTAATGCGGCAGAATTCACT
ATTAACAAGCCTAAAGGATACGTTGGACAAGAGTTTCCTCTTAACATTAAAGCTGGAACAGTTAGCGCTA
CAGATACTAAAGATGCTTCCATCGATTACCATGAGTGGCAAGCAAGCTTGGCTTTGTCTTACAGACTGAA
TATGTTCACTCCTTACATTGGAGTTAAGTGGTCTAGAGCAAGCTTTGATGCCGACACTATCCGCATTGCG
CAGCCTAAGCTTGAGACCTCTATCTTAAAAATGACCACTTGGAACCCAACGATCTCTGGATCTGGTATAG
ACGTTGATACAAAAATCACGGATACATTACAAATTGTTTCCTTGCAGCTCAACAAGATGAAATCCAGAAA
ATCTTGCGGTCTTGCAATTGGAACAACAATTGTAGATGCTGATAAATATGCAGTTACTGTTGAGACACGC
TTGATCGATGAAAGAGCAGCTCACGTAAATGCTCAGTTCCGTTTC

FIG. 16

LLNL codon optimized *Chlamydia muridarum* MOMP nucleic acid sequence

CTGCCGGTTGGTAACCCGGCTGAACCGTCTCTGATGATCGATGGTATCCTGTGGGAAGGTTTCGGTGGTG
ATCCGTGTGATCCGTGTACTACTTGGTGTGATGCTATCTCTCTGCGTCTGGGTTACTACGGTGATTTCGT
TTTCGATCGTGTTCTGAAAACTGACGTTAACAAACAGTTCGAAATGGGTGCTGCTCCGACTGGTGACGCT
GACCTGACCACTGCTCCGACTCCGGCTTCTCGTGAAACCCGGCTTACGGTAAACACATGCAGGACGCTG
AAATGTTCACTAACGCTGCTTACATGGCTCTGAACATCTGGGACCGTTTCGACGTTTTCTGCACTCTGGG
TGCTACTTCTGGTTACCTGAAAGGTAACTCTGCTGCTTTCAACCTGGTTGGTCTGTTCGGTCGTGACGAA
ACTGCTGTTGCTGCTGACGACATCCCGAACGTTTCTCTGTCTCAGGCTGTTGTTGAACTGTACACTGACA
CTGCTTTCGCTTGGTCTGTTGGTGCTCGTGCTGCTCTGTGGGAATGTGGTTGCGCTACTCTGGGTGCTTC
TTTCCAGTACGCTCAGTCTAAACCGAAAGTTGAAGAACTGAACGTTCTGTGTAACGCTGCTGAATTCACC
ATCAACAAACCGAAAGGCTACGTTGGCCAGGAATTCCCGCTGAACATCAAAGCTGGTACCGTTTCTGCTA
CTGACACCAAAGACGCTTCCATCGACTACCACGAATGGCAGGCTTCCCTGGCTCTGTCCTACCGTCTGAA
CATGTTCACTCCGTACATCGGTGTTAAATGGTCTCGTGCTTCTTTCGACGCTGACACTATCCGTATCGCT
CAGCCGAAACTGGAAACTTCTATCCTGAAAATGACTACCTGGAACCCGACTATCTCTGGTTCTGGTATCG
ACGTTGACACCAAAATCACCGACACCCTGCAGATCGTTTCCCTGCAGCTGAACAAAATGAAATCCCGTAA
ATCCTGCGGCCTGGCTATCGGTACCACCATCGTTGACGCTGACAAATACGCTGTTACCGTTGAAACCCGT
CTGATCGACGAACGTGCTGCTCACGTTAACGCTCAGTTCCGTTTC

FIG. 17

SEQUENCE LISTING

<160> NUMBER OF SEQ ID NOS: 70

<210> SEQ ID NO 1
<211> LENGTH: 1164
<212> TYPE: DNA
<213> ORGANISM: Chlamydia muridarum

<400> SEQUENCE: 1

```
atgaaaaaac tcttgaaatc ggtattagca tttgccgttt tgggttctgc ttcctccttg      60
catgctctgc ctgtggggaa tcctgctgaa ccaagcctta tgattgacgg gattctttgg     120
```

```
gaaggtttcg gtggagatcc ttgcgatcct tgcacaactt ggtgtgatgc catcagccta    180
cgtctcggct actatgggga cttcgttttt gatcgtgttt tgaaaacaga cgtgaacaaa    240
cagttcgaaa tgggagcagc tcctacagga gatgcagacc ttactacagc acctactcct    300
gcatcaagag agaatcccgc ttatggcaag catatgcaag atgcagaaat gttcactaat    360
gctgcgtaca tggcttttaaa catttgggac cgtttcgatg tattttgtac attgggagca   420
actagcggat atcttaaagg taattctgcc gcctttaact tagttggtct gtttggaaga    480
gatgaaactg cagttgcagc tgacgacata cctaacgtca gcttgtctca agctgttgtc    540
gaactctaca cagacacagc tttcgcttgg agcgtcggtg ctagagcagc tttatgggag    600
tgcggatgtg caactttagg agcttccttc caatatgctc aatctaagcc aaaagtagag    660
gaattaaacg ttctctgtaa tgcggcagaa ttcactatta caagcctaa aggatacgtt     720 ggacaagagt ttcctcttaa cattaaagct ggaacagtta gcgctacaga tactaaagat    780
gcttccatcg attaccatga gtggcaagca agcttggctt tgtcttacag actgaatatg    840
ttcactcctt acattggagt taagtggtct agagcaagct tgatgccga cactatccgc     900 attgcgcagc ctaagcttga gacctctatc ttaaaaatga ccacttggaa cccaacgatc    960
tctggatctg gtatagacgt tgatacaaaa atcacggata cattacaaat tgtttccttg   1020
cagctcaaca gatgaaatc cagaaaatct tgcggtcttg caattggaac aacaattgta    1080
gatgctgata aatatgcagt tactgttgag acacgcttga tcgatgaaag agcagctcac   1140
gtaaatgctc agttccgttt ctaa                                          1164
```

<210> SEQ ID NO 2
<211> LENGTH: 387
<212> TYPE: PRT
<213> ORGANISM: Chlamydia muridarum

<400> SEQUENCE: 2

```
Met Lys Lys Leu Leu Lys Ser Val Leu Ala Phe Ala Val Leu Gly Ser
1               5                   10

Gly Ala Arg Ala Ala Leu Trp Glu Cys Gly Cys Ala Thr Leu Gly Ala
            195                 200                 205

Ser Phe Gln Tyr Ala Gln Ser Lys Pro Lys Val Glu Glu Leu Asn Val
    210                 215                 220

Leu Cys Asn Ala Ala Glu Phe Thr Ile Asn Lys Pro Lys Gly Tyr Val
225                 230                 235                 240

Gly Gln Glu Phe Pro Leu Asn Ile Lys Ala Gly Thr Val Ser Ala Thr
                245                 250                 255

Asp Thr Lys Asp Ala Ser Ile Asp Tyr His Glu Trp Gln Ala Ser Leu
            260                 265                 270

Ala Leu Ser Tyr Arg Leu Asn Met Phe Thr Pro Tyr Ile Gly Val Lys
        275                 280                 285

Trp Ser Arg Ala Ser Phe Asp Ala Asp Thr Ile Arg Ile Ala Gln Pro
290                 295                 300

Lys Leu Glu Thr Ser Ile Leu Lys Met Thr Thr Trp Asn Pro Thr Ile
305                 310                 315                 320

Ser Gly Ser Gly Ile Asp Val Asp Thr Lys Ile Thr Asp Thr Leu Gln
                325                 330                 335

Ile Val Ser Leu Gln Leu Asn Lys Met Lys Ser Arg Lys Ser Cys Gly
            340                 345                 350

Leu Ala Ile Gly Thr Thr Ile Val Asp Ala Asp Lys Tyr Ala Val Thr
        355                 360                 365

Val Glu Thr Arg Leu Ile Asp Glu Arg Ala Ala His Val Asn Ala Gln
370                 375                 380

Phe Arg Phe
385

<210> SEQ ID NO 3
<211> LENGTH: 779
<212> TYPE: DNA
<213> ORGANISM: Chlamydia trachomatis strain A/Har-1

<400> SEQUENCE: 3
tttgtacatt gggagcaact accggttatt taaaaggaaa ctccgcttcc ttcaacttag      60
ttggattatt cggaacaaaa acacaatctt ctggctttga tacagcgaat attgttccta     120
acactgcttt gaatcaagct gtggttgagc tttatacaga cactaccttt gcttggagcg     180
taggtgctcg tgcagctctc tgggaatgtg gtgtgcaac gttaggagct tctttccaat      240
atgctcaatc taaacctaaa gtagaagagt tgaatgttct ttgtaatgca tccgaattta     300
ctattaataa gccgaaagga tatgttgggg cggaatttcc acttgatatt accgcaggaa     360
cagaagctgc gacagggact aaggatgcct ctattgacta ccatgagtgg caagcaagtt     420
tagccctttc ttacagatta aatatgttca ctccttacat tggagttaaa tggtctagag     480
taagttttga tgccgacacg atccgtatcg ctcagcctaa attggctaaa ccagtcttgg     540
ataccactac tctaaacccg accatcgctg gtaaaggaac tgtggtctct tccgcagaaa     600
acgaactggc tgatacaatg caaatcgttt ccttgcagtt gaacaagatg aaatctagaa     660
aatcttgcgg tattgcagta ggaacaactg ttgtagatgc agataaatac gcagttacaa     720
ttgagactcg cttgatcgat gagagagcag ctcacgtaaa tgcacaattc cgcttctaa      779

<210> SEQ ID NO 4
<211> LENGTH: 396
<212> TYPE: PRT
<213> ORGANISM: Chlamydia trachomatis strain A/Har-1

<400> SEQUENCE: 4

Met Lys Lys Leu Leu Lys Ser Val Leu Val Phe Ala Ala Leu Ser Ser
1               5                   10                  15

Ala Ser Ser Leu Gln Ala Leu Pro Val Gly Asn Pro Ala Glu Pro Ser
            20                  25                  30

Leu Met Ile Asp Gly Ile Leu Trp Glu Gly Phe Gly Gly Asp Pro Cys
        35                  40                  45

Asp Pro Cys Thr Thr Trp Cys Asp Ala Ile Ser Met Arg Met Gly Tyr
    50                  55                  60

Tyr Gly Asp Phe Val Phe Asp Arg Val Leu Lys Thr Asp Val Asn Lys
65                  70                  75                  80

Glu Phe Gln Met Gly Ala Ala Pro Thr Thr Ser Asp Val Ala Gly Leu
                85                  90                  95

Glu Lys Asp Pro Val Ala Asn Val Ala Arg Pro Asn Pro Ala Tyr Gly
            100                 105                 110

Lys His Met Gln Asp Ala Glu Met Phe Thr Asn Ala Ala Tyr Met Ala
        115                 120                 125

Leu Asn Ile Trp Asp Arg Phe Asp Val Phe Cys Thr Leu Gly Ala Thr
    130                 135                 140

Thr Gly Tyr Leu Lys Gly Asn Ser Ala Ser Phe Asn Leu Val Gly Leu
145                 150                 155                 160

Phe Gly Thr Lys Thr Gln Ser Ser Gly Phe Asp Thr Ala Asn Ile Val
                165                 170                 175

Pro Asn Thr Ala Leu Asn Gln Ala Val Val Glu Leu Tyr Thr Asp Thr
            180                 185                 190

Thr Phe Ala Trp Ser Val Gly Ala Arg Ala Ala Leu Trp Glu Cys Gly
        195                 200                 205

Cys Ala Thr Leu Gly Ala Ser Phe Gln Tyr Ala Gln Ser Lys Pro Lys
    210                 215                 220

Val Glu Glu Leu Asn Val Leu Cys Asn Ala Ser Glu Phe Thr Ile Asn
225                 230                 235                 240

Lys Pro Lys Gly Tyr Val Gly Ala Glu Phe Pro Leu Asp Ile Thr Ala
                245                 250                 255

Gly Thr Glu Ala Ala Thr Gly Thr Lys Asp Ala Ser Ile Asp Tyr His
            260                 265                 270

Glu Trp Gln Ala Ser Leu Ala Leu Ser Tyr Arg Leu Asn Met Phe Thr
        275                 280                 285

Pro Tyr Ile Gly Val Lys Trp Ser Arg Val Ser Phe Asp Ala Asp Thr
    290                 295                 300

Ile Arg Ile Ala Gln Pro Lys Leu Ala Lys Pro Val Leu Asp Thr Thr
305                 310                 315                 320

Thr Leu Asn Pro Thr Ile Ala Gly Lys Gly Thr Val Val Ser Ser Ala
                325                 330                 335

Glu Asn Glu Leu Ala Asp Thr Met Gln Ile Val Ser Leu Gln Leu Asn
            340                 345                 350

Lys Met Lys Ser Arg Lys Ser Cys Gly Ile Ala Val Gly Thr Thr Val
        355                 360                 365

Val Asp Ala Asp Lys Tyr Ala Val Thr Ile Glu Thr Arg Leu Ile Asp
    370                 375                 380

Glu Arg Ala Ala His Val Asn Ala Gln Phe Arg Phe
385                 390                 395

<210> SEQ ID NO 5
<211> LENGTH: 1185
<212> TYPE: DNA
<213> ORGANISM: Chlamydia trachomatis strain B/Tunis-864

<400> SEQUENCE: 5

```
atgaaaaaac tcttgaaatc ggtattagta tttgccgctt tgagttctgc ttcctccttg      60
caagctctgc ctgtggggaa tcctgctgaa ccaagcctta tgatcgacgg aattctgtgg     120
gaaggtttcg gcggagatcc ttgcgatcct tgcaccactt ggtgtgacgc tatcagcatg     180
cgtatgggtt actatggtga ctttgttttc gaccgtgttt tgaaaacaga tgtgaataaa     240
gaattccaaa tgggtgccaa gcctacagct actacaggca atgctacagc tccatccact     300
cttacagcaa gagagaatcc tgcttacggc cgacatatgc aggatgctga gatgtttaca     360
aatgccgctt gcatggcatt gaatatttgg gatcgctttg atgtattctg tacactagga     420
gcctctagcg gataccttaa aggaaactct gcttctttca atttagtggg gttattcgga     480
aataatgaga accagactaa agtttcaaat ggtacgtttg taccaaatat gagcttagat     540
caatctgttg ttgagttgta tacagatact gcttttgcgt ggagcgtcgg cgctcgcgca     600
gctttgtggg aatgtggatg tgcaacttta ggagcttctt tccaatatgc tcaatctaaa     660
cctaaagtag aagaattaaa cgttctctgc aatgcagcag agtttactat taataaacct     720
aaagggtatg taggtaagga gttgcctctt gatcttacag caggaacaga tgctgcgaca     780
ggaactaagg atgcctctat tgattaccat gaatggcaag caagtttagc tctctcttac     840
agattgaata tgttcactcc ttacattgga gttaaatggt ctcgagcaag ctttgatgca     900
gacacgattc gtattgctca gccgaagtca gccgagacta tctttgatgt taccactctg     960
aacccaacta ttgctggagc tggcgatgtg aaaactagcg cagagggtca gctcggagac    1020
acaatgcaaa tcgtctcctt gcaattgaac aagatgaaat ctagaaaatc ttgcggtatt    1080
gcagtaggaa caactattgt ggatgcagac aaatacgcag ttacagttga gactcgcttg    1140
atcgatgaga gagctgctca cgtaaatgca caattccgct tctaa                   1185
```

<210> SEQ ID NO 6
<211> LENGTH: 394
<212> TYPE: PRT
<213> ORGANISM: Chlamydia trachomatis strain B/Tunis-864

<400> SEQUENCE: 6

```
Met Lys Lys Leu Leu Lys Ser Val Leu Val Phe Ala Ala Leu Ser Ser
1               5                   10                  15

Ala Ser Ser Leu Gln Ala Leu Pro Val Gly Asn Pro Ala Glu Pro Ser
            20                  25                  30

Leu Met Ile Asp Gly Ile Leu Trp Glu Gly Phe Gly Gly Asp Pro Cys
        35                  40                  45

Asp Pro Cys Thr Thr Trp Cys Asp Ala Ile Ser Met Arg Met Gly Tyr
    50                  55                  60

Tyr Gly Asp Phe Val Phe Asp Arg Val Leu Lys Thr Asp Val Asn Lys
65                  70                  75                  80

Glu Phe Gln Met Gly Ala Lys Pro Thr Ala Thr Thr Gly Asn Ala Thr
                85                  90                  95

Ala Pro Ser Thr Leu Thr Ala Arg Glu Asn Pro Ala Tyr Gly Arg His
            100                 105                 110

Met Gln Asp Ala Glu Met Phe Thr Asn Ala Ala Cys Met Ala Leu Asn
        115                 120                 125
```

Ile Trp Asp Arg Phe Asp Val Phe Cys Thr Leu Gly Ala Ser Ser Gly
130                 135                 140

Tyr Leu Lys Gly Asn Ser Ala Ser Phe Asn Leu Val Gly Leu Phe Gly
145                 150                 155                 160

Asn Asn Glu Asn Gln Thr Lys Val Ser Asn Gly Thr Phe Val Pro Asn
                165                 170                 175

Met Ser Leu Asp Gln Ser Val Val Glu Leu Tyr Thr Asp Thr Ala Phe
                180                 185                 190

Ala Trp Ser Val Gly Ala Arg Ala Ala Leu Trp Glu Cys Gly Cys Ala
            195                 200                 205

Thr Leu Gly Ala Ser Phe Gln Tyr Ala Gln Ser Lys Pro Lys Val Glu
210                 215                 220

Glu Leu Asn Val Leu Cys Asn Ala Ala Glu Phe Thr Ile Asn Lys Pro
225                 230                 235                 240

Lys Gly Tyr Val Gly Lys Glu Leu Pro Leu Asp Leu Thr Ala Gly Thr
                245                 250                 255

Asp Ala Ala Thr Gly Thr Lys Asp Ala Ser Ile Asp Tyr His Glu Trp
                260                 265                 270

Gln Ala Ser Leu Ala Leu Ser Tyr Arg Leu Asn Met Phe Thr Pro Tyr
                275                 280                 285

Ile Gly Val Lys Trp Ser Arg Ala Ser Phe Asp Ala Asp Thr Ile Arg
290                 295                 300

Ile Ala Gln Pro Lys Ser Ala Glu Thr Ile Phe Asp Val Thr Thr Leu
305                 310                 315                 320

Asn Pro Thr Ile Ala Gly Ala Gly Asp Val Lys Thr Ser Ala Glu Gly
                325                 330                 335

Gln Leu Gly Asp Thr Met Gln Ile Val Ser Leu Gln Leu Asn Lys Met
                340                 345                 350

Lys Ser Arg Lys Ser Cys Gly Ile Ala Val Gly Thr Thr Ile Val Asp
            355                 360                 365

Ala Asp Lys Tyr Ala Val Thr Val Glu Thr Arg Leu Ile Asp Glu Arg
            370                 375                 380

Ala Ala His Val Asn Ala Gln Phe Arg Phe
385                 390

<210> SEQ ID NO 7
<211> LENGTH: 25
<212> TYPE: PRT
<213> ORGANISM: artificial sequence
<220> FEATURE:
<223> OTHER INFORMATION: synthetic peptide

<400> SEQUENCE: 7

Glu Met Gly Ala Ala Pro Thr Gly Asp Ala Asp Leu Thr Thr Ala Pro
1               5                   10                  15

Thr Pro Ala Ser Arg Glu Asn Pro Ala
            20                  25

<210> SEQ ID NO 8
<211> LENGTH: 25
<212> TYPE: PRT
<213> ORGANISM: artificial sequence
<220> FEATURE:
<223> OTHER INFORMATION: synthetic peptide

<400> SEQUENCE: 8

Pro Thr Pro Ala Ser Arg Glu Asn Pro Ala Thr Gly Lys His Met Gln
1               5                   10                  15

```
Asp Ala Glu Met Phe Thr Asn Ala Ala
            20                  25

<210> SEQ ID NO 9
<211> LENGTH: 25
<212> TYPE: PRT
<213> ORGANISM: artificial sequence
<220> FEATURE:
<223> OTHER INFORMATION: synthetic peptide

<400> SEQUENCE: 9

Phe Gly Arg Asp Glu Thr Ala Val Ala Ala Asp Asp Ile Pro Asn Val
1               5                   10                  15

Ser Leu Ser Gln Ala Val Val Glu Leu
            20                  25

<210> SEQ ID NO 10
<211> LENGTH: 25
<212> TYPE: PRT
<213> ORGANISM: artificial sequence
<220> FEATURE:
<223> OTHER INFORMATION: synthetic peptide

<400> SEQUENCE: 10

Thr Ser Ile Leu Lys Met Thr Thr Trp Asn Pro Thr Ile Ser Gly Ser
1               5                   10                  15

Gly Ile Asp Val Asp Thr Lys Ile Thr
            20                  25

<210> SEQ ID NO 11
<211> LENGTH: 25
<212> TYPE: PRT
<213> ORGANISM: artificial sequence
<220> FEATURE:
<223> OTHER INFORMATION: synthetic peptide

<400> SEQUENCE: 11

Phe Val Phe Asp Arg Val Leu Lys Thr Asp Val Asn Lys Gln Phe Glu
1               5                   10                  15

Met Gly Ala Ala Pro Thr Gly Asp Ala
            20                  25

<210> SEQ ID NO 12
<211> LENGTH: 25
<212> TYPE: PRT
<213> ORGANISM: artificial sequence
<220> FEATURE:
<223> OTHER INFORMATION: synthetic peptide

<400> SEQUENCE: 12

Gly Tyr Leu Lys Gly Asn Ser Ala Ala Phe Asn Leu Val Gly Leu Phe
1               5                   10                  15

Gly Arg Asp Glu Thr Ala Val Ala Ala
            20                  25

<210> SEQ ID NO 13
<211> LENGTH: 25
<212> TYPE: PRT
<213> ORGANISM: artificial sequence
<220> FEATURE:
<223> OTHER INFORMATION: synthetic peptide

<400> SEQUENCE: 13

Gln Asp Ala Glu Met Phe Thr Asn Ala Ala Tyr Met Ala Leu Asn Ile
```

```
1               5                   10                  15
Trp Asp Arg Phe Asp Val Phe Cys Thr
            20                  25

<210> SEQ ID NO 14
<211> LENGTH: 25
<212> TYPE: PRT
<213> ORGANISM: artificial sequence
<220> FEATURE:
<223> OTHER INFORMATION: synthetic peptide

<400> SEQUENCE: 14

Leu Ala Ile Gly Thr Thr Ile Val Asp Ala Asp Lys Tyr Ala Val Thr
1               5                   10                  15
Val Glu Thr Arg Leu Ile Asp Glu Arg
            20                  25

<210> SEQ ID NO 15
<211> LENGTH: 20
<212> TYPE: PRT
<213> ORGANISM: artificial sequence
<220> FEATURE:
<223> OTHER INFORMATION: synthetic peptide

<400> SEQUENCE: 15

Thr Val Glu Thr Arg Leu Ile Asp Glu Arg Ala Ala His Val Asn Ala
1               5                   10                  15
Gln Phe Arg Phe
            20

<210> SEQ ID NO 16
<211> LENGTH: 25
<212> TYPE: PRT
<213> ORGANISM: artificial sequence
<220> FEATURE:
<223> OTHER INFORMATION: synthetic peptide

<400> SEQUENCE: 16

Lys Val Glu Glu Leu Asn Val Leu Cys Asn Ala Ala Glu Phe Thr Ile
1               5                   10                  15
Asn Lys Pro Lys Gly Tyr Val Gly Gln
            20                  25

<210> SEQ ID NO 17
<211> LENGTH: 25
<212> TYPE: PRT
<213> ORGANISM: artificial sequence
<220> FEATURE:
<223> OTHER INFORMATION: synthetic peptide
<220> FEATURE:
<221> NAME/KEY: misc_feature
<222> LOCATION: (13)..(13)
<223> OTHER INFORMATION: Xaa can be any naturally occurring amino acid

<400> SEQUENCE: 17

Ser Phe Asp Ala Asp Thr Ile Arg Ile Ala Gln Pro Xaa Leu Glu Thr
1               5                   10                  15
Ser Ile Leu Lys Met Thr Thr Trp Asn
            20                  25

<210> SEQ ID NO 18
<211> LENGTH: 25
<212> TYPE: PRT
<213> ORGANISM: artificial sequence
<220> FEATURE:
```

-continued

<223> OTHER INFORMATION: synthetic peptide

<400> SEQUENCE: 18

Ser Gly Ile Asp Val Asp Thr Lys Ile Thr Asp Thr Leu Gln Ile Val
1 5 10 15

Ser Leu Gln Leu Asn Lys Met Lys Ser
20 25

<210> SEQ ID NO 19
<211> LENGTH: 25
<212> TYPE: PRT
<213> ORGANISM: artificial sequence
<220> FEATURE:
<223> OTHER INFORMATION: synthetic peptide

<400> SEQUENCE: 19

Val Ser Leu Gln Leu Asn Lys Met Lys Ser Arg Lys Ser Cys Gly Leu
1 5 10 15

Ala Ile Gly Thr Thr Ile Val Asp Ala
20 25

<210> SEQ ID NO 20
<211> LENGTH: 4383
<212> TYPE: DNA
<213> ORGANISM: Chlamydia muridarum

<400> SEQUENCE: 20
atgaagtttt tatcagctac cgctgtattt gctgcagctc ttccctctat cacaagtgct 60
agctccgttg aatcccaaat agaaacaaaa gatctaaact ctagtagaac aggatcctca 120
tcatcgcaat ccttcactga aataattcca gaaaatggcg cagaatatag ggtatctgga 180
gatgtttcat tttctgattt ttcaaatata ccagaagaag cagagactct tgctatatcg 240
cacaaagaac agcctaataa cgaagtagta ctctccgaag aaaaccacca agcatccttt 300
caagattctg cacaaaacca aactgaaaat gcctctgaag gaaactctcc taatagcgag 360
aatactaacc agtcatctac cacagaaacc gagtctataa ctactgatga acaagtgcag 420
aatgataatg aatctgcagc ttctgtacct actactgtag aaacagcaac agctatgcgc 480
ctcccctctt accatctaca aacagaatca ttagtagaag ggctacaga agaagatcaa 540 aatcaaccga actctcaaaa tacatctagt ggcggcggag cattttataa ctctcaacaa 600
ggacctttat cctttatcaa tgatcccgat aaagacagtt ctctcacctt atcaaaaatt 660
cgagtaatag gagagggtgg tgccatttac tcgaaaggac cattaagcat aacaggtctt 720
aaaaaattag ctttaaaaga aaacttatcc caaaaggctg gaggagctat ttgtgcagaa 780
tccactattt caataagtag tgtagattct atcatttttt ctaagaatac agtcactcct 840
ccagctgcca ataaacctga actccctaac gatccctctg ggagtaatgg taatgatggt 900
tctgatgaca gtaactcctc aggtaatact gactcaaatg aaagcaaccc taacaacagc 960
gcttctaata acactggctc tgaaaatgag ctttcttcca gtaccccatc cgcacaactt 1020
cccaatcccg caacaccatt tttatcatct gtttctacaa actctcaacc tatagacaca 1080
gaaccagaaa atgcatggca tgctgaatca gggtctggag gagctatcta ttctaaaggc 1140
aagctttcta tcgcaagctc taaagaagta gtcttcgatc acaactcggc caccaaaaat 1200
ggaggagcta tcttcggaga ggaagaaatt gctctcgaaa aaatagcgtc tctgaaattc 1260
gattccaaca ctaccggtga aaaaggtggg gctattcatg cgaaaaacagt tacactatct 1320 gatatcaaaa acactttgat tttcgttaat aatacggcta aaacaccgga agaaaactct 1380

```
ctaaaatctt ctcaactaaa caaccaaaat ccttccgaag aagagcacca agatactagt    1440
gagggtgaag aaagccagtc tcttgaaacg tcacctataa ctaatcaaga ctctgcatcc    1500
tctcatgtag ccattttccg ttctatagca gcatcctcct ctcaatctaa tagcgaaaat    1560
atccctaatg cagatgggtc tacatctgct gggggagacg caggaagctc ttcacaacca    1620
tcgacaccag gatccgattc ttcgataaat catgtgattg gaggaggagc tatctatgga    1680
gaggcagtca aaatcgagaa cctctctgga tatggaacat tctccaacaa taacgctgtt    1740
gatcatcaaa tttctggatc tacatccgat gttttaggag gagctatcta tgctaaaaca    1800
tcactaacta tcgatagcgg gaactctagt ggaaccatta cattctctga aaataccact    1860
tcttccaaat ctacaacagg acaggttgct ggaggagcca tcttctcccc tagtgtaacc    1920
atcaccacac cagtgacctt ttctaaaaac tctgcgataa atgccacaac cagttctaaa    1980
aaggatacct ttgggggagc tatcggtgca atctctacag tttctctatc caaaggagct    2040
cgattctcag aaaatattgc cgatcttgga tctgctattg gattagtacc tactacacaa    2100
gatgcagaaa ctgttcagct aacaacaggt tcttactatt ttgaaaagaa taaagcacta    2160
aaacgagcaa ctgtttacgc tcctatcgta tctatcaaag ctcataccgc aacattcgat    2220
caaaatatct ctgcagaaga aggaagcgcg atttatttca ctaaagaagc caccattgag    2280
tctttgggat ccgttctttt tacagggaac ttggtaaccc caatacaaag cacaacagtg    2340
ttaacttctg gaaacacctc aaaatacggg gctgctattt ttggacaaat agcgaatgca    2400
agcggatctc aaactgataa cctccccctc aaactgatcg cttctggagg gaatatcagc    2460
ttccgaaata acgaataccg tccagatgcc actaatactg gacaatctac tttctgtagt    2520
atcgctggag atattaaatt aaccatgcag gctgcagaag gcaaagtaat cagtttcttt    2580
gatgctatac gaacttccac taagaaaaca ggaactctgg cctctgctta tgacacacta    2640
gatatcaata atcgaatgat tcagggtcc ataaattcag cctttacagg gaccattatg    2700
ttctcctctg aattacatga gaacaaatcc tatattccac aaaacgtagt cttacacagt    2760
ggctctctca tattgaaagc aaatacggaa cttcatgtgc tttcgtttga tcagaaagaa    2820
ggctcttctc ttattatgga acctggatct gttctttcaa atcaagatat tgctgatggt    2880
tctttagtag taaatagtct taccattgat ttatcgagtg ttggaagaaa cagtgcctct    2940
ggagacaata tcttcatgcc tccagaatta agaatcgtag atacctctac aaattctgga    3000
aacagctctt ctaccccgcc ctcatcgaat acaccaccaa actcaactcc gacagcacaa    3060
gctcctattt ccaaaaattt tgctgccaca accacgacac caacaacacc tccgacaaca    3120
gggaacatcg ttttccttaa cggagttatt aaactgattg atccgaatgg gacatttttc    3180
caaaaccctg cattaggatc tgaccaaaaa atctctctac tagtactccc ttcagatcaa    3240
acaaaactcc aagctcagaa agttgtgcta acaggagaca tctctcctaa gaaaggatac    3300
acaggaacat taactcttga tcctcaacaa ttacaaaatg gagtaatcca agctttatgg    3360
acattcaaat cctacagaca gtgggcctat attcctaggg ataatcactt ttatgccaac    3420
tcgattctgg gatcccaaat gtctatggct actgtcaaac aaggattaat caatgataaa    3480
ttgaatcttg ctcgctttga tgaggttgct tacaataatt tgtggatatc aggactagga    3540
accatgctct ctcaaagagg aggccagcga tcagaggaaa tgacttatta cagtagagga    3600
gcttctgttg ctttagatgc gaaacctacc caagatttga tcattggagc agcatttagt    3660
aaaatgatcg gaagaagcaa atctttgaaa ctagagcgta actacaccca caagggatcg    3720
```

-continued

```
gaatattcct accaagcatc ggtttatgga ggtagtcctt tctatcttac aattaacaaa    3780
gaagcaggcc gatccctccc tctcttatta caaggggtta tctcctacgg atacatcaaa    3840
cacgatacag ttacccacta tcctacaatt cgtgaattaa acaaaggaga gtgggaagac    3900
ttaggatggt tgaccgctct tcgagtctct tccatcttaa aaacacctaa acaaggagac    3960
tccaaacgca ttactgttta cggagaagtt gaatattcta gcatccgtca aaacaatttt    4020
acggaaacgg aatatgatcc tcgttacttc agtaactgca cctatagaaa cttagcagtt    4080
cctgtaggat tagccttaga gggagaattc aaaggtaacg atattttgat gtacaacaga    4140
ttctctgtag cttacatgcc atccatctat cgaaactctc cagtatgcaa gtaccaagta    4200
ctctcatctg gagaaggtgg agaaatcgtc tgtggtgttc ccaccagaaa ctcctctcga    4260
gcagaatata gtacgcagtt ataccttggt cctctatgga ctttatatgg atcctacaca    4320
ttagaagcgg acgctcacac gttagccaat atgattaact gtggggctcg catgacattc    4380
taa                                                                  4383
```

<210> SEQ ID NO 21
<211> LENGTH: 1460
<212> TYPE: PRT
<213> ORGANISM: Chlamydia muridarum

<400> SEQUENCE: 21

```
Met Lys Phe Leu Ser Ala Thr Ala Val Phe Ala Ala Leu Pro Ser
1               5                   10                  15

Ile Thr Ser Ala Ser Ser Val Glu Ser Gln Ile Glu Thr Lys Asp Leu
            20                  25                  30

Asn Ser Ser Arg Thr Gly Ser Ser Ser Gln Ser Phe Thr Glu Ile
        35                  40                  45

Ile Pro Glu Asn Gly Ala Glu Tyr Arg Val Ser Gly Asp Val Ser Phe
    50                  55                  60

Ser Asp Phe Ser Asn Ile Pro Glu Glu Ala Glu Thr Leu Ala Ile Ser
65                  70                  75                  80

His Lys Glu Gln Pro Asn Asn Glu Val Val Leu Ser Glu Glu Asn His
                85                  90                  95

Gln Ala Ser Phe Gln Asp Ser Ala Gln Asn Gln Thr Glu Asn Ala Ser
            100                 105                 110

Glu Gly Asn Ser Pro Asn Ser Glu Asn Thr Asn Gln Ser Ser Thr Thr
        115                 120                 125

Glu Thr Glu Ser Ile Thr Thr Asp Glu Gln Val Gln Asn Asp Asn Glu
    130                 135                 140

Ser Ala Ala Ser Val Pro Thr Thr Val Glu Thr Ala Thr Ala Met Arg
145                 150                 155                 160

Leu Pro Ser Tyr His Leu Gln Thr Glu Leu Val Glu Gly Ala Thr
                165                 170                 175

Glu Glu Asp Gln Asn Gln Pro Asn Ser Gln Asn Thr Ser Ser Gly Gly
            180                 185                 190

Gly Ala Phe Tyr Asn Ser Gln Gln Gly Pro Leu Ser Phe Ile Asn Asp
        195                 200                 205

Pro Asp Lys Asp Ser Ser Leu Thr Leu Ser Lys Ile Arg Val Ile Gly
    210                 215                 220

Glu Gly Gly Ala Ile Tyr Ser Lys Gly Pro Leu Ser Ile Thr Gly Leu
225                 230                 235                 240

Lys Lys Leu Ala Leu Lys Glu Asn Leu Ser Gln Lys Ala Gly Gly Ala
                245                 250                 255
```

-continued

```
Ile Cys Ala Glu Ser Thr Ile Ser Ile Ser Ser Val Asp Ser Ile Ile
            260                 265                 270

Phe Ser Lys Asn Thr Val Thr Pro Ala Ala Asn Lys Pro Glu Leu
    275                 280                 285

Pro Asn Asp Pro Ser Gly Ser Asn Gly Asn Asp Gly Ser Asp Ser
    290                 295                 300

Asn Ser Ser Gly Asn Thr Asp Ser Asn Glu Ser Asn Pro Asn Ser
305                 310                 315                 320

Ala Ser Asn Asn Thr Gly Ser Glu Asn Glu Leu Ser Ser Thr Pro
            325                 330                 335

Ser Ala Gln Leu Pro Asn Pro Ala Thr Pro Phe Leu Ser Val Ser
            340                 345                 350

Thr Asn Ser Gln Pro Ile Asp Thr Glu Pro Glu Asn Ala Trp His Ala
    355                 360                 365

Glu Ser Gly Ser Gly Gly Ala Ile Tyr Ser Lys Gly Lys Leu Ser Ile
    370                 375                 380

Ala Ser Ser Lys Glu Val Val Phe Asp His Asn Ser Ala Thr Lys Asn
385                 390                 395                 400

Gly Gly Ala Ile Phe Gly Glu Glu Ile Ala Leu Glu Lys Ile Ala
            405                 410                 415

Ser Leu Lys Phe Asp Ser Asn Thr Thr Gly Glu Lys Gly Ala Ile
            420                 425                 430

His Ala Lys Thr Val Thr Leu Ser Asp Ile Lys Asn Thr Leu Ile Phe
    435                 440                 445

Val Asn Asn Thr Ala Lys Thr Pro Glu Glu Asn Ser Leu Lys Ser Ser
    450                 455                 460

Gln Leu Asn Asn Gln Asn Pro Ser Glu Glu His Gln Asp Thr Ser
465                 470                 475                 480

Glu Gly Glu Glu Ser Gln Ser Leu Glu Thr Ser Pro Ile Thr Asn Gln
            485                 490                 495

Asp Ser Ala Ser Ser His Val Ala Ile Phe Arg Ser Ile Ala Ala Ser
            500                 505                 510

Ser Ser Gln Ser Asn Ser Glu Asn Ile Pro Asn Ala Asp Gly Ser Thr
    515                 520                 525

Ser Ala Gly Gly Asp Ala Gly Ser Ser Gln Pro Ser Thr Pro Gly
    530                 535                 540

Ser Asp Ser Ser Ile Asn His Val Ile Gly Gly Ala Ile Tyr Gly
545                 550                 555                 560

Glu Ala Val Lys Ile Glu Asn Leu Ser Gly Tyr Gly Thr Phe Ser Asn
            565                 570                 575

Asn Asn Ala Val Asp His Gln Ile Ser Gly Ser Thr Ser Asp Val Leu
            580                 585                 590

Gly Gly Ala Ile Tyr Ala Lys Thr Ser Leu Thr Ile Asp Ser Gly Asn
    595                 600                 605

Ser Ser Gly Thr Ile Thr Phe Ser Glu Asn Thr Thr Ser Ser Lys Ser
    610                 615                 620

Thr Thr Gly Gln Val Ala Gly Gly Ala Ile Phe Ser Pro Ser Val Thr
625                 630                 635                 640

Ile Thr Thr Pro Val Thr Phe Ser Lys Asn Ser Ala Ile Asn Ala Thr
            645                 650                 655

Thr Ser Ser Lys Lys Asp Thr Phe Gly Gly Ile Gly Ala Ile Ser
            660                 665                 670
```

```
Thr Val Ser Leu Ser Lys Gly Ala Arg Phe Ser Glu Asn Ile Ala Asp
            675                 680                 685

Leu Gly Ser Ala Ile Gly Leu Val Pro Thr Thr Gln Asp Ala Glu Thr
    690                 695                 700

Val Gln Leu Thr Thr Gly Ser Tyr Tyr Phe Glu Lys Asn Lys Ala Leu
705                 710                 715                 720

Lys Arg Ala Thr Val Tyr Ala Pro Ile Val Ser Ile Lys Ala His Thr
                725                 730                 735

Ala Thr Phe Asp Gln Asn Ile Ser Ala Glu Gly Ser Ala Ile Tyr
                740                 745                 750

Phe Thr Lys Glu Ala Thr Ile Glu Ser Leu Gly Ser Val Leu Phe Thr
        755                 760                 765

Gly Asn Leu Val Thr Pro Ile Gln Ser Thr Thr Val Leu Thr Ser Gly
    770                 775                 780

Asn Thr Ser Lys Tyr Gly Ala Ala Ile Phe Gly Gln Ile Ala Asn Ala
785                 790                 795                 800

Ser Gly Ser Gln Thr Asp Asn Leu Pro Leu Lys Leu Ile Ala Ser Gly
                805                 810                 815

Gly Asn Ile Ser Phe Arg Asn Asn Glu Tyr Arg Pro Asp Ala Thr Asn
                820                 825                 830

Thr Gly Gln Ser Thr Phe Cys Ser Ile Ala Gly Asp Ile Lys Leu Thr
            835                 840                 845

Met Gln Ala Ala Glu Gly Lys Val Ile Ser Phe Phe Asp Ala Ile Arg
    850                 855                 860

Thr Ser Thr Lys Lys Thr Gly Thr Leu Ala Ser Ala Tyr Asp Thr Leu
865                 870                 875                 880

Asp Ile Asn Lys Ser Asn Asp Ser Gly Ser Ile Asn Ser Ala Phe Thr
                885                 890                 895

Gly Thr Ile Met Phe Ser Ser Glu Leu His Glu Asn Lys Ser Tyr Ile
            900                 905                 910

Pro Gln Asn Val Val Leu His Ser Gly Ser Leu Ile Leu Lys Ala Asn
    915                 920                 925

Thr Glu Leu His Val Leu Ser Phe Asp Gln Lys Glu Gly Ser Ser Leu
    930                 935                 940

Ile Met Glu Pro Gly Ser Val Leu Ser Asn Gln Asp Ile Ala Asp Gly
945                 950                 955                 960

Ser Leu Val Val Asn Ser Leu Thr Ile Asp Leu Ser Ser Val Gly Arg
                965                 970                 975

Asn Ser Ala Ser Gly Asp Asn Ile Phe Met Pro Pro Glu Leu Arg Ile
            980                 985                 990

Val Asp Thr Ser Thr Asn Ser Gly Asn Ser Ser Ser Thr Pro Pro Ser
    995                 1000                1005

Ser Asn Thr Pro Pro Asn Ser Thr Pro Thr Ala Gln Ala Pro Ile
    1010                1015                1020

Ser Lys Asn Phe Ala Ala Thr Thr Thr Thr Pro Thr Thr Pro Pro
    1025                1030                1035

Thr Thr Gly Asn Ile Val Phe Leu Asn Gly Val Ile Lys Leu Ile
    1040                1045                1050

Asp Pro Asn Gly Thr Phe Phe Gln Asn Pro Ala Leu Gly Ser Asp
    1055                1060                1065

Gln Lys Ile Ser Leu Leu Val Leu Pro Ser Asp Gln Thr Lys Leu
    1070                1075                1080

Gln Ala Gln Lys Val Val Leu Thr Gly Asp Ile Ser Pro Lys Lys
```

```
                1085                1090                1095
Gly Tyr Thr Gly Thr Leu Thr Leu Asp Pro Gln Gln Leu Gln Asn
            1100                1105                1110
Gly Val Ile Gln Ala Leu Trp Thr Phe Lys Ser Tyr Arg Gln Trp
            1115                1120                1125
Ala Tyr Ile Pro Arg Asp Asn His Phe Tyr Ala Asn Ser Ile Leu
            1130                1135                1140
Gly Ser Gln Met Ser Met Ala Thr Val Lys Gln Gly Leu Ile Asn
            1145                1150                1155
Asp Lys Leu Asn Leu Ala Arg Phe Asp Glu Val Ala Tyr Asn Asn
            1160                1165                1170
Leu Trp Ile Ser Gly Leu Gly Thr Met Leu Ser Gln Arg Gly Gly
            1175                1180                1185
Gln Arg Ser Glu Glu Met Thr Tyr Tyr Ser Arg Gly Ala Ser Val
            1190                1195                1200
Ala Leu Asp Ala Lys Pro Thr Gln Asp Leu Ile Ile Gly Ala Ala
            1205                1210                1215
Phe Ser Lys Met Ile Gly Arg Ser Lys Ser Leu Lys Leu Glu Arg
            1220                1225                1230
Asn Tyr Thr His Lys Gly Ser Glu Tyr Ser Tyr Gln Ala Ser Val
            1235                1240                1245
Tyr Gly Gly Ser Pro Phe Tyr Leu Thr Ile Asn Lys Glu Ala Gly
            1250                1255                1260
Arg Ser Leu Pro Leu Leu Leu Gln Gly Val Ile Ser Tyr Gly Tyr
            1265                1270                1275
Ile Lys His Asp Thr Val Thr His Tyr Pro Thr Ile Arg Glu Leu
            1280                1285                1290
Asn Lys Gly Glu Trp Glu Asp Leu Gly Trp Leu Thr Ala Leu Arg
            1295                1300                1305
Val Ser Ser Ile Leu Lys Thr Pro Lys Gln Gly Asp Ser Lys Arg
            1310                1315                1320
Ile Thr Val Tyr Gly Glu Val Glu Tyr Ser Ser Ile Arg Gln Lys
            1325                1330                1335
Gln Phe Thr Glu Thr Glu Tyr Asp Pro Arg Tyr Phe Ser Asn Cys
            1340                1345                1350
Thr Tyr Arg Asn Leu Ala Val Pro Val Gly Leu Ala Leu Glu Gly
            1355                1360                1365
Glu Phe Lys Gly Asn Asp Ile Leu Met Tyr Asn Arg Phe Ser Val
            1370                1375                1380
Ala Tyr Met Pro Ser Ile Tyr Arg Asn Ser Pro Val Cys Lys Tyr
            1385                1390                1395
Gln Val Leu Ser Ser Gly Gly Gly Glu Ile Val Cys Gly Val
            1400                1405                1410
Pro Thr Arg Asn Ser Ser Arg Ala Glu Tyr Ser Thr Gln Leu Tyr
            1415                1420                1425
Leu Gly Pro Leu Trp Thr Leu Tyr Gly Ser Tyr Thr Leu Glu Ala
            1430                1435                1440
Asp Ala His Thr Leu Ala Asn Met Ile Asn Cys Gly Ala Arg Met
            1445                1450                1455
Thr Phe
1460

<210> SEQ ID NO 22
```

<211> LENGTH: 4335
<212> TYPE: DNA
<213> ORGANISM: artificial sequence
<220> FEATURE:
<223> OTHER INFORMATION: synthetic polynucleotide

<400> SEQUENCE: 22

| | | | | |
|---|---|---|---|---|
| catatgagca | gcgttgaatc | ccaaatagaa | acaaaagatc | tgaactctag tcgcacaggc | 60 |
| tcctcatcat | cgcaatcctt | cactgaaata | attccagaaa | atggcgcaga atatcgcgta | 120 |
| tctggagatg | tttcattttc | tgattttca | aatataccag | aagaagcaga gactcttgct | 180 |
| atatcgcaca | agaacagcc | taataacgaa | gtagtactct | ccgaagaaaa ccaccaagca | 240 |
| tcctttcaag | attctgcaca | aaccaaact | gaaaatgcct | ctgaaggaaa ctctcctaat | 300 |
| agcgagaata | ctaaccagtc | atctaccaca | gaaaccgagt | ctataactac tgatgaacaa | 360 |
| gtgcagaatg | ataatgaatc | tgcagcttct | gtacctacta | ctgtagaaac agcaacagct | 420 |
| atgcgcctcc | cctcttacca | tctgcaaaca | gaatcattag | tagaaggggc tacagaagaa | 480 |
| gatcaaaatc | aaccgaactc | tcaaaataca | tctagtggcg | gcggagcatt ttataactct | 540 |
| caacaaggac | ctttatcctt | tatcaatgat | cccgataaag | acagttctct caccttatca | 600 |
| aaaattcgag | taataggaga | gggtggtgcc | atttactcga | aaggaccatt aagcataaca | 660 |
| ggtcttaaaa | aattagcttt | aaaagaaaac | ttatcccaaa | aggctggagg agctatttgt | 720 |
| gcagaatcca | ctatttcaat | aagtagtgta | gattctatca | ttttttctaa gaatacagtc | 780 |
| actcctccag | ctgccaataa | acctgaactc | cctaacgatc | cctctgggag taatggtaat | 840 |
| gatggttctg | atgacagtaa | ctcctcaggt | aatactgact | caaatgaaag caaccctaac | 900 |
| aacagcgctt | ctaataacac | tggctctgaa | atgagctttt | cttccagtac cccatccgca | 960 |
| caacttccca | tcccgcaac | accattttta | tcatctgttt | ctacaaactc tcaacctata | 1020 |
| gacacagaac | cagaaaatgc | atggcatgct | gaatcagggt | ctggaggagc tatctattct | 1080 |
| aaaggcaaac | tttctatcgc | aagctctaaa | gaagtagtct | tcgatcacaa ctcggccacc | 1140 |
| aaaaatggag | gagctatctt | cggagaggaa | gaaattgctc | tcgaaaaaat agcgtctctg | 1200 |
| aaattcgatt | ccaacactac | cggtgaaaaa | ggtggggcta | ttcatgcgaa acagttaca | 1260 |
| ctgtctgaca | tcaaaaacac | tttgattttc | gttaataata | cggctaaaac accggaagaa | 1320 |
| aactctctga | atcttctca | actgaacaac | caaaatcctt | ccgaagaaga gcaccaagat | 1380 |
| actagtgagg | gtgaagaaag | ccagtctctt | gaaacgtcac | ctataactaa tcaagactct | 1440 |
| gcatcctctc | atgtagccat | tttccgttct | atagcagcat | cctcctctca atctaatagc | 1500 |
| gaaaatatcc | ctaatgcaga | tgggtctaca | tctgctgggg | gagacgcagg aagctcttca | 1560 |
| caaccatcga | caccaggctc | cgattcttcg | ataaatcatg | tgattggagg aggagctatc | 1620 |
| tatggagagg | cagtcaaaat | cgagaacctc | tctggatatg | aacattctc caacaataac | 1680 |
| gctgttgatc | atcaaatttc | tggatctaca | tccgatgttt | taggaggagc tatctatgct | 1740 |
| aaaacatcac | tgactatcga | tagcgggaac | tctagtggaa | ccattacatt ctctgaaaat | 1800 |
| accacttctt | ccaaatctac | aacaggacag | gttgctggag | gagccatctt ctcccctagt | 1860 |
| gtaaccatca | ccacaccagt | gacctttct | aaaaactctg | cgataaatgc cacaaccagt | 1920 |
| tctaaaaagg | atacctttgg | gggagctatc | ggtgcaatct | ctacagtttc tctgtccaaa | 1980 |
| ggagcccgat | tctcagaaaa | tattgccgat | cttggatctg | ctattggatt agtacctact | 2040 |
| acacaagatg | cagaaactgt | tcagctgaca | acaggttctt | actattttga aaagaataaa | 2100 |
| gcactgaaac | gagcaactgt | ttacgctcct | atcgtatcta | tcaaagctca taccgcaaca | 2160 |

```
ttcgatcaaa atatctctgc agaagaagga agcgcgattt atttcactaa agaagccacc    2220
attgagtctt tgggttccgt tcttttttaca gggaacttgg taaccccaat acaaagcaca    2280
acagtgttaa cttctggaaa cacctcaaaa tacggggctg ctattttttgg acaaatagcg   2340
aatgcaagcg gatctcaaac tgataacctc ccccctcaaac tgatcgcttc tggagggaat   2400
atcagcttcc gaaataacga ataccgtcca gatgccacta atactggaca atctactttc    2460
tgtagtatcg ctggagatat taaattaacc atgcaggctg cagaaggcaa agtaatcagt    2520
ttctttgatg ctatacgaac ttccactaag aaaacaggaa ctctggcctc tgcttatgac    2580
acactggata tcaataaatc gaatgattca gggtccataa attcagcctt tacagggacc   2640
attatgttct cctctgagct ccatgagaac aaatcctata ttccacaaaa cgtagtctta    2700
cacagtggct ctctcatatt gaaagcaaat acggaacttc atgtgctttc gtttgatcag    2760
aaagaaggct cttctcttat tatggaacct ggatctgttc tttcaaatca agatattgct    2820
gatggttctt tagtagtaaa tagtcttacc attgatttat cgagtgttgg acgcaacagt    2880
gcctctggag acaatatctt catgcctcca gaattacgca tcgtagatac ctctacaaat    2940
tctggaaaca gctcttctac cccgccctca tcgaatacac caccaaactc aactccgaca    3000
gcacaagctc ctatttccaa aaattttgct gccacaacca cgacaccaac aacacctccg    3060
acaacaggga acatcgtttt ccttaacgga gttattaaac tgattgatcc gaatgggaca    3120
tttttccaaa accctgcatt aggatctgac caaaaaatct ctctgctggt actcccttca    3180
gatcaaacaa aactccaagc tcagaaagtt gtgctgacag gagacatctc tcctaagaaa    3240
ggatacacag gaacattaac tcttgatcct caacaattac aaaatggagt aatccaagcc    3300
ttatggacat tcaaatccta ccgccagtgg gcctatattc ctcgcgataa tcacttttat    3360
gccaactcga ttctgggttc ccaaatgtcc atggctactg tcaaacaagg attaatcaat    3420
gataaattga atcttgctcg ctttgatgag gttgcttaca ataatttgtg gatatcagga    3480
ctgggaacca tgctctctca acgcggaggc cagcgatcag aggaaatgac ttattacagt    3540
cgcggagctt ctgttgcttt agatgcgaaa cctacccaag atttgatcat tggagcagca   3600
tttagtaaaa tgatcggacg cagcaaatct ttgaaactgg agcgtaacta cacccacaag    3660
ggatcggaat attcctacca agcatcggtt tatggaggta gtccttttcta tcttacaatt    3720
aacaaagaag caggccgatc cctccctctc ttattacaag gggttatctc ctacggatac    3780
atcaaacacg atacagttac ccactatcct acaattcgtg aattaaacaa aggagagtgg    3840
gaagacttag gatggttgac cgctcttcga gtctcttcca tcttaaaaac acctaaacaa    3900
ggagactcca aacgcattac tgtttacgga gaagttgaat attctagcat ccgtcaaaaa    3960
caatttacgg aaacggaata tgatcctcgt tacttcagta actgcaccta tcgcaactta    4020
gcagttcctg taggattagc cttagaggga gaattcaaag gtaacgatat tttgatgtac    4080
aaccgcttct ctgtagctta catgccatcc atctatcgaa actctccagt atgcaagtac    4140
caagtactct catctggaga aggtggagaa atcgtctgtg tgttcccac ccgcaactcc     4200
tcccgagcag aatatagtac gcagttatac cttggtcctc tgtggacttt atatggctcc    4260
tacacattag aagcggacgc tcacacgtta gccaatatga ttaactgtgg ggctcgcatg    4320
acattctaag gatcc                                                    4335
```

<210> SEQ ID NO 23
<211> LENGTH: 1441
<212> TYPE: PRT

<213> ORGANISM: artificial sequence
<220> FEATURE:
<223> OTHER INFORMATION: synthetic peptide

<400> SEQUENCE: 23

```
Met Ser Ser Val Glu Ser Gln Ile Glu Thr Lys Asp Leu Asn Ser Ser
1               5                   10                  15

Arg Thr Gly Ser Ser Ser Gln Ser Phe Thr Glu Ile Ile Pro Glu
            20                  25                  30

Asn Gly Ala Glu Tyr Arg Val Ser Gly Asp Val Ser Phe Ser Asp Phe
            35                  40                  45

Ser Asn Ile Pro Glu Glu Ala Glu Thr Leu Ala Ile Ser His Lys Glu
        50                  55                  60

Gln Pro Asn Asn Glu Val Val Leu Ser Glu Glu Asn His Gln Ala Ser
65                  70                  75                  80

Phe Gln Asp Ser Ala Gln Asn Gln Thr Glu Asn Ala Ser Glu Gly Asn
                85                  90                  95

Ser Pro Asn Ser Glu Asn Thr Asn Gln Ser Ser Thr Thr Glu Thr Glu
            100                 105                 110

Ser Ile Thr Thr Asp Glu Gln Val Gln Asn Asp Asn Glu Ser Ala Ala
            115                 120                 125

Ser Val Pro Thr Thr Val Glu Thr Ala Thr Ala Met Arg Leu Pro Ser
        130                 135                 140

Tyr His Leu Gln Thr Glu Ser Leu Val Glu Gly Ala Thr Glu Glu Asp
145                 150                 155                 160

Gln Asn Gln Pro Asn Ser Gln Asn Thr Ser Ser Gly Gly Gly Ala Phe
                165                 170                 175

Tyr Asn Ser Gln Gln Gly Pro Leu Ser Phe Ile Asn Asp Pro Asp Lys
            180                 185                 190

Asp Ser Ser Leu Thr Leu Ser Lys Ile Arg Val Ile Gly Glu Gly Gly
            195                 200                 205

Ala Ile Tyr Ser Lys Gly Pro Leu Ser Ile Thr Gly Leu Lys Lys Leu
        210                 215                 220

Ala Leu Lys Glu Asn Leu Ser Gln Lys Ala Gly Gly Ala Ile Cys Ala
225                 230                 235                 240

Glu Ser Thr Ile Ser Ile Ser Ser Val Asp Ser Ile Ile Phe Ser Lys
                245                 250                 255

Asn Thr Val Thr Pro Pro Ala Ala Asn Lys Pro Glu Leu Pro Asn Asp
            260                 265                 270

Pro Ser Gly Ser Asn Gly Asn Asp Gly Ser Asp Ser Asn Ser Ser
        275                 280                 285

Gly Asn Thr Asp Ser Asn Glu Ser Asn Pro Asn Asn Ser Ala Ser Asn
        290                 295                 300

Asn Thr Gly Ser Glu Asn Glu Leu Ser Ser Ser Thr Pro Ser Ala Gln
305                 310                 315                 320

Leu Pro Asn Pro Ala Thr Pro Phe Leu Ser Ser Val Ser Thr Asn Ser
                325                 330                 335

Gln Pro Ile Asp Thr Glu Pro Glu Asn Ala Trp His Ala Glu Ser Gly
            340                 345                 350

Ser Gly Gly Ala Ile Tyr Ser Lys Gly Lys Leu Ser Ile Ala Ser Ser
            355                 360                 365

Lys Glu Val Val Phe Asp His Asn Ser Ala Thr Lys Asn Gly Gly Ala
        370                 375                 380

Ile Phe Gly Glu Glu Glu Ile Ala Leu Glu Lys Ile Ala Ser Leu Lys
```

-continued

```
                385                 390                 395                 400
        Phe Asp Ser Asn Thr Thr Gly Glu Lys Gly Gly Ala Ile His Ala Lys
                        405                 410                 415

Thr Val Thr Leu Ser Asp Ile Lys Asn Thr Leu Ile Phe Val Asn Asn
                        420                 425                 430

Thr Ala Lys Thr Pro Glu Glu Asn Ser Leu Lys Ser Ser Gln Leu Asn
                        435                 440                 445

Asn Gln Asn Pro Ser Glu Glu His Gln Asp Thr Ser Glu Gly Glu
        450                 455                 460

Glu Ser Gln Ser Leu Glu Thr Ser Pro Ile Thr Asn Gln Asp Ser Ala
        465                 470                 475                 480

Ser Ser His Val Ala Ile Phe Arg Ser Ile Ala Ala Ser Ser Gln
                        485                 490                 495

Ser Asn Ser Glu Asn Ile Pro Asn Ala Asp Gly Ser Thr Ser Ala Gly
                        500                 505                 510

Gly Asp Ala Gly Ser Ser Ser Gln Pro Ser Thr Pro Gly Ser Asp Ser
                        515                 520                 525

Ser Ile Asn His Val Ile Gly Gly Ala Ile Tyr Gly Glu Ala Val
                        530                 535                 540

Lys Ile Glu Asn Leu Ser Gly Tyr Gly Thr Phe Ser Asn Asn Asn Ala
        545                 550                 555                 560

Val Asp His Gln Ile Ser Gly Ser Thr Ser Asp Val Leu Gly Gly Ala
                        565                 570                 575

Ile Tyr Ala Lys Thr Ser Leu Thr Ile Asp Ser Gly Asn Ser Ser Gly
                        580                 585                 590

Thr Ile Thr Phe Ser Glu Asn Thr Thr Ser Ser Lys Ser Thr Thr Gly
                        595                 600                 605

Gln Val Ala Gly Gly Ala Ile Phe Ser Pro Ser Val Thr Ile Thr Thr
                        610                 615                 620

Pro Val Thr Phe Ser Lys Asn Ser Ala Ile Asn Ala Thr Thr Ser Ser
        625                 630                 635                 640

Lys Lys Asp Thr Phe Gly Gly Ala Ile Gly Ala Ile Ser Thr Val Ser
                        645                 650                 655

Leu Ser Lys Gly Ala Arg Phe Ser Glu Asn Ile Ala Asp Leu Gly Ser
                        660                 665                 670

Ala Ile Gly Leu Val Pro Thr Thr Gln Asp Ala Glu Thr Val Gln Leu
                        675                 680                 685

Thr Thr Gly Ser Tyr Tyr Phe Glu Lys Asn Lys Ala Leu Lys Arg Ala
                        690                 695                 700

Thr Val Tyr Ala Pro Ile Val Ser Ile Lys Ala His Thr Ala Thr Phe
        705                 710                 715                 720

Asp Gln Asn Ile Ser Ala Glu Glu Gly Ser Ala Ile Tyr Phe Thr Lys
                        725                 730                 735

Glu Ala Thr Ile Glu Ser Leu Gly Ser Val Leu Phe Thr Gly Asn Leu
                        740                 745                 750

Val Thr Pro Ile Gln Ser Thr Thr Val Leu Thr Ser Gly Asn Thr Ser
                        755                 760                 765

Lys Tyr Gly Ala Ala Ile Phe Gly Gln Ile Ala Asn Ala Ser Gly Ser
                        770                 775                 780

Gln Thr Asp Asn Leu Pro Leu Lys Leu Ile Ala Ser Gly Gly Asn Ile
        785                 790                 795                 800

Ser Phe Arg Asn Asn Glu Tyr Arg Pro Asp Ala Thr Asn Thr Gly Gln
                        805                 810                 815
```

```
Ser Thr Phe Cys Ser Ile Ala Gly Asp Ile Lys Leu Thr Met Gln Ala
            820                 825                 830

Ala Glu Gly Lys Val Ile Ser Phe Phe Asp Ala Ile Arg Thr Ser Thr
            835                 840                 845

Lys Lys Thr Gly Thr Leu Ala Ser Ala Tyr Asp Thr Leu Asp Ile Asn
        850                 855                 860

Lys Ser Asn Asp Ser Gly Ser Ile Asn Ser Ala Phe Thr Gly Thr Ile
865                 870                 875                 880

Met Phe Ser Ser Glu Leu His Glu Asn Lys Ser Tyr Ile Pro Gln Asn
                885                 890                 895

Val Val Leu His Ser Gly Ser Leu Ile Leu Lys Ala Asn Thr Glu Leu
            900                 905                 910

His Val Leu Ser Phe Asp Gln Lys Glu Gly Ser Ser Leu Ile Met Glu
            915                 920                 925

Pro Gly Ser Val Leu Ser Asn Gln Asp Ile Ala Asp Gly Ser Leu Val
        930                 935                 940

Val Asn Ser Leu Thr Ile Asp Leu Ser Ser Val Gly Arg Asn Ser Ala
945                 950                 955                 960

Ser Gly Asp Asn Ile Phe Met Pro Pro Glu Leu Arg Ile Val Asp Thr
                965                 970                 975

Ser Thr Asn Ser Gly Asn Ser Ser Thr Pro Pro Ser Ser Asn Thr
            980                 985                 990

Pro Pro Asn Ser Thr Pro Thr Ala  Gln Ala Pro Ile Ser  Lys Asn Phe
            995                 1000                1005

Ala Ala Thr Thr Thr Thr Pro  Thr Thr Pro Pro Thr  Thr Gly Asn
        1010                1015                1020

Ile Val Phe Leu Asn Gly Val  Ile Lys Leu Ile Asp  Pro Asn Gly
        1025                1030                1035

Thr Phe Phe Gln Asn Pro Ala  Leu Gly Ser Asp Gln  Lys Ile Ser
        1040                1045                1050

Leu Leu Val Leu Pro Ser Asp  Gln Thr Lys Leu Gln  Ala Gln Lys
        1055                1060                1065

Val Val Leu Thr Gly Asp Ile  Ser Pro Lys Lys Gly  Tyr Thr Gly
        1070                1075                1080

Thr Leu Thr Leu Asp Pro Gln  Gln Leu Gln Asn Gly  Val Ile Gln
        1085                1090                1095

Ala Leu Trp Thr Phe Lys Ser  Tyr Arg Gln Trp Ala  Tyr Ile Pro
        1100                1105                1110

Arg Asp Asn His Phe Tyr Ala  Asn Ser Ile Leu Gly  Ser Gln Met
        1115                1120                1125

Ser Met Ala Thr Val Lys Gln  Gly Leu Ile Asn Asp  Lys Leu Asn
        1130                1135                1140

Leu Ala Arg Phe Asp Glu Val  Ala Tyr Asn Asn Leu  Trp Ile Ser
        1145                1150                1155

Gly Leu Gly Thr Met Leu Ser  Gln Arg Gly Gly Gln  Arg Ser Glu
        1160                1165                1170

Glu Met Thr Tyr Tyr Ser Arg  Gly Ala Ser Val Ala  Leu Asp Ala
        1175                1180                1185

Lys Pro Thr Gln Asp Leu Ile  Ile Gly Ala Ala Phe  Ser Lys Met
        1190                1195                1200

Ile Gly Arg Ser Lys Ser Leu  Lys Leu Glu Arg Asn  Tyr Thr His
        1205                1210                1215
```

```
Lys Gly Ser Glu Tyr Ser Tyr Gln Ala Ser Val Tyr Gly Gly Ser
1220                1225                1230

Pro Phe Tyr Leu Thr Ile Asn Lys Glu Ala Gly Arg Ser Leu Pro
    1235                1240                1245

Leu Leu Leu Gln Gly Val Ile Ser Tyr Gly Tyr Ile Lys His Asp
1250                1255                1260

Thr Val Thr His Tyr Pro Thr Ile Arg Glu Leu Asn Lys Gly Glu
    1265                1270                1275

Trp Glu Asp Leu Gly Trp Leu Thr Ala Leu Arg Val Ser Ser Ile
1280                1285                1290

Leu Lys Thr Pro Lys Gln Gly Asp Ser Lys Arg Ile Thr Val Tyr
    1295                1300                1305

Gly Glu Val Glu Tyr Ser Ser Ile Arg Gln Lys Gln Phe Thr Glu
1310                1315                1320

Thr Glu Tyr Asp Pro Arg Tyr Phe Ser Asn Cys Thr Tyr Arg Asn
    1325                1330                1335

Leu Ala Val Pro Val Gly Leu Ala Leu Glu Gly Glu Phe Lys Gly
1340                1345                1350

Asn Asp Ile Leu Met Tyr Asn Arg Phe Ser Val Ala Tyr Met Pro
    1355                1360                1365

Ser Ile Tyr Arg Asn Ser Pro Val Cys Lys Tyr Gln Val Leu Ser
1370                1375                1380

Ser Gly Glu Gly Gly Glu Ile Val Cys Gly Val Pro Thr Arg Asn
    1385                1390                1395

Ser Ser Arg Ala Glu Tyr Ser Thr Gln Leu Tyr Leu Gly Pro Leu
1400                1405                1410

Trp Thr Leu Tyr Gly Ser Tyr Thr Leu Glu Ala Asp Ala His Thr
    1415                1420                1425

Leu Ala Asn Met Ile Asn Cys Gly Ala Arg Met Thr Phe
1430                1435                1440
```

<210> SEQ ID NO 24
<211> LENGTH: 3729
<212> TYPE: DNA
<213> ORGANISM: artificial sequence
<220> FEATURE:
<223> OTHER INFORMATION: synthetic polynucleotide

<400> SEQUENCE: 24

```
catatgagca gcgttgaatc ccaaatagaa acaaaagatc tgaactctag tcgcacaggc      60
tcctcatcat cgcaatcctt cactgaaata attccagaaa atggcgcaga atatcgcgta     120
tctggagatg tttcattttc tgattttca aatataccag aagaagcaga gactcttgct     180
atatcgcaca agaacagcc taataacgaa gtagtactct ccgaagaaaa ccaccaagca     240
tcctttcaag attctgcaca aaaccaaact gaaaatgcct ctgaaggaaa ctctcctaat     300
agcgagaata ctaaccagtc atctaccaca gaaaccgagt ctataactac tgatgaacaa     360
gtgcagaatg ataatgaatc tgcagcttct gtacctacta ctgtagaaac agcaacagct     420
atgcgcctcc cctcttacca tctgcaaaca gaatcattag tagaaggggc tacagaagaa     480
gatcaaaatc aaccgaactc tcaaaataca tctagtggcg gcggagcatt ttataactct     540
caacaaggac ctttatcctt tatcaatgat cccgataaag acagttctct caccttatca     600
aaaattcgag taataggaga gggtggtgcc atttactcga aaggaccatt aagcataaca     660
ggtcttaaaa aattagcttt aaaagaaaac ttatcccaaa aggctggagg agctatttgt     720
```

```
gcagaatcca ctatttcaat aagtagtgta gattctatca ttttttctaa gaatacagtc    780
actcctccag ctgccaataa acctgaactc cctaacgatc cctctgggag taatggtaat    840
gatggttctg atgacagtaa ctcctcaggt aatactgact caaatgaaag caaccctaac    900
aacagcgctt ctaataacac tggctctgaa aatgagcttt cttccagtac cccatccgca    960
caacttccca atcccgcaac accattttta tcatctgttt ctacaaactc tcaacctata   1020
gacacagaac cagaaaatgc atggcatgct gaatcagggt ctggaggagc tatctattct   1080
aaaggcaaac tttctatcgc aagctctaaa gaagtagtct tcgatcacaa ctcggccacc   1140
aaaaatggag gagctatctt cggagaggaa gaaattgctc tcgaaaaaat agcgtctctg   1200
aaattcgatt ccaacactac cggtgaaaaa ggtgggggcta ttcatgcgaa aacagttaca   1260
ctgtctgaca tcaaaaacac tttgattttc gttaataata cggctaaaac accggaagaa   1320
aactctctga atcttctca actgaacaac caaaatcctt ccgaagaaga gcaccaagat   1380
actagtgagg gtgaagaaag ccagtctctt gaaacgtcac ctataactaa tcaagactct   1440
gcatcctctc atgtagccat tttccgttct atagcagcat cctcctctca atctaatagc   1500
gaaaatatcc ctaatgcaga tgggtctaca tctgctgggg gagacgcagg aagctcttca   1560
caaccatcga caccaggctc cgattcttcg ataaatcatg tgattggagg aggagctatc   1620
tatggagagg cagtcaaaat cgagaacctc tctggatatg gaacattctc caacaataac   1680
gctgttgatc atcaaatttc tggatctaca tccgatgttt taggaggagc tatctatgct   1740
aaaacatcac tgactatcga tagcgggaac tctagtggaa ccattacatt ctctgaaaat   1800
accacttctt ccaaatctac aacaggacag gttgctggag gagccatctt ctcccctagt   1860
gtaaccatca ccacaccagt gaccttttct aaaaactctg cgataaatgc cacaaccagt   1920
tctaaaaagg atacctttgg gggagctatc ggtgcaatct ctacagtttc tctgtccaaa   1980
ggagcccgat tctcagaaaa tattgccgat cttggatctg ctattggatt agtacctact   2040
acacaagatg cagaaactgt tcagctgaca acaggttctt actattttga aaagaataaa   2100
gcactgaaac gagcaactgt ttacgctcct atcgtatcta tcaaagctca taccgcaaca   2160
ttcgatcaaa atatctctgc agaagaagga agcgcgattc atttcactaa agaagccacc   2220
attgagtctt tgggttccgt tcttttttaca gggaacttgg taaccccaat acaaagcaca   2280
acagtgttaa cttctggaaa cacctcaaaa tacggggctg ctattttttgg acaaatagcg   2340 aatgcaagcg atctcaaac tgataacctc cccctcaaac tgatcgcttc tggagggaat   2400
atcagcttcc gaaataacga ataccgtcca gatgccacta atactggaca atctactttc   2460
tgtagtatcg ctggagatat taaattaacc atgcaggctg cagaaggcaa agtaatcagt   2520
ttctttgatg ctatacgaac ttccactaag aaaacaggaa ctctggcctc tgcttatgac   2580
acactggata tcaataaatc gaatgattca gggtccataa attcagcctt tacagggacc   2640
attatgttct cctctgagct ccatgagaac aaatcctata ttccacaaaa cgtagtctta   2700
cacagtaaat cctaccgcca gtgggcctat attcctcgcg ataatcactt ttatgccaac   2760
tcgattctgg gttcccaaat gtccatggct actgtcaaac aaggattaat caatgataaa   2820
ttgaatcttg ctcgctttga tgaggttgct tacaataatt tgtggatatc aggactggga   2880
accatgctct ctcaacgcgg aggccagcga tcagaggaaa tgacttatta cagtcgcgga   2940
gcttctgttg ctttagatgc gaaacctacc caagatttga tcattggagc agcatttagt   3000
aaaatgatcg gacgcagcaa atctttgaaa ctggagcgta actacaccca caagggatcg   3060
gaatattcct accaagcatc ggtttatgga ggtagtcctt tctatcttac aattaacaaa   3120
```

-continued

```
gaagcaggcc gatccctccc tctcttatta caaggggtta tctcctacgg atacatcaaa    3180
cacgatacag ttacccacta tcctacaatt cgtgaattaa acaaaggaga gtgggaagac    3240
ttaggatggt tgaccgctct tcgagtctct tccatcttaa aaacacctaa acaaggagac    3300
tccaaacgca ttactgttta cggagaagtt gaatattcta gcatccgtca aaacaattt     3360 acggaaacgg aatatgatcc tcgttacttc agtaactgca cctatcgcaa cttagcagtt    3420
cctgtaggat tagccttaga gggagaattc aaaggtaacg atattttgat gtacaaccgc    3480
ttctctgtag cttacatgcc atccatctat cgaaactctc cagtatgcaa gtaccaagta    3540
ctctcatctg gagaaggtgg agaaatcgtc tgtggtgttc ccacccgcaa ctcctcccga    3600
gcagaatata gtacgcagtt ataccttggt cctctgtgga ctttatatgg ctcctacaca    3660
ttagaagcgg acgctcacac gttagccaat atgattaact gtggggctcg catgacattc    3720
taaggatcc                                                            3729
```

<210> SEQ ID NO 25
<211> LENGTH: 1239
<212> TYPE: PRT
<213> ORGANISM: artificial sequence
<220> FEATURE:
<223> OTHER INFORMATION: synthetic peptide

<400> SEQUENCE: 25

```
Met Ser Ser Val Glu Ser Gln Ile Glu Thr Lys Asp Leu Asn Ser Ser
1               5                   10                  15

Arg Thr Gly Ser Ser Ser Gln Ser Phe Thr Glu Ile Ile Pro Glu
            20                  25                  30

Asn Gly Ala Glu Tyr Arg Val Ser Gly Asp Val Ser Phe Ser Asp Phe
        35                  40                  45

Ser Asn Ile Pro Glu Glu Ala Glu Thr Leu Ala Ile Ser His Lys Glu
    50                  55                  60

Gln Pro Asn Asn Glu Val Val Leu Ser Glu Glu Asn His Gln Ala Ser
65                  70                  75                  80

Phe Gln Asp Ser Ala Gln Asn Gln Thr Glu Asn Ala Ser Glu Gly Asn
                85                  90                  95

Ser Pro Asn Ser Glu Asn Thr Asn Gln Ser Ser Thr Thr Glu Thr Glu
            100                 105                 110

Ser Ile Thr Thr Asp Glu Gln Val Gln Asn Asp Asn Glu Ser Ala Ala
        115                 120                 125

Ser Val Pro Thr Thr Val Glu Thr Ala Thr Ala Met Arg Leu Pro Ser
    130                 135                 140

Tyr His Leu Gln Thr Glu Ser Leu Val Glu Gly Ala Thr Glu Glu Asp
145                 150                 155                 160

Gln Asn Gln Pro Asn Ser Gln Asn Thr Ser Ser Gly Gly Gly Ala Phe
                165                 170                 175

Tyr Asn Ser Gln Gln Gly Pro Leu Ser Phe Ile Asn Asp Pro Asp Lys
            180                 185                 190

Asp Ser Ser Leu Thr Leu Ser Lys Ile Arg Val Ile Gly Glu Gly Gly
        195                 200                 205

Ala Ile Tyr Ser Lys Gly Pro Leu Ser Ile Thr Gly Leu Lys Lys Leu
    210                 215                 220

Ala Leu Lys Glu Asn Leu Ser Gln Lys Ala Gly Gly Ala Ile Cys Ala
225                 230                 235                 240

Glu Ser Thr Ile Ser Ile Ser Ser Val Asp Ser Ile Ile Phe Ser Lys
```

```
                        245                 250                 255
Asn Thr Val Thr Pro Ala Ala Asn Lys Pro Glu Leu Pro Asn Asp
                    260                 265                 270
Pro Ser Gly Ser Asn Gly Asn Asp Gly Ser Asp Ser Asn Ser Ser
                275                 280                 285
Gly Asn Thr Asp Ser Asn Glu Ser Asn Pro Asn Asn Ser Ala Ser Asn
            290                 295                 300
Asn Thr Gly Ser Glu Asn Glu Leu Ser Ser Thr Pro Ser Ala Gln
305                 310                 315                 320
Leu Pro Asn Pro Ala Thr Pro Phe Leu Ser Ser Val Ser Thr Asn Ser
                325                 330                 335
Gln Pro Ile Asp Thr Glu Pro Glu Asn Ala Trp His Ala Glu Ser Gly
                340                 345                 350
Ser Gly Gly Ala Ile Tyr Ser Lys Gly Lys Leu Ser Ile Ala Ser Ser
                355                 360                 365
Lys Glu Val Val Phe Asp His Asn Ser Ala Thr Lys Asn Gly Gly Ala
            370                 375                 380
Ile Phe Gly Glu Glu Glu Ile Ala Leu Glu Lys Ile Ala Ser Leu Lys
385                 390                 395                 400
Phe Asp Ser Asn Thr Thr Gly Glu Lys Gly Ala Ile His Ala Lys
                    405                 410                 415
Thr Val Thr Leu Ser Asp Ile Lys Asn Thr Leu Ile Phe Val Asn Asn
                420                 425                 430
Thr Ala Lys Thr Pro Glu Glu Asn Ser Leu Lys Ser Gln Leu Asn
                435                 440                 445
Asn Gln Asn Pro Ser Glu Glu His Gln Asp Thr Ser Glu Gly Glu
            450                 455                 460
Glu Ser Gln Ser Leu Glu Thr Ser Pro Ile Thr Asn Gln Asp Ser Ala
465                 470                 475                 480
Ser Ser His Val Ala Ile Phe Arg Ser Ile Ala Ala Ser Ser Ser Gln
                485                 490                 495
Ser Asn Ser Glu Asn Ile Pro Asn Ala Asp Gly Ser Thr Ser Ala Gly
                500                 505                 510
Gly Asp Ala Gly Ser Ser Ser Gln Pro Ser Thr Pro Gly Ser Asp Ser
            515                 520                 525
Ser Ile Asn His Val Ile Gly Gly Ala Ile Tyr Gly Glu Ala Val
            530                 535                 540
Lys Ile Glu Asn Leu Ser Gly Tyr Gly Thr Phe Ser Asn Asn Ala
545                 550                 555                 560
Val Asp His Gln Ile Ser Gly Ser Thr Ser Asp Val Leu Gly Gly Ala
                565                 570                 575
Ile Tyr Ala Lys Thr Ser Leu Thr Ile Asp Ser Gly Asn Ser Ser Gly
                580                 585                 590
Thr Ile Thr Phe Ser Glu Asn Thr Thr Ser Ser Lys Ser Thr Thr Gly
                595                 600                 605
Gln Val Ala Gly Gly Ala Ile Phe Ser Pro Ser Val Thr Ile Thr Thr
            610                 615                 620
Pro Val Thr Phe Ser Lys Asn Ser Ala Ile Asn Ala Thr Thr Ser Ser
625                 630                 635                 640
Lys Lys Asp Thr Phe Gly Gly Ala Ile Gly Ala Ile Ser Thr Val Ser
                645                 650                 655
Leu Ser Lys Gly Ala Arg Phe Ser Glu Asn Ile Ala Asp Leu Gly Ser
                660                 665                 670
```

```
Ala Ile Gly Leu Val Pro Thr Gln Asp Ala Glu Thr Val Gln Leu
            675                 680                 685

Thr Thr Gly Ser Tyr Tyr Phe Glu Lys Asn Lys Ala Leu Lys Arg Ala
    690                 695                 700

Thr Val Tyr Ala Pro Ile Val Ser Ile Lys Ala His Thr Ala Thr Phe
705                 710                 715                 720

Asp Gln Asn Ile Ser Ala Glu Glu Gly Ser Ala Ile Tyr Phe Thr Lys
                725                 730                 735

Glu Ala Thr Ile Glu Ser Leu Gly Ser Val Leu Phe Thr Gly Asn Leu
            740                 745                 750

Val Thr Pro Ile Gln Ser Thr Thr Val Leu Thr Ser Gly Asn Thr Ser
            755                 760                 765

Lys Tyr Gly Ala Ala Ile Phe Gly Gln Ile Ala Asn Ala Ser Gly Ser
    770                 775                 780

Gln Thr Asp Asn Leu Pro Leu Lys Leu Ile Ala Ser Gly Gly Asn Ile
785                 790                 795                 800

Ser Phe Arg Asn Asn Glu Tyr Arg Pro Asp Ala Thr Asn Thr Gly Gln
                805                 810                 815

Ser Thr Phe Cys Ser Ile Ala Gly Asp Ile Lys Leu Thr Met Gln Ala
            820                 825                 830

Ala Glu Gly Lys Val Ile Ser Phe Phe Asp Ala Ile Arg Thr Ser Thr
            835                 840                 845

Lys Lys Thr Gly Thr Leu Ala Ser Ala Tyr Asp Thr Leu Asp Ile Asn
850                 855                 860

Lys Ser Asn Asp Ser Gly Ser Ile Asn Ser Ala Phe Thr Gly Thr Ile
865                 870                 875                 880

Met Phe Ser Ser Glu Leu His Glu Asn Lys Ser Tyr Ile Pro Gln Asn
                885                 890                 895

Val Val Leu His Ser Lys Ser Tyr Arg Gln Trp Ala Tyr Ile Pro Arg
            900                 905                 910

Asp Asn His Phe Tyr Ala Asn Ser Ile Leu Gly Ser Gln Met Ser Met
            915                 920                 925

Ala Thr Val Lys Gln Gly Leu Ile Asn Asp Lys Leu Asn Leu Ala Arg
930                 935                 940

Phe Asp Glu Val Ala Tyr Asn Asn Leu Trp Ile Ser Gly Leu Gly Thr
945                 950                 955                 960

Met Leu Ser Gln Arg Gly Gly Gln Arg Ser Glu Glu Met Thr Tyr Tyr
                965                 970                 975

Ser Arg Gly Ala Ser Val Ala Leu Asp Ala Lys Pro Thr Gln Asp Leu
            980                 985                 990

Ile Ile Gly Ala Ala Phe Ser Lys Met Ile Gly Arg Ser Lys Ser Leu
            995                 1000                1005

Lys Leu Glu Arg Asn Tyr Thr His Lys Gly Ser Glu Tyr Ser Tyr
    1010                1015                1020

Gln Ala Ser Val Tyr Gly Gly Ser Pro Phe Tyr Leu Thr Ile Asn
    1025                1030                1035

Lys Glu Ala Gly Arg Ser Leu Pro Leu Leu Leu Gln Gly Val Ile
    1040                1045                1050

Ser Tyr Gly Tyr Ile Lys His Asp Thr Val Thr His Tyr Pro Thr
    1055                1060                1065

Ile Arg Glu Leu Asn Lys Gly Glu Trp Glu Asp Leu Gly Trp Leu
    1070                1075                1080
```

| | | | | | | | | | | |
|---|---|---|---|---|---|---|---|---|---|---|
|Thr|Ala|Leu|Arg|Val|Ser|Ser|Ile|Leu|Lys|Thr|Pro|Lys|Gln|Gly|
| |1085| | | |1090| | | |1095| | | | | |

Asp Ser Lys Arg Ile Thr Val Tyr Gly Glu Val Glu Tyr Ser Ser
    1100            1105                1110

Ile Arg Gln Lys Gln Phe Thr Glu Thr Glu Tyr Asp Pro Arg Tyr
    1115            1120                1125

Phe Ser Asn Cys Thr Tyr Arg Asn Leu Ala Val Pro Val Gly Leu
    1130            1135                1140

Ala Leu Glu Gly Glu Phe Lys Gly Asn Asp Ile Leu Met Tyr Asn
    1145            1150                1155

Arg Phe Ser Val Ala Tyr Met Pro Ser Ile Tyr Arg Asn Ser Pro
    1160            1165                1170

Val Cys Lys Tyr Gln Val Leu Ser Ser Gly Glu Gly Gly Glu Ile
    1175            1180                1185

Val Cys Gly Val Pro Thr Arg Asn Ser Ser Arg Ala Glu Tyr Ser
    1190            1195                1200

Thr Gln Leu Tyr Leu Gly Pro Leu Trp Thr Leu Tyr Gly Ser Tyr
    1205            1210                1215

Thr Leu Glu Ala Asp Ala His Thr Leu Ala Asn Met Ile Asn Cys
    1220            1225                1230

Gly Ala Arg Met Thr Phe
    1235

<210> SEQ ID NO 26
<211> LENGTH: 4563
<212> TYPE: DNA
<213> ORGANISM: Chlamydia muridarum

<400> SEQUENCE: 26

```
atgagttccg agaaagataa aaaaaactcc tgttctaagt tttccttatc ggtagtagca      60
gctattctcg cttctatgag tggtttatcg aattgttccg atctttatgc cgtaggaagt     120
tctgcagacc atcctgccta cttgattcct caagcggggt tattattgga tcatattaag     180
gatatattca ttggccctaa agatagtcag gataaggggc agtataagtt gattattggt     240
gaggctggct ctttccaaga tagtaatgca gagactcttc ctcaaaaggt agagcacagc     300
actttgtttt cagttacaac acctataatt gtgcaaggaa tagatcaaca agatcaggtc     360
tcttcgcagg gattggtctg taattttttca ggagatcatt cagaggagat ttttgagaga     420
gaatcctttt tagggatcgc tttcctaggg aatggtagca aggatggaat cacgttaaca     480
gatataaaat cttcgttatc tggtgctgcc ttgtattctt cagatgatct tattttttgaa     540 agaattaagg gagatataga gctttcttct tgttcatctt tagaaagagg aggagcttgt     600
tcagctcaaa gtattttaat tcatgattgt caaggattaa cggtaaaaca ttgtgccgca     660
ggggtgaatg ttgaaggagt tagtgctagc gaccatctcg gatttggggg cggggccttc     720
tctactacaa gttctctttc tggagagaag agtttgtata tgcctgcagg cgatattgtg     780
gtggctacct gcgatggtcc tgtgtgtttc gaaggaaata gtgctcagtt agcaaatggt     840
ggcgctattg ccgcttctgg taaagttctt tttgtagcta cgaaaaaaaa gatttccttt     900
acagacaacc aagctttgtc tggaggagct atttctgcat cttctagtat ttctttccaa     960
aattgtgctg agcttgtgtt caagagtaat cttgcaaaag gagttaaaga taatgttct    1020 ttgggaggag gtgctttagc ctctttagaa tccgtagttt tgaaagataa tctcggtatt    1080
acttatgaaa aaaatcagtc ctattcggaa ggagggcta tttttgggaa ggattgtgag    1140
```

```
attttttgaaa acaggggcc tgttgtattc agagataata cagctgcttt aggaggcgga    1200 gctatttttgg cgcaacaaac tgtggcgatt tgtggtaata agtctggaat atcttttgaa   1260
ggaagtaagt ctagttttgg aggggccatt gcttgtggaa atttctcttc tgagaataat    1320
tcttcagctt tgggatcaat tgatatctct aacaatctag gagatatctc ttttcttcgg    1380
actctgtgta ctacttcgga tttagggcaa acggattacc aaggggggagg ggccttattc   1440 gctgaaaata tttctctttc tgagaatgct ggtgcaatta ctttcaaaga caatattgtg    1500
aagacatttg cctcaaatgg aaaaatgttg ggtggagggg caattttagc ttcaggaaat    1560
gttttgatta gcaaaaactc tggagagatt tcttttgtag ggaatgctcg agctcctcag    1620
gctattccga ctcgttcatc tgacgaattg tcttttggcg cacaattaac tcaaactact    1680
tcaggatgtt ctggaggagg agctcttttt ggtaaagagg ttgccattgt tcaaaatgcc    1740
actgttgtat tcgagcaaaa tcgcttacag tgtggcgagc aggaaacaca tggtggaggc    1800
ggtgctgttt atggtatgga gagtgcctct attattggaa actcttttgt gagattcgga    1860
aataattacg ctgtagggaa tcagatttct ggaggagctc ttttatccaa gaaggtccgt    1920
ttagctgaaa atacaagggt agattttttct cgaaatatcg ctactttctg cggcggggct   1980
gttcaagttt ctgatggaag ttgcgaattg atcaacaatg ggtatgtgct attcagagat    2040
aaccgagggc agacatttgg tggggctatt tcttgcttga aaggagatgt gatcatttcc    2100
ggaaataaag atagggttga gtttagagat aacattgtga cgcggcctta ttttgaagaa    2160
aatgaagaaa aagttgagac agcagatatt aattcagata gcaagaagc agaagagcgc     2220 tcttttattag agaacattga gcagagcttt attactgcaa ctaatcagac ctttttctta    2280
gaggaagaga aactcccatc agaagctttt atctctgctg aagaactttc aaagagaaga    2340
gaatgtgctg tgggggcgat ttttgcaaaa cgggtctaca ttacggataa taagaaccct    2400
atcttgtttt cgcataattt ttctgatgtt tatgggggag ctattttttac gggttctcta   2460 caggaaactg ataaacaaga tgttgtaact cctgaagttg tgatatcagg caacgatggg    2520
gatgtcattt tttctggaaa tgcagctaaa catgataagc atttacctga tacaggtggt    2580
ggagccattt gtacacagaa tttgacgatt tcccaaaaca atgggaatgt cttgttcttg    2640
aacaattttg cttgttctgg tggagcagtt cgcatagagg atcatggaga agttcttta    2700 gaggcttttg ggggagatat tattttcaat ggaaactctt cttttcagagc tcaaggatcg    2760 gatgcgatct attttgctgg taaggactct agaattaaag ctttaaatgc tactgaagga    2820
catgcgattg tgttccaaga tgcattggtg tttgaaaata tagaagaaag aaagtcttcg    2880
ggactattgg tgattaactc tcaggaaaat gagggttata cgggatccgt ccgatttta    2940 ggatctgaaa gtaaggttcc tcaatggatt catgtgcaac agggaggtct tgagttgcta    3000
catggagcta ttttatgtag ttatgggggtt aaacaagatc ctagagctaa aatagtatta   3060
tctgctggat ctaaattgaa gattctagat tcagagcaag aaaataacgc agaaattgga    3120
gatcttgaag attctgttaa ttcagaaaaa acaccatctc tttggattgg gaagaacgct    3180
caagcaaaag tccctctggt tgatatccat actatttcta ttgatttagc atcatttttct   3240 tctaaagctc aggaaacccc tgaggaagct ccacaagtca tcgtccctaa gggaagttgt    3300
gtccactcgg gagagttaag tttggagttg gttaatacaa caggaaaagg ttatgagaat    3360
catgcgttgt taaaaaatga tactcaggtt tctctcatgt cttttcaaaga ggaaaatgat    3420 ggatctttag aagatttgag taagttgtct gtttcggatt tacgcattaa agttttctact  3480 ccagatattg tagaagaaac ttatggccat atgggggatt ggtctgaagc tacaattcaa    3540
```

-continued

```
gatgggctc ttgtcattaa ttggcatcct actggatata aattagatcc gcaaaaagct    3600
ggttctttgg tattcaatgc attatgggag gaagaggctg tattgtctac tctaaaaaat    3660
gctcggattg cccataacct taccattcag agaatggaat ttgattattc tacaaatgct    3720
tggggattag cttttagtag ctttagagag ctatcttcag agaagcttgt ttctgttgat    3780
ggatatagag gctcttatat aggggcttct gcaggcattg atactcagtt gatggaagat    3840
tttgttttgg gaatcagcac ggcttccttc ttcgggaaaa tgcatagtca gaattttgat    3900
gcagagattt ctcgacatgg ttttgttggt tcggtctata caggcttcct agctggggcc    3960
tggttcttca aggggcagta cagtcttggc gaaacacata acgatatgac aactcgttac    4020
ggggttttgg gagaatctaa tgctacttgg aagtctcgag gagtactagc agatgcttta    4080
gttgaatatc gtagtttagt cggtccagca cgacctaaat tttatgcttt gcattttaat    4140
ccttatgtcg aggtatctta tgcatctgcg aagttcccta gttttgtaga acaaggagga    4200
gaagctcgtg cttttgaaga aacctcttta acaaacatta ccgttccctt tggtatgaaa    4260
tttgaactat cttttacaaa aggacagttt tcagagacta attctcttgg aataggttgt    4320
gcatgggaaa tgtatcggaa agtcgaagga agatctgtag agctactaga agctggtttt    4380
gattgggaag atctcctat agatctccct aaacaagagc tgagagtggc tttagaaaac    4440
aatacggaat ggagttcgta ttttagtaca gctctaggag taacagcatt ttgtggagga    4500
ttttcttcta tggataataa actaggatac gaagcgaatg ctggaatgcg tttgattttc    4560
tag                                                                  4563
```

<210> SEQ ID NO 27
<211> LENGTH: 1520
<212> TYPE: PRT
<213> ORGANISM: Chlamydia muridarum

<400> SEQUENCE: 27

Met Ser Ser Glu Lys Asp Lys Lys Asn Ser Cys Ser Lys Phe Ser Leu
1               5                   10                  15

Ser Val Val Ala Ala Ile Leu Ala Ser Met Ser Gly Leu Ser Asn Cys
            20                  25                  30

Ser Asp Leu Tyr Ala Val Gly Ser Ser Ala Asp His Pro Ala Tyr Leu
        35                  40                  45

Ile Pro Gln Ala Gly Leu Leu Leu Asp His Ile Lys Asp Ile Phe Ile
    50                  55                  60

Gly Pro Lys Asp Ser Gln Asp Lys Gly Gln Tyr Lys Leu Ile Ile Gly
65                  70                  75                  80

Glu Ala Gly Ser Phe Gln Asp Ser Asn Ala Glu Thr Leu Pro Gln Lys
                85                  90                  95

Val Glu His Ser Thr Leu Phe Ser Val Thr Thr Pro Ile Ile Val Gln
            100                 105                 110

Gly Ile Asp Gln Gln Asp Gln Val Ser Ser Gln Gly Leu Val Cys Asn
        115                 120                 125

Phe Ser Gly Asp His Ser Glu Glu Ile Phe Glu Arg Glu Ser Phe Leu
    130                 135                 140

Gly Ile Ala Phe Leu Gly Asn Gly Ser Lys Asp Gly Ile Thr Leu Thr
145                 150                 155                 160

Asp Ile Lys Ser Ser Leu Ser Gly Ala Ala Leu Tyr Ser Ser Asp Asp
                165                 170                 175

Leu Ile Phe Glu Arg Ile Lys Gly Asp Ile Glu Leu Ser Ser Cys Ser

```
                180                 185                 190
Ser Leu Glu Arg Gly Gly Ala Cys Ser Ala Gln Ser Ile Leu Ile His
            195                 200                 205

Asp Cys Gln Gly Leu Thr Val Lys His Cys Ala Ala Gly Val Asn Val
            210                 215                 220

Glu Gly Val Ser Ala Ser Asp His Leu Gly Phe Gly Gly Gly Ala Phe
225                 230                 235                 240

Ser Thr Thr Ser Ser Leu Ser Gly Glu Lys Ser Leu Tyr Met Pro Ala
            245                 250                 255

Gly Asp Ile Val Val Ala Thr Cys Asp Gly Pro Val Cys Phe Glu Gly
            260                 265                 270

Asn Ser Ala Gln Leu Ala Asn Gly Gly Ala Ile Ala Ala Ser Gly Lys
            275                 280                 285

Val Leu Phe Val Ala Asn Glu Lys Lys Ile Ser Phe Thr Asp Asn Gln
            290                 295                 300

Ala Leu Ser Gly Gly Ala Ile Ser Ala Ser Ser Ile Ser Phe Gln
305                 310                 315                 320

Asn Cys Ala Glu Leu Val Phe Lys Ser Asn Leu Ala Lys Gly Val Lys
            325                 330                 335

Asp Lys Cys Ser Leu Gly Gly Ala Leu Ala Ser Leu Glu Ser Val
            340                 345                 350

Val Leu Lys Asp Asn Leu Gly Ile Thr Tyr Glu Lys Asn Gln Ser Tyr
            355                 360                 365

Ser Glu Gly Gly Ala Ile Phe Gly Lys Asp Cys Glu Ile Phe Glu Asn
            370                 375                 380

Arg Gly Pro Val Val Phe Arg Asp Asn Thr Ala Ala Leu Gly Gly
385                 390                 395                 400

Ala Ile Leu Ala Gln Gln Thr Val Ala Ile Cys Gly Asn Lys Ser Gly
            405                 410                 415

Ile Ser Phe Glu Gly Ser Lys Ser Ser Phe Gly Gly Ala Ile Ala Cys
            420                 425                 430

Gly Asn Phe Ser Ser Glu Asn Asn Ser Ser Ala Leu Gly Ser Ile Asp
            435                 440                 445

Ile Ser Asn Asn Leu Gly Asp Ile Ser Phe Leu Arg Thr Leu Cys Thr
            450                 455                 460

Thr Ser Asp Leu Gly Gln Thr Asp Tyr Gln Gly Gly Ala Leu Phe
465                 470                 475                 480

Ala Glu Asn Ile Ser Leu Ser Glu Asn Ala Gly Ala Ile Thr Phe Lys
            485                 490                 495

Asp Asn Ile Val Lys Thr Phe Ala Ser Asn Gly Lys Met Leu Gly Gly
            500                 505                 510

Gly Ala Ile Leu Ala Ser Gly Asn Val Leu Ile Ser Lys Asn Ser Gly
            515                 520                 525

Glu Ile Ser Phe Val Gly Asn Ala Arg Ala Pro Gln Ala Ile Pro Thr
            530                 535                 540

Arg Ser Ser Asp Glu Leu Ser Phe Gly Ala Gln Leu Thr Gln Thr Thr
545                 550                 555                 560

Ser Gly Cys Ser Gly Gly Ala Leu Phe Gly Lys Glu Val Ala Ile
            565                 570                 575

Val Gln Asn Ala Thr Val Val Phe Glu Gln Asn Arg Leu Gln Cys Gly
            580                 585                 590

Glu Gln Glu Thr His Gly Gly Gly Ala Val Tyr Gly Met Glu Ser
            595                 600                 605
```

```
Ala Ser Ile Ile Gly Asn Ser Phe Val Arg Phe Gly Asn Asn Tyr Ala
    610                 615                 620

Val Gly Asn Gln Ile Ser Gly Gly Ala Leu Leu Ser Lys Lys Val Arg
625                 630                 635                 640

Leu Ala Glu Asn Thr Arg Val Asp Phe Ser Arg Asn Ile Ala Thr Phe
                645                 650                 655

Cys Gly Gly Ala Val Gln Val Ser Asp Gly Ser Cys Glu Leu Ile Asn
                660                 665                 670

Asn Gly Tyr Val Leu Phe Arg Asp Asn Arg Gly Gln Thr Phe Gly Gly
            675                 680                 685

Ala Ile Ser Cys Leu Lys Gly Asp Val Ile Ile Ser Gly Asn Lys Asp
690                 695                 700

Arg Val Glu Phe Arg Asp Asn Ile Val Thr Arg Pro Tyr Phe Glu Glu
705                 710                 715                 720

Asn Glu Glu Lys Val Glu Thr Ala Asp Ile Asn Ser Asp Lys Gln Glu
                725                 730                 735

Ala Glu Glu Arg Ser Leu Leu Glu Asn Ile Glu Gln Ser Phe Ile Thr
                740                 745                 750

Ala Thr Asn Gln Thr Phe Phe Leu Glu Glu Lys Leu Pro Ser Glu
    755                 760                 765

Ala Phe Ile Ser Ala Glu Glu Leu Ser Lys Arg Arg Glu Cys Ala Gly
    770                 775                 780

Gly Ala Ile Phe Ala Lys Arg Val Tyr Ile Thr Asp Asn Lys Glu Pro
785                 790                 795                 800

Ile Leu Phe Ser His Asn Phe Ser Asp Val Tyr Gly Gly Ala Ile Phe
                805                 810                 815

Thr Gly Ser Leu Gln Glu Thr Asp Lys Gln Asp Val Val Thr Pro Glu
            820                 825                 830

Val Val Ile Ser Gly Asn Asp Gly Asp Val Ile Phe Ser Gly Asn Ala
            835                 840                 845

Ala Lys His Asp Lys His Leu Pro Asp Thr Gly Gly Gly Ala Ile Cys
    850                 855                 860

Thr Gln Asn Leu Thr Ile Ser Gln Asn Asn Gly Asn Val Leu Phe Leu
865                 870                 875                 880

Asn Asn Phe Ala Cys Ser Gly Gly Ala Val Arg Ile Glu Asp His Gly
                885                 890                 895

Glu Val Leu Leu Glu Ala Phe Gly Gly Asp Ile Ile Phe Asn Gly Asn
            900                 905                 910

Ser Ser Phe Arg Ala Gln Gly Ser Asp Ala Ile Tyr Phe Ala Gly Lys
            915                 920                 925

Asp Ser Arg Ile Lys Ala Leu Asn Ala Thr Glu Gly His Ala Ile Val
    930                 935                 940

Phe Gln Asp Ala Leu Val Phe Glu Asn Ile Glu Glu Arg Lys Ser Ser
945                 950                 955                 960

Gly Leu Leu Val Ile Asn Ser Gln Glu Asn Glu Gly Tyr Thr Gly Ser
                965                 970                 975

Val Arg Phe Leu Gly Ser Glu Ser Lys Val Pro Gln Trp Ile His Val
            980                 985                 990

Gln Gln Gly Gly Leu Glu Leu Leu His Gly Ala Ile Leu Cys Ser Tyr
    995                 1000                1005

Gly Val Lys Gln Asp Pro Arg Ala Lys Ile Val Leu Ser Ala Gly
    1010                1015                1020
```

```
Ser Lys Leu Lys Ile Leu Asp Ser Glu Gln Glu Asn Asn Ala Glu
    1025                1030                1035

Ile Gly Asp Leu Glu Asp Ser Val Asn Ser Glu Lys Thr Pro Ser
    1040                1045                1050

Leu Trp Ile Gly Lys Asn Ala Gln Ala Lys Val Pro Leu Val Asp
    1055                1060                1065

Ile His Thr Ile Ser Ile Asp Leu Ala Ser Phe Ser Ser Lys Ala
    1070                1075                1080

Gln Glu Thr Pro Glu Glu Ala Pro Gln Val Ile Val Pro Lys Gly
    1085                1090                1095

Ser Cys Val His Ser Gly Glu Leu Ser Leu Glu Leu Val Asn Thr
    1100                1105                1110

Thr Gly Lys Gly Tyr Glu Asn His Ala Leu Leu Lys Asn Asp Thr
    1115                1120                1125

Gln Val Ser Leu Met Ser Phe Lys Glu Glu Asn Asp Gly Ser Leu
    1130                1135                1140

Glu Asp Leu Ser Lys Leu Ser Val Ser Asp Leu Arg Ile Lys Val
    1145                1150                1155

Ser Thr Pro Asp Ile Val Glu Glu Thr Tyr Gly His Met Gly Asp
    1160                1165                1170

Trp Ser Glu Ala Thr Ile Gln Asp Gly Ala Leu Val Ile Asn Trp
    1175                1180                1185

His Pro Thr Gly Tyr Lys Leu Asp Pro Gln Lys Ala Gly Ser Leu
    1190                1195                1200

Val Phe Asn Ala Leu Trp Glu Glu Ala Val Leu Ser Thr Leu
    1205                1210                1215

Lys Asn Ala Arg Ile Ala His Asn Leu Thr Ile Gln Arg Met Glu
    1220                1225                1230

Phe Asp Tyr Ser Thr Asn Ala Trp Gly Leu Ala Phe Ser Ser Phe
    1235                1240                1245

Arg Glu Leu Ser Ser Glu Lys Leu Val Ser Val Asp Gly Tyr Arg
    1250                1255                1260

Gly Ser Tyr Ile Gly Ala Ser Ala Gly Ile Asp Thr Gln Leu Met
    1265                1270                1275

Glu Asp Phe Val Leu Gly Ile Ser Thr Ala Ser Phe Phe Gly Lys
    1280                1285                1290

Met His Ser Gln Asn Phe Asp Ala Glu Ile Ser Arg His Gly Phe
    1295                1300                1305

Val Gly Ser Val Tyr Thr Gly Phe Leu Ala Gly Ala Trp Phe Phe
    1310                1315                1320

Lys Gly Gln Tyr Ser Leu Gly Glu Thr His Asn Asp Met Thr Thr
    1325                1330                1335

Arg Tyr Gly Val Leu Gly Glu Ser Asn Ala Thr Trp Lys Ser Arg
    1340                1345                1350

Gly Val Leu Ala Asp Ala Leu Val Glu Tyr Arg Ser Leu Val Gly
    1355                1360                1365

Pro Ala Arg Pro Lys Phe Tyr Ala Leu His Phe Asn Pro Tyr Val
    1370                1375                1380

Glu Val Ser Tyr Ala Ser Ala Lys Phe Pro Ser Phe Val Glu Gln
    1385                1390                1395

Gly Gly Glu Ala Arg Ala Phe Glu Glu Thr Ser Leu Thr Asn Ile
    1400                1405                1410

Thr Val Pro Phe Gly Met Lys Phe Glu Leu Ser Phe Thr Lys Gly
```

| | | |
|---|---|---|
| 1415 | 1420 | 1425 |

Gln Phe Ser Glu Thr Asn Ser Leu Gly Ile Gly Cys Ala Trp Glu
       1430            1435            1440

Met Tyr Arg Lys Val Glu Gly Arg Ser Val Glu Leu Leu Glu Ala
       1445            1450            1455

Gly Phe Asp Trp Glu Gly Ser Pro Ile Asp Leu Pro Lys Gln Glu
       1460            1465            1470

Leu Arg Val Ala Leu Glu Asn Asn Thr Glu Trp Ser Ser Tyr Phe
       1475            1480            1485

Ser Thr Ala Leu Gly Val Thr Ala Phe Cys Gly Gly Phe Ser Ser
       1490            1495            1500

Met Asp Asn Lys Leu Gly Tyr Glu Ala Asn Ala Gly Met Arg Leu
       1505            1510            1515

Ile Phe
       1520

<210> SEQ ID NO 28
<211> LENGTH: 4515
<212> TYPE: DNA
<213> ORGANISM: artificial sequence
<220> FEATURE:
<223> OTHER INFORMATION: synthetic polynucleotide

<400> SEQUENCE: 28

| | | |
|---|---|---|
| catatggcta ttctggcttc tatgagtggt ttatcgaatt gttccgatct gtatgccgta | 60 |
| ggaagttctg cagaccatcc tgcctacttg attcctcaag cggggttatt attggatcat | 120 |
| attaaggata ttttcattgg ccctaaagat agtcaggata aggggcagta taagttgatt | 180 |
| attggtgagg ctggctcttt ccaagatagt aatgcagaga ctctgcctca aaaggtagag | 240 |
| cacagcactt tgttttcagt tacaacacct attattgtgc aaggaattga tcaacaagat | 300 |
| caggtctctt cgcagggatt ggtctgtaat ttttcaggag atcattcaga ggagattttt | 360 |
| gagcgcgaat cctttttagg gatcgctttc ctggggaatg gtagcaagga tggaatcacg | 420 |
| ttaacagata ttaaatcttc gttatctggt gctgccttgt attcttcaga tgatctgatt | 480 |
| tttgaacgca ttaagggaga tattgagctg tcttcttgtt catctttaga acgcggagga | 540 |
| gcttgttcag ctcaaagtat tttaattcat gattgtcaag gattaacggt aaaacattgt | 600 |
| gccgcagggg tgaatgttga aggagttagt gctagcgacc atctgggatt tggggcggg | 660 |
| gccttctcta ctacaagttc tctgtctgga gagaagagtt tgtatatgcc tgcaggcgat | 720 |
| attgtggtgg ctacctgcga tggtcctgtg tgtttcgaag gaatagtgc tcagttagca | 780 |
| aatggtggcg ctattgccgc ttctggtaaa gttctgtttg tagctaacga aaaaaagatt | 840 |
| tcctttacag acaaccaagc tttgtctgga ggagctattt ctgcatcttc tagtatttct | 900 |
| ttccaaaatt gtgctgagct ggtgttcaag agtaatctgg caaaaggagt taagataaaa | 960 |
| tgttctttgg gaggaggtgc tttagcctct ttagaatccg tagttttgaa agataatctg | 1020 |
| ggtattactt atgaaaaaaa tcagtcctat tcggaaggag gggctatttt tgggaaggat | 1080 |
| tgtgagattt tgaaaaccg cgggcctgtt gtattccgcg ataatacagc tgctttagga | 1140 |
| ggcggagcta ttttggcgca acaaactgtg gcgatttgtg gtaataagtc tggaatttct | 1200 |
| tttgaaggaa gtaagtctag ttttggaggg gccattgctt gtggaaattt ctcttctgag | 1260 |
| aataattctt cagctttggg atcaattgat atctctaaca atctgggaga tatctctttt | 1320 |
| ctgcggactc tgtgtactac ttcggattta gggcaaacgg attaccaagg ggagggggcc | 1380 |

-continued

```
ttattcgctg aaaatatttc tctgtctgag aatgctggtg caattacttt caaagacaat    1440
attgtgaaga catttgcctc aaatggaaaa atgttgggtg gagggcaat tttagcttca     1500
ggaaatgttt tgattagcaa aaactctgga gagatttctt ttgtagggaa tgcccgtgct    1560
cctcaggcta ttccgactcg ttcatctgac gaattgtctt ttggcgcaca attaactcaa    1620
actacttcag gatgttctgg aggaggtgct ctgtttggta agaggttgc cattgttcaa     1680
aatgccactg ttgtattcga gcaaaatcgc ttacagtgtg gcgagcagga aacacatggt    1740
ggaggcggtg ctgtttatgg tatggagagt gcctctatta ttggaaactc ttttgtgcgc    1800
ttcggaaata attacgctgt agggaatcag atttctggag gtgctctgtt atccaagaag    1860
gtccgtttag ctgaaaatac acgcgtagat ttttctcgca atatcgctac tttctgcggc    1920
ggggctgttc aagtttctga tggaagttgc gaattgatca acaatgggta tgtgctgttc    1980
cgcgataacc gcgggcagac atttggtggg gctatttctt gcttgaaagg agatgtgatc    2040
atttccggaa ataaagatcg cgttgagttt cgcgataaca ttgtgacgcg gccttatttt    2100
gaagaaaatg aagaaaaagt tgagacagca gatattaatt cagataagca agaagcagaa    2160
gagcgctctt tattagagaa cattgagcag agctttatta ctgcaactaa tcagacccttt    2220
ttcttagagg aagagaaact gccatcagaa gcttttatct ctgctgaaga actgtcaaag    2280
cgccgcgaat gtgctggtgg ggcgattttt gcaaaacggg tctacattac ggataataaa    2340
gaacctatct tgttttcgca taattttct gatgtttatg ggggagctat ttttacgggt     2400
tctctgcagg aaactgataa acaagatgtt gtaactcctg aagttgtgat tcaggcaac    2460
gatgggatg tcattttttc tggaaatgca gctaaacatg ataagcattt acctgataca     2520
ggtggtggag ccatttgtac acagaatttg acgatttccc aaaacaatgg gaatgtcttg    2580
ttcttgaaca attttgcttg ttctggtgga gcagttcgca ttgaggatca tggagaagtt    2640
ctgttagagg cttttggggg agatattatt ttcaatggaa actcttcttt ccgcgctcaa    2700
ggatcggatg cgatctattt tgctggtaag gactctcgca ttaaagcttt aaatgctact    2760
gaaggacatg cgattgtgtt ccaagatgca ttggtgtttg aaaatattga agaacgcaag    2820
tcttcgggac tgttggtgat taactctcag gaaaatgagc tctatacggg atctgtccgc    2880
ttttttaggat ctgaaagtaa ggttcctcaa tggattcatg tgcaacaggg aggtctggag    2940
ttgctgcatg gagctatttt atgtagttat ggggttaaac aagatcctcg cgctaaaatt    3000
gtattatctg ctggatctaa attgaagatt ctggattcag agcaagaaaa taacgcagaa    3060
attggagatc tggaagattc tgttaattca gaaaaaacac catctctgtg gattgggaag    3120
aacgctcaag caaaagtccc tctggttgat atccatacta tttctattga tttagcatca    3180
ttttcttcta agctcagga aacccctgag gaagctccac aagtcatcgt ccctaaggga    3240
agttgtgtcc actcgggaga gttaagtttg gagttggtta atacaacagg aaaaggttat    3300
gagaatcatg cgttgttaaa aaatgatact caggtttctc tgatgtcttt caaagaggaa    3360
aatgatggat ctttagaaga tttgagtaag ttgtctgttt cggatttacg cattaaagtt    3420
tctactccag atattgtaga agaaacttat ggccacatgg gggattggtc tgaagctaca    3480
attcaagatg gggctctggt cattaattgg catcctactg gatataaatt agatccgcaa    3540
aaagctggtt cttgtggtatt caatgcatta tgggaggaag aggctgtatt gtccatggtg    3600
aaaaatgctc ggattgcccaa taacctgacc attcagcgca tggaatttga ttattctaca    3660
aatgcttggg gattagcttt tagtagcttt cgcgagctgt cttcagagaa actggtttct    3720
gttgatggat atcgcggctc ttatattggg gcttctgcag gcattgatac tcagttgatg    3780
```

```
gaagattttg ttttgggaat cagcacggct tccttcttcg ggaaaatgca tagtcagaat    3840
tttgatgcag agatttctcg ccacggtttt gttggttcgg tctatacagg cttcctggct    3900
ggggcctggt tcttcaaggg gcagtacagt ctgggcgaaa cacataacga tatgacaact    3960
cgttacgggg ttttgggaga atctaatgct acttggaagt ctcgcggagt actggcagat    4020
gctttagttg aatatcgtag tttagtcggt ccagcacgcc ctaaatttta tgctttgcat    4080
tttaatcctt atgtcgaggt atcttatgca tctgcgaagt ccctagttt tgtagaacaa     4140 ggaggagaag ctcgtgcttt tgaagaaacc tctttaacaa acattaccgt tccgtttggt    4200
atgaaatttg aactgtcttt tacaaaagga cagttttcag agactaattc tctgggaatt    4260
ggttgtgcat gggaaatgta tcggaaagtc gaaggacgct ctgtagagct gctggaagct    4320
ggttttgatt gggaaggatc tcctattgat ctgcctaaac aagagctgcg cgtggcttta    4380
gaaaacaata cggaatggag ttcgtatttt agtacagctc tgggagtaac agcattttgt    4440
ggaggatttt cttctatgga taataaactg ggatacgaag cgaatgctgg aatgcgtttg    4500
attttctaag gatcc                                                     4515
```

<210> SEQ ID NO 29
<211> LENGTH: 1501
<212> TYPE: PRT
<213> ORGANISM: artificial sequence
<220> FEATURE:
<223> OTHER INFORMATION: synthetic peptide

<400> SEQUENCE: 29

```
Met Ala Ile Leu Ala Ser Met Ser Gly Leu Ser Asn Cys Ser Asp Leu
1               5                   10                  15

Tyr Ala Val Gly Ser Ser Ala Asp His Pro Ala Tyr Leu Ile Pro Gln
            20                  25                  30

Ala Gly Leu Leu Leu Asp His Ile Lys Asp Ile Phe Ile Gly Pro Lys
        35                  40                  45

Asp Ser Gln Asp Lys Gly Gln Tyr Lys Leu Ile Ile Gly Glu Ala Gly
    50                  55                  60

Ser Phe Gln Asp Ser Asn Ala Glu Thr Leu Pro Gln Lys Val Glu His
65                  70                  75                  80

Ser Thr Leu Phe Ser Val Thr Thr Pro Ile Ile Val Gln Gly Ile Asp
                85                  90                  95

Gln Gln Asp Gln Val Ser Ser Gln Gly Leu Val Cys Asn Phe Ser Gly
            100                 105                 110

Asp His Ser Glu Glu Ile Phe Glu Arg Glu Ser Phe Leu Gly Ile Ala
        115                 120                 125

Phe Leu Gly Asn Gly Ser Lys Asp Gly Ile Thr Leu Thr Asp Ile Lys
    130                 135                 140

Ser Ser Leu Ser Gly Ala Ala Leu Tyr Ser Ser Asp Asp Leu Ile Phe
145                 150                 155                 160

Glu Arg Ile Lys Gly Asp Ile Glu Leu Ser Ser Cys Ser Ser Leu Glu
                165                 170                 175

Arg Gly Gly Ala Cys Ser Ala Gln Ser Ile Leu Ile His Asp Cys Gln
            180                 185                 190

Gly Leu Thr Val Lys His Cys Ala Ala Gly Val Asn Val Glu Gly Val
        195                 200                 205

Ser Ala Ser Asp His Leu Gly Phe Gly Gly Gly Ala Phe Ser Thr Thr
    210                 215                 220
```

-continued

Ser Ser Leu Ser Gly Glu Lys Ser Leu Tyr Met Pro Ala Gly Asp Ile
225                 230                 235                 240

Val Val Ala Thr Cys Asp Gly Pro Val Cys Phe Glu Gly Asn Ser Ala
            245                 250                 255

Gln Leu Ala Asn Gly Gly Ala Ile Ala Ala Ser Gly Lys Val Leu Phe
        260                 265                 270

Val Ala Asn Glu Lys Lys Ile Ser Phe Thr Asp Asn Gln Ala Leu Ser
    275                 280                 285

Gly Gly Ala Ile Ser Ala Ser Ser Ile Ser Phe Gln Asn Cys Ala
290                 295                 300

Glu Leu Val Phe Lys Ser Asn Leu Ala Lys Gly Val Lys Asp Lys Cys
305                 310                 315                 320

Ser Leu Gly Gly Gly Ala Leu Ala Ser Leu Glu Ser Val Val Leu Lys
            325                 330                 335

Asp Asn Leu Gly Ile Thr Tyr Glu Lys Asn Gln Ser Tyr Ser Glu Gly
        340                 345                 350

Gly Ala Ile Phe Gly Lys Asp Cys Glu Ile Phe Glu Asn Arg Gly Pro
        355                 360                 365

Val Val Phe Arg Asp Asn Thr Ala Ala Leu Gly Gly Ala Ile Leu
370                 375                 380

Ala Gln Gln Thr Val Ala Ile Cys Gly Asn Lys Ser Gly Ile Ser Phe
385                 390                 395                 400

Glu Gly Ser Lys Ser Ser Phe Gly Gly Ala Ile Ala Cys Gly Asn Phe
            405                 410                 415

Ser Ser Glu Asn Asn Ser Ser Ala Leu Gly Ser Ile Asp Ile Ser Asn
        420                 425                 430

Asn Leu Gly Asp Ile Ser Phe Leu Arg Thr Leu Cys Thr Thr Ser Asp
        435                 440                 445

Leu Gly Gln Thr Asp Tyr Gln Gly Gly Ala Leu Phe Ala Glu Asn
    450                 455                 460

Ile Ser Leu Ser Glu Asn Ala Gly Ala Ile Thr Phe Lys Asp Asn Ile
465                 470                 475                 480

Val Lys Thr Phe Ala Ser Asn Gly Lys Met Leu Gly Gly Gly Ala Ile
            485                 490                 495

Leu Ala Ser Gly Asn Val Leu Ile Ser Lys Asn Ser Gly Glu Ile Ser
        500                 505                 510

Phe Val Gly Asn Ala Arg Ala Pro Gln Ala Ile Pro Thr Arg Ser Ser
        515                 520                 525

Asp Glu Leu Ser Phe Gly Ala Gln Leu Thr Gln Thr Ser Gly Cys
    530                 535                 540

Ser Gly Gly Gly Ala Leu Phe Gly Lys Glu Val Ala Ile Val Gln Asn
545                 550                 555                 560

Ala Thr Val Val Phe Glu Gln Asn Arg Leu Gln Cys Gly Glu Gln Glu
            565                 570                 575

Thr His Gly Gly Gly Ala Val Tyr Gly Met Glu Ser Ala Ser Ile
        580                 585                 590

Ile Gly Asn Ser Phe Val Arg Phe Gly Asn Asn Tyr Ala Val Gly Asn
        595                 600                 605

Gln Ile Ser Gly Gly Ala Leu Leu Ser Lys Lys Val Arg Leu Ala Glu
        610                 615                 620

Asn Thr Arg Val Asp Phe Ser Arg Asn Ile Ala Thr Phe Cys Gly Gly
625                 630                 635                 640

Ala Val Gln Val Ser Asp Gly Ser Cys Glu Leu Ile Asn Asn Gly Tyr

```
                    645                 650                 655
Val Leu Phe Arg Asp Asn Arg Gly Gln Thr Phe Gly Gly Ala Ile Ser
            660                 665                 670

Cys Leu Lys Gly Asp Val Ile Ile Ser Gly Asn Lys Asp Arg Val Glu
            675                 680                 685

Phe Arg Asp Asn Ile Val Thr Arg Pro Tyr Phe Glu Glu Asn Glu Glu
            690                 695                 700

Lys Val Glu Thr Ala Asp Ile Asn Ser Asp Lys Gln Glu Ala Glu Glu
705                 710                 715                 720

Arg Ser Leu Leu Glu Asn Ile Glu Gln Ser Phe Ile Thr Ala Thr Asn
                725                 730                 735

Gln Thr Phe Phe Leu Glu Glu Glu Lys Leu Pro Ser Glu Ala Phe Ile
            740                 745                 750

Ser Ala Glu Glu Leu Ser Lys Arg Arg Glu Cys Ala Gly Gly Ala Ile
            755                 760                 765

Phe Ala Lys Arg Val Tyr Ile Thr Asp Asn Lys Glu Pro Ile Leu Phe
            770                 775                 780

Ser His Asn Phe Ser Asp Val Tyr Gly Gly Ala Ile Phe Thr Gly Ser
785                 790                 795                 800

Leu Gln Glu Thr Asp Lys Gln Asp Val Val Thr Pro Glu Val Val Ile
                805                 810                 815

Ser Gly Asn Asp Gly Asp Val Ile Phe Ser Gly Asn Ala Ala Lys His
            820                 825                 830

Asp Lys His Leu Pro Asp Thr Gly Gly Gly Ala Ile Cys Thr Gln Asn
            835                 840                 845

Leu Thr Ile Ser Gln Asn Asn Gly Asn Val Leu Phe Leu Asn Asn Phe
850                 855                 860

Ala Cys Ser Gly Gly Ala Val Arg Ile Glu Asp His Gly Glu Val Leu
865                 870                 875                 880

Leu Glu Ala Phe Gly Gly Asp Ile Ile Phe Asn Gly Asn Ser Ser Phe
                885                 890                 895

Arg Ala Gln Gly Ser Asp Ala Ile Tyr Phe Ala Gly Lys Asp Ser Arg
            900                 905                 910

Ile Lys Ala Leu Asn Ala Thr Glu Gly His Ala Ile Val Phe Gln Asp
            915                 920                 925

Ala Leu Val Phe Glu Asn Ile Glu Glu Arg Lys Ser Ser Gly Leu Leu
            930                 935                 940

Val Ile Asn Ser Gln Glu Asn Glu Leu Tyr Thr Gly Ser Val Arg Phe
945                 950                 955                 960

Leu Gly Ser Glu Ser Lys Val Pro Gln Trp Ile His Val Gln Gln Gly
                965                 970                 975

Gly Leu Glu Leu Leu His Gly Ala Ile Leu Cys Ser Tyr Gly Val Lys
            980                 985                 990

Gln Asp Pro Arg Ala Lys Ile Val Leu Ser Ala Gly Ser Lys Leu Lys
            995                 1000                1005

Ile Leu Asp Ser Glu Gln Glu Asn Asn Ala Glu Ile Gly Asp Leu
    1010                1015                1020

Glu Asp Ser Val Asn Ser Glu Lys Thr Pro Ser Leu Trp Ile Gly
    1025                1030                1035

Lys Asn Ala Gln Ala Lys Val Pro Leu Val Asp Ile His Thr Ile
    1040                1045                1050

Ser Ile Asp Leu Ala Ser Phe Ser Ser Lys Ala Gln Glu Thr Pro
    1055                1060                1065
```

```
Glu Glu Ala Pro Gln Val Ile Val Pro Lys Gly Ser Cys Val His
    1070            1075            1080

Ser Gly Glu Leu Ser Leu Glu Leu Val Asn Thr Thr Gly Lys Gly
    1085            1090            1095

Tyr Glu Asn His Ala Leu Leu Lys Asn Asp Thr Gln Val Ser Leu
    1100            1105            1110

Met Ser Phe Lys Glu Glu Asn Asp Gly Ser Leu Glu Asp Leu Ser
    1115            1120            1125

Lys Leu Ser Val Ser Asp Leu Arg Ile Lys Val Ser Thr Pro Asp
    1130            1135            1140

Ile Val Glu Glu Thr Tyr Gly His Met Gly Asp Trp Ser Glu Ala
    1145            1150            1155

Thr Ile Gln Asp Gly Ala Leu Val Ile Asn Trp His Pro Thr Gly
    1160            1165            1170

Tyr Lys Leu Asp Pro Gln Lys Ala Gly Ser Leu Val Phe Asn Ala
    1175            1180            1185

Leu Trp Glu Glu Glu Ala Val Leu Ser Met Val Lys Asn Ala Arg
    1190            1195            1200

Ile Ala His Asn Leu Thr Ile Gln Arg Met Glu Phe Asp Tyr Ser
    1205            1210            1215

Thr Asn Ala Trp Gly Leu Ala Phe Ser Ser Phe Arg Glu Leu Ser
    1220            1225            1230

Ser Glu Lys Leu Val Ser Val Asp Gly Tyr Arg Gly Ser Tyr Ile
    1235            1240            1245

Gly Ala Ser Ala Gly Ile Asp Thr Gln Leu Met Glu Asp Phe Val
    1250            1255            1260

Leu Gly Ile Ser Thr Ala Ser Phe Phe Gly Lys Met His Ser Gln
    1265            1270            1275

Asn Phe Asp Ala Glu Ile Ser Arg His Gly Phe Val Gly Ser Val
    1280            1285            1290

Tyr Thr Gly Phe Leu Ala Gly Ala Trp Phe Phe Lys Gly Gln Tyr
    1295            1300            1305

Ser Leu Gly Glu Thr His Asn Asp Met Thr Thr Arg Tyr Gly Val
    1310            1315            1320

Leu Gly Glu Ser Asn Ala Thr Trp Lys Ser Arg Gly Val Leu Ala
    1325            1330            1335

Asp Ala Leu Val Glu Tyr Arg Ser Leu Val Gly Pro Ala Arg Pro
    1340            1345            1350

Lys Phe Tyr Ala Leu His Phe Asn Pro Tyr Val Glu Val Ser Tyr
    1355            1360            1365

Ala Ser Ala Lys Phe Pro Ser Phe Val Glu Gln Gly Gly Glu Ala
    1370            1375            1380

Arg Ala Phe Glu Glu Thr Ser Leu Thr Asn Ile Thr Val Pro Phe
    1385            1390            1395

Gly Met Lys Phe Glu Leu Ser Phe Thr Lys Gly Gln Phe Ser Glu
    1400            1405            1410

Thr Asn Ser Leu Gly Ile Gly Cys Ala Trp Glu Met Tyr Arg Lys
    1415            1420            1425

Val Glu Gly Arg Ser Val Glu Leu Leu Glu Ala Gly Phe Asp Trp
    1430            1435            1440

Glu Gly Ser Pro Ile Asp Leu Pro Lys Gln Glu Leu Arg Val Ala
    1445            1450            1455
```

| Leu | Glu | Asn | Asn | Thr | Glu | Trp | Ser | Ser | Tyr | Phe | Ser | Thr | Ala | Leu |
|---|---|---|---|---|---|---|---|---|---|---|---|---|---|---|
| 1460 | | | | | 1465 | | | | | 1470 | | | | |

| Gly | Val | Thr | Ala | Phe | Cys | Gly | Gly | Phe | Ser | Met | Asp | Asn | Lys |
|---|---|---|---|---|---|---|---|---|---|---|---|---|---|
| 1475 | | | | | 1480 | | | | 1485 | | | | |

| Leu | Gly | Tyr | Glu | Ala | Asn | Ala | Gly | Met | Arg | Leu | Ile | Phe |
|---|---|---|---|---|---|---|---|---|---|---|---|---|
| 1490 | | | | | 1495 | | | | 1500 | | | |

<210> SEQ ID NO 30
<211> LENGTH: 3927
<212> TYPE: DNA
<213> ORGANISM: artificial sequence
<220> FEATURE:
<223> OTHER INFORMATION: synthetic polynucleotide

<400> SEQUENCE: 30

| | | | | | |
|---|---|---|---|---|---|
| catatggcta | ttctggcttc | tatgagtggt | ttatcgaatt | gttccgatct | gtatgccgta | 60 |
| ggaagttctg | cagaccatcc | tgcctacttg | attcctcaag | cggggttatt | attggatcat | 120 |
| attaaggata | ttttcattgg | ccctaaagat | agtcaggata | aggggcagta | taagttgatt | 180 |
| attggtgagg | ctggctcttt | ccaagatagt | aatgcagaga | ctctgcctca | aaaggtagag | 240 |
| cacagcactt | tgttttcagt | tacaacacct | attattgtgc | aaggaattga | tcaacaagat | 300 |
| caggtctctt | cgcagggatt | ggtctgtaat | ttttcaggag | atcattcaga | ggagattttt | 360 |
| gagcgcgaat | cctttttagg | gatcgctttc | ctggggaatg | gtagcaagga | tggaatcacg | 420 |
| ttaacagata | ttaaatcttc | gttatctggt | gctgccttgt | attcttcaga | tgatctgatt | 480 |
| tttgaacgca | ttaagggaga | tattgagctg | tcttcttgtt | catctttaga | acgcggagga | 540 |
| gcttgttcag | ctcaaagtat | tttaattcat | gattgtcaag | gattaacggt | aaaacattgt | 600 |
| gccgcagggg | tgaatgttga | aggagttagt | gctagcgacc | atctgggatt | tggggcggg | 660 |
| gccttctcta | ctacaagttc | tctgtctgga | gagaagagtt | tgtatatgcc | tgcaggcgat | 720 |
| attgtggtgg | ctacctgcga | tggtcctgtg | tgtttcgaag | gaaatagtgc | tcagttagca | 780 |
| aatggtggcg | ctattgccgc | ttctggtaaa | gttctgtttg | tagctaacga | aaaaaagatt | 840 |
| tcctttacag | acaaccaagc | tttgtctgga | ggagctattt | ctgcatcttc | tagtatttct | 900 |
| ttccaaaatt | gtgctgagct | ggtgttcaag | agtaatctgg | caaaaggagt | taagataaaa | 960 |
| tgttctttgg | gaggaggtgc | tttagcctct | ttagaatccg | tagttttgaa | agataatctg | 1020 |
| ggtattactt | atgaaaaaaa | tcagtcctat | tcggaaggag | gggctatttt | tgggaaggat | 1080 |
| tgtgagattt | tgaaaaccg | cgggcctgtt | gtattccgcg | ataatacagc | tgctttagga | 1140 |
| ggcggagcta | ttttggcgca | acaaactgtg | gcgatttgtg | gtaataagtc | tggaatttct | 1200 |
| tttgaaggaa | gtaagtctag | ttttggaggg | gccattgctt | gtggaaattt | ctcttctgag | 1260 |
| aataattctt | cagctttggg | gatcaattgat | atctctaaca | atctgggaga | tatctctttt | 1320 |
| ctgcggactc | tgtgtactac | ttcggattta | gggcaaacgg | attaccaagg | ggagggggcc | 1380 |
| ttattcgctg | aaaatatttc | tctgtctgag | aatgctggtg | caattacttt | caaagacaat | 1440 |
| attgtgaaga | catttgcctc | aaatggaaaa | atgttgggtg | gaggggcaat | tttagcttca | 1500 |
| ggaaatgttt | tgattagcaa | aaactctgga | gagatttctt | ttgtagggaa | tgcccgtgct | 1560 |
| cctcaggcta | ttccgactcg | ttcatctgac | gaattgtctt | ttggcgcaca | attaactcaa | 1620 |
| actacttcag | gatgttctgg | aggaggtgct | ctgtttggta | agaggttgc | cattgttcaa | 1680 |
| aatgccactg | ttgtattcga | gcaaaatcgc | ttacagtgtg | gcgagcagga | aacacatggt | 1740 |
| ggaggcggtg | ctgtttatgg | tatggagagt | gcctctatta | ttggaaactc | ttttgtgcgc | 1800 |

```
ttcggaaata attacgctgt agggaatcag atttctggag gtgctctgtt atccaagaag    1860
gtccgtttag ctgaaaatac acgcgtagat ttttctcgca atatcgctac tttctgcggc    1920
ggggctgttc aagtttctga tggaagttgc gaattgatca caatgggta tgtgctgttc    1980 cgcgataacc gcgggcagac atttggtggg gctatttctt gcttgaaagg agatgtgatc    2040
atttccggaa ataaagatcg cgttgagttt cgcgataaca ttgtgacgcg gccttatttt    2100
gaagaaaatg aagaaaaagt tgagacagca gatattaatt cagataagca agaagcagaa    2160
gagcgctctt tattagagaa cattgagcag agctttatta ctgcaactaa tcagacctttt   2220 ttcttagagg aagagaaact gccatcagaa gcttttatct ctgctgaaga actgtcaaag    2280
cgccgcgaat gtgctggtgg ggcgattttt gcaaaacggg tctacattac ggataataaa    2340
gaacctatct tgttttcgca taattttttct gatgttatg ggggagctat ttttacgggt    2400
tctctgcagg aaactgataa acaagatgtt gtaactcctg aagttgtgat ttcaggcaac    2460
gatggggatg tcattttttc tggaaatgca gctaaacatg ataagcattt acctgataca    2520
ggtggtggag ccatttgtac acagaatttg acgatttccc aaaacaatgg gaatgtcttg    2580
ttcttgaaca ttttttgcttg ttctggtgga gcagttcgca ttgaggatca tggagaagtt    2640
ctgttagagg cttttggggg agatattatt ttcaatggaa actcttcttt ccgcgctcaa    2700
ggatcggatg cgatctattt tgctggtaag gactctcgca ttaaagcttt aaatgctact    2760
gaaggacatg cgattgtgtt ccaagatgca ttggtgtttg aaaatattga agaacgcaag    2820
tcttcgggac tgttggtgat taactctcag gaaaatgagc tctatacggg atctgtccgc    2880 ttttttaggat ctgaaagtaa ggttcctcaa tggattcatg tgcaacagac tggatataaa    2940
ttagatccgc aaaaagctgg ttctttggta ttcaatgcat tatgggagga agaggctgta    3000
ttgtccatgg tgaaaaatgc tcggattgcc cataacctga ccattcagcg catggaatttt   3060 gattattcta caaatgcttg gggattagct tttagtagct ttcgcgagct gtcttcagag    3120
aaactggttt ctgttgatgg atatcgcggc tcttatattg gggcttctgc aggcattgat    3180
actcagttga tggaagattt tgtttttggga atcagcacgg cttccttctt cgggaaaatg    3240
catagtcaga attttgatgc agagatttct cgccacggtt ttgttggttc ggtctataca    3300
ggcttcctgg ctggggcctg gttcttcaag gggcagtaca gtctgggcga acacataac    3360 gatatgacaa ctcgttacgg ggttttggga gaatctaatg ctacttggaa gtctcgcgga    3420
gtactggcag atgctttagt tgaatatcgt agtttagtcg gtccagcacg ccctaaattt    3480
tatgctttgc attttaatcc ttatgtcgag gtatcttatg catctgcgaa gttccctagt    3540
tttgtagaac aaggaggaga agctcgtgct tttgaagaaa cctctttaac aaacattacc    3600
gttccgtttg gtatgaaatt tgaactgtct tttacaaaag acagttttc agagactaat    3660 tctctgggaa ttggttgtgc atgggaaatg tatcggaaag tcgaaggacg ctctgtagag    3720
ctgctgaaag ctggttttga ttgggaagga tctcctattg atctgcctaa caagagctg    3780 cgcgtggctt tagaaaacaa tacgaatgg agttcgtatt ttagtacagc tctgggagta    3840
acagcatttt gtggaggatt ttcttctatg gataataaac tgggatacga agcgaatgct    3900
ggaatgcgtt tgatttctca aggatcc                                         3927
```

<210> SEQ ID NO 31
<211> LENGTH: 1305
<212> TYPE: PRT
<213> ORGANISM: artificial sequence
<220> FEATURE:
<223> OTHER INFORMATION: synthetic peptide

<400> SEQUENCE: 31

```
Met Ala Ile Leu Ala Ser Met Ser Gly Leu Ser Asn Cys Ser Asp Leu
1               5                   10                  15

Tyr Ala Val Gly Ser Ser Ala Asp His Pro Ala Tyr Leu Ile Pro Gln
            20                  25                  30

Ala Gly Leu Leu Leu Asp His Ile Lys Asp Ile Phe Ile Gly Pro Lys
        35                  40                  45

Asp Ser Gln Asp Lys Gly Gln Tyr Lys Leu Ile Ile Gly Glu Ala Gly
    50                  55                  60

Ser Phe Gln Asp Ser Asn Ala Glu Thr Leu Pro Gln Lys Val Glu His
65                  70                  75                  80

Ser Thr Leu Phe Ser Val Thr Thr Pro Ile Ile Val Gln Gly Ile Asp
                85                  90                  95

Gln Gln Asp Gln Val Ser Ser Gln Gly Leu Val Cys Asn Phe Ser Gly
            100                 105                 110

Asp His Ser Glu Glu Ile Phe Glu Arg Glu Ser Phe Leu Gly Ile Ala
        115                 120                 125

Phe Leu Gly Asn Gly Ser Lys Asp Gly Ile Thr Leu Thr Asp Ile Lys
    130                 135                 140

Ser Ser Leu Ser Gly Ala Ala Leu Tyr Ser Ser Asp Asp Leu Ile Phe
145                 150                 155                 160

Glu Arg Ile Lys Gly Asp Ile Glu Leu Ser Ser Cys Ser Ser Leu Glu
                165                 170                 175

Arg Gly Gly Ala Cys Ser Ala Gln Ser Ile Leu Ile His Asp Cys Gln
            180                 185                 190

Gly Leu Thr Val Lys His Cys Ala Ala Gly Val Asn Val Glu Gly Val
        195                 200                 205

Ser Ala Ser Asp His Leu Gly Phe Gly Gly Ala Phe Ser Thr Thr
    210                 215                 220

Ser Ser Leu Ser Gly Glu Lys Ser Leu Tyr Met Pro Ala Gly Asp Ile
225                 230                 235                 240

Val Val Ala Thr Cys Asp Gly Pro Val Cys Phe Glu Gly Asn Ser Ala
                245                 250                 255

Gln Leu Ala Asn Gly Ala Ile Ala Ala Ser Gly Lys Val Leu Phe
            260                 265                 270

Val Ala Asn Glu Lys Lys Ile Ser Phe Thr Asp Asn Gln Ala Leu Ser
        275                 280                 285

Gly Gly Ala Ile Ser Ala Ser Ser Ile Ser Phe Gln Asn Cys Ala
    290                 295                 300

Glu Leu Val Phe Lys Ser Asn Leu Ala Lys Gly Val Lys Asp Lys Cys
305                 310                 315                 320

Ser Leu Gly Gly Gly Ala Leu Ala Ser Leu Glu Ser Val Val Leu Lys
                325                 330                 335

Asp Asn Leu Gly Ile Thr Tyr Glu Lys Asn Gln Ser Tyr Ser Glu Gly
            340                 345                 350

Gly Ala Ile Phe Gly Lys Asp Cys Glu Ile Phe Glu Asn Arg Gly Pro
        355                 360                 365

Val Val Phe Arg Asp Asn Thr Ala Ala Leu Gly Gly Gly Ala Ile Leu
    370                 375                 380

Ala Gln Gln Thr Val Ala Ile Cys Gly Asn Lys Ser Gly Ile Ser Phe
385                 390                 395                 400

Glu Gly Ser Lys Ser Ser Phe Gly Gly Ala Ile Ala Cys Gly Asn Phe
```

```
              405                 410                 415
Ser Ser Glu Asn Asn Ser Ser Ala Leu Gly Ser Ile Asp Ile Ser Asn
            420                 425                 430

Asn Leu Gly Asp Ile Ser Phe Leu Arg Thr Leu Cys Thr Thr Ser Asp
            435                 440                 445

Leu Gly Gln Thr Asp Tyr Gln Gly Gly Ala Leu Phe Ala Glu Asn
            450                 455                 460

Ile Ser Leu Ser Glu Asn Ala Gly Ala Ile Thr Phe Lys Asp Asn Ile
465                 470                 475                 480

Val Lys Thr Phe Ala Ser Asn Gly Lys Met Leu Gly Gly Ala Ile
                485                 490                 495

Leu Ala Ser Gly Asn Val Leu Ile Ser Lys Asn Ser Gly Glu Ile Ser
            500                 505                 510

Phe Val Gly Asn Ala Arg Ala Pro Gln Ala Ile Pro Thr Arg Ser Ser
            515                 520                 525

Asp Glu Leu Ser Phe Gly Ala Gln Leu Thr Gln Thr Thr Ser Gly Cys
            530                 535                 540

Ser Gly Gly Gly Ala Leu Phe Gly Lys Glu Val Ala Ile Val Gln Asn
545                 550                 555                 560

Ala Thr Val Val Phe Glu Gln Asn Arg Leu Gln Cys Gly Glu Gln Glu
                565                 570                 575

Thr His Gly Gly Gly Ala Val Tyr Gly Met Glu Ser Ala Ser Ile
            580                 585                 590

Ile Gly Asn Ser Phe Val Arg Phe Gly Asn Asn Tyr Ala Val Gly Asn
            595                 600                 605

Gln Ile Ser Gly Gly Ala Leu Leu Ser Lys Lys Val Arg Leu Ala Glu
            610                 615                 620

Asn Thr Arg Val Asp Phe Ser Arg Asn Ile Ala Thr Phe Cys Gly Gly
625                 630                 635                 640

Ala Val Gln Val Ser Asp Gly Ser Cys Glu Leu Ile Asn Asn Gly Tyr
                645                 650                 655

Val Leu Phe Arg Asp Asn Arg Gly Gln Thr Phe Gly Gly Ala Ile Ser
            660                 665                 670

Cys Leu Lys Gly Asp Val Ile Ile Ser Gly Asn Lys Asp Arg Val Glu
            675                 680                 685

Phe Arg Asp Asn Ile Val Thr Arg Pro Tyr Phe Glu Glu Asn Glu Glu
            690                 695                 700

Lys Val Glu Thr Ala Asp Ile Asn Ser Asp Lys Gln Glu Ala Glu Glu
705                 710                 715                 720

Arg Ser Leu Leu Glu Asn Ile Glu Gln Ser Phe Ile Thr Ala Thr Asn
            725                 730                 735

Gln Thr Phe Phe Leu Glu Glu Lys Leu Pro Ser Glu Ala Phe Ile
            740                 745                 750

Ser Ala Glu Glu Leu Ser Lys Arg Arg Glu Cys Ala Gly Gly Ala Ile
            755                 760                 765

Phe Ala Lys Arg Val Tyr Ile Thr Asp Asn Lys Glu Pro Ile Leu Phe
            770                 775                 780

Ser His Asn Phe Ser Asp Val Tyr Gly Gly Ala Ile Phe Thr Gly Ser
785                 790                 795                 800

Leu Gln Glu Thr Asp Lys Gln Asp Val Val Thr Pro Glu Val Val Ile
                805                 810                 815

Ser Gly Asn Asp Gly Asp Val Ile Phe Ser Gly Asn Ala Ala Lys His
            820                 825                 830
```

-continued

Asp Lys His Leu Pro Asp Thr Gly Gly Gly Ala Ile Cys Thr Gln Asn
        835                 840                 845

Leu Thr Ile Ser Gln Asn Asn Gly Asn Val Leu Phe Leu Asn Asn Phe
850                 855                 860

Ala Cys Ser Gly Gly Ala Val Arg Ile Glu Asp His Gly Glu Val Leu
865                 870                 875                 880

Leu Glu Ala Phe Gly Gly Asp Ile Ile Phe Asn Gly Asn Ser Ser Phe
                885                 890                 895

Arg Ala Gln Gly Ser Asp Ala Ile Tyr Phe Ala Gly Lys Asp Ser Arg
            900                 905                 910

Ile Lys Ala Leu Asn Ala Thr Glu Gly His Ala Ile Val Phe Gln Asp
        915                 920                 925

Ala Leu Val Phe Glu Asn Ile Glu Glu Arg Lys Ser Ser Gly Leu Leu
    930                 935                 940

Val Ile Asn Ser Gln Glu Asn Glu Leu Tyr Thr Gly Ser Val Arg Phe
945                 950                 955                 960

Leu Gly Ser Glu Ser Lys Val Pro Gln Trp Ile His Val Gln Gln Thr
                965                 970                 975

Gly Tyr Lys Leu Asp Pro Gln Lys Ala Gly Ser Leu Val Phe Asn Ala
            980                 985                 990

Leu Trp Glu Glu Glu Ala Val Leu Ser Met Val Lys Asn Ala Arg Ile
        995                 1000                1005

Ala His Asn Leu Thr Ile Gln Arg Met Glu Phe Asp Tyr Ser Thr
    1010                1015                1020

Asn Ala Trp Gly Leu Ala Phe Ser Ser Phe Arg Glu Leu Ser Ser
    1025                1030                1035

Glu Lys Leu Val Ser Val Asp Gly Tyr Arg Gly Ser Tyr Ile Gly
    1040                1045                1050

Ala Ser Ala Gly Ile Asp Thr Gln Leu Met Glu Asp Phe Val Leu
    1055                1060                1065

Gly Ile Ser Thr Ala Ser Phe Phe Gly Lys Met His Ser Gln Asn
    1070                1075                1080

Phe Asp Ala Glu Ile Ser Arg His Gly Phe Val Gly Ser Val Tyr
    1085                1090                1095

Thr Gly Phe Leu Ala Gly Ala Trp Phe Phe Lys Gly Gln Tyr Ser
    1100                1105                1110

Leu Gly Glu Thr His Asn Asp Met Thr Thr Arg Tyr Gly Val Leu
    1115                1120                1125

Gly Glu Ser Asn Ala Thr Trp Lys Ser Arg Gly Val Leu Ala Asp
    1130                1135                1140

Ala Leu Val Glu Tyr Arg Ser Leu Val Gly Pro Ala Arg Pro Lys
    1145                1150                1155

Phe Tyr Ala Leu His Phe Asn Pro Tyr Val Glu Val Ser Tyr Ala
    1160                1165                1170

Ser Ala Lys Phe Pro Ser Phe Val Glu Gln Gly Gly Glu Ala Arg
    1175                1180                1185

Ala Phe Glu Glu Thr Ser Leu Thr Asn Ile Thr Val Pro Phe Gly
    1190                1195                1200

Met Lys Phe Glu Leu Ser Phe Thr Lys Gly Gln Phe Ser Glu Thr
    1205                1210                1215

Asn Ser Leu Gly Ile Gly Cys Ala Trp Glu Met Tyr Arg Lys Val
    1220                1225                1230

```
Glu Gly  Arg Ser Val Glu Leu  Leu Glu Ala Gly Phe  Asp Trp Glu
    1235                 1240                 1245

Gly Ser  Pro Ile Asp Leu Pro  Lys Gln Glu Leu Arg  Val Ala Leu
    1250                 1255                 1260

Glu Asn  Asn Thr Glu Trp Ser  Ser Tyr Phe Ser Thr  Ala Leu Gly
    1265                 1270                 1275

Val Thr  Ala Phe Cys Gly Gly  Phe Ser Ser Met Asp  Asn Lys Leu
    1280                 1285                 1290

Gly Tyr  Glu Ala Asn Ala Gly  Met Arg Leu Ile Phe
    1295                 1300                 1305

<210> SEQ ID NO 32
<211> LENGTH: 2931
<212> TYPE: DNA
<213> ORGANISM: Chlamydia muridarum

<400> SEQUENCE: 32
atgaaaaaac tgttcttttt tgtccttatt ggaagctcta tactgggatt tactcgagaa     60
gtccctcctt cgattctttt aaagcctata ctaaatccat accatatgac cgggttattt    120
tttcccaagg ttaatttgct tggagacaca cataatctca ctgattacca tttggataat    180
ctaaaatgca ttctggcttg cctacaaaga actccttatg aaggagctgc tttcacagta    240
accgattact taggtttttc agatacacaa aaggatggta ttttttgttt taaaaatctt    300
actccagaga gtggaggggt tattggttcc ccaactcaaa acactcctac tataaaaatt    360
cataatacaa tcggccccgt tcttttcgaa aataatacct gtcatagact gtggacacag    420
accgatcccg aaaatgaagg aaacaaagca cgcgaaggcg gggcaattca tgctggggac    480
gtttacataa gcaataacca gaaccttgtc ggattcataa agaactttgc ttatgttcaa    540
ggtggagcta ttagtgctaa tacttttgcc tataaagaaa ataaatcgag ctttctttgc    600
ctaaataact cttgtataca aactaagacg ggagggaaag gtggtgctat ttacgttagt    660
acgagctgct ctttcgagaa caataacaag gatctgcttt tcatccaaaa ctccggctgt    720
gcaggaggag ctatcttctc tccaacctgt tctctaatag gaaaccaagg agatattgtt    780
ttttacagca accacggttt taaaaatgtt gataatgcaa ctaacgaatc tggggatgga    840
ggagctatta aagtaactac ccgcttggac atcaccaata atggtagtca aatctttttt    900
tctgataata tctcaagaaa ttttggagga gctattcatg ctccttgtct tcatcttgtt    960
ggtaatgggc caacctattt tacaaacaat atagctaatc acacaggtgg ggctatttat   1020
ataacaggaa cagaaacctc aaagatttct gcagatcacc atgctattat ttttgataat   1080
aacatttctg caaacgccac caatgcggac ggatctagca gcaacactaa tcctcctcac   1140
agaaatgcga tcactatgga caattccgct ggaggaatag aacttggtgc agggaagagc   1200
cagaatctta ttttctatga tcctattcaa gtgacgaatg ctggagttac cgtagacttc   1260
aataaggatg cctcccaaac cggatgtgta gttttctctg gagcgactgt cctttctgca   1320
gatatttctc aggctaattt gcaaactaaa acacctgcaa cgcttactct cagtcacggt   1380
cttctgtgta tcgaagatcg tgctcagctc acagtgaaca attttacaca aacaggaggg   1440
attgtagcct taggaaatgg agcagtttta agcagctacc aacacagcac tacagacgcc   1500
actcaaactc cccctacaac caccactaca gatgcttccg taactcttaa tcacattgga   1560
ttaaatctcc cctctattct taaggatgga gcagagatgc ctctattatg ggtagaacct   1620
ataagcacaa ctcaaggtaa cactacaaca tatacgtcag ataccgcggc ttccttctca   1680

-continued

```
ttaaatggag ccacactctc tctcattgat gaagatggaa attctcccta tgaaaacacg   1740
gacctctctc gtgcattgta cgctcaacct atgctagcaa tttctgaggc cagtgataac   1800
caattgcaat ccgaaagcat ggacttttct aaagttaatg ttcctcacta tggatggcaa   1860
ggactttgga cctgggggtg ggcaaaaact gaaaatccaa caacaactcc tccagcaaca   1920
attactgatc cgaaaaaagc taatcagttt catagaactt tattattaac gtggctccct   1980
gctggttata tccccagccc taaacataaa agccctttaa tagctaatac cttgtggggg   2040
aatatacttt ttgcaacgga aaacttaaaa aatagctcag ggcaagaact tcttgatcgt   2100
cctttctggg gaattacagg agggggcttg ggatgatgg tctatcaaga acctagaaaa   2160
gaccatcctg gattccacat gcatacctcc ggatattcag caggaatgat tacaggaaac   2220
acacatacct tctcattacg attcagccag tcctatacaa aactcaatga acgttatgcc   2280
aagaactatg tgtcttctaa aaattactct tgccaagggg aaatgctttt gtccttacaa   2340
gaaggactca tgctgactaa actaattggt ctctatagtt atgggaatca caacagccac   2400
catttctata cccaaggaga agacctatcg tctcaagggg agttccatag tcagactttt   2460
ggaggggctg tctttttga tctacctctg aaaccttttg gaagaacaca catacttaca   2520
gctcctttct taggtgccat tggtatgtat tctaagctgt ctagctttac agaagtagga   2580
gcctatccaa gaacctttat tacagaaacg cctttaatca atgtcctgat tcctatcgga   2640
gtaaaaggta gcttcatgaa tgccacccat agacctcagg cctggactgt agagcttgct   2700
taccaacctg ttctttacag acaagaacct agtatctcta cccaattact cgctggtaaa   2760
ggtatgtggt ttgggcatgg aagtcctgca tctcgccacg ctctagctta taaaatttca   2820
cagaaaacac agcttttgcg atttgcaaca cttcaactcc agtatcacgg atactattcg   2880
tcttccactt tctgtaatta tctgaatgga gaggtatctt tacgtttcta a            2931
```

```
<210> SEQ ID NO 33
<211> LENGTH: 976
<212> TYPE: PRT
<213> ORGANISM: Chlamydia muridarum

<400> SEQUENCE: 33

Met Lys Lys Leu Phe Phe Phe Val Leu Ile Gly Ser Ser Ile Leu Gly
1               5                   10                  15

Phe Thr Arg Glu Val Pro Pro Ser Ile Leu Leu Lys Pro Ile Leu Asn
            20                  25                  30

Pro Tyr His Met Thr Gly Leu Phe Phe Pro Lys Val Asn Leu Leu Gly
        35                  40                  45

Asp Thr His Asn Leu Thr Asp Tyr His Leu Asp Asn Leu Lys Cys Ile
    50                  55                  60

Leu Ala Cys Leu Gln Arg Thr Pro Tyr Glu Gly Ala Ala Phe Thr Val
65                  70                  75                  80

Thr Asp Tyr Leu Gly Phe Ser Asp Thr Gln Lys Asp Gly Ile Phe Cys
                85                  90                  95

Phe Lys Asn Leu Thr Pro Glu Ser Gly Gly Val Ile Gly Ser Pro Thr
            100                 105                 110

Gln Asn Thr Pro Thr Ile Lys Ile His Asn Thr Ile Gly Pro Val Leu
        115                 120                 125

Phe Glu Asn Asn Thr Cys His Arg Leu Trp Thr Gln Thr Asp Pro Glu
    130                 135                 140

Asn Glu Gly Asn Lys Ala Arg Glu Gly Gly Ala Ile His Ala Gly Asp
145                 150                 155                 160
```

```
Val Tyr Ile Ser Asn Asn Gln Asn Leu Val Gly Phe Ile Lys Asn Phe
                165                 170                 175

Ala Tyr Val Gln Gly Gly Ala Ile Ser Ala Asn Thr Phe Ala Tyr Lys
            180                 185                 190

Glu Asn Lys Ser Ser Phe Leu Cys Leu Asn Asn Ser Cys Ile Gln Thr
        195                 200                 205

Lys Thr Gly Gly Lys Gly Gly Ala Ile Tyr Val Ser Thr Ser Cys Ser
    210                 215                 220

Phe Glu Asn Asn Asn Lys Asp Leu Leu Phe Ile Gln Asn Ser Gly Cys
225                 230                 235                 240

Ala Gly Gly Ala Ile Phe Ser Pro Thr Cys Ser Leu Ile Gly Asn Gln
                245                 250                 255

Gly Asp Ile Val Phe Tyr Ser Asn His Gly Phe Lys Asn Val Asp Asn
            260                 265                 270

Ala Thr Asn Glu Ser Gly Asp Gly Gly Ala Ile Lys Val Thr Thr Arg
        275                 280                 285

Leu Asp Ile Thr Asn Asn Gly Ser Gln Ile Phe Phe Ser Asp Asn Ile
    290                 295                 300

Ser Arg Asn Phe Gly Gly Ala Ile His Ala Pro Cys Leu His Leu Val
305                 310                 315                 320

Gly Asn Gly Pro Thr Tyr Phe Thr Asn Asn Ile Ala Asn His Thr Gly
                325                 330                 335

Gly Ala Ile Tyr Ile Thr Gly Thr Glu Thr Ser Lys Ile Ser Ala Asp
            340                 345                 350

His His Ala Ile Ile Phe Asp Asn Asn Ile Ser Ala Asn Ala Thr Asn
        355                 360                 365

Ala Asp Gly Ser Ser Ser Asn Thr Asn Pro Pro His Arg Asn Ala Ile
    370                 375                 380

Thr Met Asp Asn Ser Ala Gly Gly Ile Glu Leu Gly Ala Gly Lys Ser
385                 390                 395                 400

Gln Asn Leu Ile Phe Tyr Asp Pro Ile Gln Val Thr Asn Ala Gly Val
                405                 410                 415

Thr Val Asp Phe Asn Lys Asp Ala Ser Gln Thr Gly Cys Val Val Phe
            420                 425                 430

Ser Gly Ala Thr Val Leu Ser Ala Asp Ile Ser Gln Ala Asn Leu Gln
        435                 440                 445

Thr Lys Thr Pro Ala Thr Leu Thr Leu Ser His Gly Leu Leu Cys Ile
    450                 455                 460

Glu Asp Arg Ala Gln Leu Thr Val Asn Asn Phe Thr Gln Thr Gly Gly
465                 470                 475                 480

Ile Val Ala Leu Gly Asn Gly Ala Val Leu Ser Ser Tyr Gln His Ser
                485                 490                 495

Thr Thr Asp Ala Thr Gln Thr Pro Thr Thr Thr Thr Asp Ala
            500                 505                 510

Ser Val Thr Leu Asn His Ile Gly Leu Asn Leu Pro Ser Ile Leu Lys
        515                 520                 525

Asp Gly Ala Glu Met Pro Leu Leu Trp Val Glu Pro Ile Ser Thr Thr
    530                 535                 540

Gln Gly Asn Thr Thr Thr Tyr Thr Ser Asp Thr Ala Ala Ser Phe Ser
545                 550                 555                 560

Leu Asn Gly Ala Thr Leu Ser Leu Ile Asp Glu Asp Gly Asn Ser Pro
                565                 570                 575
```

```
Tyr Glu Asn Thr Asp Leu Ser Arg Ala Leu Tyr Ala Gln Pro Met Leu
            580                 585                 590

Ala Ile Ser Glu Ala Ser Asp Asn Gln Leu Gln Ser Glu Ser Met Asp
        595                 600                 605

Phe Ser Lys Val Asn Val Pro His Tyr Gly Trp Gln Gly Leu Trp Thr
            610                 615                 620

Trp Gly Trp Ala Lys Thr Glu Asn Pro Thr Thr Pro Pro Ala Thr
625                 630                 635                 640

Ile Thr Asp Pro Lys Lys Ala Asn Gln Phe His Arg Thr Leu Leu Leu
            645                 650                 655

Thr Trp Leu Pro Ala Gly Tyr Ile Pro Ser Pro Lys His Lys Ser Pro
            660                 665                 670

Leu Ile Ala Asn Thr Leu Trp Gly Asn Ile Leu Phe Ala Thr Glu Asn
            675                 680                 685

Leu Lys Asn Ser Ser Gly Gln Glu Leu Leu Asp Arg Pro Phe Trp Gly
            690                 695                 700

Ile Thr Gly Gly Gly Leu Gly Met Met Val Tyr Gln Glu Pro Arg Lys
705                 710                 715                 720

Asp His Pro Gly Phe His Met His Thr Ser Gly Tyr Ser Ala Gly Met
            725                 730                 735

Ile Thr Gly Asn Thr His Thr Phe Ser Leu Arg Phe Ser Gln Ser Tyr
            740                 745                 750

Thr Lys Leu Asn Glu Arg Tyr Ala Lys Asn Tyr Val Ser Ser Lys Asn
            755                 760                 765

Tyr Ser Cys Gln Gly Glu Met Leu Leu Ser Leu Gln Glu Gly Leu Met
            770                 775                 780

Leu Thr Lys Leu Ile Gly Leu Tyr Ser Tyr Gly Asn His Asn Ser His
785                 790                 795                 800

His Phe Tyr Thr Gln Gly Glu Asp Leu Ser Ser Gln Gly Glu Phe His
            805                 810                 815

Ser Gln Thr Phe Gly Gly Ala Val Phe Phe Asp Leu Pro Leu Lys Pro
            820                 825                 830

Phe Gly Arg Thr His Ile Leu Thr Ala Pro Phe Leu Gly Ala Ile Gly
            835                 840                 845

Met Tyr Ser Lys Leu Ser Ser Phe Thr Glu Val Gly Ala Tyr Pro Arg
850                 855                 860

Thr Phe Ile Thr Glu Thr Pro Leu Ile Asn Val Leu Ile Pro Ile Gly
865                 870                 875                 880

Val Lys Gly Ser Phe Met Asn Ala Thr His Arg Pro Gln Ala Trp Thr
            885                 890                 895

Val Glu Leu Ala Tyr Gln Pro Val Leu Tyr Arg Gln Glu Pro Ser Ile
            900                 905                 910

Ser Thr Gln Leu Leu Ala Gly Lys Gly Met Trp Phe Gly His Gly Ser
            915                 920                 925

Pro Ala Ser Arg His Ala Leu Ala Tyr Lys Ile Ser Gln Lys Thr Gln
            930                 935                 940

Leu Leu Arg Phe Ala Thr Leu Gln Leu Gln Tyr His Gly Tyr Tyr Ser
945                 950                 955                 960

Ser Ser Thr Phe Cys Asn Tyr Leu Asn Gly Glu Val Ser Leu Arg Phe
            965                 970                 975

<210> SEQ ID NO 34
<211> LENGTH: 2889
<212> TYPE: DNA
```

<213> ORGANISM: artificial sequence
<220> FEATURE:
<223> OTHER INFORMATION: synthetic polynucleotide

<400> SEQUENCE: 34

| | |
|---|---:|
| catatgcgcg aagtccctcc ttcgattctg ttaaagccta ttctgaatcc ataccacatg | 60 |
| accgggttat ttttccgaa ggttaatttg ctgggagaca cacataatct gactgattac | 120 |
| catttggata atctgaaatg cattctggct tgcctgcaac gcactcctta tgaaggagct | 180 |
| gctttcacag taaccgatta cttaggtttt tcagatacac aaaaggatgg tatttttgt | 240 |
| tttaaaaatc tgactccaga gagtggaggg gttattggtt ccccaactca aaacactcct | 300 |
| actattaaaa ttcataatac aatcggcccg gttctgttcg aaaataatac ctgtcatcgc | 360 |
| ctgtggacac agaccgatcc ggaaaatgaa ggaaacaaag cacgcgaagg cggggcaatt | 420 |
| catgctgggg acgtttacat tagcaataac cagaacctgg tcggattcat taagaacttt | 480 |
| gcttatgttc aaggtggagc tattagtgct aatacttttg cctataaaga aaataaatcg | 540 |
| agctttctgt gcctgaataa ctcttgtatt caaactaaga cggagggaa aggtggtgct | 600 |
| atttacgtta gtacgagctg ctcttcgag aacaataaca aggatctgct gttcatccaa | 660 |
| aactccggct gtgcaggagg agctatcttc tctccaacct gttctctgat tggaaaccaa | 720 |
| ggagatattg ttttttacag caaccacggt tttaaaaatg ttgataatgc aactaacgaa | 780 |
| tctggggatg gaggagctat taagtaact acccgcttgg acatcaccaa taatggtagt | 840 |
| caaatctttt tttctgataa tatctcacgc aattttggag gagctattca tgctccttgt | 900 |
| ctgcatctgg ttggtaatgg gccaacctat tttacaaaca atattgctaa tcacacaggt | 960 |
| ggggctattt atattacagg aacagaaacc tcaaagattt ctgcagatca ccatgctatt | 1020 |
| attttgata ataacatttc tgcaaacgcc accaatgcgg acggatctag cagcaacact | 1080 |
| aatcctcctc accgcaatgc gatcactatg acaattccg ctggaggaat tgaactgggt | 1140 |
| gcagggaaga gccagaatct gattttctat gatcctattc aagtgacgaa tgctggagtt | 1200 |
| accgtagact tcaataagga tgcctcccaa accggatgtg tagttttctc tggagcgact | 1260 |
| gtcctgtctg cagatatttc tcaggctaat ttgcaaacta aaacacctgc agagctcact | 1320 |
| ctgagtcacg gtctgctgtg tatcgaagat cgtgctcagc tgacagtgaa caatttaca | 1380 |
| caaacaggag ggattgtagc cttaggaaat ggagcagttt taagcagcta ccaacacagc | 1440 |
| actacagacg ccactcaaac tccgcctaca accaccacta cagatgcttc cgtaactctg | 1500 |
| aatcacattg gattaaatct gccgtctatt ctgaaggatg gagcagagat gcctctgtta | 1560 |
| tgggtagaac ctattagcac aactcaaggt aacactacaa catatacgtc agataccgcg | 1620 |
| gcttccttct cattaaatgg agccacactg tctctgattg atgaagatgg aaattctccg | 1680 |
| tatgaaaaca cggacctgtc tcgtgcattg tacgctcaac ctatgctggc aatttctgag | 1740 |
| gccagtgata accaattgca atccgaaagc atggactttt ctaaagttaa tgttcctcac | 1800 |
| tatggatggc aaggactgtg gacctggggg tgggcaaaaa ctgaaaatcc aacaacaact | 1860 |
| cctccagcaa caattactga tccgaaaaaa gctaatcagt ttcatcgcac tttattatta | 1920 |
| acgtggctgc ctgctggtta tcccgagc cctaaacata aaagccctt aattgctaat | 1980 |
| accttgtggg ggaatattgc catggcaacg gaaaacttaa aaaatagctc agggcaagaa | 2040 |
| ctgctggatc gtccttctctg gggaattaca ggaggggggct tggggatgat ggtctatcaa | 2100 |
| gaacctcgca aagaccatcc tggattccac atgcatacct ccggatattc agcaggaatg | 2160 |
| attacaggaa acacacatac cttctcatta cgcttcagcc agtcctatac aaaactgaat | 2220 |

```
gaacgttatg ccaagaacta tgtgtcttct aaaaattact cttgccaagg ggaaatgctg    2280
ttgtccttac aagaaggact gatgctgact aaactgattg gtctgtatag ttatgggaat    2340
cacaacagcc accatttcta tacccaagga gaagacctgt cgtctcaagg ggagttccat    2400
agtcagactt tggagggggc tgtcttttt gatctgcctc tgaaaccttt tggacgcaca    2460
cacattctga cagctccttt cttaggtgcc attggtatgt attctaagct gtctagcttt    2520
acagaagtag gagcctatcc acgcaccttt attacagaaa cgcctttaat caatgtcctg    2580
attcctatcg gagtaaaagg tagcttcatg aatgccaccc atcgccctca ggcctggact    2640
gtagagctgg cttaccaacc tgttctgtac cgccaagaac ctagtatctc tacccaatta    2700
ctggctggta aaggtatgtg gtttgggcat ggaagtcctg catctcgcca cgctctggct    2760
tataaaattt cacagaaaac acagctgttg cgctttgcaa cactgcaact gcagtatcac    2820
ggatactatt cgtcttccac tttctgtaat tatctgaatg gagaggtatc tttacgtttc    2880
taaggatcc                                                           2889
```

<210> SEQ ID NO 35
<211> LENGTH: 959
<212> TYPE: PRT
<213> ORGANISM: artificial sequence
<220> FEATURE:
<223> OTHER INFORMATION: synthetic peptide

<400> SEQUENCE: 35

```
Met Arg Glu Val Pro Pro Ser Ile Leu Leu Lys Pro Ile Leu Asn Pro
1               5                   10                  15

Tyr His Met Thr Gly Leu Phe Phe Pro Lys Val Asn Leu Leu Gly Asp
            20                  25                  30

Thr His Asn Leu Thr Asp Tyr His Leu Asp Asn Leu Lys Cys Ile Leu
        35                  40                  45

Ala Cys Leu Gln Arg Thr Pro Tyr Glu Gly Ala Ala Phe Thr Val Thr
    50                  55                  60

Asp Tyr Leu Gly Phe Ser Asp Thr Gln Lys Asp Gly Ile Phe Cys Phe
65                  70                  75                  80

Lys Asn Leu Thr Pro Glu Ser Gly Gly Val Ile Gly Ser Pro Thr Gln
                85                  90                  95

Asn Thr Pro Thr Ile Lys Ile His Asn Thr Ile Gly Pro Val Leu Phe
            100                 105                 110

Glu Asn Asn Thr Cys His Arg Leu Trp Thr Gln Thr Asp Pro Glu Asn
        115                 120                 125

Glu Gly Asn Lys Ala Arg Glu Gly Gly Ala Ile His Ala Gly Asp Val
    130                 135                 140

Tyr Ile Ser Asn Asn Gln Asn Leu Val Gly Phe Ile Lys Asn Phe Ala
145                 150                 155                 160

Tyr Val Gln Gly Gly Ala Ile Ser Ala Asn Thr Phe Ala Tyr Lys Glu
                165                 170                 175

Asn Lys Ser Ser Phe Leu Cys Leu Asn Asn Ser Cys Ile Gln Thr Lys
            180                 185                 190

Thr Gly Gly Lys Gly Gly Ala Ile Tyr Val Ser Thr Ser Cys Ser Phe
        195                 200                 205

Glu Asn Asn Asn Lys Asp Leu Leu Phe Ile Gln Asn Ser Gly Cys Ala
    210                 215                 220

Gly Gly Ala Ile Phe Ser Pro Thr Cys Ser Leu Ile Gly Asn Gln Gly
225                 230                 235                 240
```

```
Asp Ile Val Phe Tyr Ser Asn His Gly Phe Lys Asn Val Asp Asn Ala
                245                 250                 255

Thr Asn Glu Ser Gly Asp Gly Gly Ala Ile Lys Val Thr Thr Arg Leu
            260                 265                 270

Asp Ile Thr Asn Asn Gly Ser Gln Ile Phe Phe Ser Asp Asn Ile Ser
        275                 280                 285

Arg Asn Phe Gly Gly Ala Ile His Ala Pro Cys Leu His Leu Val Gly
    290                 295                 300

Asn Gly Pro Thr Tyr Phe Thr Asn Asn Ile Ala Asn His Thr Gly Gly
305                 310                 315                 320

Ala Ile Tyr Ile Thr Gly Thr Glu Thr Ser Lys Ile Ser Ala Asp His
                325                 330                 335

His Ala Ile Ile Phe Asp Asn Asn Ile Ser Ala Asn Ala Thr Asn Ala
            340                 345                 350

Asp Gly Ser Ser Ser Asn Thr Asn Pro Pro His Arg Asn Ala Ile Thr
        355                 360                 365

Met Asp Asn Ser Ala Gly Gly Ile Glu Leu Gly Ala Gly Lys Ser Gln
    370                 375                 380

Asn Leu Ile Phe Tyr Asp Pro Ile Gln Val Thr Asn Ala Gly Val Thr
385                 390                 395                 400

Val Asp Phe Asn Lys Asp Ala Ser Gln Thr Gly Cys Val Val Phe Ser
                405                 410                 415

Gly Ala Thr Val Leu Ser Ala Asp Ile Ser Gln Ala Asn Leu Gln Thr
            420                 425                 430

Lys Thr Pro Ala Glu Leu Thr Leu Ser His Gly Leu Leu Cys Ile Glu
        435                 440                 445

Asp Arg Ala Gln Leu Thr Val Asn Asn Phe Thr Gln Thr Gly Gly Ile
    450                 455                 460

Val Ala Leu Gly Asn Gly Ala Val Leu Ser Ser Tyr Gln His Ser Thr
465                 470                 475                 480

Thr Asp Ala Thr Gln Thr Pro Pro Thr Thr Thr Thr Asp Ala Ser
                485                 490                 495

Val Thr Leu Asn His Ile Gly Leu Asn Leu Pro Ser Ile Leu Lys Asp
            500                 505                 510

Gly Ala Glu Met Pro Leu Leu Trp Val Glu Pro Ile Ser Thr Thr Gln
        515                 520                 525

Gly Asn Thr Thr Thr Tyr Thr Ser Asp Thr Ala Ala Ser Phe Ser Leu
    530                 535                 540

Asn Gly Ala Thr Leu Ser Leu Ile Asp Glu Asp Gly Asn Ser Pro Tyr
545                 550                 555                 560

Glu Asn Thr Asp Leu Ser Arg Ala Leu Tyr Ala Gln Pro Met Leu Ala
                565                 570                 575

Ile Ser Glu Ala Ser Asp Asn Gln Leu Gln Ser Glu Ser Met Asp Phe
            580                 585                 590

Ser Lys Val Asn Val Pro His Tyr Gly Trp Gln Gly Leu Trp Thr Trp
        595                 600                 605

Gly Trp Ala Lys Thr Glu Asn Pro Thr Thr Pro Pro Ala Thr Ile
    610                 615                 620

Thr Asp Pro Lys Lys Ala Asn Gln Phe His Arg Thr Leu Leu Leu Thr
625                 630                 635                 640

Trp Leu Pro Ala Gly Tyr Ile Pro Ser Pro Lys His Lys Ser Pro Leu
                645                 650                 655
```

Ile Ala Asn Thr Leu Trp Gly Asn Ile Ala Met Ala Thr Glu Asn Leu
            660                 665                 670

Lys Asn Ser Ser Gly Gln Glu Leu Leu Asp Arg Pro Phe Trp Gly Ile
        675                 680                 685

Thr Gly Gly Gly Leu Gly Met Met Val Tyr Gln Glu Pro Arg Lys Asp
    690                 695                 700

His Pro Gly Phe His Met His Thr Ser Gly Tyr Ser Ala Gly Met Ile
705                 710                 715                 720

Thr Gly Asn Thr His Thr Phe Ser Leu Arg Phe Ser Gln Ser Tyr Thr
                725                 730                 735

Lys Leu Asn Glu Arg Tyr Ala Lys Asn Tyr Val Ser Ser Lys Asn Tyr
            740                 745                 750

Ser Cys Gln Gly Glu Met Leu Leu Ser Leu Gln Glu Gly Leu Met Leu
        755                 760                 765

Thr Lys Leu Ile Gly Leu Tyr Ser Tyr Gly Asn His Asn Ser His His
    770                 775                 780

Phe Tyr Thr Gln Gly Glu Asp Leu Ser Ser Gln Gly Glu Phe His Ser
785                 790                 795                 800

Gln Thr Phe Gly Gly Ala Val Phe Phe Asp Leu Pro Leu Lys Pro Phe
                805                 810                 815

Gly Arg Thr His Ile Leu Thr Ala Pro Phe Leu Gly Ala Ile Gly Met
            820                 825                 830

Tyr Ser Lys Leu Ser Ser Phe Thr Glu Val Gly Ala Tyr Pro Arg Thr
        835                 840                 845

Phe Ile Thr Glu Thr Pro Leu Ile Asn Val Leu Ile Pro Ile Gly Val
    850                 855                 860

Lys Gly Ser Phe Met Asn Ala Thr His Arg Pro Gln Ala Trp Thr Val
865                 870                 875                 880

Glu Leu Ala Tyr Gln Pro Val Leu Tyr Arg Gln Glu Pro Ser Ile Ser
                885                 890                 895

Thr Gln Leu Leu Ala Gly Lys Gly Met Trp Phe Gly His Gly Ser Pro
            900                 905                 910

Ala Ser Arg His Ala Leu Ala Tyr Lys Ile Ser Gln Lys Thr Gln Leu
        915                 920                 925

Leu Arg Phe Ala Thr Leu Gln Leu Gln Tyr His Gly Tyr Tyr Ser Ser
    930                 935                 940

Ser Thr Phe Cys Asn Tyr Leu Asn Gly Glu Val Ser Leu Arg Phe
945                 950                 955

<210> SEQ ID NO 36
<211> LENGTH: 2289
<212> TYPE: DNA
<213> ORGANISM: artificial sequence
<220> FEATURE:
<223> OTHER INFORMATION: synthetic polynucleotide

<400> SEQUENCE: 36
catatgcgcg aagtccctcc ttcgattctg ttaaagccta ttctgaatcc ataccacatg    60
accgggttat tttttccgaa ggttaatttg ctgggagaca cacataatct gactgattac   120
catttggata atctgaaatg cattctggct tgcctgcaac gcactcctta tgaaggagct   180
gctttcacag taaccgatta cttaggtttt tcagatacac aaaaggatgg tatttttttgt   240 tttaaaaatc tgactccaga gagtggaggg gttattggtt ccccaactca aaacactcct   300
actattaaaa ttcataatac aatcggcccg gttctgttcg aaaataatac ctgtcatcgc   360

```
ctgtggacac agaccgatcc ggaaaatgaa ggaaacaaag cacgcgaagg cggggcaatt    420
catgctgggg acgtttacat tagcaataac cagaacctgg tcggattcat taagaacttt    480
gcttatgttc aaggtggagc tattagtgct aatactttg cctataaaga aaataaatcg    540
agctttctgt gcctgaataa ctcttgtatt caaactaaga cggggagggaa aggtggtgct    600
atttacgtta gtacgagctg ctctttcgag aacaataaca aggatctgct gttcatccaa    660
aactccggct gtgcaggagg agctatcttc tctccaacct gttctctgat ggaaaccaa     720
ggagatattg ttttttacag caaccacggt tttaaaaatg ttgataatgc aactaacgaa    780
tctggggatg gaggagctat taaagtaact acccgcttgg acatcaccaa taatggtagt    840
caaatctttt tttctgataa tatctcacgc aattttggag gagctattca tgctccttgt    900
ctgcatctgg ttggtaatgg gccaacctat tttacaaaca atattgctaa tcacacaggt    960
ggggctattt atattacagg aacagaaacc tcaaagattt ctgcagatca ccatgctatt   1020
attttgata taacatttc tgcaaacgcc accaatgcgg acggatctag cagcaacact    1080
aatcctcctc accgcaatgc gatcactatg gacaattccg ctggaggaat tgaactgggt   1140
gcagggaaga gccagaatct gattttctat gatcctattc aagtgacgaa tgctggagtt   1200
accgtagact tcaataagga tgcctcccaa accggatgtg tagttttctc tggagcgact   1260
gtcctgtctg cagatatttc tcaggctaat ttgcaaacta aacacctgc agagctcact    1320
ctgagtcacc ctgctggtta tccccgagc cctaaacata aaagcccttt aattgctaat    1380
accttgtggg ggaatattgc catggcaacg gaaaacttaa aaaatagctc agggcaagaa   1440
ctgctggatc gtcctttctg gggaattaca ggaggggggct tggggatgat ggtctatcaa   1500
gaacctcgca agaccatcc tggattccac atgcatacct ccggatattc agcaggaatg   1560
attacaggaa acacacatac cttctcatta cgcttcagcc agtcctatac aaaactgaat   1620
gaacgttatg ccaagaacta tgtgtcttct aaaaattact cttgccaagg gaaatgctg    1680
ttgtccttac aagaaggact gatgctgact aaactgattg gtctgtatag ttatgggaat   1740
cacaacagcc accatttcta tacccaagga aagacctgt cgtctcaagg ggagttccat    1800
agtcagactt tggaggggc tgtctttttt gatctgcctc tgaaaccttt tggacgcaca    1860
cacattctga cagctccttt cttaggtgcc attggtatgt attctaagct gtctagcttt   1920
acagaagtag gagcctatcc acgcaccttt attacagaaa cgcctttaat caatgtcctg    1980
attcctatcg gagtaaaagg tagcttcatg aatgccaccc atcgccctca ggcctggact   2040
gtagagctgg cttaccaacc tgttctgtac cgccaagaac ctagtatctc tacccaatta   2100
ctggctggta aggtatgtg gtttgggcat ggaagtcctg catctcgcca cgctctggct    2160
tataaaattt cacagaaaac acagctgttg cgctttgcaa cactgcaact gcagtatcac   2220
ggatactatt cgtcttccac tttctgtaat tatctgaatg gagaggtatc tttacgtttc   2280
taaggatcc                                                            2289
```

<210> SEQ ID NO 37
<211> LENGTH: 759
<212> TYPE: PRT
<213> ORGANISM: artificial sequence
<220> FEATURE:
<223> OTHER INFORMATION: synthetic peptide

<400> SEQUENCE: 37

Met Arg Glu Val Pro Pro Ser Ile Leu Leu Lys Pro Ile Leu Asn Pro
1               5                   10                  15

```
Tyr His Met Thr Gly Leu Phe Phe Pro Lys Val Asn Leu Leu Gly Asp
             20                  25                  30

Thr His Asn Leu Thr Asp Tyr His Leu Asp Asn Leu Lys Cys Ile Leu
             35                  40                  45

Ala Cys Leu Gln Arg Thr Pro Tyr Glu Gly Ala Ala Phe Thr Val Thr
 50                  55                  60

Asp Tyr Leu Gly Phe Ser Asp Thr Gln Lys Asp Gly Ile Phe Cys Phe
 65                  70                  75                  80

Lys Asn Leu Thr Pro Glu Ser Gly Gly Val Ile Gly Ser Pro Thr Gln
                 85                  90                  95

Asn Thr Pro Thr Ile Lys Ile His Asn Thr Ile Gly Pro Val Leu Phe
                100                 105                 110

Glu Asn Asn Thr Cys His Arg Leu Trp Thr Gln Thr Asp Pro Glu Asn
                115                 120                 125

Glu Gly Asn Lys Ala Arg Glu Gly Gly Ala Ile His Ala Gly Asp Val
                130                 135                 140

Tyr Ile Ser Asn Asn Gln Asn Leu Val Gly Phe Ile Lys Asn Phe Ala
145                 150                 155                 160

Tyr Val Gln Gly Gly Ala Ile Ser Ala Asn Thr Phe Ala Tyr Lys Glu
                165                 170                 175

Asn Lys Ser Ser Phe Leu Cys Leu Asn Asn Ser Cys Ile Gln Thr Lys
                180                 185                 190

Thr Gly Gly Lys Gly Gly Ala Ile Tyr Val Ser Thr Ser Cys Ser Phe
                195                 200                 205

Glu Asn Asn Asn Lys Asp Leu Leu Phe Ile Gln Asn Ser Gly Cys Ala
210                 215                 220

Gly Gly Ala Ile Phe Ser Pro Thr Cys Ser Leu Ile Gly Asn Gln Gly
225                 230                 235                 240

Asp Ile Val Phe Tyr Ser Asn His Gly Phe Lys Asn Val Asp Asn Ala
                245                 250                 255

Thr Asn Glu Ser Gly Asp Gly Gly Ala Ile Lys Val Thr Thr Arg Leu
                260                 265                 270

Asp Ile Thr Asn Asn Gly Ser Gln Ile Phe Phe Ser Asp Asn Ile Ser
                275                 280                 285

Arg Asn Phe Gly Gly Ala Ile His Ala Pro Cys Leu His Leu Val Gly
                290                 295                 300

Asn Gly Pro Thr Tyr Phe Thr Asn Asn Ile Ala Asn His Thr Gly Gly
305                 310                 315                 320

Ala Ile Tyr Ile Thr Gly Thr Glu Thr Ser Lys Ile Ser Ala Asp His
                325                 330                 335

His Ala Ile Ile Phe Asp Asn Asn Ile Ser Ala Asn Ala Thr Asn Ala
                340                 345                 350

Asp Gly Ser Ser Ser Asn Thr Asn Pro Pro His Arg Asn Ala Ile Thr
                355                 360                 365

Met Asp Asn Ser Ala Gly Gly Ile Glu Leu Gly Ala Gly Lys Ser Gln
370                 375                 380

Asn Leu Ile Phe Tyr Asp Pro Ile Gln Val Thr Asn Ala Gly Val Thr
385                 390                 395                 400

Val Asp Phe Asn Lys Asp Ala Ser Gln Thr Gly Cys Val Val Phe Ser
                405                 410                 415

Gly Ala Thr Val Leu Ser Ala Asp Ile Ser Gln Ala Asn Leu Gln Thr
                420                 425                 430

Lys Thr Pro Ala Glu Leu Thr Leu Ser His Pro Ala Gly Tyr Ile Pro
```

-continued

```
        435                 440                 445

Ser Pro Lys His Lys Ser Pro Leu Ile Ala Asn Thr Leu Trp Gly Asn
    450                 455                 460

Ile Ala Met Ala Thr Glu Asn Leu Lys Asn Ser Ser Gly Gln Glu Leu
465                 470                 475                 480

Leu Asp Arg Pro Phe Trp Gly Ile Thr Gly Gly Gly Leu Gly Met Met
                485                 490                 495

Val Tyr Gln Glu Pro Arg Lys Asp His Pro Gly Phe His Met His Thr
            500                 505                 510

Ser Gly Tyr Ser Ala Gly Met Ile Thr Gly Asn Thr His Thr Phe Ser
        515                 520                 525

Leu Arg Phe Ser Gln Ser Tyr Thr Lys Leu Asn Glu Arg Tyr Ala Lys
    530                 535                 540

Asn Tyr Val Ser Ser Lys Asn Tyr Ser Cys Gln Gly Glu Met Leu Leu
545                 550                 555                 560

Ser Leu Gln Glu Gly Leu Met Leu Thr Lys Leu Ile Gly Leu Tyr Ser
                565                 570                 575

Tyr Gly Asn His Asn Ser His His Phe Tyr Thr Gln Gly Glu Asp Leu
            580                 585                 590

Ser Ser Gln Gly Glu Phe His Ser Gln Thr Phe Gly Gly Ala Val Phe
        595                 600                 605

Phe Asp Leu Pro Leu Lys Pro Phe Gly Arg Thr His Ile Leu Thr Ala
    610                 615                 620

Pro Phe Leu Gly Ala Ile Gly Met Tyr Ser Lys Leu Ser Ser Phe Thr
625                 630                 635                 640

Glu Val Gly Ala Tyr Pro Arg Thr Phe Ile Thr Glu Thr Pro Leu Ile
                645                 650                 655

Asn Val Leu Ile Pro Ile Gly Val Lys Gly Ser Phe Met Asn Ala Thr
            660                 665                 670

His Arg Pro Gln Ala Trp Thr Val Glu Leu Ala Tyr Gln Pro Val Leu
        675                 680                 685

Tyr Arg Gln Glu Pro Ser Ile Ser Thr Gln Leu Leu Ala Gly Lys Gly
    690                 695                 700

Met Trp Phe Gly His Gly Ser Pro Ala Ser Arg His Ala Leu Ala Tyr
705                 710                 715                 720

Lys Ile Ser Gln Lys Thr Gln Leu Leu Arg Phe Ala Thr Leu Gln Leu
                725                 730                 735

Gln Tyr His Gly Tyr Tyr Ser Ser Ser Thr Phe Cys Asn Tyr Leu Asn
            740                 745                 750

Gly Glu Val Ser Leu Arg Phe
        755

<210> SEQ ID NO 38
<211> LENGTH: 3078
<212> TYPE: DNA
<213> ORGANISM: Chlamydia muridarum

<400> SEQUENCE: 38
atgactcgca gaattctccc tctttcactt gttttcattc ctttatcttg tatttcggcc      60
agtgaaaccg atacactcaa acttccgaac ttgacttttg gtggtagaga gattgaattc     120
atagttactc cgcctagctc cattgctgct caatacatca cttacgcaaa tgtttctaat     180
tatagaggga actttactat ttcaagttgt acgcaggatc aatggttttc gagaggttta     240
agcactacaa actctagtgg agcttttgtt gagtctatga cttctttcac agccattgac     300
```

```
aatgcagact tgttttttg taacaattat tgcacccatc agggaggagg gggagctata    360
aatgctacag gccttattag ctttaaaaac aaccaaaaca tattgttcta taataataca    420
actattggaa ctcaatttac aggagtagca ttaagaaccg aaaggaatcg cggaggggct    480
ttatacggat caagcatcga gctaattaat aatcatagct taaattttat caataacact    540
tctggggata tgggaggagc cgtatccaca atccaaaacc tagttatcaa aaatacgtcc    600
ggaatagttg cttttgaaaa taaccatact actgatcaca tacccaacac atttgctaca    660
attcttgctc gaggaggagc tgttggctgc caaggtgcct gcgaaatctc acacaatact    720
ggtccggtag tcttcaattc caactatgga ggatacggag gagctatcag caccggggga    780
cagtgtattt ttagagataa taaggataag cttattttta taaataatag cgctttagga    840
tggcataaca ctagtgctca aggaaatgga gcagttataa gcgcaggagg agagtttggt    900
cttctaaata ataaaggccc tatctacttt gagaataata atgcctcata catagcagga    960
gctatttcct gcaacaacct taattttcaa gaaaatggtc ctatctattt tcttaataat   1020
tcggctctgt atggaggagc ttttcaccta tttgcaagcc cagctgcgaa ctatattcat   1080
actggctctg gggatattat cttcaacaat aatacagagc tttcaactac cggaatgtca   1140
gcaggtttgc gaaaactttt ttatattcct ggaacaacca acaataaccc tatcacccta   1200
tctcttggtg ctaagaaaga tactcgcatc tattttttatg atcttttttca atggggaggc   1260 ttaaaaaaag ctaatacacc ccctgaaaat agcccgcaca ccgttaccat caatccttcg   1320
gatgagttct ctggcgctgt tgtgttttca tacaaaaaca tatccagtga tctacaagct   1380
cacatgattg ccagtaaaac tcataaccaa attaaagact cccccactac cttgaagttt   1440
gggactatgt ccatagaaaa tggcgcagag tttgaattttt tcaatggccc tcttactcaa   1500
gaaagcacta gccttcttgc tttaggacaa gattctattc ttactgtagg gaaagacgct   1560
tctctcacta ttacgcatct tggaatcatt ttgccaggtc ttctcaatga ccaaggtact   1620
acagctccac gtattcgtgt taatccccaa gatatgacac agaatacaaa ctctaaccaa   1680
gctccagtaa gcacagagaa cgtggcaact caaaagatct ttttctccgg tcttgtctcg   1740
ttagtagatg aaaattacga atcagtttat gacagctgcg acctatcccg aggaaaagca   1800
aatcaaccca ttttacatat cgaaacgact aatgatgcgc agttaagcaa tgattggaaa   1860
aacactctca ataccctcgct atattcttta ccacattacg gataccaagg actctggaca   1920
tctaattgga tgacaaccac ccgtacggtc tctcttacca atagtacaga gactcaaaca   1980
gccaacaatt ctattcaaga acaaaaaaac actagcgaaa cttttgattc caacagtaca   2040
actacagcta agattccttc cattagagct tctacaggag gaacaactcc tcttgctaca   2100
acggacgtaa cagtcactag acactcctta gtagtgagct ggaccccaat cggatatata   2160
gcagatcctg ctcgtagagg ggatcttatt gcgaataatt tagtgtcttc tggaagaaat   2220
acaaccctgt acttacgttc attactacca gatgactctt ggttcgcttt acaaggatct   2280
gcagctacgc tattcaccaa acagcagaaa cgcttagatt atcacggata ttcttctgca   2340
tcgaaaggat atgctatatc ttcacaagca tcaggagcac acggacataa gttttttattt   2400 tccttttccc aatcctccga cacaatgaaa gagaaacgta ccaataataa atttcttct    2460 cgttattatc tctccgctct gtgttttgaa caacctatgt ttgatcgtat cgctcttatt    2520
ggagcagctg cttataacta tggtactcat aaaacatata acttctatgg aacgaaaaag   2580
ttttctaaag ggaactttca ctctacgact ctggggggct ctctacgttg cgaactgcgg   2640
```

-continued

```
gatagtatgc ctttccaatc gattatgttg acaccattca ttcaagctct catctcccga    2700
acagagcctg catctatcca ggagcaggga gacctggcta gattattttc gttaaaacaa    2760
ccacatacag ctgttgtttc tccaatagga attaaaggtg tttattcttc gaataaatgg    2820
ccaactgtat cctgcgaaat ggaggtagca taccagccta ctctttactg gaagcgcccc    2880
attcttaata ccgttttaat caaaaacaat ggttcttggg aaacaacaaa cactcccttta   2940 gctaagcatt ccttttatgg gagaggatca tcttctctaa aattctctta tcttaaacta    3000
ttcgctaatt atcaagcgca ggtggctact tctacagtct cacactacat gaatgcagga    3060
ggggctctgg tcttttaa                                                  3078
```

```
<210> SEQ ID NO 39
<211> LENGTH: 1025
<212> TYPE: PRT
<213> ORGANISM: Chlamydia muridarum

<400> SEQUENCE: 39
```

Met Thr Arg Arg Ile Leu Pro Leu Ser Leu Val Phe Ile Pro Leu Ser
1               5                   10                  15

Cys Ile Ser Ala Ser Glu Thr Asp Thr Leu Lys Leu Pro Asn Leu Thr
            20                  25                  30

Phe Gly Gly Arg Glu Ile Glu Phe Ile Val Thr Pro Pro Ser Ser Ile
        35                  40                  45

Ala Ala Gln Tyr Ile Thr Tyr Ala Asn Val Ser Asn Tyr Arg Gly Asn
    50                  55                  60

Phe Thr Ile Ser Ser Cys Thr Gln Asp Gln Trp Phe Ser Arg Gly Leu
65                  70                  75                  80

Ser Thr Thr Asn Ser Ser Gly Ala Phe Val Glu Ser Met Thr Ser Phe
                85                  90                  95

Thr Ala Ile Asp Asn Ala Asp Leu Phe Phe Cys Asn Asn Tyr Cys Thr
            100                 105                 110

His Gln Gly Gly Gly Ala Ile Asn Ala Thr Gly Leu Ile Ser Phe
        115                 120                 125

Lys Asn Asn Gln Asn Ile Leu Phe Tyr Asn Asn Thr Thr Ile Gly Thr
    130                 135                 140

Gln Phe Thr Gly Val Ala Leu Arg Thr Glu Arg Asn Arg Gly Gly Ala
145                 150                 155                 160

Leu Tyr Gly Ser Ser Ile Glu Leu Ile Asn Asn His Ser Leu Asn Phe
                165                 170                 175

Ile Asn Asn Thr Ser Gly Asp Met Gly Gly Ala Val Ser Thr Ile Gln
            180                 185                 190

Asn Leu Val Ile Lys Asn Thr Ser Gly Ile Val Ala Phe Glu Asn Asn
        195                 200                 205

His Thr Thr Asp His Ile Pro Asn Thr Phe Ala Thr Ile Leu Ala Arg
    210                 215                 220

Gly Gly Ala Val Gly Cys Gln Gly Ala Cys Glu Ile Ser His Asn Thr
225                 230                 235                 240

Gly Pro Val Val Phe Asn Ser Asn Tyr Gly Gly Tyr Gly Gly Ala Ile
                245                 250                 255

Ser Thr Gly Gly Gln Cys Ile Phe Arg Asp Asn Lys Asp Lys Leu Ile
            260                 265                 270

Phe Ile Asn Asn Ser Ala Leu Gly Trp His Asn Thr Ser Ala Gln Gly
        275                 280                 285

Asn Gly Ala Val Ile Ser Ala Gly Gly Glu Phe Gly Leu Leu Asn Asn

```
                  290                 295                 300
Lys Gly Pro Ile Tyr Phe Glu Asn Asn Asn Ala Ser Tyr Ile Ala Gly
305                 310                 315                 320

Ala Ile Ser Cys Asn Asn Leu Asn Phe Gln Glu Asn Gly Pro Ile Tyr
                    325                 330                 335

Phe Leu Asn Asn Ser Ala Leu Tyr Gly Gly Ala Phe His Leu Phe Ala
                340                 345                 350

Ser Pro Ala Ala Asn Tyr Ile His Thr Gly Ser Gly Asp Ile Ile Phe
            355                 360                 365

Asn Asn Asn Thr Glu Leu Ser Thr Thr Gly Met Ser Ala Gly Leu Arg
        370                 375                 380

Lys Leu Phe Tyr Ile Pro Gly Thr Thr Asn Asn Pro Ile Thr Leu
385                 390                 395                 400

Ser Leu Gly Ala Lys Lys Asp Thr Arg Ile Tyr Phe Tyr Asp Leu Phe
                405                 410                 415

Gln Trp Gly Gly Leu Lys Lys Ala Asn Thr Pro Pro Glu Asn Ser Pro
                420                 425                 430

His Thr Val Thr Ile Asn Pro Ser Asp Glu Phe Ser Gly Ala Val Val
            435                 440                 445

Phe Ser Tyr Lys Asn Ile Ser Ser Asp Leu Gln Ala His Met Ile Ala
        450                 455                 460

Ser Lys Thr His Asn Gln Ile Lys Asp Ser Pro Thr Thr Leu Lys Phe
465                 470                 475                 480

Gly Thr Met Ser Ile Glu Asn Gly Ala Glu Phe Glu Phe Phe Asn Gly
                485                 490                 495

Pro Leu Thr Gln Glu Ser Thr Ser Leu Leu Ala Leu Gly Gln Asp Ser
            500                 505                 510

Ile Leu Thr Val Gly Lys Asp Ala Ser Leu Thr Ile Thr His Leu Gly
        515                 520                 525

Ile Ile Leu Pro Gly Leu Leu Asn Asp Gln Gly Thr Thr Ala Pro Arg
            530                 535                 540

Ile Arg Val Asn Pro Gln Asp Met Thr Gln Asn Thr Asn Ser Asn Gln
545                 550                 555                 560

Ala Pro Val Ser Thr Glu Asn Val Ala Thr Gln Lys Ile Phe Phe Ser
                565                 570                 575

Gly Leu Val Ser Leu Val Asp Glu Asn Tyr Glu Ser Val Tyr Asp Ser
            580                 585                 590

Cys Asp Leu Ser Arg Gly Lys Ala Asn Gln Pro Ile Leu His Ile Glu
        595                 600                 605

Thr Thr Asn Asp Ala Gln Leu Ser Asn Asp Trp Lys Asn Thr Leu Asn
610                 615                 620

Thr Ser Leu Tyr Ser Leu Pro His Tyr Gly Tyr Gln Gly Leu Trp Thr
625                 630                 635                 640

Ser Asn Trp Met Thr Thr Thr Arg Thr Val Ser Leu Thr Asn Ser Thr
                645                 650                 655

Glu Thr Gln Thr Ala Asn Asn Ser Ile Gln Glu Gln Lys Asn Thr Ser
            660                 665                 670

Glu Thr Phe Asp Ser Asn Ser Thr Thr Ala Lys Ile Pro Ser Ile
        675                 680                 685

Arg Ala Ser Thr Gly Gly Thr Thr Pro Leu Ala Thr Thr Asp Val Thr
            690                 695                 700

Val Thr Arg His Ser Leu Val Val Ser Trp Thr Pro Ile Gly Tyr Ile
705                 710                 715                 720
```

Ala Asp Pro Ala Arg Arg Gly Asp Leu Ile Ala Asn Asn Leu Val Ser
                725                 730                 735

Ser Gly Arg Asn Thr Thr Leu Tyr Leu Arg Ser Leu Leu Pro Asp Asp
            740                 745                 750

Ser Trp Phe Ala Leu Gln Gly Ser Ala Ala Thr Leu Phe Thr Lys Gln
        755                 760                 765

Gln Lys Arg Leu Asp Tyr His Gly Tyr Ser Ser Ala Ser Lys Gly Tyr
    770                 775                 780

Ala Ile Ser Ser Gln Ala Ser Gly Ala His Gly His Lys Phe Leu Phe
785                 790                 795                 800

Ser Phe Ser Gln Ser Ser Asp Thr Met Lys Glu Lys Thr Asn Asn
                805                 810                 815

Lys Ile Ser Ser Arg Tyr Tyr Leu Ser Ala Leu Cys Phe Glu Gln Pro
            820                 825                 830

Met Phe Asp Arg Ile Ala Leu Ile Gly Ala Ala Ala Tyr Asn Tyr Gly
        835                 840                 845

Thr His Lys Thr Tyr Asn Phe Tyr Gly Thr Lys Lys Phe Ser Lys Gly
    850                 855                 860

Asn Phe His Ser Thr Thr Leu Gly Gly Ser Leu Arg Cys Glu Leu Arg
865                 870                 875                 880

Asp Ser Met Pro Phe Gln Ser Ile Met Leu Thr Pro Phe Ile Gln Ala
                885                 890                 895

Leu Ile Ser Arg Thr Glu Pro Ala Ser Ile Gln Glu Gln Gly Asp Leu
            900                 905                 910

Ala Arg Leu Phe Ser Leu Lys Gln Pro His Thr Ala Val Val Ser Pro
        915                 920                 925

Ile Gly Ile Lys Gly Val Tyr Ser Ser Asn Lys Trp Pro Thr Val Ser
    930                 935                 940

Cys Glu Met Glu Val Ala Tyr Gln Pro Thr Leu Tyr Trp Lys Arg Pro
945                 950                 955                 960

Ile Leu Asn Thr Val Leu Ile Lys Asn Asn Gly Ser Trp Glu Thr Thr
                965                 970                 975

Asn Thr Pro Leu Ala Lys His Ser Phe Tyr Gly Arg Gly Ser Ser Ser
            980                 985                 990

Leu Lys Phe Ser Tyr Leu Lys Leu Phe Ala Asn Tyr Gln Ala Gln Val
        995                 1000                1005

Ala Thr Ser Thr Val Ser His Tyr Met Asn Ala Gly Gly Ala Leu
    1010                1015                1020

Val Phe
    1025

<210> SEQ ID NO 40
<211> LENGTH: 3030
<212> TYPE: DNA
<213> ORGANISM: artificial sequence
<220> FEATURE:
<223> OTHER INFORMATION: synthetic polynucleotide

<400> SEQUENCE: 40
catatgagtg aaaccgatac actgaaactg ccgaacttga cttttggtgg tcgcgagatt    60
gaattcattg ttactccgcc tagctccatt gctgctcaat acatcactta cgcaaatgtt   120
tctaattatc gcgggaactt tactatttca agttgtacgc aggatcaatg gttttcgcgc   180
ggtttaagca ctacaaactc tagtggagct tttgttgagt ctatgacttc tttcacagcc   240

```
attgacaatg cagacttgtt tttttgtaac aattattgca cccatcaggg aggagggggga    300 gctattaatg ctacaggcct gattagcttt aaaaacaacc aaaacatttt gttctataat    360
aatacaacta ttggaactca atttacagga gtagcattac gcaccgaacg caatcgcgga    420
ggggctttat acgatcaag catcgagctg attaataatc atagcttaaa ttttatcaat    480
aacacttctg gggatatggg aggagccgta tccacaatcc aaaacctggt tatcaaaaat    540
acgtccggaa ttgttgcttt tgaaaataac catactactg atcacattcc gaacacattt    600
gctacaattc tggctcgcgg aggagctgtt ggctgccaag gtgcctgcga aatctcacac    660
aatactggtc cggtagtctt caattccaac tatggaggat acggaggagc tatcagcacc    720 ggggacagt gtattttcg cgataataag gataagctga ttttattaa taatagcgct    780 ttaggatggc ataacactag tgctcaagga aatggagcag ttattagcgc aggaggagag    840
tttggtctgc tgaataataa aggccctatc tactttgaga ataataatgc ctcatacatt    900
gcaggagcta tttcctgcaa caacctgaat tttcaagaaa atggtcctat ctattttctg    960
aataattcgg ctctgtatgg aggagctttt cacctgtttg caagcccagc tgcgaactat   1020
attcatactg gctctgggga tattatcttc aacaataata cagagctgtc aactaccgga   1080
atgtcagcag gtttgcgcaa actgtttat attcctggaa caaccaacaa taaccctatc   1140
accctgtctc tgggtgctaa gaaagatact cgcatctatt tttatgatct gtttcaatgg   1200
ggaggcttaa aaaagctaa tacaccgcct gaaaatagcc cgcacaccgt taccatcaat   1260
ccttcggatg agttctctgg cgctgttgtg ttttcataca aaaacatttc cagtgagctc   1320
caagctcaca tgattgccag taaaactcat aaccaaatta aagactcccc gactaccttg   1380
aagtttggga ctatgtccat tgaaaatggc gcagagtttg aattttcaa tggccctctg   1440 actcaagaaa gcactagcct gctggcttta ggacaagatt ctattctgac tgtagggaaa   1500
gacgcttctc tgactattac gcatctggga atcattttgc caggtctgct gaatgaccaa   1560
ggtactacag ctccacgtat tcgtgttaat ccgcaagata tgacacagaa tacaaactct   1620
aaccaagctc cagtaagcac agagaacgtg gcaactcaaa agatctttt ctccggtctg   1680 gtctcgttag tagatgaaaa ttacgaatca gtttatgaca gctgcgacct gtcccgcgga   1740
aaagcaaatc aaccgatttt acatatcgaa acgactaatg atgcgcagtt aagcaatgat   1800
tggaaaaaca ctctgaatac ctcgctgtat tctttaccac attacggata ccaaggactg   1860
tggacatcta attggatgac aaccacccgt acggtctctc tgaccaatag tacagagact   1920
caaacagcca acaattctat tcaagaacaa aaaaacacta gcgaaacttt tgattccaac   1980
agtacaacta cagctaagat tccttccatt cgcgcttcta caggaggaac aactcccatg   2040
gctacaacgg acgtaacagt cactcgccac tccttagtag tgagctggac cccaatcgga   2100
tatattgcag atcctgctcg tcgcggggat ctgattgcga ataatttagt gtcttctgga   2160
cgcaatacaa ccctgtactt acgttcatta ctgccagatg actcttggtt cgctttacaa   2220
ggatctgcag ctacgctgtt caccaaacag cagaaacgct tagattatca cggatattct   2280
tctgcatcga aaggatatgc tatttcttca caagcatcag gagcacacgg acataagttt   2340
ttatttccct ttcccaatc ctccgacaca atgaaagaga aacgtaccaa taataaaatt   2400
tcttctcgtt attatctgtc cgctctgtgt tttgaacaac ctatgtttga tcgtatcgct   2460
ctgattggag cagctgctta taactatggt actcataaaa catataactt ctatggaacg   2520
aaaaagtttt ctaaagggaa cttttcactct acgactctgg ggggctctct gcgttgcgaa   2580
ctgcgggata gtatgccttt ccaatcgatt atgttgacac cattcattca agctctgatc   2640
```

```
tcccgcacag agcctgcatc tatccaggag cagggagacc tggctcgctt attttcgtta    2700
aaacaaccac atacagctgt tgtttctcca attggaatta aggtgtttta ttcttcgaat    2760
aaatggccaa ctgtatcctg cgaaatggag gtagcatacc agcctactct gtactggaag    2820
cgcccgattc tgaataccgt tttaatcaaa acaatggtt cttgggaaac aacaaacact    2880
cctttagcta agcattcctt ttatgggcgc ggatcatctt ctctgaaatt ctcttatctg    2940
aaactgttcg ctaattatca agcgcaggtg gctacttcta cagtctcaca ctacatgaat    3000
gcaggagggg ctctggtctt ttaaggatcc                                    3030
```

<210> SEQ ID NO 41
<211> LENGTH: 1006
<212> TYPE: PRT
<213> ORGANISM: artificial sequence
<220> FEATURE:
<223> OTHER INFORMATION: synthetic peptide

<400> SEQUENCE: 41

```
Met Ser Glu Thr Asp Thr Leu Lys Leu Pro Asn Leu Thr Phe Gly Gly
1               5                   10                  15

Arg Glu Ile Glu Phe Ile Val Thr Pro Pro Ser Ser Ile Ala Ala Gln
            20                  25                  30

Tyr Ile Thr Tyr Ala Asn Val Ser Asn Tyr Arg Gly Asn Phe Thr Ile
        35                  40                  45

Ser Ser Cys Thr Gln Asp Gln Trp Phe Ser Arg Gly Leu Ser Thr Thr
    50                  55                  60

Asn Ser Ser Gly Ala Phe Val Glu Ser Met Thr Ser Phe Thr Ala Ile
65                  70                  75                  80

Asp Asn Ala Asp Leu Phe Phe Cys Asn Asn Tyr Cys Thr His Gln Gly
                85                  90                  95

Gly Gly Gly Ala Ile Asn Ala Thr Gly Leu Ile Ser Phe Lys Asn Asn
            100                 105                 110

Gln Asn Ile Leu Phe Tyr Asn Asn Thr Thr Ile Gly Thr Gln Phe Thr
        115                 120                 125

Gly Val Ala Leu Arg Thr Glu Arg Asn Arg Gly Ala Leu Tyr Gly
    130                 135                 140

Ser Ser Ile Glu Leu Ile Asn Asn His Ser Leu Asn Phe Ile Asn Asn
145                 150                 155                 160

Thr Ser Gly Asp Met Gly Gly Ala Val Ser Thr Ile Gln Asn Leu Val
                165                 170                 175

Ile Lys Asn Thr Ser Gly Ile Val Ala Phe Glu Asn Asn His Thr Thr
            180                 185                 190

Asp His Ile Pro Asn Thr Phe Ala Thr Ile Leu Ala Arg Gly Gly Ala
        195                 200                 205

Val Gly Cys Gln Gly Ala Cys Glu Ile Ser His Asn Thr Gly Pro Val
    210                 215                 220

Val Phe Asn Ser Asn Tyr Gly Gly Tyr Gly Gly Ala Ile Ser Thr Gly
225                 230                 235                 240

Gly Gln Cys Ile Phe Arg Asp Asn Lys Asp Lys Leu Ile Phe Ile Asn
                245                 250                 255

Asn Ser Ala Leu Gly Trp His Asn Thr Ser Ala Gln Gly Asn Gly Ala
            260                 265                 270

Val Ile Ser Ala Gly Gly Glu Phe Gly Leu Leu Asn Asn Lys Gly Pro
        275                 280                 285
```

```
Ile Tyr Phe Glu Asn Asn Ala Ser Tyr Ile Ala Gly Ala Ile Ser
    290                 295                 300

Cys Asn Asn Leu Asn Phe Gln Glu Asn Gly Pro Ile Tyr Phe Leu Asn
305                 310                 315                 320

Asn Ser Ala Leu Tyr Gly Gly Ala Phe His Leu Phe Ala Ser Pro Ala
                325                 330                 335

Ala Asn Tyr Ile His Thr Gly Ser Gly Asp Ile Ile Phe Asn Asn Asn
            340                 345                 350

Thr Glu Leu Ser Thr Thr Gly Met Ser Ala Gly Leu Arg Lys Leu Phe
        355                 360                 365

Tyr Ile Pro Gly Thr Thr Asn Asn Pro Ile Thr Leu Ser Leu Gly
370                 375                 380

Ala Lys Lys Asp Thr Arg Ile Tyr Phe Tyr Asp Leu Phe Gln Trp Gly
385                 390                 395                 400

Gly Leu Lys Lys Ala Asn Thr Pro Pro Glu Asn Ser Pro His Thr Val
                405                 410                 415

Thr Ile Asn Pro Ser Asp Glu Phe Ser Gly Ala Val Val Phe Ser Tyr
            420                 425                 430

Lys Asn Ile Ser Ser Glu Leu Gln Ala His Met Ile Ala Ser Lys Thr
        435                 440                 445

His Asn Gln Ile Lys Asp Ser Pro Thr Thr Leu Lys Phe Gly Thr Met
    450                 455                 460

Ser Ile Glu Asn Gly Ala Glu Phe Glu Phe Phe Asn Gly Pro Leu Thr
465                 470                 475                 480

Gln Glu Ser Thr Ser Leu Leu Ala Leu Gly Gln Asp Ser Ile Leu Thr
                485                 490                 495

Val Gly Lys Asp Ala Ser Leu Thr Ile Thr His Leu Gly Ile Ile Leu
            500                 505                 510

Pro Gly Leu Leu Asn Asp Gln Gly Thr Thr Ala Pro Arg Ile Arg Val
        515                 520                 525

Asn Pro Gln Asp Met Thr Gln Asn Thr Asn Ser Asn Gln Ala Pro Val
    530                 535                 540

Ser Thr Glu Asn Val Ala Thr Gln Lys Ile Phe Phe Ser Gly Leu Val
545                 550                 555                 560

Ser Leu Val Asp Glu Asn Tyr Glu Ser Val Tyr Asp Ser Cys Asp Leu
                565                 570                 575

Ser Arg Gly Lys Ala Asn Gln Pro Ile Leu His Ile Glu Thr Thr Asn
            580                 585                 590

Asp Ala Gln Leu Ser Asn Asp Trp Lys Asn Thr Leu Asn Thr Ser Leu
        595                 600                 605

Tyr Ser Leu Pro His Tyr Gly Tyr Gln Gly Leu Trp Thr Ser Asn Trp
    610                 615                 620

Met Thr Thr Thr Arg Thr Val Ser Leu Thr Asn Ser Thr Glu Thr Gln
625                 630                 635                 640

Thr Ala Asn Asn Ser Ile Gln Glu Gln Lys Asn Thr Ser Glu Thr Phe
                645                 650                 655

Asp Ser Asn Ser Thr Thr Thr Ala Lys Ile Pro Ser Ile Arg Ala Ser
            660                 665                 670

Thr Gly Gly Thr Thr Pro Met Ala Thr Thr Asp Val Thr Val Thr Arg
        675                 680                 685

His Ser Leu Val Val Ser Trp Thr Pro Ile Gly Tyr Ile Ala Asp Pro
    690                 695                 700

Ala Arg Arg Gly Asp Leu Ile Ala Asn Asn Leu Val Ser Ser Gly Arg
```

```
705                 710                 715                 720
Asn Thr Thr Leu Tyr Leu Arg Ser Leu Leu Pro Asp Asp Ser Trp Phe
                725                 730                 735
Ala Leu Gln Gly Ser Ala Ala Thr Leu Phe Thr Lys Gln Gln Lys Arg
                740                 745                 750
Leu Asp Tyr His Gly Tyr Ser Ala Ser Lys Gly Tyr Ala Ile Ser
                755                 760                 765
Ser Gln Ala Ser Gly Ala His Gly His Lys Phe Leu Phe Ser Phe Ser
770                 775                 780
Gln Ser Ser Asp Thr Met Lys Glu Lys Arg Thr Asn Asn Lys Ile Ser
785                 790                 795                 800
Ser Arg Tyr Tyr Leu Ser Ala Leu Cys Phe Glu Gln Pro Met Phe Asp
                805                 810                 815
Arg Ile Ala Leu Ile Gly Ala Ala Tyr Asn Tyr Gly Thr His Lys
                820                 825                 830
Thr Tyr Asn Phe Tyr Gly Thr Lys Lys Phe Ser Lys Gly Asn Phe His
                835                 840                 845
Ser Thr Thr Leu Gly Gly Ser Leu Arg Cys Glu Leu Arg Asp Ser Met
850                 855                 860
Pro Phe Gln Ser Ile Met Leu Thr Pro Phe Ile Gln Ala Leu Ile Ser
865                 870                 875                 880
Arg Thr Glu Pro Ala Ser Ile Gln Glu Gln Gly Asp Leu Ala Arg Leu
                885                 890                 895
Phe Ser Leu Lys Gln Pro His Thr Ala Val Val Ser Pro Ile Gly Ile
                900                 905                 910
Lys Gly Val Tyr Ser Ser Asn Lys Trp Pro Thr Val Ser Cys Glu Met
                915                 920                 925
Glu Val Ala Tyr Gln Pro Thr Leu Tyr Trp Lys Arg Pro Ile Leu Asn
                930                 935                 940
Thr Val Leu Ile Lys Asn Asn Gly Ser Trp Glu Thr Thr Asn Thr Pro
945                 950                 955                 960
Leu Ala Lys His Ser Phe Tyr Gly Arg Gly Ser Ser Ser Leu Lys Phe
                965                 970                 975
Ser Tyr Leu Lys Leu Phe Ala Asn Tyr Gln Ala Gln Val Ala Thr Ser
                980                 985                 990
Thr Val Ser His Tyr Met Asn Ala Gly Gly Ala Leu Val Phe
                995                 1000                1005

<210> SEQ ID NO 42
<211> LENGTH: 2484
<212> TYPE: DNA
<213> ORGANISM: artificial sequence
<220> FEATURE:
<223> OTHER INFORMATION: synthetic polynucleotide

<400> SEQUENCE: 42
catatgagtg aaaccgatac actgaaactg ccgaacttga cttttggtgg tcgcgagatt      60
gaattcattg ttactccgcc tagctccatt gctgctcaat acatcactta cgcaaatgtt     120
tctaattatc gcgggaactt tactatttca agttgtacgc aggatcaatg gttttcgcgc     180
ggtttaagca ctacaaactc tagtggagct tttgttgagt ctatgacttc tttcacagcc     240
attgacaatg cagacttgtt tttttgtaac aattattgca cccatcaggg aggaggggga     300
gctattaatg ctacaggcct gattagcttt aaaaacaacc aaaacatttt gttctataat     360
aatacaacta ttggaactca atttacagga gtagcattac gcaccgaacg caatcgcgga     420
```

| | | |
|---|---|---|
| ggggctttat acggatcaag catcgagctg attaataatc atagcttaaa ttttatcaat | 480 | |
| aacacttctg gggatatggg aggagccgta tccacaatcc aaaacctggt tatcaaaaat | 540 | |
| acgtccggaa ttgttgcttt tgaaaataac catactactg atcacattcc gaacacattt | 600 | |
| gctacaattc tggctcgcgg aggagctgtt ggctgccaag gtgcctgcga aatctcacac | 660 | |
| aatactggtc cggtagtctt caattccaac tatggaggat acggaggagc tatcagcacc | 720 | |
| gggggacagt gtattttcg cgataataag gataagctga tttttattaa taatagcgct | 780 | |
| ttaggatggc ataacactag tgctcaagga aatggagcag ttattagcgc aggaggagag | 840 | |
| tttggtctgc tgaataataa aggccctatc tactttgaga ataataatgc ctcatacatt | 900 | |
| gcaggagcta tttcctgcaa caacctgaat tttcaagaaa atggtcctat ctattttctg | 960 | |
| aataattcgg ctctgtatgg aggagctttt cacctgtttg caagcccagc tgcgaactat | 1020 | |
| attcatactg gctctgggga tattatcttc aacaataata cagagctgtc aactaccgga | 1080 | |
| atgtcagcag gtttgcgcaa actgttttat attcctggaa caaccaacaa taaccctatc | 1140 | |
| accctgtctc tgggtgctaa gaaagatact cgcatctatt tttatgatct gtttcaatgg | 1200 | |
| ggaggcttaa aaaagctaa tacaccgcct gaaaatagcc cgcacaccgt taccatcaat | 1260 | |
| ccttcggatg agttctctgg cgctgttgtg ttttcataca aaaacatttc cagtgagctc | 1320 | |
| caagctcaca tgattgccag taaaactcat aaccaaatta aagactcccc gactaccttg | 1380 | |
| aagtttaatt ctattcaaga acaaaaaaac actagcgaaa cttttgattc caacagtaca | 1440 | |
| actacagcta agattccttc cattcgcgct tctacaggag gaacaactcc catggctaca | 1500 | |
| acggacgtaa cagtcactcg ccactcctta gtagtgagct ggaccccaat cggatatatt | 1560 | |
| gcagatcctg ctcgtcgcgg ggatctgatt gcgaataatt tagtgtcttc tggacgcaat | 1620 | |
| acaaccctgt acttacgttc attactgcca gatgactctt ggttcgcttt acaaggatct | 1680 | |
| gcagctacgc tgttcaccaa acagcagaaa cgcttagatt atcacggata ttcttctgca | 1740 | |
| tcgaaaggat atgctatttc ttcacaagca tcaggagcac acggacataa gttttattt | 1800 | |
| tccttttccc aatcctccga cacaatgaaa gagaaacgta ccaataataa aatttcttct | 1860 | |
| cgttattatc tgtccgctct gtgttttgaa caacctatgt tgatcgtat cgctctgatt | 1920 | |
| ggagcagctg cttataacta tggtactcat aaaacatata acttctatgg aacgaaaaag | 1980 | |
| ttttctaaag gaactttca ctctacgact ctgggggggct ctctgcgttg cgaactgcgg | 2040 | |
| gatagtatgc ctttccaatc gattatgttg acaccattca ttcaagctct gatctcccgc | 2100 | |
| acagagcctg catctatcca ggagcaggga gacctggctc gcttattttc gttaaaacaa | 2160 | |
| ccacatacag ctgttgtttc tccaattgga attaaaggtg tttattcttc gaataaatgg | 2220 | |
| ccaactgtat cctgcgaaat ggaggtagca taccagccta ctctgtactg gaagcgcccg | 2280 | |
| attctgaata ccgttttaat caaaaacaat ggttcttggg aaacaacaaa cactcctta | 2340 | |
| gctaagcatt cctttatgg gcgcggatca tcttctctga aattctctta tctgaaactg | 2400 | |
| ttcgctaatt atcaagcgca ggtggctact tctacagtct cacactacat gaatgcagga | 2460 | |
| ggggctctgg tcttttaagg atcc | 2484 | |

<210> SEQ ID NO 43
<211> LENGTH: 2961
<212> TYPE: DNA
<213> ORGANISM: Chlamydia muridarum

<400> SEQUENCE: 43

-continued

```
atgcaaacgc ctttcataa gttctttctt ctagcaatgc tatcttactc tttattgcaa    60
ggagggcatg cggcagatat ttccatgcct ccgggaattt atgatgggac aacattgacg   120
gcgccatttc cctacactgt gatcggagat cccagaggga caaaggttac ttcatcggga   180
tcgctagagt tgaaaaacct ggacaattcc attgcgactt tacctctaag ttgttttggt   240
aatttgttgg ggaatttcac tattgcagga agagggcatt cgttagtatt tgagaatata   300
cgaacatcta caaatggggc ggcattgagt aatcatgctc cttctggact gtttgtaatt   360
gaagctttg atgaactctc tcttttgaat tgtaattcat tggtatctgt agttcctcaa    420
acaggggta cgactacttc tgttccttct aatgggacga tctattctag aacagatctt    480
gttctaagag atatcaagaa ggtttctttc tatagtaact tagtttctgg agatggggga   540
gctatagatg cacaaagttt aatggttaac ggaattgaaa aactttgtac cttccaagaa   600
aatgtagcgc agtccgatgg gggagcgtgt caggtaacaa agaccttctc tgctgtgggc   660
aataaggttc ctttgtcttt tttaggcaat gttgctggta ataagggggg aggagttgct   720
gctgtcaaag atggtcaggg ggcaggaggg gcgactgatc tatcggttaa ttttgccaat   780
aatactgctg tagaatttga gggaaatagt gctcgaatag gtggagggat ctactcggac   840
ggaaatattt cctttttagg gaatgcaaag acagttttcc taagtaacgt agcttcgcct   900
atttatgttg accctgctgc tgcaggagga cagcccctg cagataaaga taactatgga   960
gatggaggag ccatcttctg caaaaatgat actaacatag tgaagtctc tttcaaagac  1020
gagggtgttg ttttctttag taaaaatatt gccgcaggaa agggggcgc tatttatgct  1080
aagaaactga caatttctga ctgtggtccg gtccagtttc ttggtaatgt cgcgaatgac  1140
gggggcgcta tttatctagt agatcagggg gaacttagtc tatctgctga tcgcggagat  1200
attattttg atggaaattt aaagagaatg gctacgcaag gcgctgccac cgtccatgat  1260
gtaatggttg catcgaatgc tatctctatg ctacaggggg gcaaatcac aacattaagg  1320
gctaaggaag tcgccgaat tcttttaat gaccctattg aaatggcgaa tggacaacct  1380
gtaatacaaa ctcttacagt aaacgagggc gaaggatata cggggacat tgttttgct  1440
aaaggtgata atgttttgta ctcaagtatt gagctgagtc agggaagaat tattctccga  1500
gagcaaacaa aattattggt taactccctg actcagactg gagggagtgt acatatggaa  1560
gggggagta cactagactt tgcagtaaca acgccaccag ctgctaattc gatggctctt  1620
actaatgtac acttctcctt agcttcttta ctaaaaaata tgggggttac aaatcctcca  1680
acgaatcctc cagtacaggt ttctagtcca gctgtaattg gtaatacagc tgctggtact  1740
gttacgattt ctggtccgat cttttttgaa gatttagatg aaactgctta cgataataat  1800
cagtggttag gtgcggatca aactattgat gtgctgcagt tgcatttagg agcgaatcct  1860
ccggctaacg ctccaactga tttgacttta gggaacgaaa gttctaaata tgggtatcaa  1920
ggaagttgga cacttcaatg gaaccagat cctgcgaatc ctccacagaa caatagctac  1980
atgttgaagg caagctggac taaaacaggt tataatcctg gtccggagcg cgtagcttct  2040
ctggtctcta atagtctttg gggatccatt ttagatgtgc gttccgcgca ttctgcgatt  2100
caagcaagta tagatggacg agcttattgt cggggtattt ggattctgg gatttcgaac  2160
tttttctatc atgatcagga tgctttagga caggggtatc gtcatattag tgggggatat  2220
tcgataggag caaactctta tttcgggtct tctatgtttg gacttgcttt tactgaaact  2280
tttggtaggt ccaagagtta tgtggtctgt cgatctaacg atcacacttg tgtaggctct  2340
gtttacttat ccactagaca agcgttatgc ggatcctgtt tatttggaga tgcttttgtt  2400
```

```
cgggcgagtt acggatttgg aaatcagcat atgaagacct cttatacatt tgctgaagag    2460
agtaatgtgc gttgggataa taactgtgta gtgggagaag ttggagctgg gctccctatc    2520
atgctcgctg catctaagct ttatctaaat gagttgcgtc ccttcgtgca agcagagttt    2580
gcttatgcag agcatgaatc ttttacagag agagggatc aggctaggga gtttaagagt     2640
gggcatctta tgaatctatc tattccagtt ggggtgaagt ttgatcgatg ctctagtaaa    2700
catcctaaca agtatagttt tatgggagct tatatctgtg atgcttaccg gtccatttct    2760
ggaacggaga caacactcct gtctcataaa gagacttgga caacagatgc tttccattta    2820
gcaaggcatg gagttatggt cagaggatct atgtatgctt ctttaacagg taatatagaa    2880
gtctatggcc atggaaaata tgaatacagg gatgcctctc gagggtatgg tttaagtatt    2940
ggaagtaaaa tccgattcta a                                              2961
```

<210> SEQ ID NO 44
<211> LENGTH: 987
<212> TYPE: PRT
<213> ORGANISM: Chlamydia muridarum

<400> SEQUENCE: 44

```
Met Met Gln Thr Pro Phe His Lys Phe Phe Leu Leu Ala Met Leu Ser
1               5                   10                  15

Tyr Ser Leu Leu Gln Gly Gly His Ala Ala Asp Ile Ser Met Pro Pro
            20                  25                  30

Gly Ile Tyr Asp Gly Thr Thr Leu Thr Ala Pro Phe Pro Tyr Thr Val
        35                  40                  45

Ile Gly Asp Pro Arg Gly Thr Lys Val Thr Ser Ser Gly Ser Leu Glu
    50                  55                  60

Leu Lys Asn Leu Asp Asn Ser Ile Ala Thr Pro Leu Ser Cys Phe
65                  70                  75                  80

Gly Asn Leu Leu Gly Asn Phe Thr Ile Ala Gly Arg Gly His Ser Leu
                85                  90                  95

Val Phe Glu Asn Ile Arg Thr Ser Thr Asn Gly Ala Ala Leu Ser Asn
            100                 105                 110

His Ala Pro Ser Gly Leu Phe Val Ile Glu Ala Phe Asp Glu Leu Ser
        115                 120                 125

Leu Leu Asn Cys Asn Ser Leu Val Ser Val Pro Gln Thr Gly Gly
    130                 135                 140

Thr Thr Thr Ser Val Pro Ser Asn Gly Thr Ile Tyr Ser Arg Thr Asp
145                 150                 155                 160

Leu Val Leu Arg Asp Ile Lys Lys Val Ser Phe Tyr Ser Asn Leu Val
                165                 170                 175

Ser Gly Asp Gly Gly Ala Ile Asp Ala Gln Ser Leu Met Val Asn Gly
            180                 185                 190

Ile Glu Lys Leu Cys Thr Phe Gln Glu Asn Val Ala Gln Ser Asp Gly
        195                 200                 205

Gly Ala Cys Gln Val Thr Lys Thr Phe Ser Ala Val Gly Asn Lys Val
    210                 215                 220

Pro Leu Ser Phe Leu Gly Asn Val Ala Gly Asn Lys Gly Gly Val
225                 230                 235                 240

Ala Ala Val Lys Asp Gly Gln Gly Ala Gly Gly Ala Thr Asp Leu Ser
                245                 250                 255

Val Asn Phe Ala Asn Asn Thr Ala Val Glu Phe Glu Gly Asn Ser Ala
            260                 265                 270
```

```
Arg Ile Gly Gly Gly Ile Tyr Ser Asp Gly Asn Ile Ser Phe Leu Gly
    275                 280                 285

Asn Ala Lys Thr Val Phe Leu Ser Asn Val Ala Ser Pro Ile Tyr Val
    290                 295                 300

Asp Pro Ala Ala Ala Gly Gly Gln Pro Pro Ala Asp Lys Asp Asn Tyr
305                 310                 315                 320

Gly Asp Gly Gly Ala Ile Phe Cys Lys Asn Asp Thr Asn Ile Gly Glu
                325                 330                 335

Val Ser Phe Lys Asp Glu Gly Val Val Phe Phe Ser Lys Asn Ile Ala
            340                 345                 350

Ala Gly Lys Gly Gly Ala Ile Tyr Ala Lys Lys Leu Thr Ile Ser Asp
        355                 360                 365

Cys Gly Pro Val Gln Phe Leu Gly Asn Val Ala Asn Asp Gly Gly Ala
    370                 375                 380

Ile Tyr Leu Val Asp Gln Gly Glu Leu Ser Leu Ser Ala Asp Arg Gly
385                 390                 395                 400

Asp Ile Ile Phe Asp Gly Asn Leu Lys Arg Met Ala Thr Gln Gly Ala
                405                 410                 415

Ala Thr Val His Asp Val Met Val Ala Ser Asn Ala Ile Ser Met Ala
            420                 425                 430

Thr Gly Gly Gln Ile Thr Thr Leu Arg Ala Lys Glu Gly Arg Arg Ile
        435                 440                 445

Leu Phe Asn Asp Pro Ile Glu Met Ala Asn Gly Gln Pro Val Ile Gln
    450                 455                 460

Thr Leu Thr Val Asn Glu Gly Glu Gly Tyr Thr Gly Asp Ile Val Phe
465                 470                 475                 480

Ala Lys Gly Asp Asn Val Leu Tyr Ser Ser Ile Glu Leu Ser Gln Gly
                485                 490                 495

Arg Ile Ile Leu Arg Glu Gln Thr Lys Leu Leu Val Asn Ser Leu Thr
            500                 505                 510

Gln Thr Gly Gly Ser Val His Met Glu Gly Gly Ser Thr Leu Asp Phe
        515                 520                 525

Ala Val Thr Thr Pro Pro Ala Ala Asn Ser Met Ala Leu Thr Asn Val
    530                 535                 540

His Phe Ser Leu Ala Ser Leu Leu Lys Asn Asn Gly Val Thr Asn Pro
545                 550                 555                 560

Pro Thr Asn Pro Pro Val Gln Val Ser Ser Pro Ala Val Ile Gly Asn
                565                 570                 575

Thr Ala Ala Gly Thr Val Thr Ile Ser Gly Pro Ile Phe Phe Glu Asp
            580                 585                 590

Leu Asp Glu Thr Ala Tyr Asp Asn Asn Gln Trp Leu Gly Ala Asp Gln
        595                 600                 605

Thr Ile Asp Val Leu Gln Leu His Leu Gly Ala Asn Pro Pro Ala Asn
    610                 615                 620

Ala Pro Thr Asp Leu Thr Leu Gly Asn Glu Ser Ser Lys Tyr Gly Tyr
625                 630                 635                 640

Gln Gly Ser Trp Thr Leu Gln Trp Glu Pro Asp Pro Ala Asn Pro Pro
                645                 650                 655

Gln Asn Asn Ser Tyr Met Leu Lys Ala Ser Trp Thr Lys Thr Gly Tyr
            660                 665                 670

Asn Pro Gly Pro Glu Arg Val Ala Ser Leu Val Ser Asn Ser Leu Trp
        675                 680                 685
```

Gly Ser Ile Leu Asp Val Arg Ser Ala His Ser Ala Ile Gln Ala Ser
            690                 695                 700
Ile Asp Gly Arg Ala Tyr Cys Arg Gly Ile Trp Ile Ser Gly Ile Ser
705                 710                 715                 720
Asn Phe Phe Tyr His Asp Gln Asp Ala Leu Gly Gln Gly Tyr Arg His
                    725                 730                 735
Ile Ser Gly Gly Tyr Ser Ile Gly Ala Asn Ser Tyr Phe Gly Ser Ser
            740                 745                 750
Met Phe Gly Leu Ala Phe Thr Glu Thr Phe Gly Arg Ser Lys Asp Tyr
            755                 760                 765
Val Val Cys Arg Ser Asn Asp His Thr Cys Val Gly Ser Val Tyr Leu
770                 775                 780
Ser Thr Arg Gln Ala Leu Cys Gly Ser Cys Leu Phe Gly Asp Ala Phe
785                 790                 795                 800
Val Arg Ala Ser Tyr Gly Phe Gly Asn Gln His Met Lys Thr Ser Tyr
                    805                 810                 815
Thr Phe Ala Glu Glu Ser Asn Val Arg Trp Asp Asn Asn Cys Val Val
            820                 825                 830
Gly Glu Val Gly Ala Gly Leu Pro Ile Met Leu Ala Ala Ser Lys Leu
            835                 840                 845
Tyr Leu Asn Glu Leu Arg Pro Phe Val Gln Ala Glu Phe Ala Tyr Ala
850                 855                 860
Glu His Glu Ser Phe Thr Glu Arg Gly Asp Gln Ala Arg Glu Phe Lys
865                 870                 875                 880
Ser Gly His Leu Met Asn Leu Ser Ile Pro Val Gly Val Lys Phe Asp
                    885                 890                 895
Arg Cys Ser Ser Lys His Pro Asn Lys Tyr Ser Phe Met Gly Ala Tyr
            900                 905                 910
Ile Cys Asp Ala Tyr Arg Ser Ile Ser Gly Thr Glu Thr Thr Leu Leu
            915                 920                 925
Ser His Lys Glu Thr Trp Thr Thr Asp Ala Phe His Leu Ala Arg His
930                 935                 940
Gly Val Met Val Arg Gly Ser Met Tyr Ala Ser Leu Thr Gly Asn Ile
945                 950                 955                 960
Glu Val Tyr Gly His Gly Lys Tyr Glu Tyr Arg Asp Ala Ser Arg Gly
                    965                 970                 975
Tyr Gly Leu Ser Ile Gly Ser Lys Ile Arg Phe
            980                 985

<210> SEQ ID NO 45
<211> LENGTH: 2901
<212> TYPE: DNA
<213> ORGANISM: artificial sequence
<220> FEATURE:
<223> OTHER INFORMATION: synthetic polynucleotide

<400> SEQUENCE: 45
catatggcag atatttccat gcctccggga atttatgatg ggacaacatt gacggcgcca      60
tttccgtaca ctgtgatcgg agatccgcgc gggacaaagg ttacttcatc gggatcgctg     120
gagttgaaaa acctgacaa ttccattgcg actttacctc tgagttgttt tggtaatttg     180
ttggggaatt tcactattgc aggacgcggg cattcgttag tatttgagaa tattcgcaca     240
tctacaaatg gggcggcatt gagtaatcat gctccttctg gactgtttgt aattgaagct     300
tttgatgaac tgtctctgtt gaattgtaat tcattggtat ctgtagttcc tcaaacaggg     360

-continued

```
ggtacgacta cttctgttcc ttctaatggg acgatctatt cccgcacaga tctggttctg    420
cgcgatatca agaaggtttc tttctatagt aacttagttt ctggagatgg gggagctatt    480
gatgcacaaa gtttaatggt taacggaatt gaaaaactgt gtaccttcca agaaaatgta    540
gcgcagtccg atgggggagc gtgtcaggta acaaagacct tctctgctgt gggcaataag    600
gttcctttgt cttttttagg caatgttgct ggtaataagg ggggaggagt tgctgctgtc    660
aaagatggtc aggggcagg aggggcgact gatctgtcgg ttaattttgc caataatact    720
gctgtagaat ttgagggaaa tagtgctcgc attggtggag ggatctactc ggacggaaat    780
atttcctttt tagggaatgc aaagacagtt ttcctgagta acgtagcttc gcctatttat    840
gttgaccctg ctgctgcagg aggacagccg cctgcagata aagataacta tggagatgga    900
ggagccatct tctgcaaaaa tgatactaac attggtgaag tctctttcaa agacgagggt    960
gttgttttct ttagtaaaaa tattgccgca ggaaagggg gcgctatta tgctaagaaa    1020 ctgacaattt ctgactgtgg tccggtccag tttctgggta atgtcgcgaa tgacgggggc    1080
gctatttatc tggtagatca gggggaactg agtctgtctg ctgatcgcgg agatattatt    1140
tttgatggaa atttaaagcg catggctacg caaggcgctg ccaccgtcca tgatgtaatg    1200
gttgcatcga atgctatctc tatggctaca ggggggcaaa tcacaacatt acgcgctaag    1260
gaaggtcgcc gcattctgtt taatgaccct attgaaatgg cgaatggaca acctgtaatt    1320
caaactctga cagtaaacga gggcgaagga tacgggggg acattgtttt tgctaaaggt    1380
gataatgttt tgtactcaag tattgagctc agtcagggac gcattattct gcgcgagcaa    1440
acaaaattat tggttaactc cctgactcag actggaggga gtgtacacat ggaagggggg    1500
agtacactgg actttgcagt aacaacgcca ccagctgcta attcgatggc tctgactaat    1560
gtacacttct ccttagcttc tttactgaaa aataatgggg ttacaaatcc tccaacgaat    1620
cctccagtac aggtttctag tccagctgta attggtaata cagctgctgg tactgttacg    1680
atttctggtc cgatcttttt tgaagattta gatgaaactg cttacgataa taatcagtgg    1740
ttaggtgcgg atcaaactat tgatgtgctg cagttgcatt taggagcgaa tcctccggct    1800
aacgctccaa ctgatttgac tttagggaac gaaagttcta aatatgggta tcaaggaagt    1860
tggacactgc aatgggaacc agatcctgcg aatcctccac agaacaatag ctacatgttg    1920
aaggcaagct ggactaaaac aggttataat cctggtccgg agcgcgtagc ttctctggtc    1980
tctaatagtc ccatgggttc catttagat gtgcgttccg cgcattctgc gattcaagca    2040
agtattgatg gacgcgctta ttgtcggggt atttggattt ctgggatttc gaacttttc    2100 tatcatgatc aggatgcttt aggacagggg tatcgtcata ttagtggggg atattcgatt    2160
ggagcaaact cttatttcgg gtcttctatg tttggactgg cttttactga aacttttggt    2220
cgctccaaag attatgtggt ctgtcgctct aacgatcaca cttgtgtagg ctctgtttac    2280
ttatccactc gccaagcgtt atgcgggtcc tgtttatttg gagatgcttt tgttcgggcg    2340
agttacggat ttggaaatca gcacatgaag acctcttata catttgctga agagagtaat    2400
gtgcgttggg ataataactg tgtagtggga gaagttggag ctgggctgcc tatcatgctg    2460
gctgcatcta gctgtatct gaatgagttg cgtccgttcg tgcaagcaga gtttgcttat    2520
gcagagcatg aatctttac agagcgcggg gatcaggctc gcgagtttaa gagtgggcat    2580
ctgatgaatc tgtctattcc agttggggtg aagtttgatc gctgctctag taaacatcct    2640
aacaagtata gttttatggg agcttatatc tgtgatgctt accggtccat ttctggaacg    2700
gagacaacac tgctgtctca taaagagact tggacaacag atgctttcca tttagcacgt    2760
```

```
catggagtta tggtccgcgg atctatgtat gcttctttaa caggtaatat tgaagtctat   2820
gggcatggaa aatatgaata ccgcgatgcc tctcgcgggt atggtttaag tattggaagt   2880
aaaatccgct tctaaggatc c                                             2901
```

<210> SEQ ID NO 46
<211> LENGTH: 963
<212> TYPE: PRT
<213> ORGANISM: artificial sequence
<220> FEATURE:
<223> OTHER INFORMATION: synthetic peptide

<400> SEQUENCE: 46

```
Met Ala Asp Ile Ser Met Pro Pro Gly Ile Tyr Asp Gly Thr Thr Leu
1               5                   10                  15

Thr Ala Pro Phe Pro Tyr Thr Val Ile Gly Asp Pro Arg Gly Thr Lys
            20                  25                  30

Val Thr Ser Ser Gly Ser Leu Glu Leu Lys Asn Leu Asp Asn Ser Ile
        35                  40                  45

Ala Thr Leu Pro Leu Ser Cys Phe Gly Asn Leu Gly Asn Phe Thr
    50                  55                  60

Ile Ala Gly Arg Gly His Ser Leu Val Phe Glu Asn Ile Arg Thr Ser
65                  70                  75                  80

Thr Asn Gly Ala Ala Leu Ser Asn His Ala Pro Ser Gly Leu Phe Val
                85                  90                  95

Ile Glu Ala Phe Asp Glu Leu Ser Leu Leu Asn Cys Asn Ser Leu Val
            100                 105                 110

Ser Val Val Pro Gln Thr Gly Gly Thr Thr Thr Ser Val Pro Ser Asn
        115                 120                 125

Gly Thr Ile Tyr Ser Arg Thr Asp Leu Val Leu Arg Asp Ile Lys Lys
    130                 135                 140

Val Ser Phe Tyr Ser Asn Leu Val Ser Gly Asp Gly Ala Ile Asp
145                 150                 155                 160

Ala Gln Ser Leu Met Val Asn Gly Ile Glu Lys Leu Cys Thr Phe Gln
                165                 170                 175

Glu Asn Val Ala Gln Ser Asp Gly Gly Ala Cys Gln Val Thr Lys Thr
            180                 185                 190

Phe Ser Ala Val Gly Asn Lys Val Pro Leu Ser Phe Leu Gly Asn Val
        195                 200                 205

Ala Gly Asn Lys Gly Gly Val Ala Ala Val Lys Asp Gly Gln Gly
    210                 215                 220

Ala Gly Gly Ala Thr Asp Leu Ser Val Asn Phe Ala Asn Asn Thr Ala
225                 230                 235                 240

Val Glu Phe Glu Gly Asn Ser Ala Arg Ile Gly Gly Gly Ile Tyr Ser
                245                 250                 255

Asp Gly Asn Ile Ser Phe Leu Gly Asn Ala Lys Thr Val Phe Leu Ser
            260                 265                 270

Asn Val Ala Ser Pro Ile Tyr Val Asp Pro Ala Ala Ala Gly Gly Gln
        275                 280                 285

Pro Pro Ala Asp Lys Asp Asn Tyr Gly Asp Gly Ala Ile Phe Cys
    290                 295                 300

Lys Asn Asp Thr Asn Ile Gly Glu Val Ser Phe Lys Asp Glu Gly Val
305                 310                 315                 320

Val Phe Phe Ser Lys Asn Ile Ala Ala Gly Lys Gly Gly Ala Ile Tyr
                325                 330                 335
```

```
Ala Lys Lys Leu Thr Ile Ser Asp Cys Gly Pro Val Gln Phe Leu Gly
            340                 345                 350

Asn Val Ala Asn Asp Gly Gly Ala Ile Tyr Leu Val Asp Gln Gly Glu
            355                 360                 365

Leu Ser Leu Ser Ala Asp Arg Gly Asp Ile Ile Phe Asp Gly Asn Leu
            370                 375                 380

Lys Arg Met Ala Thr Gln Gly Ala Ala Thr Val His Asp Val Met Val
385                 390                 395                 400

Ala Ser Asn Ala Ile Ser Met Ala Thr Gly Gly Gln Ile Thr Thr Leu
            405                 410                 415

Arg Ala Lys Glu Gly Arg Arg Ile Leu Phe Asn Asp Pro Ile Glu Met
            420                 425                 430

Ala Asn Gly Gln Pro Val Ile Gln Thr Leu Thr Val Asn Glu Gly Glu
            435                 440                 445

Gly Tyr Thr Gly Asp Ile Val Phe Ala Lys Gly Asp Asn Val Leu Tyr
            450                 455                 460

Ser Ser Ile Glu Leu Ser Gln Gly Arg Ile Ile Leu Arg Glu Gln Thr
465                 470                 475                 480

Lys Leu Leu Val Asn Ser Leu Thr Gln Thr Gly Gly Ser Val His Met
            485                 490                 495

Glu Gly Gly Ser Thr Leu Asp Phe Ala Val Thr Thr Pro Pro Ala Ala
            500                 505                 510

Asn Ser Met Ala Leu Thr Asn Val His Phe Ser Leu Ala Ser Leu Leu
            515                 520                 525

Lys Asn Asn Gly Val Thr Asn Pro Pro Thr Asn Pro Val Gln Val
            530                 535                 540

Ser Ser Pro Ala Val Ile Gly Asn Thr Ala Ala Gly Thr Val Thr Ile
545                 550                 555                 560

Ser Gly Pro Ile Phe Phe Glu Asp Leu Asp Glu Thr Ala Tyr Asp Asn
                565                 570                 575

Asn Gln Trp Leu Gly Ala Asp Gln Thr Ile Asp Val Leu Gln Leu His
            580                 585                 590

Leu Gly Ala Asn Pro Pro Ala Asn Ala Pro Thr Asp Leu Thr Leu Gly
            595                 600                 605

Asn Glu Ser Ser Lys Tyr Gly Tyr Gln Gly Ser Trp Thr Leu Gln Trp
            610                 615                 620

Glu Pro Asp Pro Ala Asn Pro Pro Gln Asn Asn Ser Tyr Met Leu Lys
625                 630                 635                 640

Ala Ser Trp Thr Lys Thr Gly Tyr Asn Pro Gly Pro Glu Arg Val Ala
            645                 650                 655

Ser Leu Val Ser Asn Ser Pro Met Gly Ser Ile Leu Asp Val Arg Ser
            660                 665                 670

Ala His Ser Ala Ile Gln Ala Ser Ile Asp Gly Arg Ala Tyr Cys Arg
            675                 680                 685

Gly Ile Trp Ile Ser Gly Ile Ser Asn Phe Phe Tyr His Asp Gln Asp
            690                 695                 700

Ala Leu Gly Gln Gly Tyr Arg His Ile Ser Gly Gly Tyr Ser Ile Gly
705                 710                 715                 720

Ala Asn Ser Tyr Phe Gly Ser Ser Met Phe Gly Leu Ala Phe Thr Glu
            725                 730                 735

Thr Phe Gly Arg Ser Lys Asp Tyr Val Val Cys Arg Ser Asn Asp His
            740                 745                 750
```

```
Thr Cys Val Gly Ser Val Tyr Leu Ser Thr Arg Gln Ala Leu Cys Gly
            755                 760                 765
Ser Cys Leu Phe Gly Asp Ala Phe Val Arg Ala Ser Tyr Gly Phe Gly
        770                 775                 780
Asn Gln His Met Lys Thr Ser Tyr Thr Phe Ala Glu Glu Ser Asn Val
785                 790                 795                 800
Arg Trp Asp Asn Asn Cys Val Val Gly Glu Val Gly Ala Gly Leu Pro
                805                 810                 815
Ile Met Leu Ala Ala Ser Lys Leu Tyr Leu Asn Glu Leu Arg Pro Phe
            820                 825                 830
Val Gln Ala Glu Phe Ala Tyr Ala Glu His Glu Ser Phe Thr Glu Arg
        835                 840                 845
Gly Asp Gln Ala Arg Glu Phe Lys Ser Gly His Leu Met Asn Leu Ser
    850                 855                 860
Ile Pro Val Gly Val Lys Phe Asp Arg Cys Ser Ser Lys His Pro Asn
865                 870                 875                 880
Lys Tyr Ser Phe Met Gly Ala Tyr Ile Cys Asp Ala Tyr Arg Ser Ile
                885                 890                 895
Ser Gly Thr Glu Thr Thr Leu Leu Ser His Lys Glu Thr Trp Thr Thr
            900                 905                 910
Asp Ala Phe His Leu Ala Arg His Gly Val Met Val Arg Gly Ser Met
        915                 920                 925
Tyr Ala Ser Leu Thr Gly Asn Ile Glu Val Tyr Gly His Gly Lys Tyr
    930                 935                 940
Glu Tyr Arg Asp Ala Ser Arg Gly Tyr Gly Leu Ser Ile Gly Ser Lys
945                 950                 955                 960
Ile Arg Phe
```

<210> SEQ ID NO 47
<211> LENGTH: 2379
<212> TYPE: DNA
<213> ORGANISM: artificial sequence
<220> FEATURE:
<223> OTHER INFORMATION: synthetic polynucleotide

<400> SEQUENCE: 47

```
catatggcag atatttccat gcctccggga atttatgatg ggacaacatt gacggcgcca      60
tttccgtaca ctgtgatcgg agatccgcgc gggacaaagg ttacttcatc gggatcgctg     120
gagttgaaaa acctggacaa ttccattgcg actttacctc tgagttgttt tggtaatttg     180
ttggggaatt tcactattgc aggacgcggg cattcgttag tatttgagaa tattcgcaca     240
tctacaaatg gggcggcatt gagtaatcat gctccttctg gactgtttgt aattgaagct     300
tttgatgaac tgtctctgtt gaattgtaat tcattggtat ctgtagttcc tcaaacaggg     360
ggtacgacta cttctgttcc ttctaatggg acgatctatt cccgcacaga tctggttctg     420
cgcgatatca agaaggtttc tttctatagt aacttagttt ctggagatgg gggagctatt     480
gatgcacaaa gtttaatggt taacggaatt gaaaaactgt gtaccttcca agaaaatgta     540
gcgcagtccg atgggggagc gtgtcaggta acaaagacct ctctgctgt gggcaataag     600
gttccttttgt cttttttagg caatgttgct ggtaataagg ggggaggagt tgctgctgtc     660
aaagatggtc agggggcagg agggccgact gatctgtcgg ttaattttgc caataatact     720
gctgtagaat ttgagggaaa tagtgctcgc attggtggag ggatctactc ggacggaaat     780
atttcctttt tagggaatgc aaagacagtt ttcctgagta acgtagcttc gcctatttat     840
```

-continued

```
gttgaccctg ctgctgcagg aggacagccg cctgcagata agataaacta tggagatgga    900
ggagccatct tctgcaaaaa tgatactaac attggtgaag tctcttttcaa agacgagggt   960
gttgttttct ttagtaaaaa tattgccgca ggaaagggg gcgctattta tgctaagaaa   1020
ctgacaattt ctgactgtgg tccggtccag tttctgggta atgtcgcgaa tgacgggggc   1080
gctatttatc tggtagatca gggggaactg agtctgtctg ctgatcgcgg agatattatt   1140
tttgatggaa atttaaagcg catggctacg caaggcgctg ccaccgtcca tgatgtaatg   1200
gttgcatcga atgctatctc tatggctaca ggggggcaaa tcacaacatt acgcgctaag   1260
gaaggtcgcc gcattctgtt taatgaccct attgaaatgg cgaatggaca acctgtaatt   1320
caaactctga cagtaaacga gggcgaagga tacgggggg acattgtttt tgctaaaggt   1380
gataatgttt tgtactcaag tattgagctc agtcagacag gttataatcc tggtccggag   1440
cgcgtagctt ctctggtctc taatagtccc atgggttcca ttttagatgt gcgttccgcg   1500
cattctgcga ttcaagcaag tattgatgga cgcgcttatt gtcggggtat ttggatttct   1560
gggatttcga acttttctcta tcatgatcag gatgctttag acaggggta tcgtcatatt   1620
agtgggggat attcgattgg agcaaaactct tatttcgggt cttctatgtt tggactggct   1680
tttactgaaa cttttggtcg ctccaaagat tatgtggtct gtcgctctaa cgatcacact   1740
tgtgtaggct ctgtttactt atccactcgc caagcgttat gcgggtcctg tttatttgga   1800
gatgcttttg ttcgggcgag ttacggattt ggaaatcagc acatgaagac ctcttataca   1860
tttgctgaag agagtaatgt gcgttgggat aataactgtg tagtgggaga agttggagct   1920
gggctgccta tcatgctggc tgcatctaag ctgtatctga atgagttgcg tccgttcgtg   1980
caagcagagt ttgcttatgc agagcatgaa tcttttacag agcgcgggga tcaggctcgc   2040
gagtttaaga gtgggcatct gatgaatctg tctattccag ttggggtgaa gtttgatcgc   2100
tgctctagta acatcctaa caagtatagt tttatgggag cttatatctg tgatgcttac   2160
cggtccattc tggaacgga gacaacactg ctgtctcata aagagacttg gacaacagat   2220
gctttccatt tagcacgtca tggagttatg gtccgcggat ctatgtatgc ttcttttaaca   2280
ggtaatattg aagtctatgg gcatggaaaa tatgaatacc gcgatgcctc tcgcgggtat   2340
ggtttaagta ttggaagtaa aatccgcttc taaggatcc                          2379
```

<210> SEQ ID NO 48
<211> LENGTH: 789
<212> TYPE: PRT
<213> ORGANISM: artificial sequence
<220> FEATURE:
<223> OTHER INFORMATION: synthetic peptide

<400> SEQUENCE: 48

```
Met Ala Asp Ile Ser Met Pro Pro Gly Ile Tyr Asp Gly Thr Thr Leu
1               5                   10                  15

Thr Ala Pro Phe Pro Tyr Thr Val Ile Gly Asp Pro Arg Gly Thr Lys
            20                  25                  30

Val Thr Ser Ser Gly Ser Leu Glu Leu Lys Asn Leu Asp Asn Ser Ile
        35                  40                  45

Ala Thr Leu Pro Leu Ser Cys Phe Gly Asn Leu Gly Asn Phe Thr
    50                  55                  60

Ile Ala Gly Arg Gly His Ser Leu Val Phe Glu Asn Ile Arg Thr Ser
65                  70                  75                  80

Thr Asn Gly Ala Ala Leu Ser Asn His Ala Pro Ser Gly Leu Phe Val
                85                  90                  95
```

Ile Glu Ala Phe Asp Glu Leu Ser Leu Leu Asn Cys Asn Ser Leu Val
            100                 105                 110

Ser Val Val Pro Gln Thr Gly Gly Thr Thr Thr Ser Val Pro Ser Asn
            115                 120                 125

Gly Thr Ile Tyr Ser Arg Thr Asp Leu Val Leu Arg Asp Ile Lys Lys
130                 135                 140

Val Ser Phe Tyr Ser Asn Leu Val Ser Gly Asp Gly Ala Ile Asp
145                 150                 155                 160

Ala Gln Ser Leu Met Val Asn Gly Ile Glu Lys Leu Cys Thr Phe Gln
            165                 170                 175

Glu Asn Val Ala Gln Ser Asp Gly Gly Ala Cys Gln Val Thr Lys Thr
            180                 185                 190

Phe Ser Ala Val Gly Asn Lys Val Pro Leu Ser Phe Leu Gly Asn Val
            195                 200                 205

Ala Gly Asn Lys Gly Gly Val Ala Ala Val Lys Asp Gly Gln Gly
210                 215                 220

Ala Gly Gly Ala Thr Asp Leu Ser Val Asn Phe Ala Asn Asn Thr Ala
225                 230                 235                 240

Val Glu Phe Glu Gly Asn Ser Ala Arg Ile Gly Gly Gly Ile Tyr Ser
            245                 250                 255

Asp Gly Asn Ile Ser Phe Leu Gly Asn Ala Lys Thr Val Phe Leu Ser
            260                 265                 270

Asn Val Ala Ser Pro Ile Tyr Val Asp Pro Ala Ala Gly Gly Gln
            275                 280                 285

Pro Pro Ala Asp Lys Asp Asn Tyr Gly Asp Gly Ala Ile Phe Cys
            290                 295                 300

Lys Asn Asp Thr Asn Ile Gly Glu Val Ser Phe Lys Asp Glu Gly Val
305                 310                 315                 320

Val Phe Phe Ser Lys Asn Ile Ala Ala Gly Lys Gly Ala Ile Tyr
            325                 330                 335

Ala Lys Lys Leu Thr Ile Ser Asp Cys Gly Pro Val Gln Phe Leu Gly
            340                 345                 350

Asn Val Ala Asn Asp Gly Gly Ala Ile Tyr Leu Val Asp Gln Gly Glu
            355                 360                 365

Leu Ser Leu Ser Ala Asp Arg Gly Asp Ile Ile Phe Asp Gly Asn Leu
            370                 375                 380

Lys Arg Met Ala Thr Gln Gly Ala Ala Thr Val His Asp Val Met Val
385                 390                 395                 400

Ala Ser Asn Ala Ile Ser Met Ala Thr Gly Gln Ile Thr Thr Leu
            405                 410                 415

Arg Ala Lys Glu Gly Arg Arg Ile Leu Phe Asn Asp Pro Ile Glu Met
            420                 425                 430

Ala Asn Gly Gln Pro Val Ile Gln Thr Leu Thr Val Asn Glu Gly Glu
            435                 440                 445

Gly Tyr Thr Gly Asp Ile Val Phe Ala Lys Gly Asp Asn Val Leu Tyr
450                 455                 460

Ser Ser Ile Glu Leu Ser Gln Thr Gly Tyr Asn Pro Gly Pro Glu Arg
465                 470                 475                 480

Val Ala Ser Leu Val Ser Asn Ser Pro Met Gly Ser Ile Leu Asp Val
            485                 490                 495

Arg Ser Ala His Ser Ala Ile Gln Ala Ser Ile Asp Gly Arg Ala Tyr
            500                 505                 510

Cys Arg Gly Ile Trp Ile Ser Gly Ile Ser Asn Phe Phe Tyr His Asp
                515                 520                 525

Gln Asp Ala Leu Gly Gln Gly Tyr Arg His Ile Ser Gly Gly Tyr Ser
530                 535                 540

Ile Gly Ala Asn Ser Tyr Phe Gly Ser Ser Met Phe Gly Leu Ala Phe
545                 550                 555                 560

Thr Glu Thr Phe Gly Arg Ser Lys Asp Tyr Val Val Cys Arg Ser Asn
                565                 570                 575

Asp His Thr Cys Val Gly Ser Val Tyr Leu Ser Thr Arg Gln Ala Leu
            580                 585                 590

Cys Gly Ser Cys Leu Phe Gly Asp Ala Phe Val Arg Ala Ser Tyr Gly
        595                 600                 605

Phe Gly Asn Gln His Met Lys Thr Ser Tyr Thr Phe Ala Glu Glu Ser
    610                 615                 620

Asn Val Arg Trp Asp Asn Asn Cys Val Val Gly Glu Val Gly Ala Gly
625                 630                 635                 640

Leu Pro Ile Met Leu Ala Ala Ser Lys Leu Tyr Leu Asn Glu Leu Arg
                645                 650                 655

Pro Phe Val Gln Ala Glu Phe Ala Tyr Ala Glu His Glu Ser Phe Thr
                660                 665                 670

Glu Arg Gly Asp Gln Ala Arg Glu Phe Lys Ser Gly His Leu Met Asn
                675                 680                 685

Leu Ser Ile Pro Val Gly Val Lys Phe Asp Arg Cys Ser Ser Lys His
            690                 695                 700

Pro Asn Lys Tyr Ser Phe Met Gly Ala Tyr Ile Cys Asp Ala Tyr Arg
705                 710                 715                 720

Ser Ile Ser Gly Thr Glu Thr Thr Leu Leu Ser His Lys Glu Thr Trp
                725                 730                 735

Thr Thr Asp Ala Phe His Leu Ala Arg His Gly Val Met Val Arg Gly
                740                 745                 750

Ser Met Tyr Ala Ser Leu Thr Gly Asn Ile Glu Val Tyr Gly His Gly
                755                 760                 765

Lys Tyr Glu Tyr Arg Asp Ala Ser Arg Gly Tyr Gly Leu Ser Ile Gly
770                 775                 780

Ser Lys Ile Arg Phe
785

<210> SEQ ID NO 49
<211> LENGTH: 2943
<212> TYPE: DNA
<213> ORGANISM: Chlamydia muridarum

<400> SEQUENCE: 49
atgccttttt ctttgagatc tacatcattt tgttttttag cctgtttatg ttcttattca 60
tatggattag cgagttctcc tcaggtactg acccccaatg taatcatccc ttttaaagga 120
gacgatatct atttaaatgg ggattgcgtt tttgcaagta tctatgcagg agcagagcag 180
ggatcgatta tttctgctaa tgggcaaaat ctaacaatcg taggacaaaa ccacacttta 240
tcatttacgg attcccaagg gccagccctt caaaattgtg ctttcatttc agcagaagaa 300
aagatctctc taagagattt ttcgagcctt ttgttttcga aaaatgtttc ttgcggggag 360
aaaggaatga tttcagggaa aaccgtaagc atttcagggg gagatagtat agtttttaag 420
gataactctg ttggttattc ttcattaccc tctgtggggc aaactcctac aactccaatt 480
gttggcgatg ttttaaaggg atccattttt tgtgtggaga caggtttaga gatttctgga 540

```
gtcaaaaaag agcttgtttt cgataacact gctgggaatt ttggggcagt attctgtagt    600
cgtgccgctc aaggagacac gactttcaca gtgaaagact gtaagggtaa aattcttttt    660
caagataacg taggctcttg tggaggcggc gtaatttata aggggaagt acttttccaa     720
gataatgaag gagaaatgct tttccgagga aattcagctc atgatgattt gggaattctc    780
gatgctaacc cacagcctcc tactgaagta ggaggtgggg gtggtgtcat ttgtacccca    840
gagaaaacgg taacttttaa ggggaataaa gggcctatta cctttgatta taattttgca    900
aaaggtcgag gagggcaat ccaatcacag accttttctt tggtagctga tagtgctgtt     960
gttttcagta ataatacagc tgagaaaggt ggaggcgcca tttatgctct tgaggttaac   1020
gtgagcacaa atggaggatc tattcttttt gagggaaata gagcttctga gggtggggct   1080
atctgtgtga gcgagccgat cgctgctaat aatggagggc tcactttaca tgctgctgat   1140
ggggacatta ttttctcgaa aaatatgacg agtgatcgtc ctggagaacg cagtgcaatc   1200
cggatcttag atagtggaac aaatgtctct ttaaatgctt caggggcatc gaagatgatt   1260
ttttatgatc ctgttgtgca aaataatccc gcaactccac ctactggtac gtctggggaa   1320
attaagatca atgagtccgg gagtggatcg gttgtgttta cagcagagac tttgactcct   1380
tcggaaaaat tgaatgttat caacgctact tctaatttcc caggaaattt aacggtatct   1440
agtggagaat tagttgttac gaagggagcg acactaacag taggaaatat cacagcaaca   1500
tcaggacgag taactttagg atcaggggct tcgttatccg ccgttgcagg tactgctggc   1560
acttgtacgg tgtctaaatt agggattgat ttagagtcct tcctagtccc tacttatgag   1620
actgcaaagt tgggtgcgga tacaacagta gcggtgaata acaatcctac tttagaccta   1680
gtaatggcga atgagacgga gatgtatgat aatccgcttt ttatgaacgc tgttacaatc   1740
ccttttgtga cattggtttc tctccaaact actggtggtg ttactacaag tgccgttact   1800
ctgaataatg cagatactgc gcattatggg tatcaaggat cttggtctgc tgattggaga   1860
aggcctcctt tagctcctga tcctagcggc atgacacctc ttgataaaag taatacattg   1920
tatgtgacat ggaggccatc ctctaactac ggtgtgtata agttagatcc tcaaagaagg   1980
ggtgagttgg tcccgaattc tttatgggta tctggatctg ccttaagaac ctttacaaat   2040
ggtttgaagg aacattacgt ctctagagat gtcggattta ttgcatctgt acaagcctta   2100
ggggattatg ttctgaatta taagcagggt aaccgagatg gctttctagc taggtacgga   2160
ggttttcaag ctgttgcggc ttctcactat gaaaatgggg ggatctttgg ggtagctttc   2220
ggtcaacttt atggtcaaac taagagccgt ttgtacgatt ctaaggatgc tggaaacatt   2280
acgattttgt cctgttttgg acgaagttat atcgatgtta aaggaacaga accgttgtg    2340
tattgggaga cggcttatgg atattctgtt catagaatgc atacgcagta tttcaatgga   2400
aaaacgaata agtttgatca ttcgaaatgt cgttggcaca acaatagtta ttatgcattt   2460
gtaggtgcag aacataattt cttggagtat tgtattccta ctcgtcaatt agctagggat   2520
tatgatctta caggatttat gcgtttcgaa atgtcgggag gttggtcgag tggtgcaaaa   2580
gaaacgggtg ctttacctag acattttgat cgaggaacag gcataatat gtctcttcca    2640
ataggggttg tagctcatgc tgtttctaat ggacgaagat ctcctccatc taaattgacg   2700
attaacatgg gatatagacc agacatttgg cgggtgactc cacattgcaa tatgaaaatt   2760
attgcaaacg gagttaagac tcctatacag ggatctcctc tagctcggca cgccttcttt   2820
ttagaagttc atgatactct gtatgttcgt catttgggca gagcctatat gaattattct   2880
```

```
ttagatgctc gtcatcgaca aactacgcat ttcgtatctt taggattgaa tcgtatcttt    2940
taa                                                                  2943
```

<210> SEQ ID NO 50
<211> LENGTH: 980
<212> TYPE: PRT
<213> ORGANISM: Chlamydia muridarum

<400> SEQUENCE: 50

```
Met Pro Phe Ser Leu Arg Ser Thr Ser Phe Cys Phe Leu Ala Cys Leu
1               5                   10                  15

Cys Ser Tyr Ser Tyr Gly Leu Ala Ser Ser Pro Gln Val Leu Thr Pro
            20                  25                  30

Asn Val Ile Ile Pro Phe Lys Gly Asp Asp Ile Tyr Leu Asn Gly Asp
        35                  40                  45

Cys Val Phe Ala Ser Ile Tyr Ala Gly Ala Glu Gln Gly Ser Ile Ile
    50                  55                  60

Ser Ala Asn Gly Gln Asn Leu Thr Ile Val Gly Gln Asn His Thr Leu
65                  70                  75                  80

Ser Phe Thr Asp Ser Gln Gly Pro Ala Leu Gln Asn Cys Ala Phe Ile
                85                  90                  95

Ser Ala Glu Glu Lys Ile Ser Leu Arg Asp Phe Ser Ser Leu Leu Phe
            100                 105                 110

Ser Lys Asn Val Ser Cys Gly Glu Lys Gly Met Ile Ser Gly Lys Thr
        115                 120                 125

Val Ser Ile Ser Gly Gly Asp Ser Ile Val Phe Lys Asp Asn Ser Val
    130                 135                 140

Gly Tyr Ser Ser Leu Pro Ser Val Gly Gln Thr Pro Thr Thr Pro Ile
145                 150                 155                 160

Val Gly Asp Val Leu Lys Gly Ser Ile Phe Cys Val Glu Thr Gly Leu
                165                 170                 175

Glu Ile Ser Gly Val Lys Lys Glu Leu Val Phe Asp Asn Thr Ala Gly
            180                 185                 190

Asn Phe Gly Ala Val Phe Cys Ser Arg Ala Ala Gln Gly Asp Thr Thr
        195                 200                 205

Phe Thr Val Lys Asp Cys Lys Gly Lys Ile Leu Phe Gln Asp Asn Val
    210                 215                 220

Gly Ser Cys Gly Gly Gly Val Ile Tyr Lys Gly Glu Val Leu Phe Gln
225                 230                 235                 240

Asp Asn Glu Gly Glu Met Leu Phe Arg Gly Asn Ser Ala His Asp Asp
                245                 250                 255

Leu Gly Ile Leu Asp Ala Asn Pro Gln Pro Thr Glu Val Gly Gly
            260                 265                 270

Gly Gly Gly Val Ile Cys Thr Pro Glu Lys Thr Val Thr Phe Lys Gly
        275                 280                 285

Asn Lys Gly Pro Ile Thr Phe Asp Tyr Asn Phe Ala Lys Gly Arg Gly
    290                 295                 300

Gly Ala Ile Gln Ser Gln Thr Phe Ser Leu Val Ala Asp Ser Ala Val
305                 310                 315                 320

Val Phe Ser Asn Asn Thr Ala Glu Lys Gly Gly Ala Ile Tyr Ala
                325                 330                 335

Leu Glu Val Asn Val Ser Thr Asn Gly Gly Ser Ile Leu Phe Glu Gly
            340                 345                 350

Asn Arg Ala Ser Glu Gly Gly Ala Ile Cys Val Ser Glu Pro Ile Ala
```

-continued

```
              355                 360                 365
Ala Asn Asn Gly Gly Leu Thr Leu His Ala Ala Asp Gly Asp Ile Ile
370                 375                 380
Phe Ser Lys Asn Met Thr Ser Asp Arg Pro Gly Glu Arg Ser Ala Ile
385                 390                 395                 400
Arg Ile Leu Asp Ser Gly Thr Asn Val Ser Leu Asn Ala Ser Gly Ala
                405                 410                 415
Ser Lys Met Ile Phe Tyr Asp Pro Val Val Gln Asn Asn Pro Ala Thr
                420                 425                 430
Pro Pro Thr Gly Thr Ser Gly Glu Ile Lys Ile Asn Glu Ser Gly Ser
                435                 440                 445
Gly Ser Val Val Phe Thr Ala Glu Thr Leu Thr Pro Ser Glu Lys Leu
        450                 455                 460
Asn Val Ile Asn Ala Thr Ser Asn Phe Pro Gly Asn Leu Thr Val Ser
465                 470                 475                 480
Ser Gly Glu Leu Val Val Thr Lys Gly Ala Thr Leu Thr Val Gly Asn
                485                 490                 495
Ile Thr Ala Thr Ser Gly Arg Val Thr Leu Gly Ser Gly Ala Ser Leu
                500                 505                 510
Ser Ala Val Ala Gly Thr Ala Gly Thr Cys Thr Val Ser Lys Leu Gly
                515                 520                 525
Ile Asp Leu Glu Ser Phe Leu Val Pro Thr Tyr Glu Thr Ala Lys Leu
                530                 535                 540
Gly Ala Asp Thr Thr Val Ala Val Asn Asn Pro Thr Leu Asp Leu
545                 550                 555                 560
Val Met Ala Asn Glu Thr Glu Met Tyr Asp Asn Pro Leu Phe Met Asn
                565                 570                 575
Ala Val Thr Ile Pro Phe Val Thr Leu Val Ser Leu Gln Thr Thr Gly
                580                 585                 590
Gly Val Thr Thr Ser Ala Val Thr Leu Asn Asn Ala Asp Thr Ala His
                595                 600                 605
Tyr Gly Tyr Gln Gly Ser Trp Ser Ala Asp Trp Arg Arg Pro Leu
        610                 615                 620
Ala Pro Asp Pro Ser Gly Met Thr Pro Leu Asp Lys Ser Asn Thr Leu
625                 630                 635                 640
Tyr Val Thr Trp Arg Pro Ser Ser Asn Tyr Gly Val Tyr Lys Leu Asp
                645                 650                 655
Pro Gln Arg Arg Gly Glu Leu Val Pro Asn Ser Leu Trp Val Ser Gly
                660                 665                 670
Ser Ala Leu Arg Thr Phe Thr Asn Gly Leu Lys Glu His Tyr Val Ser
                675                 680                 685
Arg Asp Val Gly Phe Ile Ala Ser Val Gln Ala Leu Gly Asp Tyr Val
        690                 695                 700
Leu Asn Tyr Lys Gln Gly Asn Arg Asp Gly Phe Leu Ala Arg Tyr Gly
705                 710                 715                 720
Gly Phe Gln Ala Val Ala Ala Ser His Tyr Glu Asn Gly Gly Ile Phe
                725                 730                 735
Gly Val Ala Phe Gly Gln Leu Tyr Gly Gln Thr Lys Ser Arg Leu Tyr
                740                 745                 750
Asp Ser Lys Asp Ala Gly Asn Ile Thr Ile Leu Ser Cys Phe Gly Arg
                755                 760                 765
Ser Tyr Ile Asp Val Lys Gly Thr Glu Thr Val Val Tyr Trp Glu Thr
        770                 775                 780
```

```
Ala Tyr Gly Tyr Ser Val His Arg Met His Thr Gln Tyr Phe Asn Gly
785                 790                 795                 800

Lys Thr Asn Lys Phe Asp His Ser Lys Cys Arg Trp His Asn Asn Ser
            805                 810                 815

Tyr Tyr Ala Phe Val Gly Ala Glu His Asn Phe Leu Glu Tyr Cys Ile
        820                 825                 830

Pro Thr Arg Gln Leu Ala Arg Asp Tyr Asp Leu Thr Gly Phe Met Arg
    835                 840                 845

Phe Glu Met Ser Gly Gly Trp Ser Ser Gly Ala Lys Glu Thr Gly Ala
850                 855                 860

Leu Pro Arg His Phe Asp Arg Gly Thr Gly His Asn Met Ser Leu Pro
865                 870                 875                 880

Ile Gly Val Val Ala His Ala Val Ser Asn Gly Arg Arg Ser Pro Pro
            885                 890                 895

Ser Lys Leu Thr Ile Asn Met Gly Tyr Arg Pro Asp Ile Trp Arg Val
        900                 905                 910

Thr Pro His Cys Asn Met Lys Ile Ile Ala Asn Gly Val Lys Thr Pro
    915                 920                 925

Ile Gln Gly Ser Pro Leu Ala Arg His Ala Phe Phe Leu Glu Val His
930                 935                 940

Asp Thr Leu Tyr Val Arg His Leu Gly Arg Ala Tyr Met Asn Tyr Ser
945                 950                 955                 960

Leu Asp Ala Arg His Arg Gln Thr Thr His Phe Val Ser Leu Gly Leu
            965                 970                 975

Asn Arg Ile Phe
            980

<210> SEQ ID NO 51
<211> LENGTH: 2886
<212> TYPE: DNA
<213> ORGANISM: artificial sequence
<220> FEATURE:
<223> OTHER INFORMATION: synthetic polynucleotide

<400> SEQUENCE: 51
catatgagtt ctcctcaggt actgaccccg aatgtaatca tccctttaa aggagacgat      60 atctatttaa atggggattg cgttttgca agtatctatg caggagcaga gcagggatcg    120
attatttctg ctaatgggca aaatctgaca atcgtaggac aaaaccacac tttatcattt    180
acggattccc aagggccagc cctgcaaaat tgtgctttca tttcagcaga agaaaagatc    240
tctctgcgcg atttttcgag cctgttgttt tcgaaaaatg tttcttgcgg ggagaaagga    300
atgatttcag ggaaaaccgt aagcatttca gggggagata gtattgtttt taaggataac    360
tctgttggtt attcttcatt accgtctgtg gggcaaactc ctacaactcc aattgttggc    420
gatgttttaa agggttccat tttttgtgtg gagacaggtt tagagatttc tggagtcaaa    480
aaagagctgg ttttcgataa cactgctggg aattttgggg cagtattctg tagtcgtgcc    540
gctcaaggag acacgacttt cacagtgaaa gactgtaagg gtaaaattct gtttcaagat    600
aacgtaggct cttgtggagg cggcgtaatt tataaagggg aagtactgtt ccaagataat    660
gaaggagaaa tgctgttccg cggaaattca gctcatgatg atttgggaat tctggatgct    720
aacccacagc ctcctactga agtaggaggt ggggtggtg tcatttgtac cccagagaaa    780
acggtaactt ttaaggggaa taaagggcct attcctttg attataattt tgcaaaaggt    840
cgcggagggg caatccaatc acagaccttt tctttggtag ctgatagtgc tgttgttttc    900
```

-continued

```
agtaataata cagctgagaa aggtggaggc gccatttatg ctctggaggt taacgtgagc      960
acaaatggag gatctattct gtttgaggga aatcgcgctt ctgagggtgg ggctatctgt     1020
gtgagcgagc cgatcgctgc taataatgga gggctgactt tacatgctgc tgatggggac     1080
attattttct cgaaaaatat gacgagtgat cgtcctggag aacgcagtgc aatccggatc     1140
ttagatagtg aacaaatgt ctcttaaat gcttcagggg catcgaagat gatttttat        1200
gatcctgttg tgcaaaataa tccggcaact ccacctactg gtacgtctgg ggaaattaag    1260
atcaatgagt ccgggagtgg atcggttgtg tttacagcag agactttgac tccttcggaa    1320
aaattgaatg ttatcaacgc tacttctaat ttcccaggaa atttaacggt atctagtgga    1380
gagctcgttg ttacgaaggg agcgacactg acagtaggaa atatcacagc aacatcagga    1440
cgcgtaactt taggatcagg ggcttcgtta tccgccgttg caggtactgc tggcacttgt    1500
acggtgtcta aattagggat tgatttagag tccttcctgg tccctactta tgagactgca    1560
aagtggggtg cggatacaac agtagcggtg aataacaatc ctactttaga cctggtaatg    1620
gcgaatgaga cggagatgta tgataatccg ctgtttatga acgctgttac aatccctttt    1680
gtgacattgg tttctctgca aactactggt ggtgttacta caagtgccgt tactctgaat    1740
aatgcagata ctgcgcatta tgggtatcaa ggatcttggt ctgctgattg gcgccgccct    1800
cctttagctc ctgatcctag cggcatgaca cctctggata aaagtaatac attgtatgtg    1860
acatggcgcc atcctctaa ctacggtgtg tataagttag atcccatggc ccggcgtggt    1920
gagttggtcc cgaattcttt atgggtatct ggatctgcct tacgcacctt tacaaatggt    1980
ttgaaggaac attacgtctc tcgcgatgtc ggatttattg catctgtaca agccttaggg    2040
gattatgttc tgaattataa gcagggtaac cgcgatggct ttctggctcg ctacggaggt    2100
tttcaagctg ttgcggcttc tcactatgaa atgggggga tctttggggt agctttcggt    2160
caactgtatg gtcaaactaa gagccgtttg tacgattcta aggatgctgg aaacattacg    2220
atttttgtcct gttttggacg cagttatatc gatgttaaag gaacagaaac cgttgtgtat    2280
tgggagacgg cttatggata ttctgttcat cgcatgcata cgcagtattt caatggaaaa    2340
acgaataagt ttgatcattc gaaatgtcgt tggcacaaca atagttatta tgcatttgta    2400
ggtgcagaac ataatttctt ggagtattgt attcctactc gtcaattagc tcgcgattat    2460
gatctgcacag gatttatgcg tttcgaaatg tcgggaggtt ggtcgagtgg tgcaaaagaa    2520
acgggtgctt tacctcgcca ttttgatcgc ggaacagggc ataatatgtc tctgccaatt    2580
ggggttgtag ctcatgctgt ttctaatgga cgccgctctc ctccatctaa attgacgatt    2640
aacatgggat atcgcccaga catttggcgg gtgactccac attgcaatat gaaaattatt    2700
gcaaacggag ttaagactcc tattcaggga tctcctctgg ctcggcacgc cttcttttta    2760
gaagttcatg atactctgta tgttcgtcat ttgggccgcg cctatatgaa ttattcttta    2820
gatgctcgtc atcgccaaac tacgcatttc gtatctttag gattgaatcg tatcttttaa    2880
ggatcc                                                                2886
```

<210> SEQ ID NO 52
<211> LENGTH: 958
<212> TYPE: PRT
<213> ORGANISM: artificial sequence
<220> FEATURE:
<223> OTHER INFORMATION: synthetic peptide

<400> SEQUENCE: 52

-continued

```
Met Ser Ser Pro Gln Val Leu Thr Pro Asn Val Ile Ile Pro Phe Lys
1               5                   10                  15

Gly Asp Asp Ile Tyr Leu Asn Gly Asp Cys Val Phe Ala Ser Ile Tyr
            20                  25                  30

Ala Gly Ala Glu Gln Gly Ser Ile Ile Ser Ala Asn Gly Gln Asn Leu
        35                  40                  45

Thr Ile Val Gly Gln Asn His Thr Leu Ser Phe Thr Asp Ser Gln Gly
    50                  55                  60

Pro Ala Leu Gln Asn Cys Ala Phe Ile Ser Ala Glu Glu Lys Ile Ser
65                  70                  75                  80

Leu Arg Asp Phe Ser Ser Leu Leu Phe Ser Lys Asn Val Ser Cys Gly
                85                  90                  95

Glu Lys Gly Met Ile Ser Gly Lys Thr Val Ser Ile Ser Gly Gly Asp
            100                 105                 110

Ser Ile Val Phe Lys Asp Asn Ser Val Gly Tyr Ser Ser Leu Pro Ser
        115                 120                 125

Val Gly Gln Thr Pro Thr Thr Pro Ile Val Gly Asp Val Leu Lys Gly
    130                 135                 140

Ser Ile Phe Cys Val Glu Thr Gly Leu Glu Ile Ser Gly Val Lys Lys
145                 150                 155                 160

Glu Leu Val Phe Asp Asn Thr Ala Gly Asn Phe Gly Ala Val Phe Cys
                165                 170                 175

Ser Arg Ala Ala Gln Gly Asp Thr Thr Phe Thr Val Lys Asp Cys Lys
            180                 185                 190

Gly Lys Ile Leu Phe Gln Asp Asn Val Gly Ser Cys Gly Gly Gly Val
        195                 200                 205

Ile Tyr Lys Gly Glu Val Leu Phe Gln Asp Asn Glu Gly Glu Met Leu
    210                 215                 220

Phe Arg Gly Asn Ser Ala His Asp Asp Leu Gly Ile Leu Asp Ala Asn
225                 230                 235                 240

Pro Gln Pro Pro Thr Glu Val Gly Gly Gly Gly Val Ile Cys Thr
                245                 250                 255

Pro Glu Lys Thr Val Thr Phe Lys Gly Asn Lys Gly Pro Ile Thr Phe
            260                 265                 270

Asp Tyr Asn Phe Ala Lys Gly Arg Gly Gly Ala Ile Gln Ser Gln Thr
        275                 280                 285

Phe Ser Leu Val Ala Asp Ser Ala Val Phe Ser Asn Asn Thr Ala
    290                 295                 300

Glu Lys Gly Gly Gly Ala Ile Tyr Ala Leu Glu Val Asn Val Ser Thr
305                 310                 315                 320

Asn Gly Gly Ser Ile Leu Phe Glu Gly Asn Arg Ala Ser Glu Gly Gly
                325                 330                 335

Ala Ile Cys Val Ser Glu Pro Ile Ala Asn Asn Gly Gly Leu Thr
            340                 345                 350

Leu His Ala Ala Asp Gly Asp Ile Ile Phe Ser Lys Asn Met Thr Ser
        355                 360                 365

Asp Arg Pro Gly Glu Arg Ser Ala Ile Arg Ile Leu Asp Ser Gly Thr
    370                 375                 380

Asn Val Ser Leu Asn Ala Ser Gly Ala Ser Lys Met Ile Phe Tyr Asp
385                 390                 395                 400

Pro Val Val Gln Asn Asn Pro Ala Thr Pro Thr Gly Thr Ser Gly
                405                 410                 415

Glu Ile Lys Ile Asn Glu Ser Gly Ser Gly Ser Val Val Phe Thr Ala
```

-continued

```
            420                 425                 430
Glu Thr Leu Thr Pro Ser Glu Lys Leu Asn Val Ile Asn Ala Thr Ser
                435                 440                 445

Asn Phe Pro Gly Asn Leu Thr Val Ser Ser Gly Glu Leu Val Val Thr
    450                 455                 460

Lys Gly Ala Thr Leu Thr Val Gly Asn Ile Thr Ala Thr Ser Gly Arg
465                 470                 475                 480

Val Thr Leu Gly Ser Gly Ala Ser Leu Ser Ala Val Ala Gly Thr Ala
                485                 490                 495

Gly Thr Cys Thr Val Ser Lys Leu Gly Ile Asp Leu Glu Ser Phe Leu
                500                 505                 510

Val Pro Thr Tyr Glu Thr Ala Lys Leu Gly Ala Asp Thr Thr Val Ala
                515                 520                 525

Val Asn Asn Pro Thr Leu Asp Leu Val Met Ala Asn Glu Thr Glu
                530                 535                 540

Met Tyr Asp Asn Pro Leu Phe Met Asn Ala Val Thr Ile Pro Phe Val
545                 550                 555                 560

Thr Leu Val Ser Leu Gln Thr Thr Gly Gly Val Thr Thr Ser Ala Val
                565                 570                 575

Thr Leu Asn Asn Ala Asp Thr Ala His Tyr Gly Tyr Gln Gly Ser Trp
                580                 585                 590

Ser Ala Asp Trp Arg Arg Pro Pro Leu Ala Pro Asp Pro Ser Gly Met
                595                 600                 605

Thr Pro Leu Asp Lys Ser Asn Thr Leu Tyr Val Thr Trp Arg Pro Ser
                610                 615                 620

Ser Asn Tyr Gly Val Tyr Lys Leu Asp Pro Met Ala Arg Arg Gly Glu
625                 630                 635                 640

Leu Val Pro Asn Ser Leu Trp Val Ser Gly Ser Ala Leu Arg Thr Phe
                645                 650                 655

Thr Asn Gly Leu Lys Glu His Tyr Val Ser Arg Asp Val Gly Phe Ile
                660                 665                 670

Ala Ser Val Gln Ala Leu Gly Asp Tyr Val Leu Asn Tyr Lys Gln Gly
                675                 680                 685

Asn Arg Asp Gly Phe Leu Ala Arg Tyr Gly Gly Phe Gln Ala Val Ala
                690                 695                 700

Ala Ser His Tyr Glu Asn Gly Gly Ile Phe Gly Val Ala Phe Gly Gln
705                 710                 715                 720

Leu Tyr Gly Gln Thr Lys Ser Arg Leu Tyr Asp Ser Lys Asp Ala Gly
                725                 730                 735

Asn Ile Thr Ile Leu Ser Cys Phe Gly Arg Ser Tyr Ile Asp Val Lys
                740                 745                 750

Gly Thr Glu Thr Val Val Tyr Trp Glu Thr Ala Tyr Gly Tyr Ser Val
                755                 760                 765

His Arg Met His Thr Gln Tyr Phe Asn Gly Lys Thr Asn Lys Phe Asp
                770                 775                 780

His Ser Lys Cys Arg Trp His Asn Asn Ser Tyr Tyr Ala Phe Val Gly
785                 790                 795                 800

Ala Glu His Asn Phe Leu Glu Tyr Cys Ile Pro Thr Arg Gln Leu Ala
                805                 810                 815

Arg Asp Tyr Asp Leu Thr Gly Phe Met Arg Phe Glu Met Ser Gly Gly
                820                 825                 830

Trp Ser Ser Gly Ala Lys Glu Thr Gly Ala Leu Pro Arg His Phe Asp
                835                 840                 845
```

```
Arg Gly Thr Gly His Asn Met Ser Leu Pro Ile Gly Val Val Ala His
              850                 855                 860

Ala Val Ser Asn Gly Arg Arg Ser Pro Pro Ser Lys Leu Thr Ile Asn
865                 870                 875                 880

Met Gly Tyr Arg Pro Asp Ile Trp Arg Val Thr Pro His Cys Asn Met
            885                 890                 895

Lys Ile Ile Ala Asn Gly Val Lys Thr Pro Ile Gln Gly Ser Pro Leu
                900                 905                 910

Ala Arg His Ala Phe Phe Leu Glu Val His Asp Thr Leu Tyr Val Arg
            915                 920                 925

His Leu Gly Arg Ala Tyr Met Asn Tyr Ser Leu Asp Ala Arg His Arg
        930                 935                 940

Gln Thr Thr His Phe Val Ser Leu Gly Leu Asn Arg Ile Phe
945                 950                 955
```

<210> SEQ ID NO 53
<211> LENGTH: 2400
<212> TYPE: DNA
<213> ORGANISM: artificial sequence
<220> FEATURE:
<223> OTHER INFORMATION: synthetic polynucleotide

<400> SEQUENCE: 53

```
catatgagtt ctcctcaggt actgaccccg aatgtaatca tcccttttaa aggagacgat      60
atctatttaa atggggattg cgttttttgca agtatctatg caggagcaga gcagggatcg    120
attatttctg ctaatgggca aaatctgaca atcgtaggac aaaaccacac tttatcattt    180
acggattccc aagggccagc cctgcaaaat tgtgctttca tttcagcaga agaaaagatc    240
tctctgcgcg attttcgag cctgttgttt tcgaaaaatg tttcttgcgg ggagaaagga    300
atgatttcag ggaaaaccgt aagcatttca gggggagata gtattgtttt taaggataac    360
tctgttggtt attcttcatt accgtctgtg gggcaaactc ctacaactcc aattgttggc    420
gatgttttaa agggttccat ttttttgtgtg agacaggtt tagagatttc tggagtcaaa    480
aaagagctgg ttttcgataa cactgctggg aattttgggg cagtattctg tagtcgtgcc    540
gctcaaggag acacgacttt cacagtgaaa gactgtaagg gtaaaattct gtttcaagat    600
aacgtaggct cttgtggagg cggcgtaatt tataaagggg aagtactgtt ccaagataat    660
gaaggagaaa tgctgttccg cggaaattca gctcatgatg atttgggaat tctggatgct    720
aacccacagc ctcctactga gtaggaggt ggggtggtg tcatttgtac cccagagaaa    780
acggtaactt ttaaggggaa taagggcct attacctttg attataattt tgcaaaaggt    840
cgcggagggg caatccaatc acagacctt tctttggtag ctgatagtgc tgttgttttc    900
agtaataata cagctgagaa aggtggaggc gccatttatg ctctggaggt taacgtgagc    960
acaaatggag gatctattct gtttgaggga atcgcgctt ctgagggtgg ggctatctgt   1020
gtgagcgagc cgatcgctgc taataatgga gggctgactt tacatgctgc tgatggggac   1080
attatttttct cgaaaaatat gacgagtgat cgtcctggag aacgcagtgc aatccggatc   1140
ttagatagtg gaacaaatgt ctctttaaat gcttcagggg catcgaagat gattttttat   1200
gatcctgttg tgcaaaataa tccggcaact ccacctactg gtacgtctgg ggaaattaag   1260
atcaatgagt ccgggagtgg atcggttgtg tttacagcag agactttgac tccttcggaa   1320
aaattgaatg ttatcaacgc tacttctaat ttcccaggaa atttaacggt atctagtgga   1380
gagctctcct ctaactacgg tgtgtataag ttagatccca tggcccggcg tggtgagttg   1440
```

-continued

```
gtcccgaatt ctttatgggt atctggatct gccttacgca cctttacaaa tggtttgaag      1500
gaacattacg tctctcgcga tgtcggattt attgcatctg tacaagcctt agggattat       1560 gttctgaatt ataagcaggg taaccgcgat ggcttctgg ctcgctacgg aggttttcaa       1620
gctgttgcgg cttctcacta tgaaaatggg gggatctttg gggtagcttt cggtcaactg      1680
tatggtcaaa ctaagagccg tttgtacgat tctaaggatg ctggaaacat tacgattttg      1740
tcctgttttg gacgcagtta tatcgatgtt aaaggaacag aaaccgttgt gtattgggag      1800
acggcttatg gatattctgt tcatcgcatg catacgcagt atttcaatgg aaaaacgaat      1860
aagtttgatc attcgaaatg tcgttggcac aacaatagtt attatgcatt tgtaggtgca      1920
gaacataatt tcttggagta ttgtattcct actcgtcaat tagctcgcga ttatgatctg      1980
acaggattta tgcgtttcga aatgtcggga ggttggtcga gtggtgcaaa agaaacgggt      2040
gctttacctc gccatttga tcgcggaaca gggcataata tgtctctgcc aattggggtt      2100
gtagctcatg ctgtttctaa tggacgccgc tctcctccat ctaaattgac gattaacatg      2160
ggatatcgcc cagacatttg gcgggtgact ccacattgca atatgaaaat tattgcaaac      2220
ggagttaaga ctcctattca gggatctcct ctggctcggc acgccttctt tttagaagtt      2280
catgatactc tgtatgttcg tcatttgggc cgcgcctata tgaattattc tttagatgct      2340
cgtcatcgcc aaactacgca tttcgtatct ttaggattga atcgtatctt ttaaggatcc      2400
```

<210> SEQ ID NO 54
<211> LENGTH: 796
<212> TYPE: PRT
<213> ORGANISM: artificial sequence
<220> FEATURE:
<223> OTHER INFORMATION: synthetic peptide

<400> SEQUENCE: 54

```
Met Ser Ser Pro Gln Val Leu Thr Pro Asn Val Ile Ile Pro Phe Lys
1               5                   10                  15

Gly Asp Asp Ile Tyr Leu Asn Gly Asp Cys Val Phe Ala Ser Ile Tyr
            20                  25                  30

Ala Gly Ala Glu Gln Gly Ser Ile Ile Ser Ala Asn Gly Gln Asn Leu
        35                  40                  45

Thr Ile Val Gly Gln Asn His Thr Leu Ser Phe Thr Asp Ser Gln Gly
    50                  55                  60

Pro Ala Leu Gln Asn Cys Ala Phe Ile Ser Ala Glu Glu Lys Ile Ser
65                  70                  75                  80

Leu Arg Asp Phe Ser Ser Leu Leu Phe Ser Lys Asn Val Ser Cys Gly
                85                  90                  95

Glu Lys Gly Met Ile Ser Gly Lys Thr Val Ser Ile Ser Gly Gly Asp
            100                 105                 110

Ser Ile Val Phe Lys Asp Asn Ser Val Gly Tyr Ser Ser Leu Pro Ser
        115                 120                 125

Val Gly Gln Thr Pro Thr Thr Pro Ile Val Gly Asp Val Leu Lys Gly
    130                 135                 140

Ser Ile Phe Cys Val Glu Thr Gly Leu Glu Ile Ser Gly Val Lys Lys
145                 150                 155                 160

Glu Leu Val Phe Asp Asn Thr Ala Gly Asn Phe Gly Ala Val Phe Cys
                165                 170                 175

Ser Arg Ala Ala Gln Gly Asp Thr Thr Phe Thr Val Lys Asp Cys Lys
            180                 185                 190
```

-continued

```
Gly Lys Ile Leu Phe Gln Asp Asn Val Gly Ser Cys Gly Gly Val
        195                 200                 205
Ile Tyr Lys Gly Glu Val Leu Phe Gln Asp Asn Glu Gly Glu Met Leu
    210                 215                 220
Phe Arg Gly Asn Ser Ala His Asp Asp Leu Gly Ile Leu Asp Ala Asn
225                 230                 235                 240
Pro Gln Pro Pro Thr Glu Val Gly Gly Gly Gly Val Ile Cys Thr
                245                 250                 255
Pro Glu Lys Thr Val Thr Phe Lys Gly Asn Lys Gly Pro Ile Thr Phe
            260                 265                 270
Asp Tyr Asn Phe Ala Lys Gly Arg Gly Ala Ile Gln Ser Gln Thr
        275                 280                 285
Phe Ser Leu Val Ala Asp Ser Ala Val Val Phe Ser Asn Asn Thr Ala
    290                 295                 300
Glu Lys Gly Gly Gly Ala Ile Tyr Ala Leu Glu Val Asn Val Ser Thr
305                 310                 315                 320
Asn Gly Gly Ser Ile Leu Phe Glu Gly Asn Arg Ala Ser Glu Gly Gly
                325                 330                 335
Ala Ile Cys Val Ser Glu Pro Ile Ala Ala Asn Asn Gly Gly Leu Thr
            340                 345                 350
Leu His Ala Ala Asp Gly Asp Ile Ile Phe Ser Lys Asn Met Thr Ser
        355                 360                 365
Asp Arg Pro Gly Glu Arg Ser Ala Ile Arg Ile Leu Asp Ser Gly Thr
    370                 375                 380
Asn Val Ser Leu Asn Ala Ser Gly Ala Ser Lys Met Ile Phe Tyr Asp
385                 390                 395                 400
Pro Val Val Gln Asn Asn Pro Ala Thr Pro Thr Gly Thr Ser Gly
                405                 410                 415
Glu Ile Lys Ile Asn Glu Ser Gly Ser Gly Ser Val Val Phe Thr Ala
            420                 425                 430
Glu Thr Leu Thr Pro Ser Glu Lys Leu Asn Val Ile Asn Ala Thr Ser
        435                 440                 445
Asn Phe Pro Gly Asn Leu Thr Val Ser Ser Gly Glu Leu Ser Ser Asn
    450                 455                 460
Tyr Gly Val Tyr Lys Leu Asp Pro Met Ala Arg Arg Gly Glu Leu Val
465                 470                 475                 480
Pro Asn Ser Leu Trp Val Ser Gly Ser Ala Leu Arg Thr Phe Thr Asn
                485                 490                 495
Gly Leu Lys Glu His Tyr Val Ser Arg Asp Val Gly Phe Ile Ala Ser
            500                 505                 510
Val Gln Ala Leu Gly Asp Tyr Val Leu Asn Tyr Lys Gln Gly Asn Arg
        515                 520                 525
Asp Gly Phe Leu Ala Arg Tyr Gly Gly Phe Gln Ala Val Ala Ala Ser
    530                 535                 540
His Tyr Glu Asn Gly Gly Ile Phe Gly Val Ala Phe Gly Gln Leu Tyr
545                 550                 555                 560
Gly Gln Thr Lys Ser Arg Leu Tyr Asp Ser Lys Asp Ala Gly Asn Ile
                565                 570                 575
Thr Ile Leu Ser Cys Phe Gly Arg Ser Tyr Ile Asp Val Lys Gly Thr
            580                 585                 590
Glu Thr Val Val Tyr Trp Glu Thr Ala Tyr Gly Tyr Ser Val His Arg
        595                 600                 605
Met His Thr Gln Tyr Phe Asn Gly Lys Thr Asn Lys Phe Asp His Ser
```

```
                    610               615               620
Lys Cys Arg Trp His Asn Asn Ser Tyr Tyr Ala Phe Val Gly Ala Glu
625                 630               635                   640

His Asn Phe Leu Glu Tyr Cys Ile Pro Thr Arg Gln Leu Ala Arg Asp
                    645               650                   655

Tyr Asp Leu Thr Gly Phe Met Arg Phe Glu Met Ser Gly Gly Trp Ser
                660               665               670

Ser Gly Ala Lys Glu Thr Gly Ala Leu Pro Arg His Phe Asp Arg Gly
                675               680               685

Thr Gly His Asn Met Ser Leu Pro Ile Gly Val Val Ala His Ala Val
                690               695               700

Ser Asn Gly Arg Arg Ser Pro Pro Ser Lys Leu Thr Ile Asn Met Gly
705                 710               715                   720

Tyr Arg Pro Asp Ile Trp Arg Val Thr Pro His Cys Asn Met Lys Ile
                725               730               735

Ile Ala Asn Gly Val Lys Thr Pro Ile Gln Gly Ser Pro Leu Ala Arg
                740               745               750

His Ala Phe Phe Leu Glu Val His Asp Thr Leu Tyr Val Arg His Leu
                755               760               765

Gly Arg Ala Tyr Met Asn Tyr Ser Leu Asp Ala Arg His Arg Gln Thr
                770               775               780

Thr His Phe Val Ser Leu Gly Leu Asn Arg Ile Phe
785                 790               795

<210> SEQ ID NO 55
<211> LENGTH: 606
<212> TYPE: DNA
<213> ORGANISM: artificial sequence
<220> FEATURE:
<223> OTHER INFORMATION: synthetic polynucleotide

<400> SEQUENCE: 55
catatgctga atctgctgga aaactgggac accctgggct ccacggtgtc acagctgcaa      60
gaacgcctgg gtccgctgac gcgtgatttt tgggacaacc tggaaaaaga aaccgattgg    120
gttcgccagg aaatgaataa ggacctggaa gaagtgaaac agaaggttca accgtatctg    180
gatgaatttc agaaaaagtg aaagaagac gtcgaactgt accgtcagaa ggtggcaccg    240
ctgggcgctg aactgcaaga tccgcacgc cagaaactgc aagaactgca aggtcgtctg    300
tcaccggttg ctgaagaatt tcgtgatcgc atgcgtacgc atgtggattc gctgcgcacc    360
caactggcac cgcactctga acagatgcgc gaaagtctgg cgcaacgtct ggccgaactg    420
aaaagtaacc cgaccctgaa tgaataccat accgtgccaa aacgcacct gaagaccctg    480 ggtgaaaaag cacgtccggc gctgaagac ctgcgtcatt ctctgatgcc gatgctggaa    540
accctgaaaa cccaagtcca gtcggtgatt gacaaagcaa gcgaaaccct gacggcacag    600
ggatcc                                                                 606

<210> SEQ ID NO 56
<211> LENGTH: 198
<212> TYPE: PRT
<213> ORGANISM: artificial sequence
<220> FEATURE:
<223> OTHER INFORMATION: synthetic peptide

<400> SEQUENCE: 56

Leu Asn Leu Leu Glu Asn Trp Asp Thr Leu Gly Ser Thr Val Ser Gln
1               5                   10                  15
```

Leu Gln Glu Arg Leu Gly Pro Leu Thr Arg Asp Phe Trp Asn Leu
            20                  25                  30

Glu Lys Glu Thr Asp Trp Val Arg Gln Glu Met Asn Lys Asp Leu Glu
        35                  40                  45

Glu Val Lys Gln Lys Val Gln Pro Tyr Leu Asp Glu Phe Gln Lys Lys
 50                  55                  60

Trp Lys Glu Asp Val Glu Leu Tyr Arg Gln Lys Val Ala Pro Leu Gly
 65                  70                  75                  80

Ala Glu Leu Gln Glu Ser Ala Arg Gln Lys Leu Gln Glu Leu Gln Gly
                85                  90                  95

Arg Leu Ser Pro Val Ala Glu Glu Phe Arg Asp Arg Met Arg Thr His
            100                 105                 110

Val Asp Ser Leu Arg Thr Gln Leu Ala Pro His Ser Glu Gln Met Arg
            115                 120                 125

Glu Ser Leu Ala Gln Arg Leu Ala Glu Leu Lys Ser Asn Pro Thr Leu
130                 135                 140

Asn Glu Tyr His Thr Arg Ala Lys Thr His Leu Lys Thr Leu Gly Glu
145                 150                 155                 160

Lys Ala Arg Pro Ala Leu Glu Asp Leu Arg His Ser Leu Met Pro Met
                165                 170                 175

Leu Glu Thr Leu Lys Thr Gln Val Gln Ser Val Ile Asp Lys Ala Ser
            180                 185                 190

Glu Thr Leu Thr Ala Gln
        195

<210> SEQ ID NO 57
<211> LENGTH: 555
<212> TYPE: DNA
<213> ORGANISM: artificial sequence
<220> FEATURE:
<223> OTHER INFORMATION: synthetic polynucleotide

<400> SEQUENCE: 57
catatgggtg aaccggaagt gaccgatcaa ctggaatggc aatctaatca accgtgggaa      60
caagccctga accgttttg ggactatctg cgctgggtgc aaaccctgag cgatcaggtt     120
caagaagaac tgcagagctc tcaagttacc caggaactga cggcactgat ggaagacacc     180
atgacggaag tcaaagctta taaaaggaa ctggaagaac agctgggccc ggtcgcagaa     240
gaaacgcgtg ctcgcctggg taaagaagtg caagcagcac aggcacgtct gggtgcagat     300
atggaagacc tgcgtaaccg cctgggtcaa taccgtaatg aagtgcatac catgctgggc     360
cagagtacgg aagaaattcg tgcgcgcctg tccacccacc tgcgtaaaat gcgtaagcgc     420
ctgatgcgcg atgcggaaga cctgcagaaa cgtctggccg tttataaggc aggcgctcgc     480
gaaggtgccg aacgtggtgt gtcggcaatc cgtgaacgcc tgggtccgct ggttgaacaa     540
ggtcgtcagg gatcc                                                     555

<210> SEQ ID NO 58
<211> LENGTH: 185
<212> TYPE: PRT
<213> ORGANISM: artificial sequence
<220> FEATURE:
<223> OTHER INFORMATION: synthetic peptide

<400> SEQUENCE: 58

His Met Gly Glu Pro Glu Val Thr Asp Gln Leu Glu Trp Gln Ser Asn
1               5                   10                  15

Gln Pro Trp Glu Gln Ala Leu Asn Arg Phe Trp Asp Tyr Leu Arg Trp
            20                  25                  30

Val Gln Thr Leu Ser Asp Gln Val Gln Glu Leu Gln Ser Ser Gln
        35                  40                  45

Val Thr Gln Glu Leu Thr Ala Leu Met Glu Asp Thr Met Thr Glu Val
50                  55                  60

Lys Ala Tyr Lys Lys Glu Leu Glu Glu Gln Leu Gly Pro Val Ala Glu
65                  70                  75                  80

Glu Thr Arg Ala Arg Leu Gly Lys Glu Val Gln Ala Ala Gln Ala Arg
                85                  90                  95

Leu Gly Ala Asp Met Glu Asp Leu Arg Asn Arg Leu Gly Gln Tyr Arg
            100                 105                 110

Asn Glu Val His Thr Met Leu Gly Gln Ser Thr Glu Glu Ile Arg Ala
        115                 120                 125

Arg Leu Ser Thr His Leu Arg Lys Met Arg Lys Arg Leu Met Arg Asp
130                 135                 140

Ala Glu Asp Leu Gln Lys Arg Leu Ala Val Tyr Lys Ala Gly Ala Arg
145                 150                 155                 160

Glu Gly Ala Glu Arg Gly Val Ser Ala Ile Arg Glu Arg Leu Gly Pro
                165                 170                 175

Leu Val Glu Gln Gly Arg Gln Gly Ser
            180                 185

<210> SEQ ID NO 59
<211> LENGTH: 1165
<212> TYPE: DNA
<213> ORGANISM: artificial sequence
<220> FEATURE:
<223> OTHER INFORMATION: synthetic polynucleotide

<400> SEQUENCE: 59
atattttgtt tactttaaga aggagatata ccatggcaca tatgctgccg gttggtaacc      60
cggctgaacc gtctctgatg atcgatggta tcctgtggga aggtttcggt ggtgatccgt     120
gtgatccgtg tactacttgg tgtgatgcta tctctctgcg tctgggttac tacggtgatt     180
tcgttttcga tcgtgttctg aaaactgacg ttaacaaaca gttcgaaatg ggtgctgctc     240
cgactggtga cgctgacctg accactgctc gactccggc ttctcgtgaa acccggcttt     300
acggtaaaca catgcaggac gctgaaatgt tcactaacgc tgcttacatg gctctgaaca     360
tctgggaccg tttcgacgtt ttctgcactc tgggtgctac ttctggttac ctgaaaggta     420
actctgctgc tttcaacctg gttggtctgt tcggtcgtga cgaaactgct gttgctgctg     480
acgacatccc gaacgtttct ctgtctcagg ctgttgttga actgtacact gacactgctt     540
tcgcttggtc tgttggtgct cgtgctgctc tgtgggaatg tggttgcgct actctgggtg     600
cttctttcca gtacgctcag tctaaaccga agttgaaga actgaacgtt ctgtgtaacg     660
ctgctgaatt caccatcaac aaaccgaaag gctacgttgg ccaggaattc ccgctgaaca     720
tcaaagctgg taccgtttct gctactgaca ccaaagacgc ttccatcgac taccacgaat     780
ggcaggcttc cctggctctg tcctaccgtc tgaacatgtt cactccgtac atcggtgtta     840
aatggtctcg tgcttctttc gacgctgaca ctatccgtat cgctcagccg aaactggaaa     900
cttctatcct gaaaatgact acctggaacc gactatctc tggttctggt atcgacgttg     960
acaccaaaat caccgacacc ctgcagatcg tttccctgca gctgaacaaa atgaaatccc    1020
gtaaatcctg cggcctggct atcggtacca ccatcgttga cgctgacaaa tacgctgtta    1080

```
ccgttgaaac cgtctgatc gacgaacgtg ctgctcacgt taacgctcag ttccgtttcg    1140
gatccggctg ctaacaaagc ccgaa                                         1165
```

<210> SEQ ID NO 60
<211> LENGTH: 366
<212> TYPE: PRT
<213> ORGANISM: artificial sequence
<220> FEATURE:
<223> OTHER INFORMATION: synthetic peptide

<400> SEQUENCE: 60

```
Met Leu Pro Val Gly Asn Pro Ala Glu Pro Ser Leu Met Ile Asp Gly
1               5                   10                  15

Ile Leu Trp Glu Gly Phe Gly Gly Asp Pro Cys Asp Pro Cys Thr Thr
            20                  25                  30

Trp Cys Asp Ala Ile Ser Leu Arg Leu Gly Tyr Tyr Gly Asp Phe Val
        35                  40                  45

Phe Asp Arg Val Leu Lys Thr Asp Val Asn Lys Gln Phe Glu Met Gly
    50                  55                  60

Ala Ala Pro Thr Gly Asp Ala Asp Leu Thr Thr Ala Pro Thr Pro Ala
65                  70                  75                  80

Ser Arg Glu Asn Pro Ala Tyr Gly Lys His Met Gln Asp Ala Glu Met
                85                  90                  95

Phe Thr Asn Ala Ala Tyr Met Ala Leu Asn Ile Trp Asp Arg Phe Asp
            100                 105                 110

Val Phe Cys Thr Leu Gly Ala Thr Ser Gly Tyr Leu Lys Gly Asn Ser
        115                 120                 125

Ala Ala Phe Asn Leu Val Gly Leu Phe Gly Arg Asp Glu Thr Ala Val
    130                 135                 140

Ala Ala Asp Asp Ile Pro Asn Val Ser Leu Ser Gln Ala Val Val Glu
145                 150                 155                 160

Leu Tyr Thr Asp Thr Ala Phe Ala Trp Ser Val Gly Ala Arg Ala Ala
                165                 170                 175

Leu Trp Glu Cys Gly Cys Ala Thr Leu Gly Ala Ser Phe Gln Tyr Ala
            180                 185                 190

Gln Ser Lys Pro Lys Val Glu Glu Leu Asn Val Leu Cys Asn Ala Ala
        195                 200                 205

Glu Phe Thr Ile Asn Lys Pro Lys Gly Tyr Val Gly Gln Glu Phe Pro
    210                 215                 220

Leu Asn Ile Lys Ala Gly Thr Val Ser Ala Thr Asp Thr Lys Asp Ala
225                 230                 235                 240

Ser Ile Asp Tyr His Glu Trp Gln Ala Ser Leu Ala Leu Ser Tyr Arg
                245                 250                 255

Leu Asn Met Phe Thr Pro Tyr Ile Gly Val Lys Trp Ser Arg Ala Ser
            260                 265                 270

Phe Asp Ala Asp Thr Ile Arg Ile Ala Gln Pro Lys Leu Glu Thr Ser
        275                 280                 285

Ile Leu Lys Met Thr Thr Trp Asn Pro Thr Ile Ser Gly Ser Gly Ile
    290                 295                 300

Asp Val Asp Thr Lys Ile Thr Asp Thr Leu Gln Ile Val Ser Leu Gln
305                 310                 315                 320

Leu Asn Lys Met Lys Ser Arg Lys Ser Cys Gly Leu Ala Ile Gly Thr
                325                 330                 335

Thr Ile Val Asp Ala Asp Lys Tyr Ala Val Thr Val Glu Thr Arg Leu
```

```
                340                 345                 350
Ile Asp Glu Arg Ala Ala His Val Asn Ala Gln Phe Arg Phe
            355                 360                 365

<210> SEQ ID NO 61
<211> LENGTH: 594
<212> TYPE: DNA
<213> ORGANISM: mouse

<400> SEQUENCE: 61
ctgaatctcc tggaaaactg ggacactctg ggttcaaccg ttagtcagct gcaggaacgg     60
ctgggcccat tgactcggga cttctgggat aacctggaga agaaacaga ttgggtgaga    120 caggagatga acaaggacct agaggaagtg aaacagaagg tgcagcccta cctggacgaa    180
ttccagaaga atggaaaga ggatgtggag ctctaccgcc agaaggtggc gcctctgggc     240
gccgagctgc aggagagcgc gcgccagaag ctgcaggagc tgcaagggag actgtcccct    300
gtggctgagg aatttcgcga ccgcatgcgc acacacgtag actctctgcg cacacagcta    360
gcgccccaca gcgaacagat gcgcgagagc ctggcccagc gcctggctga gctcaagagc    420
aaccctacct tgaacgagta ccacaccagg gccaaaaccc acctgaagac acttggcgag    480
aaagccagac ctgcgctgga ggacctgcgc catagtctga tgcccatgct ggagacgctt    540
aagacccaag tccagagtgt gatcgacaag gccagcgaga ctctgactgc ccag          594

<210> SEQ ID NO 62
<211> LENGTH: 594
<212> TYPE: DNA
<213> ORGANISM: artificial sequence
<220> FEATURE:
<223> OTHER INFORMATION: synthetic polynucleotide

<400> SEQUENCE: 62
ctgaatctgc tggaaaactg ggacaccctg ggctccacgg tgtcacagct gcaagaacgc     60
ctgggtccgc tgacgcgtga tttttgggac aacctggaaa agaaaccga ttgggttcgc    120 caggaaatga ataaggacct ggaagaagtg aaacagaagg ttcaaccgta tctggatgaa    180
tttcagaaaa agtggaaaga agacgtcgaa ctgtaccgtc agaaggtggc accgctgggc    240
gctgaactgc aagaatccgc acgccagaaa ctgcaagaac tgcaaggtcg tctgtcaccg    300
gttgctgaag aatttcgtga tcgcatgcgt acgcatgtgg attcgctgcg cacccaactg    360
gcaccgcact ctgaacagat gcgcgaaagt ctggcgcaac gtctggccga actgaaaagt    420
aacccgaccc tgaatgaata ccatacccgt gccaaaacgc acctgaagac cctgggtgaa    480
aaagcacgtc cggcgctgga agacctgcgt cattctctga tgccgatgct ggaaaccctg    540
aaaacccaag tccagtcggt gattgacaaa gcaagcgaaa ccctgacggc acag          594

<210> SEQ ID NO 63
<211> LENGTH: 594
<212> TYPE: DNA
<213> ORGANISM: artificial sequence
<220> FEATURE:
<223> OTHER INFORMATION: synthetic polynucleotide

<400> SEQUENCE: 63
ctgaacctgc tggaaaactg ggacaccctg ggttctaccg tttctcagct gcaggaacgt     60
ctgggtccgc tgacccgtga cttctgggac aacctggaaa agaaaccga ctgggttcgt    120 caggaaatga acaagacct ggaagaagtt aaacagaaag ttcagccgta cctggacgaa    180
```

| | |
|---|---|
| ttccagaaaa aatggaaaga agacgttgaa ctgtaccgtc agaaagttgc gccgctgggt | 240 |
| gcggaactgc aggaatctgc gcgtcagaaa ctgcaggaac tgcagggtcg tctgtctccg | 300 |
| gttgcggaag aattccgtga ccgtatgcgt acccacgttg actctctgcg tacccagctg | 360 |
| gcgccgcact ctgaacagat gcgtgaatct ctggcgcagc gtctggcgga actgaaatct | 420 |
| aacccgaccc tgaacgaata ccacacccgt gcgaaaaccc acctgaaaac cctgggtgaa | 480 |
| aaagcgcgtc cggcgctgga agacctgcgt cactctctga tgccgatgct ggaaaccctg | 540 |
| aaaaccaaag cgcagtctgt tatcgacaaa gcgtctgaaa ccctgaccgc gcag | 594 |

<210> SEQ ID NO 64
<211> LENGTH: 1095
<212> TYPE: DNA
<213> ORGANISM: Chlamydia muridarum

<400> SEQUENCE: 64

| | |
|---|---|
| ctgcctgtgg ggaatcctgc tgaaccaagc cttatgattg acgggattct ttgggaaggt | 60 |
| ttcggtggag atccttgcga tccttgcaca acttggtgtg atgccatcag cctacgtctc | 120 |
| ggctactatg gggacttcgt ttttgatcgt gttttgaaaa cagacgtgaa caaacagttc | 180 |
| gaaatgggag cagctcctac aggagatgca gaccttacta cagcacctac tcctgcatca | 240 |
| agagagaatc ccgcttatgg caagcatatg caagatgcag aaatgttcac taatgctgcg | 300 |
| tacatggctt taaacatttg ggaccgtttc gatgtatttt gtacattggg agcaactagc | 360 |
| ggatatctta aggtaattc tgccgccttt aacttagttg gtctgtttgg aagagatgaa | 420 |
| actgcagttg cagctgacga catacctaac gtcagcttgt ctcaagctgt tgtcgaactc | 480 |
| tacacagaca cagctttcgc ttggagcgtc ggtgctagag cagctttatg ggagtgcgga | 540 |
| tgtgcaactt taggagcttc cttccaatat gctcaatcta agccaaaagt agaggaatta | 600 |
| aacgttctct gtaatgcggc agaattcact attaacaagc taaaggata cgttggacaa | 660 |
| gagtttcctc ttaacattaa agctggaaca gttagcgcta cagatactaa agatgcttcc | 720 |
| atcgattacc atgagtggca agcaagcttg gctttgtctt acagactgaa tatgttcact | 780 |
| ccttacattg gagttaagtg gtctagagca agctttgatg ccgacactat ccgcattgcg | 840 |
| cagcctaagc ttgagacctc tatcttaaaa atgaccactt ggaacccaac gatctctgga | 900 |
| tctggtatag acgttgatac aaaaatcacg gatacattac aaattgtttc cttgcagctc | 960 |
| aacaagatga atccagaaa atcttgcggt cttgcaattg gaacaacaat tgtagatgct | 1020 |
| gataaatatg cagttactgt tgagacacgc ttgatcgatg aaagagcagc tcacgtaaat | 1080 |
| gctcagttcc gtttc | 1095 |

<210> SEQ ID NO 65
<211> LENGTH: 1095
<212> TYPE: DNA
<213> ORGANISM: artificial sequence
<220> FEATURE:
<223> OTHER INFORMATION: synthetic polynucleotide

<400> SEQUENCE: 65

| | |
|---|---|
| ctgccggttg gtaacccggc tgaaccgtct ctgatgatcg atggtatcct gtgggaaggt | 60 |
| ttcggtggtg atccgtgtga tccgtgtact acttggtgtg atgctatctc tctgcgtctg | 120 |
| ggttactacg gtgatttcgt tttcgatcgt gttctgaaaa ctgacgttaa caaacagttc | 180 |
| gaaatgggtg ctgctccgac tggtgacgct gacctgacca ctgctccgac tccggcttct | 240 |
| cgtgaaaacc cggcttacgg taaacacatg caggacgctg aaatgttcac taacgctgct | 300 |

```
tacatggctc tgaacatctg ggaccgtttc gacgttttct gcactctggg tgctacttct    360
ggttacctga aggtaactc tgctgctttc aacctggttg gtctgttcgg tcgtgacgaa    420
actgctgttg ctgctgacga catcccgaac gtttctctgt ctcaggctgt tgttgaactg    480
tacactgaca ctgctttcgc ttggtctgtt ggtgctcgtg ctgctctgtg gaatgtggt    540
tgcgctactc tgggtgcttc tttccagtac gctcagtcta aaccgaaagt tgaagaactg    600
aacgttctgt gtaacgctgc tgaattcacc atcaacaaac cgaaaggcta cgttggccag    660
gaattcccgc tgaacatcaa agctggtacc gtttctgcta ctgacaccaa agacgcttcc    720
atcgactacc acgaatggca ggcttccctg gctctgtcct accgtctgaa catgttcact    780
ccgtacatcg gtgttaaatg gtctcgtgct tctttcgacg ctgacactat ccgtatcgct    840
cagccgaaac tggaaacttc tatcctgaaa atgactacct ggaacccgac tatctctggt    900
tctggtatcg acgttgacac caaaatcacc gacaccctgc agatcgtttc cctgcagctg    960
aacaaaatga atcccgtaa atcctgcggc tggctatcg gtaccaccat cgttgacgct   1020
gacaaatacg ctgttaccgt tgaaacccgt ctgatcgacg aacgtgctgc tcacgttaac   1080
gctcagttcc gtttc                                                   1095
```

<210> SEQ ID NO 66
<211> LENGTH: 375
<212> TYPE: PRT
<213> ORGANISM: Chlamydia tracomatis

<400> SEQUENCE: 66

```
Leu Pro Val Gly Asn Pro Ala Glu Pro Ser Leu Met Ile Asp Gly Ile
 1               5                  10                  15
Leu Trp Glu Gly Phe Gly Gly Asp Pro Cys Asp Pro Cys Thr Thr Trp
            20                  25                  30
Cys Asp Ala Ile Ser Met Arg Val Gly Tyr Tyr Gly Asp Phe Val Phe
        35                  40                  45
Asp Arg Val Leu Lys Thr Asp Val Asn Lys Glu Phe Gln Met Gly Ala
    50                  55                  60
Ala Pro Thr Thr Ser Asp Val Ala Gly Leu Gln Asn Asp Pro Thr Ile
65                  70                  75                  80
Asn Val Ala Arg Pro Asn Pro Ala Tyr Gly Lys His Met Gln Asp Ala
                85                  90                  95
Glu Met Phe Thr Asn Ala Ala Tyr Met Ala Leu Asn Ile Trp Asp Arg
           100                 105                 110
Phe Asp Val Phe Cys Thr Leu Gly Ala Thr Thr Gly Tyr Leu Lys Gly
       115                 120                 125
Asn Ser Ala Ser Phe Asn Leu Val Gly Leu Phe Gly Thr Lys Thr Gln
   130                 135                 140
Ser Ser Ser Phe Asn Thr Ala Lys Leu Ile Pro Asn Thr Ala Leu Asn
145                 150                 155                 160
Glu Ala Val Val Glu Leu Tyr Ile Asn Thr Thr Phe Ala Trp Ser Val
               165                 170                 175
Gly Ala Arg Ala Ala Leu Trp Glu Cys Gly Cys Ala Thr Leu Gly Ala
           180                 185                 190
Ser Phe Gln Tyr Ala Gln Ser Lys Pro Lys Val Glu Glu Leu Asn Val
       195                 200                 205
Leu Cys Asn Ala Ser Glu Phe Thr Ile Asn Lys Pro Lys Gly Tyr Val
   210                 215                 220
```

Gly Ala Glu Phe Pro Leu Asn Ile Thr Ala Gly Thr Glu Ala Ala Thr
225                 230                 235                 240

Gly Thr Lys Asp Ala Ser Ile Asp Tyr His Glu Trp Gln Ala Ser Leu
            245                 250                 255

Ala Leu Ser Tyr Arg Leu Asn Met Phe Thr Pro Tyr Ile Gly Val Lys
            260                 265                 270

Trp Ser Arg Val Ser Phe Asp Ala Asp Thr Ile Arg Ile Ala Gln Pro
        275                 280                 285

Lys Leu Ala Glu Ala Ile Leu Asp Val Thr Thr Leu Asn Arg Thr Thr
        290                 295                 300

Ala Gly Lys Gly Ser Val Val Ser Ala Gly Thr Asp Asn Glu Leu Ala
305                 310                 315                 320

Asp Thr Met Gln Ile Val Ser Leu Gln Leu Asn Lys Met Lys Ser Arg
                325                 330                 335

Lys Ser Cys Gly Ile Ala Val Gly Thr Thr Ile Val Asp Ala Asp Lys
            340                 345                 350

Tyr Ala Val Thr Val Glu Ala Arg Leu Ile Asp Glu Arg Ala Ala His
            355                 360                 365

Val Asn Ala Gln Phe Arg Phe
        370                 375

<210> SEQ ID NO 67
<211> LENGTH: 28
<212> TYPE: PRT
<213> ORGANISM: artificial sequence
<220> FEATURE:
<223> OTHER INFORMATION: synthetic peptide

<400> SEQUENCE: 67

Gly Asp Asn Glu Asn Gln Lys Thr Val Lys Ala Glu Ser Val Pro Asn
1               5                   10                  15

Met Ser Phe Asp Gln Ser Val Val Glu Leu Tyr Thr
            20                  25

<210> SEQ ID NO 68
<211> LENGTH: 28
<212> TYPE: PRT
<213> ORGANISM: artificial sequence
<220> FEATURE:
<223> OTHER INFORMATION: synthetic peptide

<400> SEQUENCE: 68

Gly Asp Asn Glu Asn Gln Ser Thr Val Lys Thr Asn Ser Val Pro Asn
1               5                   10                  15

Met Ser Leu Asp Gln Ser Val Val Glu Leu Tyr Thr
            20                  25

<210> SEQ ID NO 69
<211> LENGTH: 21
<212> TYPE: PRT
<213> ORGANISM: artificial sequence
<220> FEATURE:
<223> OTHER INFORMATION: synthetic peptide

<400> SEQUENCE: 69

Glu Trp Gln Ala Ser Leu Ala Leu Ser Tyr Arg Leu Asn Met Phe Thr
1               5                   10                  15

Pro Tyr Ile Gly Val
            20

```
<210> SEQ ID NO 70
<211> LENGTH: 21
<212> TYPE: PRT
<213> ORGANISM: artificial sequence
<220> FEATURE:
<223> OTHER INFORMATION: synthetic peptide

<400> SEQUENCE: 70

Glu Trp Gln Ala Ser Leu Ala Leu Ser Tyr Arg Leu Asn Met Phe Thr
1               5                   10                  15

Pro Tyr Ile Gly Val
            20
```

MOMP TELONANOPARTICLES, AND RELATED COMPOSITIONS, METHODS AND SYSTEMS

CROSS REFERENCE TO RELATED APPLICATIONS

The present application is a continuation application U.S. application Ser. No. 16/609,420 filed on Oct. 29, 2019 which is the U.S. national stage of International Patent Application PCT/US2018/030537 filed internationally on May 1, 2018, which, in turn, claims priority to U.S. Provisional Application No. 62/500,435, entitled "MOMP telonanoparticles, and related compositions, methods and systems" filed on May 2, 2017, the content of each of which is incorporated herein by reference in its entirety.

STATEMENT OF GOVERNMENT GRANT

The invention was made with Government support under Contract No. DE-AC52-07NA27344 between the U.S. Department of Energy and Lawrence Livermore National Security, LLC, for the operation of Lawrence Livermore National Security. The Government may have certain rights to the invention.

FIELD

The present disclosure relates to nanolipoprotein particles (NLPs) and, in particular, to nanolipoprotein particles comprising telodendrimers and *Chlamydia* major outer membrane protein (MOMP) as well as related compositions, methods and systems.

BACKGROUND

*Chlamydia* is a prevalent sexually transmitted infection that affects over 100 million people worldwide. Although most individuals infected with *Chlamydia trachomatis* are initially asymptomatic, symptoms can arise if left undiagnosed. Long-term infection can result in debilitating side effects such as pelvic inflammatory disease, infertility, and blindness. *Chlamydia* infection, therefore, constitutes a significant public health threat and underscores the need for a vaccine.

*Chlamydia* strains express a major outer membrane protein (MOMP) that is shown to be an effective vaccine antigen. However, in view of poor solubility, low yield and protein misfolding of the *Chlamydia* MOMP protein production of a functional recombinant MOMP protein for vaccine development has been challenging.

SUMMARY

Provided herein are nanolipoprotein particles comprising *Chlamydia* major outer membrane protein (MOMP), and related compositions, methods and systems which in several embodiments, allow production of soluble and functional MOMP antigen and can be used as a vehicle to deliver MOMP in a vaccine.

According to a first aspect, a telodendrimer-nanolipoprotein particle (t-NLP) is described. The t-NLP particle comprises one or more membrane forming lipids, one or more telodendrimers, a scaffold protein and a *Chlamydia* major outer membrane protein (MOMP) or a fragment thereof, the MOMP or the fragment thereof comprising a MOMP hydrophobic region. In the telodendrimer-nanolipoprotein particle the one or more membrane forming lipids are arranged in a discoidal membrane lipid bilayer stabilized by the scaffold protein and the one or more telodendrimers, with the membrane lipid bilayer attaching the MOMP or the fragment thereof through interaction of the MOP hydrophobic region with the membrane lipid bilayer.

According to a second aspect, a method to provide a telodendrimer-nanolipoprotein particle presenting a *Chlamydia* major outer membrane proteins (MOMP) and/or a fragment thereof is described, the MOMP and/or the fragment thereof comprising a MOMP hydrophobic region. The method comprises providing one or more membrane forming lipids, one or more telodendrimers, a polynucleotide coding for the MOMP and/or the fragment thereof and a polynucleotide coding for a scaffold protein. The method further comprises mixing the one or more membrane forming lipids and the one or more telodendrimers to provide a lipid-telodendrimer mixture, and mixing lipid-telodendrimer mixture with the polynucleotides and with an in vitro cell free translation system to provide a single reaction mixture. The method further comprises translating the polynucleotides within the single reaction mixture via the in vitro cell free translation system, the mixing and translating performed to allow self-assembly of the scaffold protein, the one or more membrane forming lipids and the one or more telodendrimers into a nanolipoprotein particle. In the method, the nanolipoprotein particle comprises the MOMP within a discoidal membrane lipid bilayer formed by the one or more membrane forming lipids and stabilized by the scaffold protein, the membrane lipid bilayer attaching the MOMP through interaction of the target protein hydrophobic region with the membrane lipid bilayer.

According to a third aspect, a method to provide a telodendrimer-nanolipoprotein particle presenting a *Chlamydia* major outer membrane proteins (MOMP) and/or a fragment thereof is described, the MOMP and/or the fragment thereof comprising a MOMP hydrophobic region. The method comprises providing one or more membrane forming lipids, one or more telodendrimers, a polynucleotide coding for the MOMP and/or the fragment thereof and a scaffold protein. The method further comprises mixing the one or more membrane forming lipids and the one or more telodendrimers to provide a lipid-telodendrimer mixture, and mixing lipid-telodendrimer mixture with the polynucleotides, the scaffold protein with an in vitro cell free translation system to provide a single reaction mixture. The method further comprises translating the polynucleotide within the single reaction mixture via the in vitro cell free translation system, the mixing and translating performed to allow self-assembly of the scaffold protein, the one or more membrane forming lipids and the one or more telodendrimers into a nanolipoprotein particle. In the method, the nanolipoprotein particle comprises the MOMP within a discoidal membrane lipid bilayer formed by the one or more membrane forming lipids and stabilized by the scaffold protein, the membrane lipid bilayer attaching the MOMP through interaction of the target protein hydrophobic region with the membrane lipid bilayer.

According to a fourth aspect, a system to provide a t-NLP comprising *Chlamydia* major outer membrane proteins (MOMP) is described. The system comprises one or more membrane forming lipids, one or more telodendrimers, a polynucleotide coding for *Chlamydia* major outer membrane proteins (MOMP), a polynucleotide coding for a scaffold protein and/or a scaffold protein for simultaneous combined or sequential use in methods to provide a t-NLP presenting a MOMP herein described.

According to a fifth aspect, a composition comprising one or more MOMP-t-NLPs of the present disclosure together with a suitable vehicle, is described. In some embodiments, the composition can further comprise one or more adjuvants. In some embodiments, the vehicle is a pharmaceutically acceptable vehicle and the composition is a pharmaceutical composition.

According to a sixth aspect, a method and system of immunizing an individual against *Chlamydia* is described. The method comprises administering to the individual an effective amount a MOMP-t-NLP herein described for a time and under conditions to allow contact of the MOMP-t-NLP with the immune system of the individual. The system comprises one or more MOMP t-NLPs herein described together with one or more adjuvant or adjuvant-NLPs herein described.

According to a seventh aspect, a method and system for treating or preventing a *Chlamydia* infection or conditions associated thereto in an individual, is described, the method comprises administering to the individual a MOMP-t-NLP herein described in an effective amount to elicit an immunitary response to the MOMP-t-NLPs in the individual. The system comprises one or more MOMP t-NLPs herein described together with one or more adjuvant or adjuvant-NLPs herein described.

Telodendrimer nanolipoproteins and related compositions, methods and systems, in several embodiments herein described allow, in several embodiments, production of a soluble recombinant MOMP antigen in a functional multimeric conformation.

Telodendrimer nanolipoproteins and related compositions, methods and systems, in several embodiments herein described allow, in several embodiments, to rapidly produce a high yield recombinant soluble mMOMP exhibiting functional multimer formation.

Telodendrimer nanolipoproteins and related compositions, methods and systems, in several embodiments herein described allow, in several embodiments, production of MOMP in particles that can also comprise immunogenic adjuvants and that can be used in the production of vaccine and/or in methods for generating an immunogenic response in individuals.

Telodendrimer nanolipoproteins and related compositions, methods and systems, in several embodiments herein described allow, in several embodiments, immunization against *Chlamydia* characterized by strong antibody titers.

Telodendrimer nanolipoproteins and related compositions, methods and systems, in several embodiments herein described can be used, as a model that can be applied to other antigens with low solubility (from 0-50% of the total amount of antigens in the reaction mixture) or requiring the use of detergents to first prepare the membrane protein additional to the scaffold protein for assembly. For example, telodendrimer nanolipoproteins and related compositions, methods and systems, in several embodiments herein described can be used, as a model for beta barrel forming membrane proteins that form multimeric complexes and tend to form inclusion bodies when over-expressed.

The MOMP-t-NLPs and related compositions, methods and systems herein described can be used in connection with various applications wherein presentation of functional MOMPs in an ordered structure is desired. For example, the MOMP-t-nanolipoprotein particles herein described and related compositions methods and systems can be used in antigen detection, generation of functional pores, receptors and membrane enzymes for use as therapeutics as well as immune modulators vaccine development and use, and/or to contain cell-targeting moieties. Additional exemplary applications include uses of nanolipoprotein particles in several fields including basic biology research, applied biology, bio-engineering, molecular biology, medical research, medical diagnostics, structural biology, therapeutics, vaccine development and in additional fields identifiable by a skilled person upon reading of the present disclosure.

The details of one or more embodiments of the disclosure are set forth in the accompanying drawings and the description below. Other features, objects, and advantages will be apparent from the description and drawings, and from the claims.

BRIEF DESCRIPTION OF THE DRAWINGS

The accompanying drawings, which are incorporated into and constitute a part of this specification, illustrate one or more embodiments of the present disclosure and, together with the detailed description and example sections, serve to explain the principles and implementations of the disclosure. Exemplary embodiments of the present disclosure will become more fully understood from the detailed description and the accompanying drawings, wherein:

FIG. 1D is a figure from Tu et al. 2014 [2]showing "an homology analysis of MOMP multiepitope Grey shading indicates identical residues, and unshaded indicates non-identical residues) (see Tu et al. 2014, FIG. 1 legend) (SEQ ID NOs: 67 to SEQ ID NO: 70)

FIG. 2 panels (210-250) mMOMP DNA, Δ49ΔpoA1 DNA, and DMPC lipids/telodendrimer were mixed in a cell free reaction chamber. FIG. 2 panel (240) Protein translation and the self-assembly of mMOMP-tNLPs in a cell free lysate. FIG. 2 panel (250) shows a schematic representation of the assembled mMOMP-tNLP product. As shown in the schematic, the cell-free expression of mMOMP from a DNA construct in presence of Δ49ApoA1 scaffold protein, lipids and telodendrimers results in the formation of a complex of soluble mMOMP in a functional porin structure within a tNLP.

FIGS. 3A-3B shows codon optimized and species matched DNA sequences of FIG. 3A shows a comparison of wild type vs. codon optimized mouse nucleic acid sequence for the encoded Δ49ApoA1 gene (SEQ ID NO: 61, SEQ ID NO: 62). FIG. 3B shows a comparison between wild type *Chlamydia muridarum* MOMP vs. codon optimized MOMP nucleic acid sequence (SEQ ID NO: 64 SEQ ID NO: 65), the asterisk symbol marks where the native sequence and the optimized sequence are the same. The wild type mouse nucleic acid sequence for the encoded Δ49ApoA1 gene is also shown in FIG. 13. The codon optimized mouse nucleic acid sequence for the encoded Δ49ApoA1 gene is also shown in FIG. 14. The wild type *Chlamydia muridarum* MOMP nucleic acid sequence is also shown in FIG. 16. The codon optimized *Chlamydia muridarum* MOMP nucleic acid sequence is also shown in FIG. 17.

FIG. 4A shows total and soluble portions of mMOMP produced in a cell-free expression system in the presence of DMPC. FIG. 4B shows total and soluble portions of mMOMP produced in a cell-free expression system, co-expressed with Δ49ApoA1 in the presence of DMPC and telodendrimer $PEG^{5k}$-$CA_8$. The presence of the mMOMP protein band in the 'S' lane of FIG. 4B indicates that the addition of telodendrimers to the cell-free expression system results in soluble mMOMP protein, with the solubility of mMOMP increasing from 10% to 75% upon insertion into tNLP.

FIGS. 5A-5C shows examples of expression and purification of mMOMP-tNLP. In particular, FIG. 5A shows a SYPRO Ruby Protein Gel stain of 4-12% SDS-PAGE of nickel affinity chromatography-purified mMOMP-tNLP. Total unpurified lysate (Total), flow through (FT), Washes (W) 1 and 6, and Elutions (E) 1 through 6. All samples were boiled for 5 minutes in the presence of 50 mM DTT. mMOMP is at 40 kDa and the Δ49ApoA1 is at 22 kDa. M: molecular weight marker. The SDS-PAGE gel densitometry analysis of FIG. 5A indicates that affinity purified mMOMP-tNLP is 95% pure, and yields 1.5 mg of purified mMOMP-tNLP per 1 mL of cell-free reaction. Distinct bands of mMOMP and Δ49ApoA1 indicate that the two proteins are co-purifying as a complex. FIG. 5B shows a diagram reporting SEC traces of mMOMP-tNLP particles from four nickel affinity column elution fractions (E1, E2, E3 and E4), where the different nickel affinity column fractions show the same SEC elution time, indicating they contain the same sized mMOMP-tNLPs. The elutions in panel A and b are the same elution fractions. X axis represents absorption at 280 nm, whereas Y axis is the time of elution. The SEC analysis of FIG. 5B confirms that each mMOMP-tNLP fraction eluted at the appropriate time (retention time ($t_r$)~7 min) without un-incorporated protein or free lipid peaks ($t_r$~15 min and 4 min, respectively), indicating that the complex was a homogenous mixture of mMOMP-tNLPs. FIG. 5C shows an image of a dot blot of SEC-purified mMOMP-tNLP samples in duplicate, probed with mAb40 and mAbHIS antibodies. The dot blots of SEC fractions of FIG. 5C show apolipoprotein and mMOMP co-localized within the SEC fractions.

FIGS. 6A-6C show examples of size distribution and cryoEM imaging of mMOMP-tNLPs. In particular, FIG. 6A shows the size distribution of empty tNLPs as measured by Dynamic Light Scattering (DLS). FIG. 6B shows the size distribution of mMOMP-tNLPs measured by DLS. The graphs of FIGS. 6A and 6B show empty tNLPs approximately 10 nm in diameter and mMOMP-tNLP particle with an almost 4-fold increase in diameter to about 40 nm. FIG. 6C shows images of cryoEM of mMOMP-tNLP and tNLP, demonstrating that the mMOMP particles are disc like in shape and that there are size differences between tNLP and mMOMP-tNLP particles. Detailed images of the discs show the distribution of mMOMP protein multimers, shown as multiple dark regions of enhanced density within the mMOMP-tNLP particle.

FIGS. 7A-7B shows images of mMOMP-tNLPs analyzed by SDS-PAGE and Western blot. In particular, FIG. 7A shows an image of a SYPRO Ruby Protein Gel stain of 4-12% SDS-PAGE of affinity purified mMOMP-tNLP and tNLP alone. mMOMP monomer shows a band at ~40 kDa and the Δ49ApoA1 shows a band at 22 kDa. The mass ratio of soluble mMOMP to apolipoprotein is ~2:1. Lane 1 shows a molecular weight marker (M). In lane 2, the protein band pattern indicates that the application of heat and reducing agent have broken down higher order mMOMP structure. In contrast, in lane 3, the presence of higher order bands indicates mMOMP multimer conformation is retained in absence of the application of heat and reducing agent. FIG. 7B shows an image of a Western blot of mMOMP-tNLP and tNLP alone. Shown is a transfer membrane probed with mAb40 (1:1000 dilution). As indicated, samples were incubated at room temperature or were boiled for 5 minutes in the presence of 50 mM DTT. Similar to the results shown in FIG. 7A, the Western blot analysis of FIG. 7B also indicates the formation of higher order oligomer structures of mMOMP in mMOMP-tNLPS, in absence of heat and denaturant.

FIG. 8 shows exemplary results of dot blot analysis of mMOMP-tNLP and tNLP assemblies treated with heat and reducing agent. The mMOMP-tNLP and tNLP assemblies were blotted in triplicate and probed with mAb40 (linear epitope antibody) and mAbHIS (penta-His antibody). Where indicated, samples were boiled for 5 minutes in the presence of 50 mM DTT. In the illustration of FIG. 8, a same intensity of signal is observed for antibodies specific for mMOMP with and without heat and reducing agent, indicating that heat and DTT do not affect the mAb40 binding to mMOMP, and that oligomers of mMOMP are broken down to monomers upon heat and DTT.

FIGS. 9A-9B shows exemplary results of conductance analysis of mMOMP-tNLPs. In particular, FIG. 9A shows conductance traces recorded at 50 mV applied voltage in physiological conditions after tNLP alone (i) and mMOMP-tNLPs (ii-iv) were added to the measurement chamber. Current increases seen after mMOMP-tNLP addition indicate pore formation. Representative traces show 1× (ii) and 3× (iii) mMOMP-tNLP incorporations. Trace (iv) shows several incorporations events occurring in quick succession. The increases shown in the traces shown in FIG. 9A indicate the formation of bilayer pore formation by mMOMP proteins, indicating functional mMOMP insertion. FIG. 9B shows a histogram of 184 conductance events. Dashed line indicates best fit to a sum of Gaussian peaks for 1× and 3× incorporation events, indicating that the mMOMP channel of FIG. 9B have a tendency to oligomerize within the membrane and form trimers (corresponding to three pores).

FIGS. 10A-10B shows exemplary results of in vivo testing of mMOMP-tNLPs. In particular.

FIGS. 11A-11B shows a schematic representation of an exemplary telodendrimer suitable to be included in MOMP-tNLPs herein described. In particular, FIG. 11A shows a schematic representation of exemplary Cys-telodendrimer suitable to be included in MOMP-t-NLPs herein described. FIG. 11B shows a schematic representation of exemplary His-telodendrimer suitable to be included in MOMP-t-NLPs herein described.

FIGS. 12A-12C shows sequences of scaffold protein and MOMP protein that can be used to provide MOMP-NLPs herein described. FIG. 12A shows codon optimized nucleotide (SEQ ID NO: 55) and amino acid sequence (SEQ ID NO: 56) for LLNL mouse Δ49ApoA1. FIG. 12B shows codon optimized nucleotide (SEQ ID NO: 57) and amino acid sequence (SEQ ID NO: 58) for LLNL Mouse ApoE4, 22 k. FIG. 12C shows codon optimized nucleotide (SEQ ID NO: 59) and amino acid sequence (SEQ ID NO: 60) for LLNL MoPn MOMP based on (NP_296436) WP_010232357 and codon optimized.

Figure 1A:
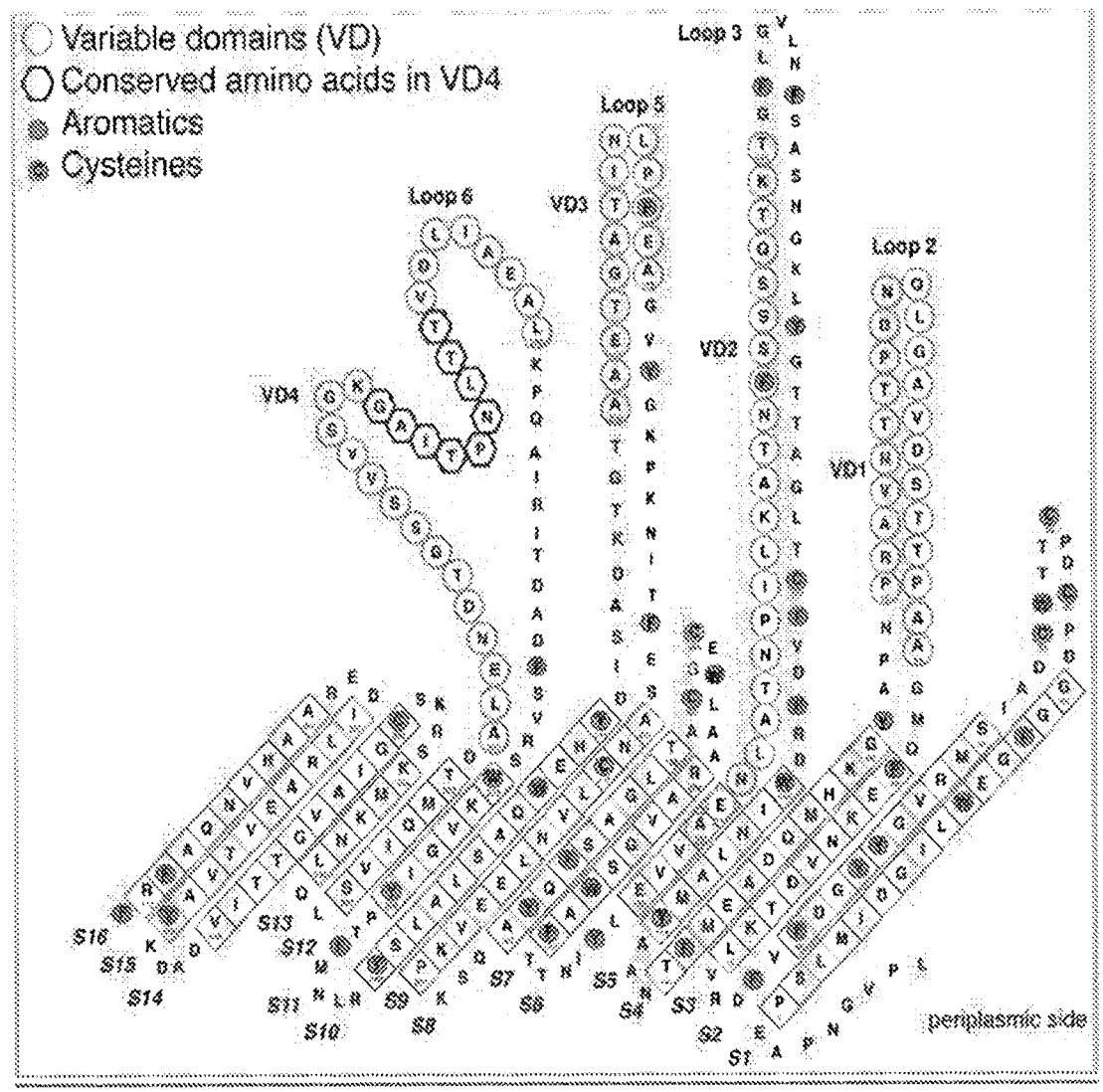
FIG. 1A is a grayscale version of a figure from Feher et al. 2013 [1] which shows a schematic representation of the secondary structure and "predicted topology of the *C. trachomatis* MOMP serovar C monomer." (see Feher et al. 2013 FIG. 4) (SEQ ID NO: 66) wherein the variable domains are shown by domains with residues in gray circles in the MOMP loops, while transmembrane domains are shown by amino acids within squares.

FIG. 13 shows a wild type mouse nucleic acid sequence (SEQ ID NO: 61) for the encoded Δ49ApoA1 gene.

FIG. 14 shows LLNL codon optimized mouse nucleic acid sequence (SEQ ID NO: 62) for the encoded Δ49ApoA1 gene.

FIG. 15 shows a LLNL codon optimized BALBC mouse nucleic acid sequence (SEQ ID NO: 63) for the encoded Δ49ApoA1 gene.

FIG. 16 shows a wild type *Chlamydia muridarum* MOMP nucleic acid sequence (SEQ ID NO:64).

FIG. 17 shows LLNL codon optimized *Chlamydia muridarum* MOMP nucleic acid sequence (SEQ ID NO: 65).

FIGS. 18A-18C shows exemplary results of in vivo testing of MOMP-NLPs formulated with CpG or CpG and $FSL_1$. FIG. 18A shows antibody tiers from immunized mice revealed from ELISA analysis. FIG. 18B shows weight loss of the immunized mice following intranasal challenge with *C. muridarum* (Cm) as a measure of protection. FIG. 18C plots the number of Cm IFU recovered from mice vaccinated with different MOMP:NLPs formulations. Each dot represents a mouse. The horizontal line corresponds to the median. * $p<0.05$.

FIG. 19 illustrates an exemplary schematic of a *Chlamydia* vaccine pipeline.

FIG. 20A shows results from the SDS-PAGE analysis following cell-free synthesis of MOMP-NLPs using varying ratios of fluorescent labeled Apo to MOMP proteins at 1:1, 1:5, 1:10, 1:25, 1:50, and 1:100.

FIG. 20B shows scanning electron microscopic images (SEM) of (A) empty NLP disc, (B) MOMP-NLP disc with 1-2 monomers of MOMP inserted, (C) MOMP-NLP disc with 1-2 trimers of MOMP inserted, and (D) MOMP-NLP disc with >3 trimers of MOMP inserted.

FIG. 21A shows SDS-PAGE images of codon-optimized fluorescent-labeled Pmps (PmpC, PmpE, PmpF, PmpG, and PmpH) having an adhesion domain (annotated as "+") and truncated versions that lack the adhesion domain (annotated as "–").

FIG. 21B shows SDS-PAGE images of cell-free expressed and nickel-purified PmpH and $ApoA_1$ $Δ49A_1$.

FIGS. 22A-22C demonstrates in an embodiment the cell-free production of MOMP co-translated with $ApoA_1$ $Δ49A_1$. FIG. 22A shows SDS-PAGE images of cell-free expressed and purified MOMP and $ApoA_1$ $Δ49A_1$. FIG. 22B shows exemplary results of dot blot analysis MOMP-NLP and NLP assemblies treated with heat and reducing agent. The MOMP-NLP and NLP assemblies were blotted in triplicate and probed with mAb40, mAbHIS and mAb18b. Addition of heat and DTT results in a decrease in signal as detected by mAb18b, a conformational trimer recognition antibody, indicating a loss in trimer formation. mAb40 recognizes both MOMP monomer and trimer as it binds to a linear epitope. The mAbHIS recognizes the HIS tag on the Δ49A1 protein. FIG. 22C shows conductance traces recorded at 50 mV applied voltage in physiological conditions after NLP alone and MOMP-NLP were added to the measurement chamber. Current increases observed after MOMP-NLP addition indicate the formation of bilayer pore formation by MOMP proteins, indicating functional MOMP insertion.

FIGS. 23A-23E shows results of experiments directed to provide a structural characterization of native MOMP. FIG. 23A shows results of TEM analysis of native MOMP.

FIG. 23B shows TEM images of trimeric MOMP particles selected using a semi-automated particle selection tool via EMAN 2.1 package. FIG. 23C shows MOMP trimer images be collected and class averaged. FIG. 23D shows raw projection images of MOMP trimer with distinct structural features (white arrows). FIG. 23E shows previously solved MOMP structures, such as MOMP from *Campylobacter jejuni* (5 LDT). Black arrow indicates the fitted edges of preliminary density map generated from class averages.

FIG. 24 shows the percentage of weight loss of the immunized mice following *C. muridarum* (Cm) challenge with two different MOMP-t-NLP formulations and two empty NLP formulations.

DETAILED DESCRIPTION

Provided herein are nanolipoprotein particles comprising telodendrimers and *Chlamydia* major outer membrane protein (MOMP) and related compositions methods and systems.

The term "nanolipoprotein particle" "nanodisc" "rHDL" or "NLP" as used herein indicates a supramolecular complex formed by a membrane forming lipid arranged in a lipid bilayer stabilized by a scaffold protein. The membrane forming lipids and scaffold protein are components of the NLP. In particular, the membrane forming lipid component is part of a total lipid component, (herein also membrane lipid component or lipid component) of the NLP together with additional lipids such as functionalized lipids and/or lysolipids, that can further be included in the NLPs as will be understood by a skilled person upon reading of the present disclosure. The scaffold protein component is part of a protein component of the NLP together with additional proteins such as membrane proteins, target proteins and other proteins that can be further included as components of the NLPs as will be understood by a skilled person upon reading of the present disclosure. Additional components can be provided as part of the NLP herein described as will be understood by a skilled person. In particular, the membrane lipid bilayer can attach membrane proteins or other amphipathic compounds through interaction of respective hydrophobic regions with the membrane lipid bilayer. The membrane lipid bilayer can also attach proteins or other molecule through anchor compounds or functionalized lipids as will be understood by a skilled person upon reading of the disclosure. In a nanolipoprotein particle, the membrane lipid bilayer can be confined in a discoidal configuration by the scaffold protein. Predominately discoidal in shape, nanolipoprotein particles typically have diameters between 5 to 25 nm, share uniform heights between 3 to 6 nm and can be produced in yields ranging between 30 to 90%.

In particular, in embodiments herein described the nanolipoprotein particle can be formed by a lipid bilayer confined in a discoidal configuration by a scaffold protein. In this configuration, the lipid bilayer confined by the scaffold protein can be 3-6 nanometers in thickness, the nanolipoprotein particle can have an overall diameter of 5-25 nanometers, and the scaffold protein on the particle can have a thickness of 1-2 nanometers. In some embodiments, an entire NLP structure can be up to 600 kilodaltons in weight.

The particular membrane forming lipid, scaffold protein, the lipid to protein ratio, and the assembly parameters determine the size and homogeneity of nanolipoprotein particles as will be understood by a skilled person. In the nanolipoprotein particle the membrane forming lipid are typically arranged in a membrane lipid bilayer confined by the scaffold protein in a discoidal configuration as will be understood by a skilled person.

The term "membrane forming lipid" or "amphipathic lipid" as used herein indicates a lipid possessing both hydrophilic and hydrophobic moieties that in an aqueous environment assembles into a lipid bilayer structure that consists of two opposing layers of amphipathic molecules known as polar lipids. Each polar lipid has a hydrophilic moiety, i.e. a polar group such as, a derivatized phosphate or a saccharide group, and a hydrophobic moiety, i.e., a long hydrocarbon chain. Exemplary polar lipids include phospholipids, sphingolipids, glycolipids, ether lipids, sterols, alkylphosphocholines and the like. Amphipathic lipids include but are not limited to membrane lipids, i.e. amphipathic lipids that are constituents of a biological membrane, such as phospholipids like dimyristoylphosphatidylcholine (DMPC) or dioleoylphosphoethanolamine (DOPE) or dioleoylphosphatidylcholine (DOPC), or dipalmitoylphosphatidylcholine (DPPC). In a preferred embodiment, the lipid is dimyristoylphosphatidylcholine (DMPC).

The term "scaffold protein" as used herein indicates any amphipathic protein that is capable of self-assembly with amphipathic lipids in an aqueous environment, organizing the amphipathic lipids into a bilayer disc, and comprise apolipoproteins, lipophorins, derivatives thereof (such as truncated and tandemly arrayed sequences) and fragments thereof (e.g. peptide fragments and synthetic peptides) which maintains the amphipathic nature and capability of self-assembly, such as apolipoprotein E4 (22 Kd fragment), lipophorin III, apolipoprotein A-1 and the like. In general, scaffold proteins have an alpha helical secondary structure in which a plurality of hydrophobic amino acids form a hydrophobic face and a plurality of hydrophilic amino acids form an opposing hydrophilic face. In some embodiments, rationally designed amphipathic peptides and synthetic apolipoproteins which maintain an amphipathic structure and capability of self-assembly can serve as a scaffold protein of the NLP.

The term "apolipoprotein" as used herein indicates an amphipathic protein that binds lipids to form lipoproteins. The term "amphipathic" pertains to a molecule containing both hydrophilic and hydrophobic properties. Exemplary amphipathic molecules comprise molecules having hydrophobic and hydrophilic regions/portions in its structure. Examples of biomolecules which are amphipathic include but not limited to phospholipids, cholesterol, glycolipids, fatty acids, bile acids, saponins, and additional lipids identifiable by a skilled person. A "lipoprotein" as used herein indicates a biomolecule assembly that contains both proteins and lipids. In particular, in lipoproteins, the protein component surrounds or solubilizes the lipid molecules enabling particle formation. Exemplary lipoproteins include the plasma lipoprotein particles classified under high-density (HDL) and low-density (LDL) lipoproteins, which enable fats and cholesterol to be carried in the blood stream, the transmembrane proteins of the mitochondrion and the chloroplast, and bacterial lipoproteins. In particular, the lipid components of lipoproteins are insoluble in water, but because of their amphipathic properties, apolipoproteins such as certain Apolipoproteins A and Apolipoproteins B and other amphipathic protein molecules can organize the lipids in a bilayer orientation with exposed hydrophilic moieties, creating the lipoprotein particle that is itself water-soluble, and can thus be carried through water-based circulation (e.g. blood, lymph in vivo or in vitro). Apolipoproteins known to provide the protein components of the lipoproteins can be divided into six classes and several sub-classes, based on the different structures and functions. Exemplary apolipoprotein known to be able to form lipoproteins comprise Apolipoproteins A (apo A-I, apo A-II, apo A-IV, and apo A-V), Apolipoproteins B (apo B48 and apo B100), Apolipoproteins C (apo C-I, apo C-II, apo C-III, and apo C-IV), Apolipoproteins D, Apolipoproteins E, and Apolipoproteins H. For example, apolipoproteins B can form low-density lipoprotein particles, and have mostly beta-sheet structure and associate with lipid droplets irreversibly, while Apolipoprotein A1 comprise alpha helices and can associate with lipid droplets reversibly forming high-density lipoprotein particles.

The term "protein" as used herein indicates a polypeptide with a particular secondary and tertiary structure that can interact with another molecule and in particular, with other biomolecules including other proteins, DNA, RNA, lipids, metabolites, hormones, chemokines, and/or small molecules. The term "polypeptide" as used herein indicates an organic linear, circular, or branched polymer composed of two or more amino acid monomers and/or analogs thereof. The term "polypeptide" includes amino acid polymers of any length including full-length proteins and peptides, as well as analogs and fragments thereof. A polypeptide of three or more amino acids is also called a protein oligomer, peptide, or oligopeptide. In particular, the terms "peptide" and "oligopeptide" usually indicate a polypeptide with less than 100 amino acid monomers. In particular, in a protein, the polypeptide provides the primary structure of the protein, wherein the term "primary structure" of a protein refers to the sequence of amino acids in the polypeptide chain covalently linked to form the polypeptide polymer. A protein "sequence" indicates the order of the amino acids that form the primary structure. Covalent bonds between amino acids within the primary structure can include peptide bonds or disulfide bonds, and additional bonds identifiable by a skilled person. Polypeptides in the sense of the present disclosure are usually composed of a linear chain of alpha-amino acid residues covalently linked by peptide bond or a synthetic covalent linkage. The two ends of the linear polypeptide chain encompassing the terminal residues and the adjacent segment are referred to as the carboxyl terminus (C-terminus) and the amino terminus (N-terminus) based on the nature of the free group on each extremity. Unless otherwise indicated, counting of residues in a polypeptide is performed from the N-terminal end ($NH_2$-group), which is the end where the amino group is not involved in a peptide bond to the C-terminal end (—COOH group) which is the end where a COOH group is not involved in a peptide bond. Proteins and polypeptides can be identified by x-ray crystallography, direct sequencing, immunoprecipitation, and a variety of other methods as understood by a person skilled in the art. Proteins can be provided in vitro or in vivo by several methods identifiable by a skilled person. In some instances where the proteins are synthetic proteins in at least a portion of the polymer two or more amino acid monomers and/or analogs thereof are joined through chemically-mediated condensation of an organic acid (—COOH) and an amine (—$NH_2$) to form an amide bond or a "peptide" bond.

As used herein the term "amino acid", "amino acid monomer", or "amino acid residue" refers to organic compounds composed of amine and carboxylic acid functional groups, along with a side-chain specific to each amino acid. In particular, alpha- or α-amino acid refers to organic compounds composed of amine (—$NH_2$) and carboxylic acid (—COOH), and a side-chain specific to each amino acid connected to an alpha carbon. Different amino acids have different side chains and have distinctive characteristics, such as charge, polarity, aromaticity, reduction potential, hydrophobicity, and pKa. Amino acids can be covalently linked to form a polymer through peptide bonds by reactions between the amine group of a first amino acid and the carboxylic acid group of a second amino acid. Amino acid in the sense of the disclosure refers to any of the twenty naturally occurring amino acids, non-natural amino acids, and includes both D an L optical isomers.

In embodiments herein described, the NLPs herein described further comprise one or more telodendrimers to form telo-nanolipoprotein particles (telo-NLPs or t-NLPs). Predominately discoidal in shape, MOMP-t-NLPS typically have diameters of less than one micron in diameter and in particular can have a diameter from 5 nm to 100 nm in diameter, and in particular from 25 nm to 50 nm. The t-NLPs herein described typically have uniform heights between 3 to 6 nm and can be produced in yields ranging between 80 to 90%.

In particular, in embodiments herein described the MOMP-t-NLPs can be formed by a lipid bilayer confined in a discoidal configuration by a scaffold protein and a telodendrimer. In this configuration, the lipid bilayer confined by the scaffold protein can be 3-6 nanometers in thickness, the nanolipoprotein particle can have an overall diameter between 5 nm to 100 nm in diameter and in particular a diameter of 25-50 nanometers, and the scaffold protein on the particle can have a thickness of 1-2 nanometers. In some embodiments, an entire NLP structure can be up to 600 kilodaltons in molecular weight.

The term "telodendrimer" refers to a dendrimer containing a hydrophilic covalently attaching a tail group T which comprises a hydrophilic polymer having a weight averaged molecular weight from 1 to 100 kDa. The term "attach" or "attached" as used herein, refers to connecting or uniting by a bond, link, force or tie in order to keep two or more components together, which encompasses either direct or indirect attachment where, for example, a first molecule is directly bound to a second molecule or material, or one or more intermediate molecules are disposed between the first molecule and the second molecule or material The term "dendrimers" used herein refer to repetitively branched molecules having three basis architectural components namely (i) a focal point or group on a dendrimer core, (ii) repetitive plurality of branched monomer units covalently linked to the dendrimer core and (iii) a plurality of end groups each covalently linked to a terminal monomer of the plurality of branched monomer units. In particular, a "dendrimer core" is a chemical moiety presenting a backbone and at least two anchor atoms, each anchor atom defining a bonding position to a head attachment atom of a branched monomer units.

In some embodiments, the dendrimer core can be formed by a branched monomer unit, for example, a lysine unit.

The term "monomer unit" or "monomer" in the sense of the disclosure is a chemical structure presenting one head attachment atom and at least one tail attachment atoms. The head attachment atom defines a bonding position to an anchor atom of a dendrimer core or a tail attachment atom of another monomer unit. The tail attachment atom defines a bonding position to a head attachment atom of another branch cell unit or to a terminal functional group with the attachment possibly performed directly or indirectly.

A "branched monomer unit", or "branched monomer" is a monomer unit having at least two tail attachment atoms as also indicated. A generation of branched monomer unit within a dendrimer defines a shell of the dendrimer as will be understood by a skilled person (see "Dendrimers and other Dendritic polymers" by Jean M. J Frechet and Donald A. Tomalia 2001 herein incorporated by reference in its entirety). The branched monomer unit of a generation typically define an interior space inside the dendrimer herein also indicated as interior of shell as will be understood by a skilled person. An "end group" of a dendrimer, is a functional group or a chemical moiety presented on the outermost part of the dendrimer attached to an end of branched monomer unit. The branched monomer unit attaching the end groups typically provide the outer shell or periphery of the dendrimer.

In the dendrimer core, the backbone of the dendrimer core can be any stable chemical moiety having the capability to present anchoring positions for the attachment of branched monomer units and a focal point for attachment to a linker moiety L, a spacer moiety A or a tail group T.

In particular, the core backbone structure can be one of aromatic, heteroaromatic rings, aliphatic, or heteroaliphatic rings or chains. In some embodiments, the backbone of the dendrimer core can be one single atom, including C, N, O, S, Si, or P.

In a dendrimer as described herein, the branched monomer unit are linked together to form arms (or "dendrons") extending from the focal point and terminating at the end groups. The focal point of the dendritic polymer can be attached to other segments of the telodendrimers, and the end groups may be further functionalized with additional chemical moieties.

In embodiments, herein described, the dendritic polymer can be any suitable dendritic polymer. The dendritic polymer can be made of branched monomer units including amino acids or other bifunctional XY2 type monomers, where X and Y are two different functional groups capable of reacting together such that the resulting polymer chain has a branch point where an X-Y covalent bond is formed. For example, in the case of lysine, when X is a carboxylic acid and Y is an amino group, an amide bond can be form between X and Y. In some embodiments, each branched monomer unit X can be a diamino carboxylic acid, a dihydroxy carboxylic acid and a hydroxylamino carboxylic acid.

In some embodiments, each diamino carboxylic acid can be 2,3-diamino propanoic acid, 2,4-diaminobutanoic acid, 2,5-diaminopentanoic acid (ornithine), 2,6-diaminohexanoic acid (lysine), (2-Aminoethyl)-cysteine, 3-amino-2-aminomethyl propanoic acid, 3-amino-2-aminomethyl-2-methyl propanoic acid, 4-amino-2-(2-aminoethyl)butyric acid or 5-amino-2-(3-aminopropyl)pentanoic acid. In some embodiments, each dihydroxy carboxylic acid can be glyceric acid, 2,4-dihydroxybutyric acid, 2,2-Bis(hydroxymethyl)propionic acid, 2,2-Bis(hydroxymethyl)butyric acid, serine or threonine.

In some embodiments, each hydroxyl amino carboxylic acid can be serine or homoserine. In some embodiments, the diamino carboxylic acid is an amino acid. In some embodiments, each branched monomer unit X is lysine.

The dendritic polymer of the telodendrimer can be any suitable generation of dendrimer, including generation 1, 2, 3, 4, 5, or more, where each "generation" of dendrimer refers to the number of branch points encountered between the focal point and the end group following one branch of the dendrimer. The dendritic polymer of the telodendrimer can also include partial-generations such as 1.5, 2.5, 3.5, 4.5, 5.5, etc., where a branch point of the dendrimer has only a single branch. The various architectures of the dendritic polymer can provide any suitable number of end groups, including, but not limited to, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31 or 32 end groups.

The telodendrimer backbone can vary, depending on the number of branches and the number and chemical nature of the end groups and R groups, which will modulate solution conformation, rheological properties, and other characteristics. The telodendrimers can have any suitable number n of end groups and any suitable number of R groups. In some embodiments, n can be 2-70, or 2-50, or 2-30, or 2-10. In some embodiment, n is 2-20.

The R groups installed at the telodendrimer periphery can be any suitable chemical moiety, including, for example, hydrophilic groups, hydrophobic groups, or amphiphilic compounds. Examples of hydrophobic groups include, but are not limited to, long-chain alkanes and fatty acids, fluorocarbons, silicones, certain steroids such as cholesterol, and many polymers including, for example, polystyrene and polyisoprene. Examples of hydrophilic groups include, but are not limited to, alcohols, short-chain carboxylic acids, amines, sulfonates, phosphates, sugars, and certain polymers such as PEG. Examples of amphiphilic compounds include, but are not limited to, molecules that have one hydrophilic face and one hydrophobic face.

Amphiphilic compounds that can be used in the preparation of MOMP-t-NLPs herein described comprise cholic acid and cholic acid analogs and derivatives. "Cholic acid" refers to (R)-4-((3R,5S,7R,8R,9S,10S,12S,13R,14S,17R)-3, 7,12-trihydroxy-10, 13-dimethylhexadecahydro-1H-cyclopenta[a]phenanthren-17-yl)pentanoic acid. Cholic acid derivatives and analogs comprise allocholic acid, pythocholic acid, avicholic acid, deoxycholic acid, and chenodeoxycholic acid. Cholic acid derivatives can be designed to modulate the properties of the nanocarriers resulting from telodendrimer assembly, such as micelle stability and membrane activity. For example, the cholic acid derivatives can have hydrophilic faces that are modified with one or more glycerol groups, aminopropanediol groups, or other groups.

In some embodiments, each R of the telodendrimer of formula (I) can be cholic acid, (3α,5(3,7α,12α)-7,12-dihydroxy-3-(2,3-dihydroxy-1-propoxy)-cholic acid, (3α, 5β,7α,12α)-7-hydroxy-3,12-di(2,3-dihydroxy-1-propoxy)-cholic acid, (3α,5β,7α,12α)-7,12-dihydroxy-3-(3-amino-2-hydroxy-1-propoxy)-cholic acid, cholesterol formate (CF), doxorubicin, or rhein. In some embodiments, each amphiphilic compound is cholic acid (CA). In some embodiments, each amphiphilic compound is cholesterol formate (CF).

In some embodiments, the tail group T can be a moiety of formula (XI)

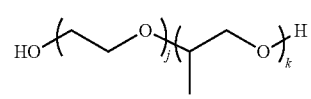

Formula (XI)

wherein i and j can be independently selected from 2-3000, preferably 22-2300, and more preferably 22-230; and wherein the polymer of Formula (XI) can be attached by way of any one of the two terminal hydroxyl groups to an end group of the dendrimer.

In some embodiments, i and j together can be independently selected from 2-3000, preferably 22-2300, and more preferably 22-230.

In some embodiments, the tail group can be polyethylene glycol, PEG, (k=0 in formula (XI)), polypropylene glycol (j=0 in Formula XI) or a polyethylene-b-polypropylene glycol (j>0, k>0) in Formula (XI).

In some embodiments herein described, the telodendrimers herein described are block copolymers having a linear poly(ethylene glycol) (PEG) moiety and a dendritic hydrophobic segment or a dendritic amphiphilic moiety. Telodendrimers can also have additional functional groups such as cholic acid groups and hydrophobic groups (e.g. hydrophobic moieties with drug properties) covalently bound to the dendritic segment.

As used herein, the term "hydrophobic group" refers to a chemical moiety that is Water-insoluble or repelled by water. Examples of hydrophobic groups include, but are not limited to, C1-C4 short-chain alkanyls, C5-C22 long-chain alkanyls, C1-C4 short-chain alkenyls, C5-C22 long-chain alkenyls, C1-C4 short-chain alkynyls, C5-C22 long-chain alkenyls and fatty acids, fluorocarbons, silicones, certain steroids such as cholesterol, and many polymers including, for example, polystyrene and polyisoprene or their derivatives.

As used herein, the term "hydrophilic group" refers to a chemical moiety that is water-soluble or attracted to water. Examples of hydrophilic groups include, but are not limited to, alcohols, short-chain carboxylic acids, quaternary amines, sulfonates, phosphates, sugars, and certain polymers such as poly(ethylene glycol) (PEG).

In some embodiments, the PEG as used herein can have 2 to 3000 ethylene glycol units, —($CH_2CH_2O$)—, preferably 22-2300 ethylene glycol units, and more preferably 22-230 ethylene glycol units.

It is also to be understood that, unless otherwise specified herein, a molecular weight of a polymer herein refers to a weight average molecular weight. In the instant disclosure molecular weight of a polymer, e.g. PEG can be indicated as a superscript together with the indication of the polymer (e.g. a PEG of 2000 DA can also be indicated as $PEG^{2k}$)

As used herein, the term "amphiphilic compound" or "amphiphilic moiety" refers to a compound or moiety having both hydrophobic portions and hydrophilic portions. For example, the amphiphilic compounds herein described can have one hydrophilic face of the compound and one hydrophobic face of the compound.

In some embodiments, in telodendrimers of the disclosure the tail group T is attached to the dendrimer through a spacer A and/or a linker L.

As used herein the term "spacer A" indicates a spacer moiety formed by one or more monomers configured to be directly covalently connected to one or more tail groups T and to one linker moiety L.

As used herein, the term "linker" or "linker moiety" refers to a chemical moiety formed by one or more monomers configured to be directly covalently bonded to a spacer A and a focal point of a dendrimer. The types of bonds used to link the linker L to the focal point of the dendrimer D and the spacer A include, but are not limited to, amides, amines, esters, carbamates, ureas, thioethers, thiocarbamates, thiocarbonates and thioureas and additional bonds as will be understood by a skilled person.

In particular, in some embodiments, the telodendrimer of the present disclosure can have general formula (I):

$$(T)_m\text{-}(A)_p\text{-}L\text{-}D\text{-}(R)_n \qquad (I)$$

wherein
D is a dendrimer
T is a tail group;
A is a spacer moiety configured to be directly covalently connected to each T and to a linker moiety L, and comprises a polymer of 1 to m number of spacer A monomers, wherein the spacer A monomer comprises a substituted or unsubstituted linear C1-C15 alkyl; branched C3-C15 alkyl; cyclic C3-C15 alkyl; linear, cyclic, or branched C2-C15 alkenyl; linear, cyclic, or branched C2-C15 alkynyl; C6-C20 substituted or unsubstituted aryl; and C6-C20 substituted or unsubstituted heteroaryl.
m is 0-20 and p is 0-1, and
wherein m is 0 or 1 when p is 0; or m is 2-20 when p is 1;

In some embodiments, L can be a polymer of 1 to m number of independently selected spacer A monomers, wherein the spacer A monomer comprises a substituted or unsubstituted linear C1-C15 alkyl; branched C3-C15 alkyl; cyclic C3-C15 alkyl; linear, cyclic, or branched C2-C15 alkenyl; linear, cyclic, or branched C2-C15 alkynyl; C6-C20 substituted or unsubstituted aryl; and C6-C20 substituted or unsubstituted heteroaryl, wherein each branch of the dendrimer is adapted to present an end group R by a covalent bond;

In some of those embodiments, each end group R is independently a hydrophobic group, a hydrophilic group, an amphiphilic group, H, or a functional group such as halo, hydroxyl, sulfhydryl, $C_1$-$C_{24}$ alkoxy, $C_2$-$C_{24}$ alkenyloxy, $C_2$-$C_{24}$ alkynyloxy, $C_5$-$C_{24}$ aryloxy, $C_6$-$C_{24}$ aralkyloxy, $C_6$-$C_{24}$ alkaryloxy, acyl (including for example $C_2$-$C_{24}$ alkylcarbonyl (—CO-alkyl) and $C_6$-$C_{24}$ arylcarbonyl (—CO-aryl)), acyloxy (—O-acyl, including for example $C_2$-$C_{24}$ alkylcarbonyloxy (—O—CO-alkyl) and $C_6$-$C_{24}$ arylcarbonyloxy (—O—CO-aryl)), $C_2$-$C_{24}$ alkoxycarbonyl (—(CO)—O-alkyl), $C_6$-$C_{24}$ aryloxycarbonyl (—(CO)—O-aryl), $C_2$-$C_{24}$ alkylcarbonato (—O—(CO)—O-alkyl), $C_6$-$C_{24}$ arylcarbonato (—O—(CO)—O-aryl), carboxy (—COOH), carboxylato (—COO—), carbamoyl (—(CO)—$NH_2$), mono-($C_1$-$C_{24}$ alkyl)-substituted carbamoyl (—(CO)—NH($C_1$-$C_{24}$ alkyl)), di-($C_1$-$C_{24}$ alkyl)-substituted carbamoyl (—(CO)—N($C_1$-$C_{24}$ alkyl)$_2$), mono-($C_5$-$C_{24}$ aryl)-substituted carbamoyl (—(CO)—NH-aryl), di-($C_5$-$C_{24}$ aryl)-substituted carbamoyl (—(CO)—N($C_5$-$C_{24}$ aryl)$_2$), di-N—($C_1$-$C_{24}$ alkyl),N—($C_5$-$C_{24}$ aryl)-substituted carbamoyl, thiocarbamoyl (—(CS)—$NH_2$), mono-($C_1$-$C_{24}$ alkyl)-substituted thiocarbamoyl (—(CO)—NH($C_1$-$C_{24}$ alkyl)), di-($C_1$-$C_{24}$ alkyl)-substituted thiocarbamoyl (—(CO)—N($C_1$-$C_{24}$ alkyl)$_2$), mono-($C_5$-$C_{24}$ aryl)-substituted thiocarbamoyl (—(CO)—NH-aryl), di-($C_5$-$C_{24}$ aryl)-substituted thiocarbamoyl (—(CO)—N($C_5$-$C_{24}$ aryl)$_2$), di-N—($C_1$-$C_{24}$ alkyl), N—($C_5$-$C_{24}$ aryl)-substituted thiocarbamoyl, carbamido (—NH—(CO)—$NH_2$), cyano(—C≡N), cyanato (—O—C≡N), thiocyanato (—S—C≡N), formyl (—(CO)—H), thioformyl (—(CS)—H), amino (—$NH_2$), mono-($C_1$-$C_{24}$ alkyl)-substituted amino, di-($C_1$-$C_{24}$ alkyl)-substituted amino, mono-($C_5$-$C_{24}$ aryl)-substituted amino, di-($C_5$-$C_{24}$ aryl)-substituted amino, $C_2$-$C_{24}$ alkylamido (—NH—(CO)-alkyl), $C_6$-$C_{24}$ arylamido (—NH—(CO)-aryl), imino (—CR=NH where R=hydrogen, $C_1$-$C_{24}$ alkyl, $C_5$-$C_{24}$ aryl, $C_6$-$C_{24}$ alkaryl, $C_6$-$C_{24}$ aralkyl, etc.), $C_2$-$C_{20}$ alkylimino (—CR=N(alkyl), where R=hydrogen, $C_1$-$C_{24}$ alkyl, $C_5$-$C_{24}$ aryl, $C_6$-$C_{24}$ alkaryl, $C_6$-$C_{24}$ aralkyl, etc.), arylimino (—CR=N(aryl), where R=hydrogen, $C_1$-$C_{20}$ alkyl, $C_5$-$C_{24}$ aryl, $C_6$-$C_{24}$ alkaryl, $C_6$-$C_{24}$ aralkyl, etc.), nitro (—$NO_2$), nitroso (—NO), sulfo (—$SO_2$—OH), sulfonato (—$SO_2$—O—), $C_1$-$C_{24}$ alkylsulfanyl (—S-alkyl; also termed "alkylthio"), $C_5$-$C_{24}$ arylsulfanyl (—S-aryl; also termed "arylthio"), $C_1$-$C_{24}$ alkylsulfinyl (—(SO)-alkyl), $C_5$-$C_{24}$ arylsulfinyl (—(SO)-aryl), $C_1$-$C_{24}$ alkylsulfonyl (—$SO_2$-alkyl), $C_5$-$C_{24}$ arylsulfonyl (—$SO_2$-aryl), boryl (—$BH_2$), borono (—B(OH)$_2$), boronato (—B(OR)$_2$ where R is alkyl or other hydrocarbyl), phosphono (—P(O)(OH)$_2$), phosphonato (—P(O)(O—)$_2$), phosphinato (—P(O)(O—)), phospho (—$PO_2$), phosphino (—PH2), silyl (—$SiR_3$ wherein R is hydrogen or hydrocarbyl), and silyloxy (—O-silyl); and the hydrocarbyl moieties $C_1$-$C_{24}$ alkyl (preferably $C_1$-$C_{12}$ alkyl, more preferably $C_1$-$C_6$ alkyl), $C_2$-$C_{24}$ alkenyl (preferably $C_2$-$C_{12}$ alkenyl, more preferably $C_2$-$C_6$ alkenyl), $C_2$-$C_{24}$ alkynyl (preferably $C_2$-$C_{12}$ alkynyl, more preferably $C_2$-$C_6$ alkynyl), $C_5$-$C_{24}$ aryl (preferably $C_5$-$C_{14}$ aryl), $C_6$-$C_{24}$ alkaryl (preferably $C_6$-$C_{16}$ alkaryl), and $C_6$-$C_{24}$ aralkyl (preferably $C_6$-$C_{16}$ aralkyl).

In some embodiments, the tail group T is polyethyleneglycol (PEG) polymers, each of the m number PEG polymer independently having a weight average molecular weight of 1-100 kDa.

In some embodiments, a telodendrimer can have the at least one tail group T having polyethyleneglycol (PEG) polymer moiety, a dendritic polymer moiety D, and at least one end group R which includes but is not limited to a hydrophobic group, a hydrophilic group, an amphiphilic compound or a drug on the dendrimer periphery or branch, wherein the dendritic polymer moiety D has a single focal group and n number of branches.

In some embodiments, a telodendrimer can comprise one or more of the following monomers in combination within a dendrimer, spacer moiety A and/or linker moiety be XY2-type monomers, where X and Y are two different functional groups capable of reacting together such that the resulting polymer chain has a branch point where an X-Y bond is formed. Exemplary monomers include a diamino carboxylic acid, a dihydroxy carboxylic acid and a hydroxyl amino carboxylic acid. Examples of diamino carboxylic acid groups include 2,3-diamino propanoic acid, 2,4-diaminobutanoic acid, 2,5-diaminopentanoic acid (ornithine), 2,6-diaminohexanoic acid (lysine), (2-Aminoethyl)-cysteine, 3-amino-2-aminomethyl propanoic acid, 3-amino-2-aminomethyl-2-methyl propanoic acid, 4-amino-2-(2-aminoethyl)butyric acid and 5-amino-2-(3-aminopropyl)pentanoic acid. Examples of dihydroxy carboxylic acid groups include glyceric acid, 2,4-dihydroxybutyric acid, and 2,2-bis(hydroxymethyl)propionic acid. Examples of hydroxyl amino carboxylic acids include serine and homoserine. One of skill in the art will appreciate other monomer units useful in the current disclosure.

In addition, the aforementioned functional groups may, if a particular group permits, be further substituted with one or more additional functional groups or with one or more hydrocarbyl moieties such as those specifically enumerated above. Analogously, the above-mentioned hydrocarbyl moieties may be further substituted with one or more functional groups or additional hydrocarbyl moieties such as those specifically enumerated.

In some embodiments, in formula (I) subscript n is an integer from 2 to 128, wherein subscript n is equal to the number of end group R; wherein each end group R is covalently linked to the dendritic polymer D, and wherein at least half the number n of R groups are each independently a hydrophobic group, a hydrophilic group, an amphiphilic group or a drug.

In formula (I) subscript p can be 0 or 1, wherein when p is 0, m can be 0 or 1; when p is 1, m can be 2 to 20 wherein each of the m number of PEG is directly covalently linked to A and each of the m number of PEGs is independently selected from a molecular weight of 1 to 100 kDa, or preferably a molecular weight of 1 kDa (PEG1000) to a molecular weight of 10 kDa (PEG 10,000).

In some embodiments, spacer moiety A can be a monomer or an oligomer presenting to at least two tail groups. As used herein, the terms "monomer" and "monomer unit" for spacer moiety A refers to repeating units that make up the spacer moiety A herein described. The monomers may be XY2-type monomers, where X and Y are two different functional groups capable of reacting together such that the resulting polymer chain has a branch point where an X-Y bond is formed.

For purpose of making spacer moiety A, one of the two Y's of a XY2-type monomer can be orthogonally protected, for example by way of Fmoc (Fluorenylmethyloxycarbonyl), Boc (t-butyloxycarbonyl), or DDE ((4,4-dimethyl-2,6-dioxocyclohex-1-ylidene)ethyl) when B is an amino group and A is a carboxylic acid.

Therefore, each of the XY2 in spacer moiety A is capable of having a covalent bond with a tail group T.

Exemplary monomers for spacer moiety A include a diamino carboxylic acid, a dihydroxy carboxylic acid and a hydroxylamino carboxylic acid. Examples of diamino carboxylic acid groups herein described comprise 2,3 diamino propanoic acid, 2,4-diaminobutanoic acid, 2,5-di aminopentanoic acid (ornithine), 2,6-diaminohexanoic acid (lysine), (2-Aminoethyl)-cysteine, 3-amino-2-aminomethyl propanoic acid, 3-amino-2-aminomethyl-2-methyl propanoic acid, 4-amino-2-(2-aminoethyl)butyric acid and 5-amino-2-(3-aminopropyl)pentanoic acid. Examples of dihydroxy carboxylic acid groups of telodendrimers of the present disclosure comprise glyceric acid, 2,4-dihydroxy butyric acid, and 2,2-bis(hydroxymethyl)propionic acid. Examples of hydroxylamino carboxylic acids include, but are not limited to, serine and homoserine as well as additional monomeric units as will be understood by a skilled person.

In some embodiments, spacer moiety A comprises an oligomer of lysine represented by $(K)_{m''}$ wherein oligomer of lysine has a peptide backbone based on an alpha amino group of lysine, wherein K is lysine and m" is 1-20 and wherein m" is an integer between m-1 to 20. In some embodiment, m" is m-1.

In some embodiment, at least one of the dendrimer, spacer moiety A and/or linker moiety L can independently comprise at least one monomer selected from XY2-type monomers, where A and B are two different functional groups capable of reacting together such that the resulting polymer chain has a branch point where an X-Y bond is formed. Exemplary monomers include a diamino carboxylic acid, a dihydroxy carboxylic acid and a hydroxylamino carboxylic acid. Examples of diamino carboxylic acid groups herein described comprise 2,3 diamino propanoic acid, 2,4-diaminobutanoic acid, 2,5-di aminopentanoic acid (ornithine), 2,6-diaminohexanoic acid (lysine), (2-Aminoethyl)-cysteine, 3-amino-2-aminomethyl propanoic acid, 3-amino-2-aminomethyl-2-methyl propanoic acid, 4-amino-2-(2-aminoethyl)butyric acid and 5-amino-2-(3-aminopropyl)pentanoic acid. Examples of dihydroxy carboxylic acid groups of telodendrimers of the present disclosure comprise glyceric acid, 2,4-dihydroxy butyric acid, and 2,2-bis(hydroxymethyl)propionic acid. Examples of hydroxylamino carboxylic acids include, but are not limited to, serine and homoserine as well as additional monomeric units as will be understood by a skilled person.

In some embodiments a dendrimer can comprise branched polymers containing a focal point, a plurality of branched monomer units, and a plurality of end groups in which the focal point of the dendritic polymer is a functional group on the branched monomer that is of equal spacing from all the end groups can be attached to another segment of the telodendrimer, including linker L, spacer A or tail group T. The end groups may be further functionalized with additional chemical moieties.

In embodiments wherein the telodendrimer has formula (I), the focal point of a telodendrimer or a telodendrimer segment can be any suitable functional group that form a covalent bond between the dendrimer and a tail group T, spacer moiety A, a linker moiety L.

In some embodiments, the functional group for the focal point can be a nucleophilic group including, but not limited to, an alcohol, an amine, a thiol, or a hydrazine. The focal point functional group can also be an electrophile such as an aldehyde, a carboxylic acid, or a carboxylic acid derivative including for example an acid chloride or an N-hydroxysuccinimidyl ester.

The telodendrimer of formula (I) can have a single type of R group on the periphery, or any combination of R groups in any suitable ratio. In general, at least half the number n of R groups are other than an end group. For example, at least half the number n of R groups can be a hydrophobic group, a hydrophilic group, an amphiphilic compound, a drug, or any combination thereof. In some embodiments, half the number n of R groups are amphiphilic compounds.

In some embodiments, all the R groups are an amphiphilic group such as cholic acid or cholesterol formate. In other embodiments, some of the R groups are an end group of the dendrimer. In some other embodiments, at least two different R groups are present, such as two different amphiphilic groups, or an amphiphilic group and a drug, or an amphiphilic group and a dendritic polymer end group, or two different drugs, or a drug and a dendritic end group.

In some embodiments, telodendrimers of t-NLPs of Formula (I), D can be lysine, L can be a bond, R can be cholic acid or cholate, m can be 1, and/or n can be 2, 4 or 8. In some embodiments, R can be formed by a detergent moiety, a lipid and/or an amino acid such as HIS, GLU.

In some embodiments, the telodendrimer of the present disclosure comprise a compound of formulas (II)-(III):

$$PEG-D-(R)_n \quad (II)$$

$$PEG-L-D-(R)_n \quad (III)$$

$$(PEG)_{m'}-A-L-D-(R)_n \quad (IV)$$

wherein D, L, R and n are as defined for formula (I) and subscript m' of formula (IV) is 2-20.

In some embodiments, the PEG in telodendrimer of any one of formula (I) to (IV) can be a PEG having a molecular weight from 1 kDA (PEG1000) to 10 kDA (PEG 10,000).

In some embodiments, MOMP-t-NLPs herein described can comprise telodendrimers such as $PEG^{2K}$-D-$CA_4$, $PEG^{5K}$-D-$CA_4$, $PEG^{10K}$-D-$CA_4$, $PEG^{2K}$-D-$CA_8$, $PEG^{5K}$-D-$CA_8$, $PEG^{10K}$-D-$CA_8$, $PEG^{2K}$-D-$CF_4$, $PEG^{5K}$-D-$CF_4$, $PEG^{10K}$-D-$CF_4$, $PEG^{2K}$-D-$CF_8$, $PEG^{5K}$-D-$CF_8$, or $PEG^{10K}$-D-$CF_8$, wherein each dendritic polymer D is a poly(lysine) dendritic polymer wherein each end group is hydroxy. In one embodiment, the telodendrimer can be $PEG^{5K}$-D-$CF_8$. Additional modifications for the telodendrimer can include attachment of lipidic and detergent moieties such as Telo-His and Telo-Cys.

In some embodiments, MOMP-t-NLPs herein described can comprise telodendrimers such as $PEG^{2K}$-D-$CA_4$, $PEG^{5K}$-D-$CA_4$, $PEG^{10K}$-D-$CA_4$, $PEG^{2K}$-D-$CA_8$, $PEG^{5K}$-D-$CA_8$, $PEG^{10K}$-D-$CA_8$, $PEG^{2K}$-D-$CF_4$, $PEG^{5K}$-D-$CF_4$, $PEG^{10K}$-D-$CF_4$, $PEG^{2K}$-D-$CF_8$, $PEG^{5K}$-D-$CF_8$, or $PEG^{10K}$-D-$CF_8$, wherein each dendritic polymer D is a poly(lysine) dendritic polymer wherein each end group is hydroxy. In one embodiment, the telodendrimer can be $PEG^{5K}$-D-$CF_8$. Additional modifications for the telodendrimer can include attachment of lipidic and detergent moieties such as Telo-His and Telo-Cys.

Figure 10B:
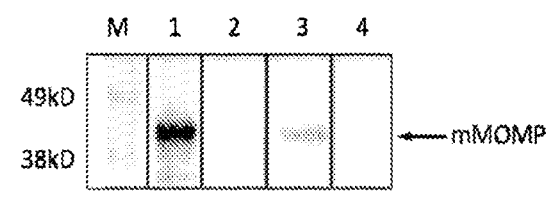
FIG. 10B shows images of four western blots, wherein mMOMP protein was loaded onto each lane equally and mouse sera from mice administered with mMOMP-CpG-tNLPs, CpG-tNLPs, *Chlamydia* EB, or PBS were then incubated with the blot overnight. Lane 1 is blotted with mouse sera immunized with mMOMP-CpG-tNLP and shows significant mMOMP antibody binding. Lane 2 is blotted with mouse sera immunized with CpG-tNLP. Lane 3 is blotted with mouse sera immunized with live *Chlamydia* EB and confirms that *Chlamydia* EB induces MOMP antibodies that bind to recombinant mMOMP. The decreased signal from this blot is because *Chlamydia* EB contains many surface antigens, not just mMOMP, therefore it induces a large variety of antibodies. Lane 4 is blotted with mice sera immunized with PBS control group and shows no mMOMP binding. M: molecular weight marker.
Figure 11A:
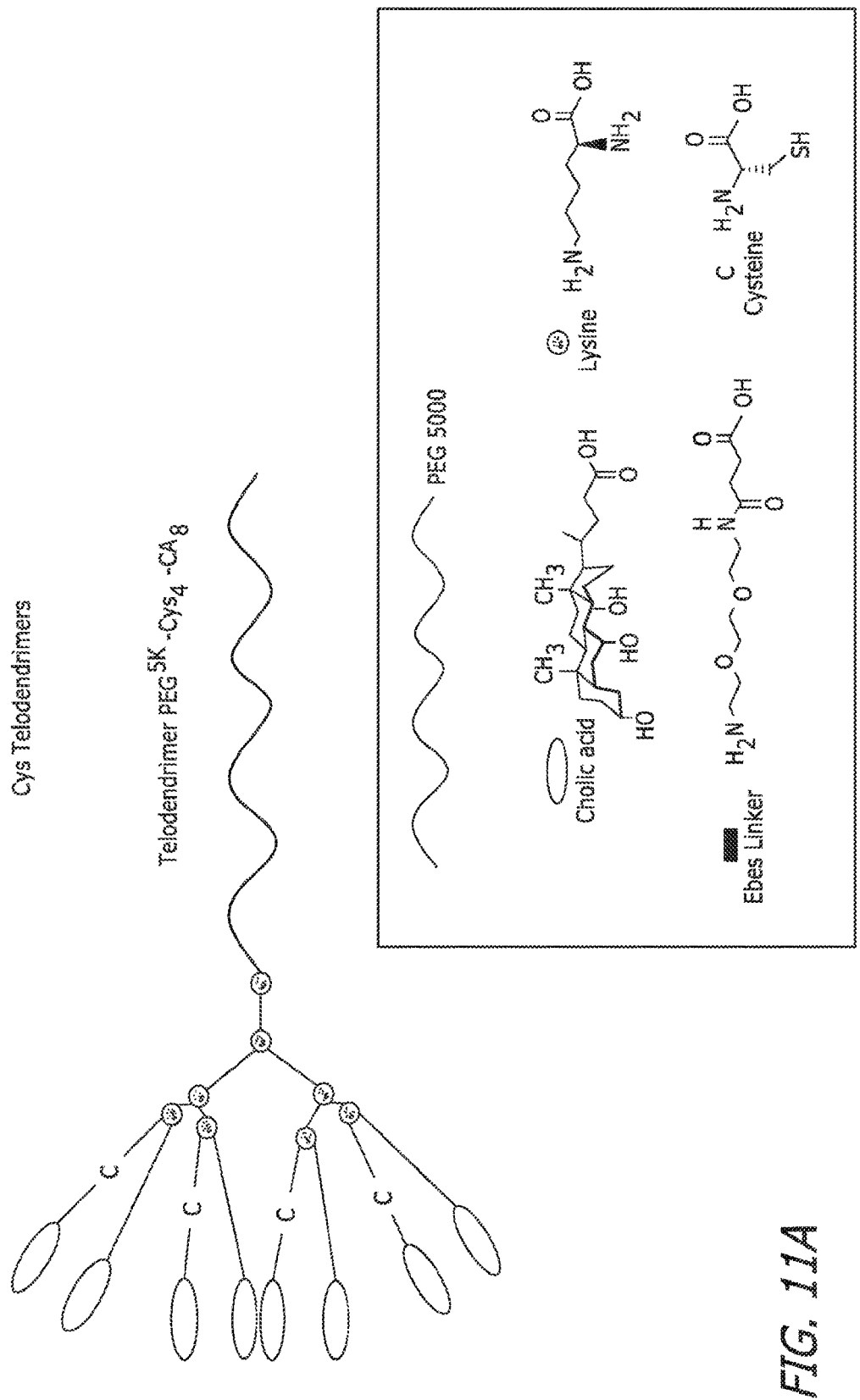

A schematic representation of an exemplary telodendrimer comprising a telo-cys is shown in FIG. 11A. A schematic representation of an exemplary telodenrimer comprising telo-His is shown in FIG. 11B. In some embodiments, in a Telo-Cys according to the schematic representation of FIG. 11A, or a in a Telo-His according to the schematic of FIG. 10B, the cholic acid is covalently linked to a cysteine amine or a lysine by amide bond; cysteine and lysine are or lysine and lysine are covalently connected by an amide bond and a core lysine monomer is covalently attached to a tail group of PEG 5000. In some embodiments, telodendrimers herein described can comprise a combination of cysteine and histidine as will be understood by a skilled person.

In some embodiments, an Ebes linker, (N-(Fmoc-8-amino-3,6-dioxa-octyl)succinamic acid), is present between the tail group PEG 5000 and the core lysine monomer by amide bond and an ester bond.

In particular, in preferred embodiments, MOMP-t-NLPs comprising one or more of $PEG^{5K}$-D-$CA_4$, $PEG^{5K}$-D-$CA_8$, $PEG^{5K}$-D-$CF_4$, and $PEG^{5K}$-D-$CF_8$, provided an improved formulation of MOMP proteins within a tNLP compared to other telodendrimers herein described. The telodendrimers useful in the preparation of t-NLPs herein described can be prepared by a variety of methods, such as those described in PCT Publication No. WO 2010/039496 herein incorporated by reference in its entirety.

In embodiments herein described the nanolipoprotein particles further comprise a *Chlamydia* major outer membrane protein (MOMP).

The term "*Chlamydia*" as used herein indicates a genus of pathogenic bacteria of the phylum Chlamydiae that are obligate intracellular bacteria as well as the bacteria belonging to said genus. *Chlamydia* bacteria are ovoid in shape and stain Gram-negative. *Chlamydia* bacteria are characterized by a developmental cycle involving an infectious elementary body (EB) and the vegetative reticulate body (RB). In particular, the EB remains within a phagosome after *Chlamydia* attaches and promotes entry into a target host cell. The EB differentiates into the RB which then redifferentiate into EB after several rounds of replication. The EB is small, dense, rigid, metabolically inert, and resistant to the hostile extracellular environment while the RB is large, low-density, less rigid, metabolically active but noninfectious (Moulder, J. W., Hatch, T. P., Kuo, C. C., Schachter, J., and Storz, J. 1984. Order II: Chlamydiales. In Bergey's manual of systematic bacteriology, Vol. 1 (eds. N. R. Krieg and J. G. Holt), pp. 729-739. Williams & Wilkins, Baltimore, MD). *Chlamydia* comprise *Chlamydia* species *Chlamydia trachomatis*, *Chlamydia pneumoniae*, and *Chlamydia psittaci* (human pathogens), *Chlamydia suis* (affects only swine), *Chlamydia pecorum* (affects cows/swine/koala) and *Chlamydia pneumonia* (affects koala) and *Chlamydia muridarum* (affects only mice and hamsters)

The term "MOMP" as used herein indicates the major outer membrane protein of a bacterium of the genus *Chlamydia* capable of folding into a beta barrel structure that can associate with other MOMP proteins. MOMP can be encoded by the gene ompA of bacteria of the *Chlamydia* genus. Typically, a MOMP beta barrel structure consists of 18 transmembrane regions. In general, MOMP has a molecular mass of ~40 kDa and can make up 60% of total outer membrane protein. Chlamydial MOMP is detectable both in the EB and in the RB of *Chlamydia* with techniques such as monoclonal antibodies (MAbs) and surface radioiodination as well as additional techniques identifiable by a skilled person. MOMPs comprise proteins with low solubility (from 0% to 50% of the total amount of MOMP protein in the mixture). In particular, MOMP can have a solubility score lower or equal to 20% and in some instances a solubility of 10% or lower.

MOMP has been identified to be a porin even if MOMP has been associated with other functions such as a potential chlamydial cytoadhesin as well as a structural protein. Porins are a family of membrane channels commonly found in the outer membranes of Gram-negative bacteria, where they serve as diffusion pathways for nutrients, waste products, and antibiotics and can also be receptors for bacteriophages. Porins have a structural topology comprised of antiparallel β-strands spanning the outer membrane, a water-filled inner channel, tight β-turns extending into the periplasmic region and flexible loops reaching beyond the extracellular surface [1]. The MOMP of *Chlamydia* genus contains four symmetrically spaced variable domains (VDs 1 to 4). The variable domain regions are predicted to be outside the trans-membrane β-strands. Detailed structural description of MOMP of *Chlamydia* can be found in Feher et al. 2014 [1].

MOMP in the sense of the disclosure encompasses a protein from a *Chlamydia* bacterium capable of oligomerization, formation of homo-trimers and functional porins, and capable of forming antigens that can elicit an immune response. In some embodiments, MOMP comprised in tNLPs described herein primarily forms homo-trimers [3].

MOMP in the sense of the disclosure encompass MOMP proteins of various bacteria within the *Chlamydia* genus as well as species-specific variants of MOMP, such as a MoPn MOMP protein (mMOMP), a type of MOMP expressed in the mouse-specific bacterium *Chlamydia* muridarum, Sequence information from various strains and species within the *Chlamydia* genus can be accessed via the National Center for Biotechnology Information website as will be understood by a person skilled in the art. For example, sequence information for the *Chlamydia muridarum* MOMP gene (ompA) can be accessed via the National Center for Biotechnology Information website at the address https://www.ncbi.nlm.nih.gov/nuccore/U60196. Sequence information for the *Chlamydia trachomatis* MOMP gene (ompA) can be accessed via the National Center for Biotechnology Information website at the address https://www.ncbi.nlm.nih.gov/gene/884473. Exemplary MOMP gene and protein sequences are listed in Table 1.

TABLE 1

Exemplary MOMPgene and protein sequences

| Origin | Sequences | SEQ ID NO |
|---|---|---|
| *Chlamydia muridarum* MOMP gene (ompA) | ATGAAAAAACTCTTGAAATCGGTATTAGCATTTGCCGTTTTGGGTTCTGCT TCCTCCTTGCATGCTCTGCCTGTGGGAATCCTGCTGAACCAAGCCTTATG ATTGACGGGATTCTTTGGGAAGGTTTCGGTGGAGATCCTTGCGATCCTTGC ACAACTTGGTGTGATGCCATCAGCCTACGTCTCGGCTACTATGGGGACTTC GTTTTTGATCGTGTTTTGAAAACAGACGTGAACAAACAGTTCGAAATGGGA GCAGCTCCTACAGGAGATGCAGACCTTACTACAGCACCTACTCCTGCATCA AGAGAGAATCCCGCTTATGGCAAGCATATGCAAGATGCAGAAATGTTCACT AATGCTGCGTACATGGCTTTAAACATTTGGGACCGTTTCGATGTATTTTGT ACATTGGGAGCAACTAGCGGATATCTTAAAGGTAATTCTGCCGCCTTTAAC TTAGTTGGTCTGTTTGGAAGAGATGAAACTGCAGTTGCAGCTGACGACATA CCTAACGTCAGCTTGTCTCAAGCTGTTGTCGAACTCTACACAGACACAGCT TTCGCTTGGAGCGTCGGTGCTAGAGCAGCTTTATGGGAGTGCGGATGTGCA ACTTTAGGAGCTTCCTTCCAATATGCTCAATCTAAGCCAAAAGTAGAGGAA TTAAACGTTCTCTGTAATGCGGCAGAATTCACTATTAACAAGCCTAAAGGA TACGTTGGACAAGAGTTTCCTCTTAACATTAAAGCTGGAACAGTTAGCGCT ACAGATACTAAAGATGCTTCCATCGATTACCATGAGTGGCAAGCAAGCTTG GCTTTGTCTTACAGACTGAATATGTTCACTCCTTACATTGGAGTTAAGTGG TCTAGAGCAAGCTTTGATGCCGACACTATCCGCATTGCGCAGCCTAAGCTT GAGACCTCTATCTTAAAAATGACCACTTGGAACCCAACGATCTCTGGATCT GGTATAGACGTTGATACAAAAATCACGGATACATTACAAATTGTTTCCTTG CAGCTCAACAAGATGAAATCCAGAAAATCTTGCGGTCTTGCAATTGGAACA ACAATTGTAGATGCTGATAAATATGCAGTTACTGTTGAGACACGCTTGATC GATGAAAGAGCAGCTCACGTAAATGCTCAGTTCCGTTTCTAA | 1 |
| *Chlamydia muridarum* MOMP protein (GenBank: AAB07068.1) | MKKLLKSVLAFAVLGSASSLHALPVGNPAEPSLMEDGILWEGFGGDPCDPC TTWCDAISLRLGYYGDFVFDRVLKTDVNKQPEMGAAPTGDADLTTAPTPAS RENPAYGKHMQDAEMFTNAAYMALNIWDRFDVFCTLGATSGYLKGNSAAFN LVGLFGRDETAVAADDIPNVSLSQAVVELYTDTAFAWSVGARAALWECGCA TLGASFQYAQSKPKVEELNVLCNAAEFTINKPKGYVGQEFPLNIKAGTVSA TDTKDASIDYHEWQASLALSYRLNMFTPYIGVKWSRASFDADTIRIAQPKL ETSILKMTTWNPTISGSGEDVDTKITDTLQIVSLQLNKMKSRKSCGLAIGT TIVDADKYAVTVETRLEDERAAHVNAQFRF | 2 |
| *Chlamydia trachomatis* strain A/Har-1 major outer membrane protein (ompA) gene (GenBank: DQ064279.1) | ATGAAAAAACTCTTGAAATCGGTATTAGTATTTGCCGCTTTGAGTTCTGCT TCCTCCTTGCAAGCTCTGCCTGTGGGAATCCTGCTGAACCAAGCCTTATG ATCGACGGAATTCTGTGGGAAGGTTTCGGCGGAGATCCTTGCGATCCTTGC ACCACTTGGTGTGACGCTATCAGCATGCGTATGGGTTACTATGGTGACTTT GTTTTCGACCGTGTTTTGAAAACAGATGTGAATAAAGAATTTCAGTAGGGA GCGGCGCCTACTACCAGCGATGTAGCAGGCTTAGAAAAGGATCCAGTAGCA AATGTTGCTCGCCCAAATCCCGCTTATGGCAAACACATGCAAGATGCTGAA ATGTTTACGAACGCTGCTTACATGGCATTAAATATCTGGGATCGTTTTGAT GTATTTTGTACATTGGGAGCAACTACCGGTTATTTAAAAGGAAACTCCGCT TCCTTCAACTTAGTTGGATTATTCGGAACAAAAACACAATCTTCTGGCTTT GATACAGCGAATATTGTTCCTAACACTGCTTTGAATCAAGCTGTGGTTGAG CTTTATACAGACACTACCTTTGCTTGGAGCGTAGGTGCTCGTGCAGCTCTC TGGGAATGTGGGTGTGCAACGTTAGGAGCTTCTTTCCAATATGCTCAATCT AAACCTAAAGTAGAAGAGTTGAATGTTCTTTGTAATGCATCCGAATTTACT ATTAATAAGCCGAAAGGATATGTTGGGCGGAATTTCCACTTGATATTACC GCAGGAACAGAAGCTGCGACAGGGACTAAGGATGCCTCTATTGACTACCAT GAGTGGCAAGCAAGTTTAGCCCTTTCTTACAGATTAAATATGTTCACTCCT TACATTGGAGTTAAATGGTCTAGAGTAAGTTTTGATGCCGACACGATCCGT ATCGCTCAGCCTAAATTGGCTAAACCAGTCTTGGATACCACTACTCTAAAC CCGACCATCGCTGGTAAAGGAACTGTGGTCTCTTCCGCAGAAAACGAACTG GCTGATACAATGCAAATCGTTTCCTTGCAGTTGAACAAGATGAAATCTAGA AAATCTTGCGGTATTGCAGTAGGAACAACTGTTGATGCAGATAAATAC GCAGTTACAATTGAGACTCGCTTGATCGATGAGAGCAGCTCACGTAAAT GCACAATTCCGCTTCTAA | 3 |
| *Chlamydia trachomatis* strain A/Har-1 major outer | MKKLLKSVLVFAALSSASSLQALPVGNPAEPSLMEDGILWEGFGGDPCDPC TTWCDAISMRMGYYGDFVFDRVLKTDVNKEFQMGAAPTTSDVAGLEKDPVA NVARPNPAYGKHMQDAEMFTNAAYMALNIWDRFDVFCTLGATTGYLKGNSA | 4 |

TABLE 1-continued

Exemplary MOMPgene and protein sequences

| Origin | Sequences | SEQ ID NO |
|---|---|---|
| membrane protein sequence (ompA) | SFNLVGLFGTKTQSSGFDTANIVPNTALNQAVVELYTDTTFAWSVGARAAL<br>WECGCATLGASFQYAQSKPKVEELNVLCNASEFTINKPKGYVGAEFPLDIT<br>AGTEAATGTKDASIDYHEWQASLALSYRLNMFTPYIGVKWSRVSFDADTIR<br>IAQPKLAKPVLDTTTLNPTIAGKGTVVSSAENELADTMQIVSLQLNKMKSR<br>KSCGIAVGTTVVDADKYAVTIETRLIDERAAHVNAQFRF | |
| *Chlamydia trachomatis* strain B/Tunis-864 major outer membrane protein (ompA) gene, complete cds (Genbank: DQ064280.1) | ATGAAAAAACTCTTGAAATCGGTATTAGTATTTGCCGCTTTGAGTTCTGCT<br>TCCTCCTTGCAAGCTCTGCCTGTGGGGAATCCTGCTGAACCAAGCCTTATG<br>ATCGACGGAATTCTGTGGGAAGGTTTCGGCGGAGATCCTTGCGATCCTTGC<br>ACCACTTGGTGTGACGCTATCAGCATGCGTATGGGTTACTATGGTGACTTT<br>GTTTTCGACCGTGTTTTGAAAACAGATGTGAATAAAGAATTCCAAATGGGT<br>GCCAAGCCTACAGCTACTACAGGCAATGCTACAGCTCCATCCACTCTTACA<br>GCAAGAGAGAATCCTGCTTACGGCCGACATATGCAGGATGCTGAGATGTTT<br>ACAAATGCCGCTTGCATGGCATTGAATATTTGGGATCGCTTTGATGTATTC<br>TGTACACTAGGAGCCTCTAGCGGATACCTTAAAGGAAACTCTGCTTCTTTC<br>AATTTAGTGGGGTTATTCGGAAATAATGAGAACCAGACTAAAGTTTCAAAT<br>GGTACGTTTGTACCAAATATGAGCTTAGATCAATCTGTTGTTGAGTTGTAT<br>ACAGATACTGCTTTTGCGTGGAGCGTCGGCGCTCGCGCAGCTTTGTGGGAA<br>TGTGGATGTGCAACTTTAGGAGCTTCTTTCCAATATGCTCAATCTAAACCT<br>AAAGTAGAAGAATTAAACGTTCTCTGCAATGCAGCAGAGTTTACTATTAAT<br>AAACCTAAAGGGTATGTAGGTAAGGAGTTGCCTCTTGATCTTACAGCAGGA<br>ACAGATGCTGCGACAGGAACTAAGGATGCCTCTATTGATTACCATGAATGG<br>CAAGCAAGTTTAGCTCTCTCTTACAGATTGAATATGTTCACTCCTTACATT<br>GGAGTTAAATGGTCTCGAGCAAGCTTTGATGCAGACACGATTCGTATTGCT<br>CAGCCGAAGTCAGCCGAGACTATCTTTGATGTTACCACTCTGAACCCAACT<br>ATTGCTGGAGCTGGCGATGTGAAAACTAGCGCAGAGGGTCAGCTCGGAGAC<br>ACAATGCAAATCGTCTCCTTGCAATTGAACAAGATGAAATCTAGAAAATCT<br>TGCGGTATTGCAGTAGGAACAACTATTGTGGATGCAGACAAATACGCAGTT<br>ACAGTTGAGACTCGCTTGATCGATGAGAGAGCTGCTCACGTAAATGCACAA<br>TTCCGCTTCTAA | 5 |
| *Chlamydia trachomatis* strain B/Tunis-864 major outer membrane protein sequence (ompA) | MKKLLKSVLVFAALSSASSLQALPVGNPAEPSLMIDGILWEGFGGDPCDPC<br>TTWCDAISMRMGYYGDFVFDRVLKTDVNKEFQMGAKPTATTGNATAPSTLT<br>ARENPAYGRHMQDAEMFTNAACMALNIWDRFDVFCTLGASSGYLKGNSASF<br>NLVGLFGNNENQTKVSNGTFVPNMSLDQSVVELYTDTAFAWSVGARAALWE<br>CGCATLGASFQYAQSKPKVEELNVLCNAAEFTINKPKGYVGKELPLDLTAG<br>TDAATGTKDASIDYHEWQASLALSYRLNMFTPYIGVKWSRASFDADTIRIA<br>QPKSAETIFDVTTLNPTIAGAGDVKTSAEGQLGDTMQIVSLQLNKMKSRKS<br>CGIAVGTTIVDADKYAVTVETRLIDERAAHVNAQFRF | 6 |

In some embodiments, the MOMP-NLPs herein described can include one or more MOMP fragments alone or in combination with MOMP protein. The term "MOMP fragment" is a portion of a MOMP protein herein described comprising a transmembrane region including for example MOMP hydrophobic amino acid configured to interact with a membrane lipid bilayer. In a MOMP fragment, the transmembrane region can be formed by at least one transmembrane domain each domain comprising 3 to 40 hydrophobic amino acid residues.

Additional sequences of the ompA gene and MOMP protein or fragments thereof are recognizable by persons skilled in the art, comprising sequences of members of the *Chlamydia* genus such as *Chlamydia trachomatis, Chlamydia muridarum* and *Chlamydia suis* and in particular the fifteen known *Chlamydia trachomatis* serovars and additional strains known to those skilled in the art, which can be found in public databases such as NCBI.

In particular, *C. trachomatis* includes three human biovars: (1) Serovars Ab, B, Ba, or C, which cause trachoma: infection of the eyes, which can lead to blindness, (2) Serovars D-K, which cause urethritis, pelvic inflammatory disease, ectopic pregnancy, neonatal pneumonia, and neonatal conjunctivitis, and (3) Serovars L1, L2, and L3, which cause lymphogranuloma venereum.

The term "biovar" as used herein refers to a variant prokaryotic strain that differs physiologically and/or biochemically from other strains in a particular species. The term "serovar" refers to strains that have antigenic properties that differ from other strains.

In some embodiments, additional ompA genes and MOMP proteins can be identified by conducting homology search of gene or protein sequences in databases such as NCBI and others known to persons skilled in the art.

Homology can be determined using available sequence analysis algorithm programs including but not limited to CLUSTAL, ALIGN, GAP, BESTFIT, BLAST, FASTA, and TFASTA among others known to a skilled person. Sequences of DNA, mRNA, or protein having at least 50% sequence identity to known ompA DNA and mRNA sequences and MOMP protein sequences can be considered homologous. The term "percent identity" refers to a quantitative measurement of the similarity between sequences of a polypeptide or a polynucleotide and, in particular, indicates the amount of characters that match between two different sequences. The similarity between sequences is typically measured by a process that comprises the steps of aligning the two polypeptide or polynucleotide sequences to form aligned sequences, then detecting the number of matched characters, i.e. characters similar or identical between the two aligned sequences, and calculating the total number of matched characters divided by the total number of aligned characters in each polypeptide or polynucleotide sequence, including gaps. The similarity result is expressed as a percentage of identity.

Homology can also be determined on the basis of protein structural similarity. Several publicly available online servers can be used to detect protein structure alignment and calculate percent structural similarity, such as FATCAT, SuperPose, iPBA, MAPSCI, and others known to a person skilled in the art. Proteins having at least 50% structural identity to known MOMP protein structures or fragments thereof can be considered homologous.

MOMP in the sense of the disclosure also includes codon-optimized sequences of MOMP expressed in a cell-free expression system, herein exemplified by an *E. coli* cell-free expression system (see e.g. the sequences illustrated in FIGS. 3A-3B and the sequences illustrated in FIGS. 12C, 16 and 17). Additional MOMP variants comprise MOMPs having a sequence that differs in all or in part from a naturally occurring MOMP and that maintain the beta barrel structure with the 18 transmembrane regions separated by loops. In particular, additional MOMP variants include modifications with respect to a natural MOMP protein which maintain the barrel structure while changing the level of immunogenicity of the MOMP. In some of these embodiments, the difference in sequence between a natural MOMP and the variant can be localized in the extra cellular loops.

MOMP in the sense of the present disclosure comprise wild type MOMP and MOMP derivatives such as MOMP including mutations, deletions, truncations and MOMP fusion protein including MOMP fused with other peptides.

In some embodiments, the MOMP in the sense of the present disclosure can be recombinant forms of MOMP in which the MOMP coding sequence has been mutated to present a unique DNA sequence, which does not alter the amino acids to enhance transcription and translation of the target protein. Exemplary sequences are shown in the illustration of FIGS. 3A-3B and are also shown in FIGS. 16 and 17. The exemplary mMOMP gene of FIGS. 3A-3B (also shown in FIG. 17) provide an *E. coli* codon-optimized version of MOMP expressed in the mouse-specific *Chlamydia muridarum*. The exemplary MoPn gene and protein sequences of FIG. 12C provide an *E. coli* codon-optimized version of MOMP expressed in the mouse-specific *Chlamydia muridarum* MoPn.

As would be understood by those skilled in the art, the term "codon optimization" as used herein refers to the introduction of synonymous mutations into codons of a protein-coding gene in order to improve protein expression in expression systems of a particular organism, such as *E. coli* in accordance with the codon usage bias of that organism. The term "codon usage bias" refers to differences in the frequency of occurrence of synonymous codons in coding DNA. The genetic codes of different organisms are often biased towards using one of the several codons that encode a same amino acid over others—thus using the one codon with, a greater frequency than expected by chance. Optimized codons in microorganisms, such as *Escherichia coli* or *Saccharomyces cerevisiae*, reflect the composition of their respective genomic tRNA pool. The use of optimized codons can help to achieve faster translation rates and high accuracy.

In the field of bioinformatics and computational biology, many statistical methods have been proposed and used to analyze codon usage bias. Methods such as the 'frequency of optimal codons' (Fop), the Relative Codon Adaptation (RCA) or the 'Codon Adaptation Index' (CAI) are used to predict gene expression levels, while methods such as the 'effective number of codons' (Nc) and Shannon entropy from information theory are used to measure codon usage evenness. Multivariate statistical methods, such as correspondence analysis and principal component analysis, are widely used to analyze variations in codon usage among genes. There are many computer programs to implement the statistical analyses enumerated above, including CodonW, GCUA, INCA, and others identifiable by those skilled in the art. Codon optimization has applications in designing synthetic genes and DNA vaccines. Several software packages are available online for codon optimization of gene sequences, including those offered by companies such as GenScript, EnCor Biotechnology, Integrated DNA Technologies, ThermoFisher Scientific, among others known those skilled in the art. Those packages can be used in providing MOMP with codon ensuring optimized expression in various cell systems as will be understood by a skilled person.

In particular, MOMP in the sense of the disclosure can comprise monomeric or multimeric MOMP such as dimeric and trimeric MOMP.

In some embodiments, MOMP-t-NLPs herein described comprise multimeric MOMP (>2 membrane proteins) embedded in nanoparticles.

In some embodiments, MOMP-t-NLP herein described comprise at least one MOMP from *Chlamydia* species *Chlamydia trachomatis Chlamydia pneumoniae*, and *Chlamydia psittaci* (human pathogens), *Chlamydia suis* (affects only swine), *Chlamydia pecorum* (affects cows/swine/koala) and *Chlamydia pneumonia* (affects koala) and *Chlamydia muridarum* (affects only mice and hamsters) or a variant thereof In some embodiments, the membrane forming lipids component of the lipid component lipids such as phospholipids, preferably including at least one phospholipid, typically soy phosphatidylcholine, egg phosphatidylcholine, soy phosphatidylglycerol, egg phosphatidylglycerol, palmitoyl-oleoyl-phosphatidylcholine distearoylphosphatidylcholine, or distearoylphosphatidylglycerol. Other useful phospholipids include, e.g., phosphatidylcholine, phosphatidylglycerol, sphingomyelin, phosphatidylserine, phosphatidic acid, phosphatidylethanolamine, lysolecithin, lysophosphatidylethanolamine, phosphatidylinositol, cephalin, cardiolipin, cerebrosides, dicetylphosphate, dioleoylphosphatidylcholine, dipalmitoylphosphatidylcholine, dipalmitoylphosphatidylglycerol, dioleoylphosphatidylglycerol, stearoyl-palmitoyl-phosphatidylcholine, di-palmitoyl-phosphatidylethanolamine, distearoyl-phosphatidylethanolamine, di-myrstoyl-phosphatidylserine, di-myrstoyl-phosphatidylserine and dioleyl-phosphatidylcholine.

Additionally exemplary membrane forming lipids that can be comprised in various combinations together with one or more lysolipids comprise 1,2-dipalmitoyl-sn-glycero-3-phosphocholine, 1,2-dimyristoyl-sn-glycero-3-phosphocholine, 1,2-dilauroyl-sn-glycero-3-phosphocholine, 1,2-didecanoyl-sn-glycero-3-phosphocholine, 1,2-dierucoyl-sn-glycero-3-phosphocholine, 1,2-dioleoyl-sn-glycero-3-phosphocholine, 1,2-dipalmitoleoyl-sn-glycero-3-phosphocholine, 1,2-dimyristoleoyl-sn-glycero-3-phosphocholine, 1-stearoyl-2-oleoyl-sn-glycero-3-phosphocholine, 1-stearoyl-2-myristoyl-sn-glycero-3-phosphocholine, 1-palmitoyl-2-oleoyl-sn-glycero-3-phosphocholine, egg phosphatidylcholine extracts, soy phosphatidylcholine extracts, heart phosphatidylcholine extracts, brain phosphatidylcholine extracts, liver phosphatidylcholine extracts, 1,2-distearoyl-sn-glycero-3-phosphate, 1,2-dipalmitoyl-sn-glycero-3-phosphate, 1,2-dimyristoyl-sn-glycero-3-phosphate, 1,2-dilauroyl-sn-glycero-3-phosphate, 1-palmitoyl-2-oleoyl-sn-glycero-3-phosphate, 1-stearoyl-2-oleoyl-sn-glycero-3- phosphate, 1,2-dipalmitoyl-sn-glycero-3-phosphoethanolamine, 1,2-dimyristoyl-sn-glycero-3-phosphoethanolamine, 1,2-dilauroyl-sn-glycero-3-phosphoethanolamine, 1,2-dioleoyl-sn-glycero-3-phosphoethanolamine, 1,2-dipalmitoleoyl-sn-glycero-3-phosphoethanolamine, Egg phosphatidylethanolamine extract, soy phosphatidylethanolamine extract, heart phosphatidylethanolamine extract, brain phosphatidylethanolamine extract, 1,2-distearoyl-sn-glycero-3-phospho-(1'-rac-glycerol), 1,2-dioleoyl-sn-glycero-3-phospho-(1'-rac-glycerol), 1,2-dipalmitoyl-sn-glycero-3-phospho-(1'-rac-glycerol), 1,2-dimyristoyl-sn-glycero-3-phospho-(1'-rac-glycerol), 1,2-dilauroyl-sn-glycero-3-phospho-(1'-rac-glycerol), 1-palmitoyl-2-oleoyl-sn-glycero-3-phospho-(1'-rac-glycerol), egg phosphatidylglycerol extract, soy phosphatidylglycerol extract, 1,2-distearoyl-sn-glycero-3-phospho-L-serine, 1,2-dioleoyl-sn-glycero-3-phospho-L-serine, 1,2-dipalmitoyl-sn-glycero-3-phospho-L-serine, 1,2-dimyristoyl-sn-glycero-3-phospho-L-serine, 1,2-dilauroyl-sn-glycero-3-phospho-L-serine, 1-palmitoyl-2-oleoyl-sn-glycero-3-phospho-L-serine, soy phosphatidylserine extract, brain phosphatidylserine extract, 2-((2,3-bis(oleoyloxy)propyl)dimethylammonio)ethyl hydrogen phosphate, cholesterol, ergosterol, sphingolipids, ceramides, sphingomyelin, gangliosides, glycosphingolipids, 1,2-dioleoyl-3-trimethylammonium-propane, 1,2-di-O-octadecenyl-3-trimethylammonium propane.

In some embodiments, non-phosphorus containing lipids can also be used as membrane forming lipids in the MOMP-t-NLPs herein described, e.g. stearylamine, docecylamine, acetyl palmitate, and fatty acid amides. Additional membrane forming lipids suitable for use in providing NLPs are well known to persons of ordinary skill in the art and are cited in a variety of well-known sources, e.g., McCutcheon's Detergents and Emulsifiers and McCutcheon's Functional Materials, Allured Publishing Co., Ridgewood, N.J., both of which are incorporated herein by reference.

In some embodiments, the scaffold proteins can contain amino acid additions, deletions, or substitutions. In other embodiments, the scaffold proteins can be derived from various species and more particularly derived from human, mouse, rat, guinea pig, rabbit, cow, horse, pig, dog, koala, and non-human primates.

In some embodiments membrane forming lipids can be comprised within a MOMP-t-NLP stabilized by scaffold proteins such as human derived apoE4, truncated versions of human derived apoE4 (e.g. apoE422k), human derived apoE3, truncated versions of human derived apoE3 (e.g. apoE322k), human derived apoE2, truncated versions of human derived apoE2 (e.g. apoE222k), human derived apoA1, truncated versions of human derived apoA1 (e.g. Δ49ApoA1, MSP1, MSP1T2, MSP1E3D1), mouse derived apoE4, truncated versions of mouse derived apoE4 (e.g. apoE422k), mouse derived apoE3, truncated versions of mouse derived apoE3 (e.g. apoE322k), mouse derived apoE2, truncated versions of mouse derived apoE2 (e.g. apoE222k), mouse derived apoA1, truncated versions of mouse derived apoA1 (e.g. Δ49ApoA1, MSP1, MSP1T2, MSP1E3D1), rat derived apoE4, truncated versions of rat derived apoE4 (e.g. apoE422k), rat derived apoE3, truncated versions of rat derived apoE3 (e.g. apoE322k), rat derived apoE2, truncated versions of rat derived apoE2 (e.g. apoE222k), rat derived apoA1, truncated versions of rat derived apoA1 (e.g. Δ49ApoA1, MSP1, MSP1T2, MSP1E3D1), lipophorins (e.g. B. mori, M. sexta), synthetic cyclic peptides that mimic the function of apolipoproteins. Other apolipoproteins, as will be understood for a skilled person, can be used to form NLP, including but not limited to apoB and apoC.

In some embodiments, the scaffold protein can be codon-optimized in order to improve protein expression in expression systems of a particular organism. Exemplary polynucleotide and amino acid sequences of E. coli codon optimized scaffold protein are shown in FIGS. 12A and 12B. Exemplary polynucleotide sequences of E. coli codon optimized scaffold protein are shown in FIGS. 14 and 15.

In some embodiments, the scaffold protein is formed by amphipathic peptides and/or synthetic apolipoproteins which are configured to maintain an amphipathic structure and capability of self-assembly. In particular, in those embodiments, the peptides and/or synthetic apolipoprotein are configured and selected to provide the a plurality of helical segments each having a primary structure configured to form an alpha helix secondary structure, In the alpha helix secondary structure of at least one helical segment, the peptides and/or synthetic apolipoprotein comprise a plurality of hydrophobic amino acids and a plurality of hydrophilic amino acids positioned in the primary structure to provide an amphipathic alpha helix secondary structure, with the plurality of hydrophobic amino acids forming an hydrophobic amino acid cluster and the plurality hydrophilic amino acids forming an hydrophilic amino acid cluster. In some of those embodiments, the scaffold proteins can be peptides derived from apolipoproteins, and can contain amino acid additions, deletions, or substitutions. In other embodiments, these peptides have no sequence homology to apolipoproteins but can be structural analogs. In some embodiments, the peptides can be prepared with L- or D-amino acids. In embodiments where the scaffold protein comprises one or more peptides the skilled person would be able to identify the ratios of peptides based on the length and number of peptides and apolipoproteins and on a desired dimension of the nanolipoprotein particles upon reading of the present disclosure. Additional description of scaffold proteins can be found in PCT/US2015/051172 published on Mar. 16, 2017 as WO2017/044899 incorporated herein by reference in its entirety.

In several embodiments herein described, MOMP-t-NLPs show different size, compositions, and homogeneity. Composition of a t-NLP can be detected by various techniques known in the art, such as high performance liquid chromatography (HPLC), reverse phase high performance liquid chromatography (RP-HPLC), mass spectrometry, thin layer chromatography, NMR spectroscopy and elemental analysis could be used to define the composition of the particles and additional techniques identifiable by a skilled person.

Size and compositions of the MOMP-t-NLPs can be characterized by SEC (size exclusion chromatography) traces which are used to separate out molecules in solution by their size and in some cases their molecular weights as will be understood by a skilled person.

In some embodiments, a MOMP-t-NLP herein described can have a size ranging between 5 nm to 100 nm in diameter. In some embodiments, a MOMP-t-NLP herein described can have a size ranging between 10 nm to 70 nm in diameter. In some embodiments, a MOMP-t-NLP herein described can have a size ranging between 25 nm to 50 nm in diameter In embodiments herein described, NLPs comprise scaffold protein and a lipid component comprising membrane forming lipids and possibly other lipids, as well telodendrimers and MOMP in ratios and proportions that would be identifiable by a skilled person upon reading of the present disclosure.

In general, assembly of telo-NLPs can be accomplished with a wide range of ratios of total membrane forming lipids to scaffold proteins as previously described. Telodendrimer can be incorporated at a ratio of 1:10 to 1:1000 telodendrimer to lipid, with a preferred ratio between 1:50 and 1:500, or more preferably between 1:100 and 1:200.

The t-NLPs here described can contain any suitable combination of lipids with telodendrimers and/or other components. In particular, the one or more membrane forming lipids mixed to form a t-NLP can be polar and/or non-polar lipids as will be understood by a skilled person upon reading of the present disclosure. The telodendrimers mixed to form the t-NLPs can comprise PEG with lengths of 1000-10000 kDa. The ratio of lipid to telodendrimer in the t-NLPs, for example, can be from about 1000:1 to about 10:1 (mol/mol). For example, the ratio can be about 1000:1, 900:1, 800:1, 700:1, 600:1, 500:1, 400:1, 300:1, 200:1, 100:1, 99:1, 95:1, 90:1, 80:1, 75:1, 70:1, 60:1, 50:1, 40:1, 30:1, 25:1, 20:1, 15:1, 14:1, 13:1, 12:1, 11:1 or 10:1 (mol/mol) wherein the term about when referred to ratios indicates the ratios ±5%. In some embodiments, the ratio of lipid to telodendrimer is from about 200:1 to about 100:1 (mol/mol). In some embodiments, the ratio of lipid to telodendrimer is about 150:1 (mol/mol). In some embodiments, the ratio of lipid to telodendrimer is about 135:1 (W/W). Other molar ratios of lipid to telodendrimer can also be useful in t-NLPs herein described as will be apparent to a skilled person upon reading of the present disclosure. In some embodiments of t-NLPs, the lipid to telodendrimer ratios within the telo-NLPs herein described can be of 1000:1 to 10:1, preferably 50:1 to 500:1

In some embodiments, a MOMP-t-NLP herein described, can have a ratio of scaffold protein to lipid is 1:30 to 1:100.

Figure 20A:
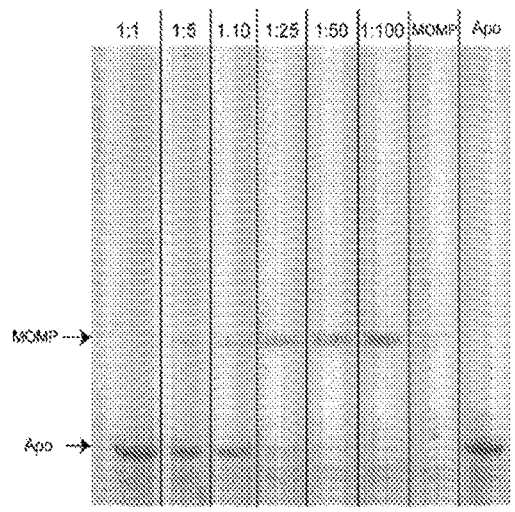
Figure 20B:
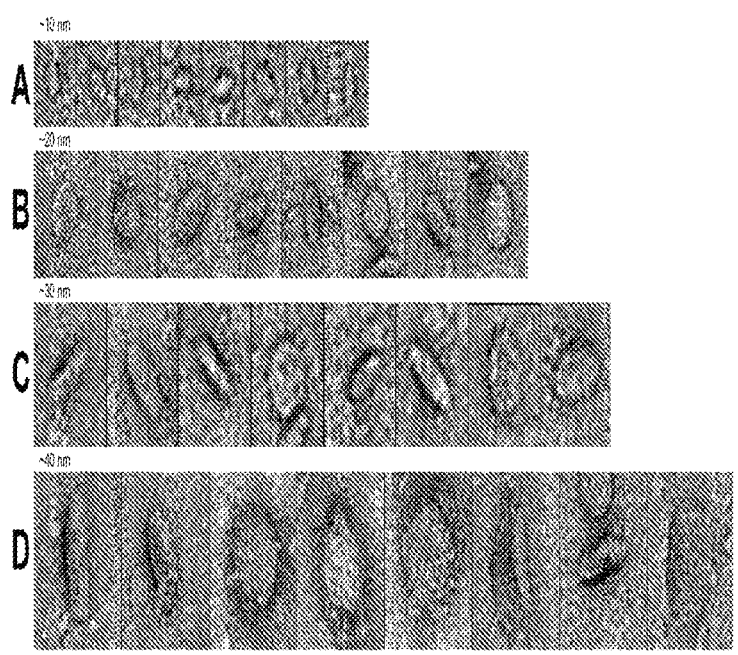

In some embodiments, a MOMP-t-NLP herein described can have a ratio of MOMP to scaffold protein of 50:1 to 1:10 (see, for example, Example 9 and FIGS. 20A-B). In some embodiments, the ratio of MOMP to scaffold protein can be 20:1 to 1:4, 5:1 to 1:2 or of 3:1 to 1:1.

In some embodiments, a MOMP-t-NLP herein described can have a ratio of MOMP to NLPs of 1:1 to 50:1. In some embodiments, the ratio of MOMP to NLPs is 1:1 to 3:1 or 6:1, 9:1 and 12:1.

Any measuring technique available in the art can be used to determine properties of the t-NLPs herein described. For example, techniques such as size exclusion chromatography (SEC), small angle X-ray scattering (SAXS), dynamic light scattering (DLS), x-ray photoelectron microscopy, powder x-ray diffraction, scanning electron microscopy (SEM), transmission electron microscopy (TEM), cryo-electron microscopy (cryo-EM), and atomic force microscopy (AFM) can be used to determine average size and dispersity of the t-NLPs.

In preferred embodiments, a MOMP-t-NLP herein described can have a size ranging between 5 nm to 100 nm in diameter with a ratio of telodendrimer to lipid is 1:10 to 1:1000, a ratio of scaffold protein to lipid of 1:30 to 1:100 and a ratio of MOMP to scaffold protein is 20:1 to 1:4.

More preferably among the most preferred embodiments, a MOMP-t-NLP herein described can have a size ranging between 10 nm to 70 nm in diameter with a ratio of telodendrimer to lipid 1:50 to 1:500, a ratio of scaffold protein to lipid 1:30 to 1:100, and a ratio of MOMP to scaffold protein 5:1 to 1:2.

In most preferred embodiments, a MOMP-t-NLP herein described has a size ranges between 25 nm to 50 nm in diameter. In the MOMP-t-NLP, the ratio of telodendrimer to lipid is 1:100 to 1:200, the ratio of scaffold protein to lipid is 1:30 to 1:100, and the ratio of MOMP to scaffold protein is 3:1 to 1:1.

In those embodiments, MOMP-t-NLPs can solubilize a MOMP with a solubility score ≤20% of the total amount of the MOMP protein in the mixture.

In particular, MOMP-t-NLP with the above preferred and in particular, most preferred ratios are capable of increasing a MOMP's solubility from a solubility score of 10% to a solubility score greater than 70% when embedded in the resulting t-NLP-MOMP particle, the percentage calculated with respect to the total amount of the MOMP protein in the mixture In some of these embodiments, the increase in solubility allows MOMP protein yield to be as high as 2 mg/mL cell-free reaction, and MOMP insertion rate in the final construct to be as high as 50% or greater with respect to the total amount of MOMP in the reaction mixture In particular, in some embodiments, MOMP-t-NLP with the above preferred and in particular, most preferred ratios can provide an increase of 5-50% for the solubility of MOMP assembled in to a tNLP compared to the solubility of MOMP in a mixture in absence of tNLP. Once the material is purified, all of the subsequent material is present at 100% solubility.

Additionally, some embodiments of the MOMP-t-NLPs with the above ratios can allow oligomer MOMP protein to be embedded in a single water soluble nanoparticle, as well as the generation of 25 nm to 50 nm size nanoparticle suitable for in vivo application. Additionally, MOMP-t-NLPs with the above ratios are particularly suitable in compositions, methods and systems directed to elicit an immunogenic response against MOMP in an individual.

In some embodiments, the MOMP-t-NLPs show a larger than expected size of approximately 40 nm then previously identified using other methods.

In some embodiments, MOMP-t-NLPs herein described can further include additional lipids such as functionalized amphipathic compounds and/or one or more target proteins that can be added during the assembly of the t-NLP herein described such as polymorphic membrane proteins (PMP) that may interact with MOMP.

The term "Polymorphic Membrane Proteins" as described herein indicates a group of membrane-bound, surface-exposed chlamydial proteins that have repetitive domains, cell binding domains and beta barrel membrane bound domain as will be understood by a skilled person. In particular, in some of these embodiments, MOMP-t-NLPs herein described comprise PMPs that are capable of forming and/or form disulfide-bond-cross-linked proteins with MOMPs and/or other PMPs. In particular, these PMPS share no homology with other bacterial proteins but do share common features among *Chlamydia* spp.

In some embodiments herein described, the MOMP-t-NLPs further comprise full-length Pmps from a same or different Chlamydial species such as *Chlamydia muridarum* or *C. trachomatis*. In particular, in some embodiments, the MOMP-t-NLPs can further comprise any combination of pmp proteins PmpA, PmpB, PmpC, PmpD, PmpE, PmpF, PmpG, PmpH, and/or PmpI from that *C. muridarum* and/or *C. trachomatis* as will be understood by a person of ordinary skill in the art. In particular the MOMP-t-NLPs can comprise one or more Pmp proteins in a same or different MOMP-t-NLPs within a composition comprising one or more MOMP-t-NLPs herein described. In particular in some embodiments, the MOMP-t-NLPs herein described can comprise one or more of Pmp C, E, F, G and H. In some embodiments, the MOMP-t-NLPs herein described can comprise one or more of Pmp A, B, D and I.

In some embodiments, MOMPs are co-translated with one or more Pmps in a cell-free method/system in presence of NLPs components to form MOMP-Pmp-t-NLPs (see Example 10). Vaccination with MOMP-Pmp-t-NLPs can provide enhanced immunogenic protection against *Chlamydia* infection.

In some embodiments, a MOMP-Pmp-t-NLP herein described can have a ratio of scaffold protein to lipid is 1:30 to 1:100.

In some embodiments, a MOMP-Pmp-t-NLP herein described can have a ratio of Pmps to scaffold protein of 50:1 to 1:10. In some embodiments, the ratio of Pmps to scaffold protein can be 20:1 to 1:4, 5:1 to 1:2 or of 3:1 to 1:1.

In some embodiments, a MOMP-Pmp-t-NLP herein described can have a ratio of Pmps to NLPs of 1:1 to 50:1. In some embodiments, the ratio of Pmps to NLPs is 1:1 to 3:1 or 6:1, 9:1 and 12:1.

In preferred embodiments, a MOMP-Pmp-t-NLP herein described can have a size ranging between 5 nm to 100 nm in diameter with a ratio of telodendrimer to lipid is 1:10 to 1:1000, a ratio of scaffold protein to lipid of 1:30 to 1:100, a ratio of MOMP to scaffold protein is 20:1 to 1:4, and a ratio of Pmps to scaffold protein is 20:1 to 1:4.

More preferably among the most preferred embodiments, a MOMP-Pmp-t-NLP herein described can have a size ranging between 10 nm to 70 nm in diameter with a ratio of telodendrimer to lipid 1:50 to 1:500, a ratio of scaffold protein to lipid 1:30 to 1:100, a ratio of MOMP to scaffold protein 5:1 to 1:2, and a ratio of Pmps to scaffold protein 5:1 to 1:2.

In most preferred embodiments, a MOMP-Pmp-t-NLP herein described has a size ranges between 25 nm to 50 nm in diameter. In the MOMP-Pmp-t-NLP, the ratio of telodendrimer to lipid is 1:100 to 1:200, the ratio of scaffold protein to lipid is 1:30 to 1:100, the ratio of MOMP to scaffold protein is 3:1 to 1:1, and the ratio of Pmps to scaffold protein is 3:1 to 1:1.

The term "functionalized amphipathic compounds" in the sense of the disclosure indicates compounds having a hydrophobic portion and a hydrophilic portion in a configuration where the hydrophobic portion anchor is able to anchor the compound to the lipid bilayer of the NLP and the hydrophilic portion is presented on the NLP bilayer face following NLP assembly. In the functionalized amphipathic compounds in the sense of the disclosure the hydrophilic portion of typically essentially consists of or comprises a hydrophilic functional group.

The term "functional group" as used herein indicates specific groups of atoms within a molecular structure that are responsible for a characteristic chemical reaction of that structure. Exemplary functional groups include hydrocarbons, groups containing double or triple bonds, groups containing halogen, groups containing oxygen, groups containing nitrogen and groups containing phosphorus and sulfur all identifiable by a skilled person.

The term "present" as used herein with reference to a compound or functional group indicates attachment performed to maintain the chemical reactivity of the compound or functional group as attached. Accordingly, a functional group presented on an amphipathic compound, is able to perform under the appropriate conditions the one or more chemical reactions that chemically characterize the functional group.

The use of functionalized amphipathic compounds enables attachment of various peptides or other biologics to the surfaces of the lipid of the NLP that allows some desired target features to be obtained, such as stability, affinity for a target molecule, and the like. Non-limiting examples of functional groups presented on functionalized lipids include: chelated Ni atoms, azide, anhydride, alkynes, thiols, halogens, carboxy, amino, hydroxyl, and phosphate groups, and additional groups identifiable by a skilled person upon reading of the present disclosure.

In some embodiments, the functional group on the functionalized amphipathic compound can be a reactive chemical groups (e.g. azide, chelated nickel, alkyne, and additional reactive chemical groups identifiable by a skilled person), a biologically active compound (e.g. DNA, peptide, carbohydrate, and additional biologically active group identifiable by a skilled person) or a small molecule (e.g. cellular targeting compound, adjuvant, drug, and additional small molecules identifiable by a skilled person). In some embodiments, the functionalized amphipathic compound is a functionalized lipid compound. Functional groups that enhance the lipid solubility are referred to as hydrophobic or lipophilic functional groups. Functional groups that lack the ability to either ionize or form hydrogen bonds tend to impart a measure of lipid solubility to a drug molecule. The functional group can be attached to the lipid polar head through covalent or ionic bonds and "weak bonds" such as dipole-dipole interactions, the London dispersion force and hydrogen bonding, preferably covalent. Moreover, functionalization of the lipid can involve hydrophobic quantum dots embedded into the lipid bilayer. The following article is incorporated by reference in its entirety: R. A. Sperling, and W. J. Parak. "Surface modification, functionalization and bioconjugation of colloidal inorganic nanoparticles". Phil. Trans. R. Soc. A 28 Mar. 2010 vol. 368 no. 1915 1333-1383 [4].

In some embodiments, functionalized amphipathic compounds can comprise one or more of 1,2-dipalmitoyl-sn-glycero-3-phosphoethanolamine-N-(6-((folate)amino) hexanoyl), 1,2-dipalmitoyl-sn-glycero-3-phosphoethanolamine-N-(6-azidohexanoyl), 1,2-dipalmitoyl-sn-glycero-3-phosphoethanolamine-N-(succinyl), 1,2-dioleoyl-sn-glycero-3-phosphoethanolamine-N-(succinyl), 1,2-dipalmitoyl-sn-glycero-3-phosphoethanolamine-N-(glutaryl), 1,2-dioleoyl-sn-glycero-3-phosphoethanolamine-N-(glutaryl), 1,2-dioleoyl-sn-glycero-3-phosphoethanolamine-N-(dodecanyl), 1,2-Dipalmitoyl-sn-Glycero-3-Phosphoethanolamine-N-(hexanoylamine), 1,2-dipalmitoyl-sn-glycero-3-phosphoethanolamine-N-(dodecanylamine), 1,2-Dipalmitoyl-sn-Glycero-3-Phosphothioethanol, 1,2-dioleoyl-sn-glycero-3-phosphoethanolamine-N-[4-(p-maleimidomethyl)cyclohexane-carboxamide], 1,2-dioleoyl-sn-glycero-3-phosphoethanolamine-N-[4-(p-maleimidophenyl)butyramide], 1,2-dioleoyl-sn-glycero-3-phosphoethanolamine-N-[3-(2-pyridyldithio)propionate], 1,2-dioleoyl-sn-glycero-3-phosphoethanolamine-N-(biotinyl), 1,2-Dioleoyl-sn-Glycero-3-Phospho(Ethylene Glycol), 1,2-dioleoyl-sn-glycero-3-phosphoethanolamine-N-lactosyl, 1,2-distearoyl-sn-glycero-3-phosphoethanolamine-N-[dibenzocyclooctyl (polyethylene glycol)-2000], 1,2-distearoyl-sn-glycero-3-phosphoethanolamine-N-[succinyl(polyethylene glycol)-2000], 1,2-distearoyl-sn-glycero-3-phosphoethanolamine-N-[carboxy(polyethylene glycol)-2000], 1,2-distearoyl-sn-glycero-3-phosphoethanolamine-N-[maleimide(polyethylene glycol)-2000], 1,2-distearoyl-sn-phosphoethanolamine-N-[PDP(polyethylene glycol)-2000], 1,2-distearoyl-sn-glycero-3-phosphoethanolamine-N-[amino (polyethylene glycol)-2000], 1,2-distearoyl-sn-glycero-3-phosphoethanolamine-N-[biotinyl(polyethylene glycol)-

2000], 1,2-distearoyl-sn-glycero-3-phosphoethanolamine-N-[cyanur(polyethylene glycol)-2000], 1,2-distearoyl-sn-glycero-3-phosphoethanolamine-N-[folate(polyethylene glycol)-2000], cholesterol modified oligonucleotides, cholesterol-PEG2000-azide, cholesterol-PEG2000-Dibenzocyclooctyl, cholesterol-PEG2000-maleimide, cholesterol-PEG2000-N-hydroxysuccinimide esters, cholesterol-PEG2000-thiol, cholesterol-azide, cholesterol-Dibenzocyclooctyl, cholesterol-maleimide, cholesterol-N-hydroxysuccinimide esters, cholesterol-thiol, C18 modified oligonucleotides, C18-PEG2000-azide, C18-PEG2000-Dibenzocyclooctyl, C18-PEG2000-maleimide, C18-PEG2000-N-hydroxysuccinimide esters, C18-PEG2000-thiol, C18-azide, C18-Dibenzocyclooctyl, C18-maleimide, C18-N-hydroxysuccinimide esters, C18-thiol.

In some embodiments, the MOMP-telo-nanolipoprotein particles herein described can further comprise one or more membrane proteins herein also indicated as target protein. The term "membrane protein" as used herein indicates any protein having a structure that is suitable for attachment to or association with a biological membrane or biomembrane (i.e. an enclosing or separating amphipathic layer that acts as a barrier within or around a cell). In particular, membrane proteins include proteins that contain large regions or structural domains that are hydrophobic (the regions that are embedded in or bound to the membrane); those proteins can be difficult to work with in aqueous systems, since when removed from their normal lipid bilayer environment those proteins tend to aggregate and become insoluble.

Methods and systems for production of MOMP-t-NLPs are also described. In the methods and systems herein described expression of MOMP and the scaffold protein of a MOMP-t-NLP herein described is performed in a cell-free method/system in presence of other NLPs components for a time and under conditions that allow assembly of the NLP.

The membrane forming lipid and the protein components of the MOMP-t-NLP are generally able to self-assemble in a biological (largely aqueous) environment according to the thermodynamics associated with water exclusion (increasing entropy) during hydrophobic association. In the methods and systems herein provided, the amphipathic lipid and the protein components of the NLP are allowed to assembly in a cell free expression system.

As used herein, the wording "cell free expression", "cell free translation", "in vitro translation" or "IVT" refer to at least one compound or reagent that, when combined with a polynucleotide encoding a polypeptide of interest, allows in vitro translation of said polypeptide/protein of interest.

The term "polynucleotide" as used herein indicates an organic polymer composed of two or more monomers including nucleotides, or analogs thereof. The term "nucleotide" refers to any of several compounds that consist of a ribose (ribonucleotide) or deoxyribose (deoxyribonucleotides) sugar joined to a purine or pyrimidine base and to a phosphate group, and that are the basic structural units of nucleic acids. The term "nucleotide analog" refers to a nucleotide in which one or more individual atoms have been replaced with a different atom with a different functional group. Accordingly, the term polynucleotide includes nucleic acids of any length of DNA or RNA analogs and fragments thereof. A polynucleotide of three or more nucleotides is also called nucleotidic oligomers or oligonucleotide.

In particular, co-expression of both scaffold protein and MOMP in presence of phospholipids with or without surfactant/detergent can be performed in a "one-pot" reaction that generates, in situ, both scaffold protein and target membrane protein; NLP self-assembly will ensue using phospholipids already in the reaction mixture.

In some embodiments, the additives used in the cell free reaction systems include any substance that improves the solubilization of the protein of interest and/or of any other protein components that are present in the reaction mixtures, any substance that may augment protein production and any substance that improves protein functions. Those additives include but are not limited to cofactors (e.g. retinal, heme) other proteins that facilitate modification (e.g. glycosylases, phosphatases, chaperonins) lipids, redox factors, detergents and protease inhibitors, and in particular, phospholipids such as dimyristoylphosphatidyl choline (DMPC) and the like, and surfactants/detergents such as cholate, triton X-100 and the like. Exemplary detergents that can be used for protein solubilization in the methods and systems herein disclosed, include Heptanoyl-N-methyl-glucamide, Octanoyl-N-methyl-glucamide, Nonanoyl-Nmethyl-glucamide, n-Nonyl-b-D-gluco-pyranoside, N-Octyl-b-D-glucopyranoside, Octyl-b-D-thiogluco-pyranoside, NN-Dimethyldodecylamine-N-oxide and Glycerol. Additional additives that might be included in the reaction mixtures include labels and labeling molecule that can be used to label or tag the target protein and thus to enable the detection of the target protein through detection of a related labeling signal.

The terms "label" and "labeled molecule" as used herein refer to a molecule capable of detection, including but not limited to radioactive isotopes, fluorophores, chemiluminescent dyes, chromophores, enzymes, enzymes substrates, enzyme cofactors, enzyme inhibitors, dyes, metal ions, nanoparticles, metal sols, ligands (such as biotin, avidin, streptavidin or haptens) and the like. The term "fluorophore" refers to a substance or a portion thereof which is capable of exhibiting fluorescence in a detectable image. As a consequence, the wording "labeling signal" as used herein indicates the signal emitted from the label that allows detection of the label, including but not limited to radioactivity, fluorescence, chemoluminescence, production of a compound in outcome of an enzymatic reaction and the like.

In some embodiments, the polynucleotides encoding MOMP and/or the scaffold protein or other proteins can comprise an engineered polynucleotide designed such that the resulting protein can be expressed as a full-length protein. In some embodiments, the polynucleotide is an engineered polynucleotide designed to encode a protein fragment. Protein fragments include one or more portions of the protein, e.g. protein domains or subdomains. In some embodiments, the polynucleotide is an engineered polynucleotide designed to encode a mutated MOMP. In particular, in some embodiments the polynucleotide can also be designed such that the resulting protein, protein fragment or mutated MOMP is expressed as a fusion, or chimeric protein product (i.e. it is joined via a peptide bond to a heterologous protein sequence of a different protein), for example to facilitate purification or detection. A chimeric product can be made by ligating the appropriate nucleic acid sequences encoding the desired amino acid sequences to each other using standard methods and expressing the chimeric product. In particular, in some embodiments, the polynucleotide can be engineered so that the MOMP is labeled or tagged. Labeling or tagging can be performed with methods that include, for example, FRET pairs, NHS-labeling, fluorescent dyes, and biotin as well as coding for a "His-tag" to enable protein isolation and purification via established Ni-affinity chromatography.

In some embodiments herein described, the polynucleotide is a DNA molecule that can be in a linear or circular form, and encodes the desired polypeptide under the control of a promoter specific to an enzyme such as an RNA polymerase, that is capable of transcribing the encoded portion of the DNA.

In embodiments where the polynucleotide is DNA, the DNA may be transcribed as part of the cell free reactions or system. In those embodiments, the DNA contains appropriate regulatory elements, including but not limited to ribosome binding site, T7 promoter, and T7 terminator, and the reagents or compounds include appropriate elements for both transcription and translation reactions. In other embodiments where the polynucleotide is RNA, the RNA can be prepared prior to addition to the cell free reactions/system, wherein the polypeptide of interest is produced, and the reagents or compounds include appropriate elements for translation reactions only.

Accordingly, as used herein, the term "cell free expression", "cell free translation", "in vitro translation" or "IVT" refer to methods and systems wherein the transcription and translation reactions are carried out independently, and to systems in which the transcription and translation reactions are carried out simultaneously in a non-cellular compartment, e.g. glass vial.

In each of these methods and systems, the reagents or compounds typically include a cell extract capable of supporting in vitro transcription and/or translation as appropriate. In any case, the cell extracts contain all the enzymes and factors to carry out the intended reactions, and in addition, be supplemented with amino acids, an energy regenerating component (e.g. ATP), and cofactors, including factors and additives that support the solubilization of the protein of interest.

These systems are known in the art and can be identified by the skilled person upon reading of the present disclosure, and exist for both eukaryotic and prokaryotic applications. Exemplary cell free expression systems that can be used in connection with the methods and systems of the present disclosure includes but are not limited to commercial kits for various species such as extracts available from Invitrogen, Ambion, Qiagen and Roche Molecular Diagnostics, cellular extracts made from *E. coli* or wheat germ or rabbit reticulocytes, or prepared following protocols, such as published laboratory protocols, identifiable by a skilled person upon reading of the present disclosure.

In some embodiments, the cell free system can operate in batch mode or in a continuous mode. In the batch mode, the reaction products remain in the system and the starting materials are not continuously introduced. Therefore, in batch mode, the system produces a limited quantity of protein. In a continuous mode instead, the reaction products are continuously removed from the system, and the starting materials are continuously restored to improve the yield of the protein products and therefore the system produces a significantly greater amount of product.

In some embodiments, MOMP-t-NLPs herein described can be assembled by a translation method, where self-assembly of the NLPs can be achieved while the apolipoprotein or other scaffold protein is provided as a protein in a mixture also comprising one or more membrane forming lipids, one or more telodendrimers, a polynucleotide coding for the MOMP and/or a MOMP fragment, and a scaffold protein. In some embodiments, the scaffold protein to telodendrimer mass ratio can be 15:1 to 1:1, preferably 5:1. In some embodiments, scaffold protein to lipids mass ratio can be 1.5:1 to 0.1:1, preferably 0.5:1. In some embodiments, scaffold protein to lipids mass ratio will be reduced when MOMP is inserted and may be altered to 1.5:0.75 to 0.1:0.75, preferably 0.5:0.75

In some embodiments, MOMP-t-NLPs herein described can be assembled by a translation method, where self-assembly of the NLPs can be achieved while the apolipoprotein or other scaffold protein is being translated from mRNA as described for example in [5-7]. In this process, expression system lysates are mixed with the lipid and telodendrimer component of the NLP and plasmid DNA encoding the scaffold protein. The reaction can then be allowed to proceed until assembly occurs during apolipoprotein expression (e.g. for approximately 4-24 hrs). The apolipoprotein typically contains an affinity tag (e.g. His-tag) for subsequent purification of the self-assembled NLP from the lysate.

In some embodiments, the ratio of lipid to telodendrimer to be added during the assembly process is 1:1 (W/W) to 1:100 (W/W). In some embodiments, the ratio of DNA encoding MOMP and/or a MOMP fragment to DNA encoding scaffolding protein is between 1:1 (W/W) to 200:1 (W/W). Preferably, the ratio of lipid to telodendrimer to be added during the assembly process is 10:1 (W/W). Preferably, the ratio of DNA encoding MOMP and/or a MOMP fragment to DNA encoding scaffolding protein is between 5:1 to 50:1, more preferably between 10:1 to 25:1.

In some embodiments, wherein the MOMP-NLP comprises a MOMP-fragment the ratio of plasmids (pApo:pMOMP-fragment) can be varied in the cell free reaction to control the amount of fragmented MOMP made and inserted during the assembly process. Normally, we use is 1:1 (W/W) to 1:250 (W/W).

In some embodiments, telodendrimers concentrations can be optimized for a MOMP and/or a MOMP fragment by mixing them with lipids at concentrations from 0.5-10 mg (telodendrimer) and 5-60 mg (lipid) per mL. In some embodiments, the telodendrimer and lipid concentration can be at a 2 mg (telodendrimer) and 20 mg (lipid) per mL prior to addition to the cell-free reaction. In some of those embodiments, the MOMP and/or MOMP fragment assembled in the NLPs form tertiary structures recognized using a conformational antibody, which has never been seen with other recombinant forms of MOMP.

In some embodiments, the methods and systems herein described are performed at predefined lipid protein ratio, assembly conditions and/or with the use of preselected protein component (formed by MOMP and Scaffold protein as polynucleotide) and lipid component (formed by Lipid and telodendrimers) so as to increase the yield, control the size and composition of the resulting NLP, provide an NLP of pre-determined dimensions, achieve desired functionality of the NLP, such as a certain level of loading capacity for a target molecule. In some embodiments, the molar ratio of lipid component to scaffold protein component is 10:1, 20:1, 30:1, 40:1, 50:1, 60:1, 70:1, 80:1, 90:1, 100:1, 110:1, 120:1, 130:1, 140:1, 150:1, 160:1, 170:1, 180:1, 190:1, 200:1, 210:1, 220:1, 230:1, and 240:1. In NLPs herein described, the lipid to scaffold protein component ratio can be determined on a case by case basis in view of the experimental design as will be understood by a skilled person.

In some embodiments, the scaffold protein is selected to define the size of empty NLPs. In particular, the scaffold protein and/or the membrane forming lipid can be selected so that the scaffold protein and the membrane forming lipid are contacted at a mass ratio of scaffold protein to membrane forming lipid from about 1:10 to about 1:1 to provide a particle having a size from 10 to 60 nm. In some embodiments, Lipophorin III lipoproteins may assemble into larger NLPs with diameters 10-30 nm range, apolipoprotein A1 NLPs range in size from 10-25 nm, truncated Δ (1-49) Apolipoprotein A1 15-35 nm. Adjustment of protein to lipid ratios by increasing lipid will also increase the size of the NLP. An exemplary, procedure is illustrated in the examples section. Inclusion of MOMP protein can cause up to 4-fold increase in size to the dimensions of an empty NLP.

In some embodiments, the method to assemble MOMP-t-NLPs herein described results in increasing MOMP to achieve detectable MOMP solubility. In particular, solubility can be measured by centrifuging the total cell-free mixtures following completion of the cell free reaction (e.g. by a table centrifuge at max speed for 10 minutes). After centrifugation, the supernatant is collected and MOMP solubility calculated as ratio of the amount MOMP protein in supernatant to the amount of MOMP protein in the total mixture. A percentage solubility can be the calculated by calculating the amount of the MOMP present in the supernatant (e.g. in term of molar concentration or mass concentration.

In particular, in some embodiments, a detectable solubility for recombinant or native MOMP can be achieved without the need of adding detergents. In particular, in some embodiments, no exogenously added detergent is required for solubilization of MOMP to a detectable solubility. In some embodiments, the increased levels of MOMP solubility are detectable with formation of NLPs within the cell free reaction.

In some embodiments, the method to assemble MOMP-t-NLPs herein described results into as high as 8:1 MOMP membrane protein and/or MOMP fragment insertion ratio to NLP, which has not been achieved previously.

In particular in some embodiments, wherein the MOMP-NLP comprises MOMP fragment, the NLP to MOMP ratio is expected to be between 1:1 and 1:25 (Apo:MOMP protein) depending on the fragment size.

In some embodiments, the method to assemble MOMP-t-NLPs herein described results in a MOMP protein and/or a MOMP fragment with a greater than 2 mg/mL of >85% purity without need of using affinity or solubilization tags directly encoded on the MOMP protein.

In some embodiments, the formulation resulting from method to assemble MOMP-t-NLPs herein described in a form susceptible to lyophilization and resolubilization, which result in MOMP-tNLPs that were intact and functional. Accordingly, in some embodiments, the method to assemble MOMP-t-NLPs herein described, the combination of the materials used therein provide stabilized MOMP-t-NLPs.

In some embodiments, any of the MOMP-t-NLP herein described can be comprised in a composition together with a suitable vehicle. The term "vehicle" as used herein indicates any of various media acting usually as solvents, carriers, binders or diluents of a MOMP-t-NLP comprised in the composition as an active ingredient.

In some embodiments, the composition of the disclosure comprises a same type of MOMP-t-NLP. In some embodiments, the composition can comprise more than one type of MOMP-t-NLP presenting different combination of MOMP, MOMP fragments, Pmps, adjuvants and/or other components, and/or presenting a same or different combination of MOMP, MOMP fragments, Pmps, adjuvants and/or other components at different ratios, as will be understood by a skilled person.

In some embodiments, MOMP-t-NLP can be included in pharmaceutical compositions (e.g. a vaccine) together with an excipient or diluent. In particular, in some embodiments, pharmaceutical compositions are described which contain MOMP-t-NLP, in combination with one or more compatible and pharmaceutically acceptable vehicle, and in particular with pharmaceutically acceptable diluents or excipients.

The term "excipient" as used herein indicates an inactive substance used as a carrier for the active ingredients of a medication. Suitable excipients for the pharmaceutical compositions herein disclosed include any substance that enhances the ability of the body of an individual to absorb the NLP. Suitable excipients also include any substance that can be used to bulk up formulations with NLP to allow for convenient and accurate dosage. In addition to their use in the single-dosage quantity, excipients can be used in the manufacturing process to aid in the handling of NLP. Depending on the route of administration, and form of medication, different excipients may be used. Exemplary excipients include but are not limited to antiadherents, binders, coatings disintegrants, fillers, flavors (such as sweeteners) and colors, glidants, lubricants, preservatives, sorbents.

The term "diluent" as used herein indicates a diluting agent which is issued to dilute or carry an active ingredient of a composition. Suitable diluents include any substance that can decrease the viscosity of a medicinal preparation.

In certain embodiments, compositions and, in particular, pharmaceutical compositions can be formulated for systemic administration, which includes parenteral administration and more particularly intravenous, intradermic, and intramuscular administration. In some embodiments, compositions and, in particular, pharmaceutical compositions can be formulated for non-parenteral administration and more particularly intranasal, intratracheal, vaginal, oral, and sublingual administration.

In some embodiments, the compositions herein described are administrated to humans or animals via mucosal vaccination routes. The compositions can be delivered to a subject through oral mucosa or intranasal inhalation, allowing a direct absorption into the systemic circulation.

Exemplary compositions for parenteral administration include but are not limited to sterile aqueous solutions, injectable solutions or suspensions including MOMP-t-NLPs. In some embodiments, a composition for parenteral administration can be prepared at the time of use by dissolving a powdered composition, previously prepared in a freeze-dried lyophilized form, in a biologically compatible aqueous liquid (distilled water, physiological solution or other aqueous solution).

The term "lyophilization" (also known as freeze-drying or cryodesiccation) indicates a dehydration process typically used to preserve a perishable material or make the material more convenient for transport. Freeze-drying works by freezing the material and then reducing the surrounding pressure and adding enough heat to allow the frozen water in the material to sublime directly from the solid phase to gas.

If a freeze-dried substance is sealed to prevent the reabsorption of moisture, the substance may be stored at room temperature without refrigeration, and be protected against spoilage for many years. Preservation is possible because the greatly reduced water content inhibits the action of microorganisms and enzymes that would normally spoil or degrade the substance.

Lyophilization can also cause less damage to the substance than other dehydration methods using higher temperatures. Freeze-drying does not usually cause shrinkage or toughening of the material being dried. In addition, flavours and smells generally remain unchanged, making the process popular for preserving food. However, water is not the only chemical capable of sublimation, and the loss of other volatile compounds such as acetic acid (vinegar) and alcohols can yield undesirable results.

Freeze-dried products can be rehydrated (reconstituted) much more quickly and easily because the process leaves microscopic pores. The pores are created by the ice crystals that sublimate, leaving gaps or pores in their place. This is especially important when it comes to pharmaceutical uses. Lyophilization can also be used to increase the shelf life of some pharmaceuticals for many years.

In pharmaceutical applications freeze-drying is often used to increase the shelf life of products, such as vaccines and other injectables. By removing the water from the material and sealing the material in a vial, the material can be easily stored, shipped, and later reconstituted to its original form for injection.

In some embodiments, MOMP-t-NLPs herein described can be used as an immunostimulatory particle and in particular as immunostimulatory particles directed to obtain an immunitary response against one or more bacteria of the genus Chlamydia.

The term immunostimulatory as used herein describes the stimulation of the immune system and in particular the ability of a compound, complex and/or particle to affect the immune system.

The immunostimulatory MOMP-t-NLPs herein described are configured to present MOMP as an immunological agent on the t-NLP alone or together with other immunological agents such as other antigens or single or multiple adjuvants. In preferred embodiments the immunostimulatory-MOMP-t-NLPs herein described comprise MOMPS primarily forming homo-trimers in effective amount to elicit an immunological response [3].

The term "immunological agent" as used herein indicates a compound that is able to interfere with the immune system of an individual, and in particular provoke, reduce, enhance or impair a response of the immune system under same or comparable conditions. Exemplary immunological agents comprise antigen and adjuvants.

The term "antigen" or "immunogen" as used herein indicates a substance that prompts the generation of antibodies and/or can cause an immune response. In particular, antigens in the sense of the present disclosure encompass all substances that can be recognized by an adaptive immune system. Exemplary antigens include exogenous antigens and endogenous antigens. Exogenous antigens are antigens that have entered the body from the outside, for example by inhalation, ingestion, or injection. By endocytosis or phagocytosis, these antigens are taken into the antigen-presenting cells (APCs) and processed into fragments. APCs then present the fragments to T helper cells (CD4$^+$) by the use of class II histocompatibility molecules on their surface. Some T cells are specific for the peptide: MHC complex. They become activated and start to secrete cytokines. Cytokines are substances that can activate cytotoxic T lymphocytes (CTL), antibody-secreting B cells, macrophages, and other particles. Endogenous antigens are antigens that have been generated within the cell, as a result of normal cell metabolism, or because of viral or intracellular bacterial infection or transformation of cells leading to cancer. The fragments are then presented on the cell surface in the complex with MHC class I molecules. If activated cytotoxic CD8$^+$ T cells recognize them, the T cells begin to secrete various toxins that cause the lysis or apoptosis of the infected cell. In order to keep the cytotoxic cells from killing cells just for presenting self-proteins, self-reactive T cells are deleted from the repertoire as a result of tolerance (also known as negative selection). They include xenogenic (heterologous), autologous and idiotypic or allogenic (homologous) antigens. Antigens are also generated between normal cells.

In some embodiments, the immunostimulatory MOMP-t-NLPs herein described comprise an immunogenic fragment of the MOMP protein or MOMP immunogenic fragment. The term "immunogenic fragment" as used herein refers to a fragment of a protein that is capable of eliciting a specific immune response, such as an epitope for a B-cell or T-cell as will be understood by a skilled person. In particular, in embodiments herein described a MOMP immunogenic fragment is a MOMP fragment in the sense of the disclosure comprising an immunogenic region including immunogenic MOMP domains in addition to a transmembrane region comprising MOMP hydrophobic amino acid configured to interact with a membrane lipid bilayer. In particular, in a MOMP immunogenic fragment the immunogenic region can be formed by one or more of the variable domains and/or one or more of the epitopes of the MOMP protein, having 1 to 100 amino acid residues each.

Reference is made in this connection to the illustration of FIG. 1A, which shows exemplary variable domains (residues circled) and exemplary transmembrane domains (residues within squares) of MOMP protein. In particular FIG. 1A shows Protein sequence of major outer membrane protein (MOMP), Chlamydia tracomatis, serovar CLPVGN-PAEPSLMIDGILWEGFGGDPCDPCTTWCDAISMRVG-YYGDFVFDRVLKTDVNKEFQMGAAPTTSDVAGLQ-NDPTINVARPNPAYGKHMQDAEMFTNAAYMALNIW-DRFDVFCTLGATTGYLKGNSASFNLVGLFGTKTQS-SSFNTAKLIPNTALNEAVVELYINTTFAWSVGARAA-LWECGCATLGASFQYAQSKPKVEELNVLCNASEFT-INKPKGYVGAEFPLNITA GTEAATGTKDASIDYHEW-QASLALSYRLNMFTPYIGVKWSRVSFDADTIRIAQ-PKLAEAILDVTTLNRTTAGKGSVVSAGTDNELADT-MQIVSLQLNKMKSRKSCGIAVGTTIVDADKYAVTV-EARLIDERAAHVNAQFRF (SEQ ID NO: 66)

Figure 1B:
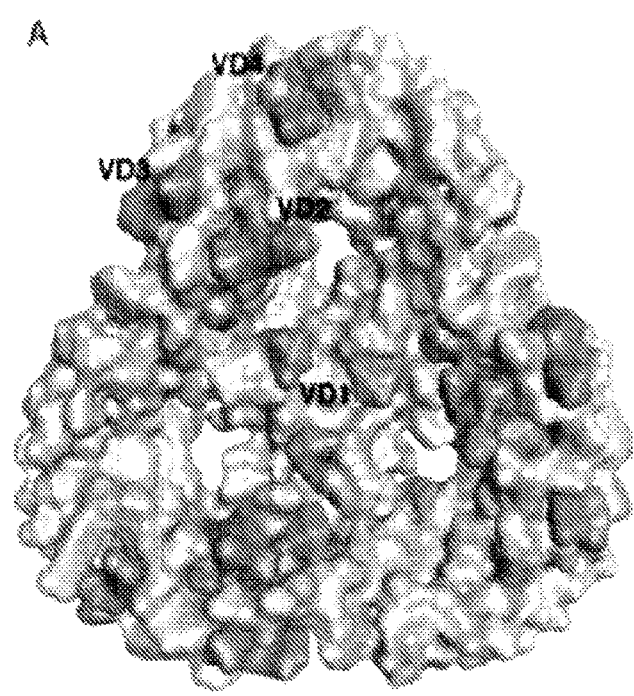
FIG. 1B is a gray scale version of a figure from Feher et al. [1] which shows a schematic representation of a "MOMP model surface, mapping of VD. Positions attaching the VDs to the barrel mapped (dark) onto the molecular surface of the MOMP trimer model" (see Feher et al. 2013 FIG. 5A legend) wherein the variable domains are designated by the V1-V4 which are known or expected to be important for immunogenicity
Figure 1C:
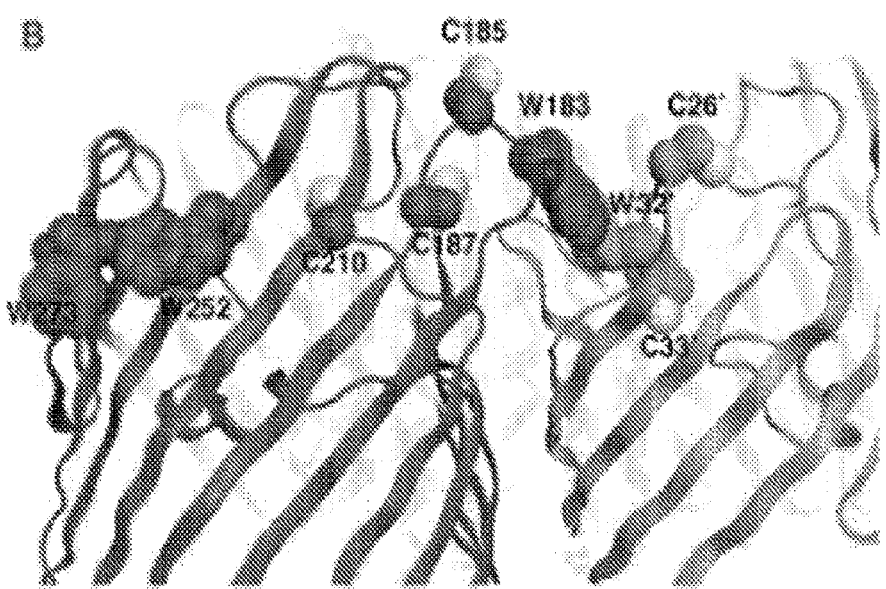
FIG. 1C is a gray scale version of a figure from Feher et al. 2013 [1] which shows "MOMP loops 1 and 4 potential inter-monomer stabilizing contacts. Two of the three monomer b-barrels (light gray on the right and dark gray on the left ribbon representation) illustrate the proximity of Loops 1 and 4. Their tryptophan and cysteine residues (space-filling atom representation) on neighboring trimer subunits are shown (C29 not modeled). Residues W252 and W273 are at the exterior membrane interface in the putative aromatic girdle" (see Feher et al. 2013 FIG. 5B legend).

Reference is also made to the illustration of FIGS. 1B and 1C showing MOMP variable domains (herein also VD) in schematic illustration of MOMP tridimensional structure from Feher et al. [1] 2013 (see FIG. 4) incorporated herein by reference in its entirety.

Reference is also made to the illustration of FIG. 1D showing a MOMP multiepitope described in Tu et al. 2013 [2] incorporated herein by reference in its entirety; the MOMP multiepitope is expected to be comprised in MOMP immunogenic fragments herein described fused to a MOMP transmembrane region in the sense of the disclosure.

The term "epitope" as used herein, also known as an "antigenic determinant" refers to the part of an antigen that is recognized by the immune system, specifically by antibodies, B cells, or T cells. For example, the epitope is the specific piece of the antigen to which an antibody binds. The part of an antibody that binds to the epitope is called a paratope. Although epitopes are usually non-self proteins, sequences derived from the host that can be recognized (as in the case of autoimmune diseases) are also epitopes.

As a person skilled in the art would understand, the epitopes of protein antigens are divided into two categories, comprising conformational epitopes and linear epitopes, based on their structure and interaction with the paratope. A conformational epitope is composed of discontinuous sections of the antigen's amino acid sequence. These epitopes interact with the paratope based on the 3-D surface features and shape or tertiary structure of the antigen. By contrast, linear epitopes interact with the paratope based on their primary structure. A linear epitope is formed by a continuous sequence of amino acids from the antigen.

domains (VD) VD1, VD2, or VD4, or constant domain (CD) CD2, CD3, CD4, or CD5; the sequences of oligomer peptide probes used to detect the epitopes and the corresponding MOMP protein domains recognized are shown in Table 2.

TABLE2

| Oligomer probe | MOMP domain | *C. muridarum* MOMP amino acid sequence | SEQ ID NO |
|---|---|---|---|
| P5 | VD1 | EMGAAPTGDADLTTAPTPASRENPA | 7 |
| P6 | VD1 | PTPASRENPATGKHMQDAEMFTNAA | 8 |
| P10 | VD2 | FGRDETAVAADDIPNVSLSQAVVEL | 9 |
| P20 | VD4 | TSILKMTTWNPTISGSGIDVDTKIT | 10 |
| P4 | VD1 | FVFDRVLKTDVNKQFEMGAAPTGDA | 11 |
| P9 | VD2 | GYLKGNSAAFNLVGLFGRDETAVAA | 12 |
| P7 | CD2 | QDAEMFTNAAYMALNIWDRFDVFCT | 13 |
| P23 | CD5 | LAIGTTIVDADKYAVTVETRLIDER | 14 |
| P24 | CD5 | TVETRLIDERAAHVNAQFRF | 15 |
| P14 | CD3 | KVEELNVLCNAAEFTINKPKGYVGQ | 16 |
| P19 | Includes regions of CD4 and VD4 | SFDADTIRIAQPXLETSILKMTTWN | 17 |
| P21 | Overlaps VD4 and CD5 | SGIDVDTKITDTLQIVSLQLNKMKS | 18 |
| P22 | CD5 | VSLQLNKMKSRKSCGLAIGTTIVDA | 19 |

For example, T cell epitopes are presented on the surface of an antigen-presenting cell, where they are bound to MHC molecules. In humans, antigen-presenting cells are specialized to present MHC class II peptides, whereas most nucleated somatic cells present MHC class I peptides. T cell epitopes presented by MHC class I molecules are typically peptides between 8 and 11 amino acids in length, whereas MHC class II molecules present longer peptides, 13-17 amino acids in length, and non-classical MHC molecules also present non-peptidic epitopes such as glycolipids.

Epitopes can be mapped, for example using protein microarrays, or with ELISA or ELISPOT techniques, among others known to those skilled in the art. Another technique involves high-throughput mutagenesis, an epitope mapping strategy developed to improve rapid mapping of conformational epitopes on structurally complex proteins [8]. In addition, MHC class I and II epitopes can be predicted by computational means [9]. Additional methods for identifying epitopes are described in U.S. Pat. Nos. 8,889,142, 8,486,411, 7,754,228 and 6,635,746 and will be understood by a person skilled in the art.

In particular, an immunogenic fragment of MOMP refers to a fragment of a MOMP protein that is capable of eliciting a *Chlamydia* specific immune response in a host. As would be understood by persons skilled in the art, an immune response in a host is typically mediated by recognition by the host immune system of a specific protein epitope.

Mapping of MOMP B-cell epitopes recognized by antibodies elicited by immunization can be performed following techniques known in the art, such as those described in Tifrea et al. 2014 [10]. Examples of MOMP immunogenic epitopes comprise those of epitopes within MOMP variable Additional exemplary immunogenic MOMP peptide fragments and epitopes of *C. trachomatis* are identifiable by those skilled in the art, in published articles such as in [2, 11-14], among others, and such as those described in U.S. Pat. Nos. 8,889,142, 8,486,411, 7,754,228 and 6,635,746.

Identification of MOMP epitopes can also be determined in part by analysis of structure of MOMP proteins. Exposed domains of MOMP are understood to be both serotyping and protective antigenic determinants [12]. The four topological models of MOMP, corresponding to *C. muridarum* and the *C. trachomatis* serovars C, D and F, have been proposed and can be used in the protein structural analysis [1, 15-17].

The immunostimulatory MOMP-t-NLP herein described can further comprise adjuvants.

The term "adjuvant" as used herein indicates an agent that stimulates the immune system but that is not antigenic in itself. Typically, adjuvants are used in connection with antigens and/or vaccine composition to increase the response to one or more antigen of choice.

Exemplary adjuvants that can be incorporated into an NLP herein described as a self-assembling component comprise; naturally occurring hydrophobic or amphipathic adjuvants, including but not limited to lipopolysaccharides (LPS), mono-phosphorylated Lipid A (MPLA), organic compounds (squalene, sorbitol oleate esters), alpha-galactosyl ceramide, and lipoteichoic acid (LTA), or hydrophilic adjuvants synthetically appended with a hydrophobic moiety, including for example microbial derivatives (e.g. CpG motifs, muramyl dipeptide (MDP), flagellin), plant derivatives (e.g. saponins), and immunostimulatory proteins (e.g. cytokines, toxins, and derivative peptides), and immunostimulatory carbohydrates and polysaccharides.

In particular, in some embodiments, immunostimulatory MOMP-t-NLP herein described present MPLA alone or in combination with additional adjuvants. MLPA is a well-established adjuvant that has been shown to induce both cellular and humoral immune responses. MPLA is a low toxicity derivative of a bacterial cell wall component, lipopolysaccharide (LPS).

In any of the above embodiments, one or more additional same or different adjuvant and/or antigen can be attached to the immunostimulatory MOMP-t-NLPs through binding the anchor compound-anchor substrate compound and/or through incorporation of an amphipathic adjuvant into the nanoparticle during self-assembly.

In some embodiments, binding or conjugation of the adjuvant or other immunological agent can be performed by chelation of the immunological agent to a functional group presented by one or more functionalized lipids in the MOMP-t-NLPs herein described. The term "chelation" as used herein indicates the binding or complexation of a bi- or multidentate ligand with a single metal ion. In particular, in some embodiments, the bi or multi-dentate ligand is part of the lipid and is capable of binding a metal ion. The ligands, which are often organic compounds, are called chelants, chelators, chelating agents, or sequestering agents. Chelating agents form multiple bonds with a single metal ion. The term "chelants" as used herein indicates a molecule that forms a stable complex with certain metal ions. Examples of chelating moieties include, but are not limited to, nitrilotriaceticacid (NTA), iminodiacetic acid (IDA), and diethylenetriamine penta-acetic acid (DTPA).

Successful binding of an immunological agent to the NLP can be readily verified and quantified through a range of techniques that include but are not limited to centrifugal filtration, size exclusion chromatography, fluorescence correlation spectroscopy, cantilever-based sensing, force spectroscopy, Fourier transform infrared spectroscopy, surface plasmon resonance, total internal reflection fluorescence, Raman spectroscopy and additional techniques identifiable by a skilled person. In addition, binding specifically to the surface can be verified using atomic force microscopy and transmission electron microscopy and additional techniques identifiable by a skilled person.

In some embodiments, the formation of immunostimulatory MOMP-t-NLPs herein described is amenable to the incorporation of multiple adjuvants, including for example compounds directed to enhance immune response e.g. non-human lipoproteins, bacterial peptides, DNA (e.g. CpG motifs), chemokines, cytokines, pattern-recognition receptors (PRR), lipids, polysaccharides, lipopolysaccharides, and the like; in general, agonists and immune stimulatory molecules, synthetic or natural, (known or unknown at this time) can be assembled in or on NLPs, providing for enhanced, specific, rapid immune stimulation at the site of NLP/antigen inoculation and spreading systemically.

In some embodiments, the formulated MOMP t-NLPs with single or multiple adjuvant result in a sustained IgG titer that are several logs higher than adjuvant-NLPs or NLPs alone. Adjuvants concentrations can be varied up to 20 µg per dose. In preferred embodiments, MOMP t-NLPs can comprise two or more adjuvants to provide MOMP t-NLPs capable of eliciting an optimal protective response with MOMP.

In some embodiments, immunostimulatory MOMP-t-NLPs herein described can be comprised of immunostimulatory compositions, including vaccines to be administered to individuals.

The term "individual" as used herein in the context of treatment includes a single biological organism, including but not limited to, animals and in particular higher animals and in particular vertebrates such as mammals and in particular human beings The immunostimulatory MOMP-t-NLPs or the immunostimulatory composition herein described can also be administered to an individual alone or in combination with additional immunostimulatory agents to immunize the individual.

In particular, in some embodiments, MOMP-t-NLPs herein described can be used in combination with NLPs comprising an adjuvant such as microbial derivatives (e.g. CpG derivatives, MPLA), muramyl dipeptide derivatives (e.g. muroctasin), and any peptide or protein adjuvants (e.g. flagellin) can be incorporated into NLP directly to create an adjuvant NLP that can be used as an adjuvant or as a platform for subunit vaccine development with enhanced potency.

In particular, an adjuvant NLP according to the present disclosure can comprise single or multiple adjuvants, such as CpGs, MPLA, and cytokines. In some embodiments, an adjuvant NLP can be customized by including for example selected adjuvants in view of the desired effect based on the ability of different adjuvants to target different toll-like receptors (TLR) for immunostimulation (e.g. MPLA targets TLR 4, CpGs target TLR9, and flagellin targets TLR5). In some of these embodiments, the customization is performed in view of a specific vaccine formulation to be used in combination with the adjuvant NLP. The customization can be made to combine in the NLP only the adjuvants that are effective for the vaccine formulation of choice, since in some vaccine formulations only certain adjuvants are successful at enhancing the efficacy of the vaccine.

In some embodiments, the MOMP-t-NLP herein described are provided in a formulation compatible with intramuscular or intranasal administration in an amount effective to elicit a protective response. In some embodiments, the MOMP-t-NLP herein described are provided in a formulation for intravaginal administration in an amount effective to elicit a protective response by vaginal exposure to a *Chlamydia* pathogen.

Immunization can be affected by simple intramuscular injection in either the shoulder area or in the gluteus maximus hind muscular region. Particles could be delivered following solubilization in sterile normal saline solution, for example. Such immunizations would be subject to practices and methods approved by the US government Food and Drug Administration (FDA).

In particular, in some embodiments, the immunostimulatory NLPs that comprise at least one antigen can be used as vaccines that can be prepared rapidly and are relatively stable affording the desired protective immune response in accordance with attached immunogen.

The term "vaccine" as used herein indicates a composition, and in particular a biological preparation, that establishes or improves immunity to a particular external pathogenic assault, or an inherent transformational incident resulting in a cancerous or autoimmune condition in mammals. Vaccines in the sense of the present description can be prophylactic, or therapeutic.

In some embodiments, the immunostimulatory MOMP-t-NLP construct is more immunogenic than the antigen alone, and can be used as a vaccine to protect against *Chlamydia* infection when injected into an appropriate recipient with or without the aid or use of an adjuvant type carrier.

In particular, in some embodiments, methods herein described allow production of a functional MOMP protein in immunostimulatory MOMP-t-NLPs for vaccine development despite MOMP poor solubility, low yield, and protein misfolding which characterize MOMP production thus provide immunogenic MOMP or fragment thereof in particular in the preferred and most preferred embodiments herein described as will be understood by a skilled person upon reading of the present disclosure. The dimension and complexity of MOMP renders it difficult to recombinantly synthesize in a correctly folded state. For example, efforts to express MOMP in bacterial systems have yielded poor results due to incorrect MOMP protein folding [15, 18, 19]. In addition, processes of extracting native MOMP from *Chlamydia* is laborious and is difficult to produce for large-scale commercial applications. Experimental MOMP vaccines based on denatured or non-native recombinant preparations have shown to yield only partial protection in a mouse model using *C. muridarum* [10, 20-22].

The cell-free expression methods and systems described herein can produce a MOMP-tNLP complex with the tNLP membrane-bound MOMP forming multimers similar to the native protein in high yield, with increased solubility (Example 2), and retained functionality and immunogenicity (Examples 5-7), while eliminating the need to overexpress insoluble MOMP proteins in cells or to reconstitute MOMP with detergent. The process described herein can also be applied to other membrane-bound proteins previously difficult to obtain antigens in vivo or difficult to produce in native higher order structures.

In several embodiments, the immunostimulatory MOMP-t-NLP presenting antigens alone or in combination with adjuvants conjugates encapsulate key requirements for vaccine formulation: non-virulence; immunostimulation; clustered antigen presentation; expression of MOMP in multimeric form required for effective immune response; simple, rapid, inexpensive production; and the means to accommodate a wide range of select-agent antigens. Furthermore, adjuvant-bearing NLPs promote both humoral and cellular immune responses.

In some embodiments, the immunostimulatory MOMP-t-NLP presenting antigens alone or in combination with adjuvants in a vaccine for treating or preventing a *Chlamydia* infection or conditions associated thereto via intramuscular or intranasal administration. In some embodiments, the immunostimulatory MOMP-t-NLP presenting antigens alone or in combination with adjuvants in a vaccine for treating or preventing a *Chlamydia* infection or conditions associated thereto via intravaginal administration.

In several embodiments, the immunostimulatory MOMP-t-NLP are herein described and related compositions, methods and systems allow cost effective and rapid development of immunostimulatory compositions that are safe, enable immunization with multivalent/or broad-spectrum response and at the same time, are able to elicit a high levels protection following an adequate stimulation of a host immune response.

In several embodiments, the immunostimulatory MOMP-t-NLP, methods and systems herein described allow incorporation in the immunogenic particles of secondary additives to enhance immune response in the individual.

In certain embodiments, an adjuvant and one or more immunostimulatory MOMP-t-NLP can also be comprised in a system to immunize an individual. In those embodiments, the system comprises: the immunostimulatory particle herein described and an adjuvant, the immunostimulatory particle and the adjuvant to be administered to the individual to immunize such individual.

The systems herein disclosed can be provided in the form of kits of parts. In kit of parts for the production of MOMP-t-NLPs herein described, the MOMP and the scaffold protein can be included in the kit as a protein alone or in the presence of lipids/detergents for transition into nanoparticles. The MOMP and/or the scaffold protein can be included as a plasmid or PCR DNA product for transcription/translation. The indicator protein may be included as encoded RNA for translation. In kit of parts for the immunization of an individual the immunostimulatory MOMP-t-NLP can be comprised together with adjuvant and/or adjuvant NLPs and additional components identifiable by a skilled person.

In a kit of parts, a polynucleotide, amphipathic lipid, target protein and/or scaffold protein, MOMP-tNLPs, adjuvants, adjuvant NLPs and additional reagents are comprised in the kit independently possibly included in a composition together with suitable vehicle carrier or auxiliary agents. For example, a polynucleotide can be included in one or more compositions alone and/or included in a suitable vector, and each polynucleotide in a composition together with a suitable vehicle carrier or auxiliary agent. Furthermore, the target protein can be included in various forms suitable for appropriate incorporation into the NPL.

Additional components can include labeled polynucleotides, labeled antibodies, labels, microfluidic chip, reference standards, and additional components identifiable by a skilled person upon reading of the present disclosure. In particular, the components of the kit can be provided, with suitable instructions and other necessary reagents, in order to perform the methods here disclosed. The kit will normally contain the compositions in separate containers. Instructions, for example written or audio instructions, on paper or electronic support such as tapes or CD-ROMs, for carrying out the assay, will usually be included in the kit. The kit can also contain, depending on the particular method used, other packaged reagents and materials (i.e. wash buffers and the like).

Further details concerning the identification of the suitable carrier agent or auxiliary agent of the compositions, and generally manufacturing and packaging of the kit, can be identified by the person skilled in the art upon reading of the present disclosure.

EXAMPLES

The methods and system herein disclosed are further illustrated in the following examples, which are provided by way of illustration and are not intended to be limiting.

In particular, mMOMP-tNLPs comprising a MoPn MOMP protein (mMOMP, a type of MOMP expressed in the mouse-specific *Chlamydia muridarum*), scaffold protein Δ49apolipoprotein A1 (Δ49ApoA1, a truncated version of mouse ApoA1), membrane-forming lipids, and telodendrimers were prepared using a cell-free expression system and characterized in vitro and in vivo. The mMOMP-tNLP particle also accommodated the co-localization of the CpG adjuvant ODN1826 for in vivo characterization. A skilled person will be able to use the membrane forming lipids, telo-dendrimers, scaffold proteins, adjuvant, and mMOMP herein described. The following materials and methods were used.

Plasmids: The truncated form of mouse Apo A1 (Δ1-49) or Δ49ApoA1 gene and mMOMP gene were assembled from oligonucleotides and cloned into NdeI/BamHI digested pIVEX2.4d vector (Roche Molecular Diagnostics, Basel, Switzerland) using Gibson Assembly. Briefly, Archetype Software was used to design 60 bp long, overlapping oligonucleotides covering the DNA sequence of interest (Δ49ApoA1 including 90 bp 5' and 3' vector overlap to pIVEX2.4d). The 60 bp oligonucleotides overlapped neighboring oligonucleotides by 30 bp. In addition, forward and reverse primers (distal primers) were designed for amplification of the DNA sequence of interest. The pIVEX2.4d vector contained a His-tag used for nickel affinity purification as previously described [23]. The codon-optimized plasmid sequences are shown (FIGS. 3A-3B; also shown in FIGS. 12A-C, 13, 14, 15, 16 and 17).

DMPC/telodendrimer preparation: $PEG^{5k}$-$CA_8$ telodendrimer was prepared according to a published method [24]. Small unilamellar vesicles of DMPC (Avanti Polar Lipids, Alabaster, Alabama) were prepared by probe sonication of a 20 mg/mL aqueous solution of DMPC until optical clarity was achieved; typically 3 intervals of 30 seconds were sufficient. After the sonication, the samples were centrifuged at 14,100 rcf for 1 minute to remove metal contamination from the probe tip. For the DMPC/$PEG^{5k}$-$CA_8$ mixtures, a total of 20 mg/mL DMPC and 2 mg/mL $PEG^{5k}$-$CA_8$ were mixed at a volume ratio of 1:1.

Cell-free Reaction: Small and large scale reactions (50 μL and 1 mL) were carried out using RTS 500 ProteoMaster *E. coli* HY Kit (Biotechrabbit GmbH, Hannover, Germany). Small scale reactions contained the same ratio of components as the large-scale reactions. Reaction components (lysate, reaction mix, feeding mix, amino acid mix, and methionine) were combined as specified by the manufacturer. For expression, 0.3-1.5 μg of Δ49ApoA1 and 15 μg mMOMP plasmid DNA was added to each 1 mL reaction. A total of 400 μL DMPC/telodendrimer mixture was then added. The reactions were incubated at 30° C., with shaking at 300 rpm for 14-18 hrs in a floor shaker.

Affinity purification of NLP-related complexes: Immobilized nickel affinity chromatography was used to isolate the mMOMP-tNLP from the cell-free reaction mixture. 1 mL of 50% slurry cOmplete His-Tag Purification Resin (Roche Molecular Diagnostics, Basel, Switzerland) was equilibrated with equilibration buffer (50 mM $NaH_2PO_4$, 300 mM NaCl, pH 8.0) with 10 mM imidazole (Sigma-Aldrich, St Louis, MO) in a 10 mL chromatography column. The total cell free reaction (1 mL) was mixed with the equilibrated resin, and was incubated/mutated at 4° C. for 1 hr. The column was then washed with equilibration buffer containing 20 mM imidazole. The column was washed with 1 mL of the same buffer 6 times. The mMOMP-tNLPs were eluted in six 300 μl fractions of equilibration buffer containing 250 mM imidazole and 1 final elution of 300 μl in 500 mM imidazole. All elutions were analyzed by SDS-PAGE and peak fractions containing protein were combined. Pooled fractions were dialyzed in PBS (pH 7.4) and then stored at 4° C. Material for mouse studies were tested for endotoxin levels using the Endosafe-PTS (Charles River, Charleston, SC) endotoxin testing system based on Limulus Amebocyte Lysate (LAL) assay. All NLP preparations have an endotoxin level between 20 and 100 EU/mg.

Size exclusion chromatography (SEC): NLPs were purified by SEC (Superdex 200, 10/300 GL column, GE Healthcare, Piscataway, NJ). SEC was run at a flow rate of 1 mL/min in PBS buffer with 0.25% PEG2000.

SDS PAGE: A total of 5-15 μL aliquots of the eluted mMOMP-tNLPs were mixed with 4× NuPAGE LDS Sample buffer and 10× NuPAGE Sample Reducing Agent (Life Technologies Corporation, Carlsbad, California), heat denatured and loaded onto a 4-12% gradient pre-made 1.0 mm Bis-Tris gel (Life Technologies Corporation, Carlsbad, California) along with the molecular weight standard SeeBlue Plus2 (Life Technologies Corporation, Carlsbad, California). The running buffer was 1×MES-SDS (Life Technologies Corporation, Carlsbad, California). Samples were run for 35 minutes at 200V. Gels were stained with SYPRO Ruby Protein Gel stain (Life Technologies Corporation, Carlsbad, California) according to manufacturer's instructions, and imaged using a LiCor Odyssey Fc Imager (LI-COR Biotechnology, Lincoln, NE).

Western blots and dot blots analysis: Western and dot blots were performed on PVDF membranes (Millipore). For western blots, samples were resolved with SDS-PAGE as described above. The gels were incubated in transfer buffer for 10 minutes and transferred at 4° C. for 65 minutes at 100V. The transfer buffer was 1× NuPAGE (Life Technologies Corporation, Carlsbad, California). Blots were incubated overnight at 4° C. in Odyssey Blocking Buffer (PBS) (LiCor Biotechnology, Lincoln, Nebraska) containing 0.2% Tween-20 and either 0.5 mg/mL mAb40 (linear, VD1) or 0.2 mg/mL Penta-His antibody (Qiagen, Hilden, Germany) diluted 1:1000 [25]. Blots were then washed for five minutes, four times, with PBS-T (50 mM $NaH_2PO_4$, 300 mM NaCl, 0.2% Tween-20, pH 7.4) while shaking. Blots were then incubated for 1 hour in blocking buffer containing 0.2% Tween-20, 0.02% SDS and 1 mg/mL IRDye 800CW Goat (polyclonal) anti-Mouse IgG (H+L) (LI-COR Biosciences, Lincoln, Nebraska) diluted to 1:10,000. Blots were washed with PBS-T four more times and imaged with LiCor Fc Imager at 800 nm. For dot blots, 3 μg of purified nanoparticles with and without mMOMP were blotted using the Bio-Dot Apparatus #1706545 (Bio-Rad), according to manufacturer's instructions. Blots were developed as mentioned above.

Conductance assays: To look at the ability of mMOMP to form functional pores, the mMOMP-tNLP complex was incorporated into planar lipid bilayer and conductance measurements were performed in a two-chamber black lipid membranes (BLM) cell (Eastern Scientific LLC, Rockville, MD, USA). A supported DMPC lipid bilayer was formed over a 200 μm diameter aperture in a Teflon film partition using a painting technique. The cis-chamber (connected to ground Ag/AgCl electrode) and trans-chamber (connected to a reference Ag/AgCl electrode) were filled with 0.2 mL and 2 mL PBS buffer (w/$Mg^{2+}$ and $Ca^{2+}$, pH 7.4) respectively. 1-2 μL mMOMP-tNLP complex in solution was added to the cis-chamber above the DMPC bilayer. A holding potential between −100 mV to +100 mV was applied to the reference electrode, and the transmembrane current signal was recorded by the Axiopatch 200B patch clamp amplifier (Axon Instruments, Milpitas, CA, USA) connected to a computer system running Clampex 10.3 software (Axon Instruments). The current traces were acquired at a sampling frequency of 10 kHz-100 kHz. The data were exported and analyzed using PClamp 10.3 software (Axon Instruments) and Igor Pro 6.31 (Wavemetrics Inc.).

Dynamic light scattering (DLS): Dynamic light scattering measurements of the NLP size were performed on a Zetasizer Nano ZS90 (Malvern Instruments, Malvern United Kingdom)) following the manufacturer's protocols. Each data point represents an average of at least 10 individual runs.

Atomic Force Microscopy (AFM): AFM is a technique known to a skilled person to investigate NLPs and membrane protein insertion[145-148]. Briefly, atomically flat mica disks are glued to metal substrates to secure them to the scanner of a stand-alone MFP-3D AFM (Asylum Research, Santa Barbara, CA). Topographical images are obtained with "Biolevers" (Olympus, Tokyo, Japan) with a spring constant of 0.03 N/m in a room temperature controlled room at 23+/−1° C. Images are taken in alternate contact (AC) mode in liquid, with very low amplitudes at the primary resonance frequency that was obtained from thermal analysis of the cantilever in solution. Heights of features in images are determined by histogram and statistical analysis as will be understood by a skilled person 60,112,113.

Transmission Electron Microscopy (TEM): Samples are harvested using both continuous carbon coated TEM grids and small silicon wafers with silicon nitride membranes (each ~3 mm in diameter). For NLP samples, a 4 μL drop of the purified sample (0.5 mg/ml) can be adsorbed to a cleaned holey-carbon-coated copper EM grid, blotted with Whatman paper and rapidly plunge frozen. The resulting cryoEM grid can then be imaged using low-dose exposure techniques on a JEOL JEM-2100F transmission electron microscope. Electron micrographs are direct images of the sample, acquiring a large dataset provides a statistical overview of the homogeneity and aggregation of the protein or complex in solution[149-151]

Cryo-electron microscopy (cryoEM): In cryoEM, a fully hydrated complex is frozen and then subjected to electron microscopy. This permits an advantage in studying hydrated complexes used for detailed and accurate image re-construction[152-157] All tNLP and mMOMP-tNLP samples were preserved as frozen hydrated specimen in the presence of saturated ammonium molybdate for scanning with a JEOL JEM-2100F transmission electron microscope (JOEL USA, Peabody, Massachusetts) at magnification of 80,000× under liquid nitrogen temperature.

Mouse immune study: All animal studies were performed at Lawrence Livermore National Laboratory in PHS-assured facilities in accordance with guidelines set by the Animal Care and Use Committee (IACUC). Female 3-week old mice (BALB/c) were purchased from Jackson Laboratory (Bar Harbor, ME). Since 3-week old mice are pre-pubescent, they are more susceptible to STI infection and more suitable than adult mice for the *Chlamydia* studies. A total of 6 mice/group were vaccinated with the following formulations: 1×10$^4$ IFU's of EB obtained from Dr. Luis de la Maza at UC Irvine, 10 μg of tNLP with 5 μg CpG adjuvant, 10 μg mMOMP-tNLP plus 5 μg of CpG adjuvant, or PBS alone. Total volumes per inoculation were 50 μL. Animals were primed on day 1 and received boosts at days 21 and 42. Whole blood was drawn prior to each inoculation. A final bleed was conducted on day 61 post initial prime. Serum antigen specific IgG antibody titers were measured using an enzyme-linked immunosorbent assay (ELISA). Immulon 2 HB microtiter plates (Thermo Labsystems, Franklin, MA) were coated with the appropriate antigen (200 ng/well), and then incubated with sera (2-fold serial dilutions starting at 1:100 dilutions) for 1 hour. Goat anti-mouse IgG HRP-conjugated antibody (KPL, Gaithersburg, MD) was added to the plates for 1 hour, and the bound HRP was detected by incubation with TMB (Sigma) quenched after 5 min with 1 M HCl. The reaction product was quantitated by a spectrophotometer at 450 nm, and values were corrected for background activity detected from wells that received diluent in place of sera. The titration curves were then fit to a power function in MS Office Excel and titers were calculated from the fit function using a cutoff absorbance value of the average background O.D.±3 S.D.

Example 1. Structural Characterization of Native MOMP

A structural characterization of MOMP was performed with TEM.

Figures 23A, 23B, 23C, 23D, 23E:
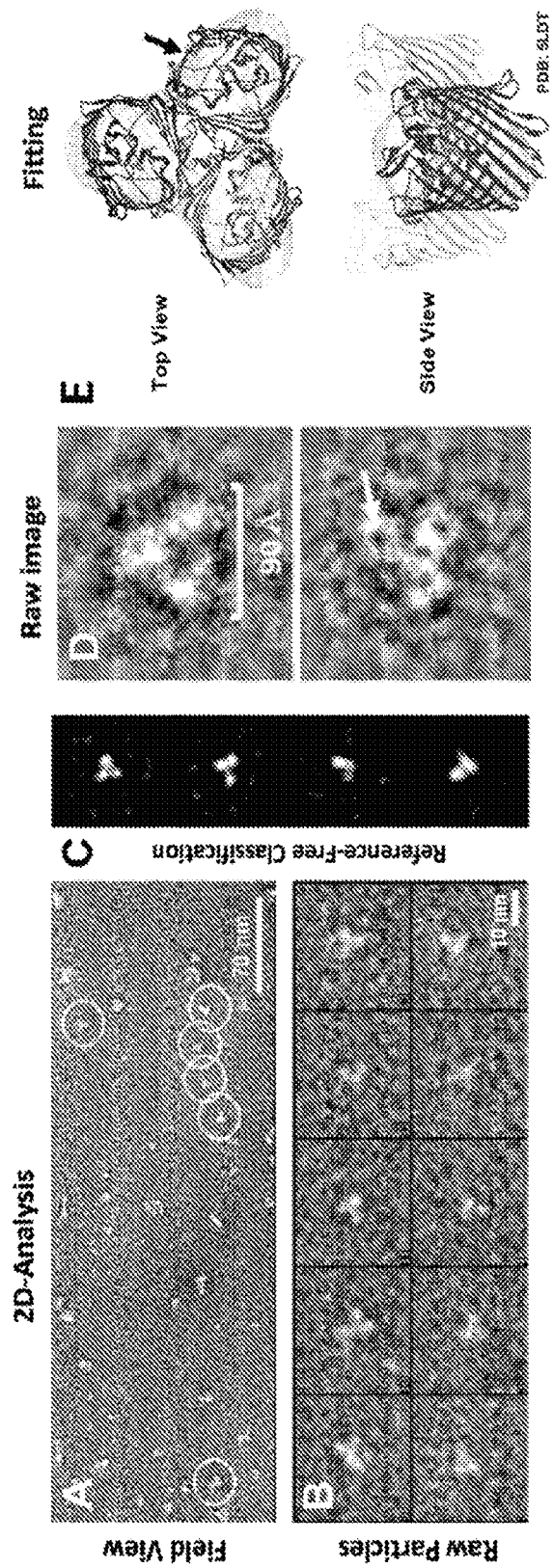

In particular, the TEM analysis performed shows monodispersed native MOMP (FIG. 23A) stained with 5% ammonium molybdate and placed on continuous carbon grids for observation. For model building, trimeric MOMP particles are selected using a semi-automated particle selection tool via EMAN 2.1 package [26] (FIG. 23B). The pre-processing of MOMP image analysis shows that the protein is predominantly in a trimeric association, with some sample heterogeneity MOMP trimer images were then collected and class averaged. The individual MOMP trimer images were processed using reference-free classification to group particles with similar orientation (FIG. 23C). The images were then aligned, rotated, and averaged.

Preliminary Raw projection images show clear trimeric association and distinct features of MOMP (FIG. 23D). In particular, in the illustration of FIG. 23D, raw projection images of MOMP trimer show distinct structural features (white arrow). The diameter of the MOMP trimer was calculated to be 90 Angstroms.

Furthermore, preliminary 3D density maps were generated for comparison to MOMP from *Campylobacter jejuni* (Protein Data Base (PDB) ID: 5LDT)[27] (FIG. 23E). Class averaged images can be used for comparison to previously solved MOMP structures, such as MOMP from *Campylobacter jejuni* (5LDT). Black arrow indicates the fitted edges of preliminary density map generated from class averages.

Example 2. Cell-Free Co-Translation Supports Soluble mMOMP Expression

Figure 2:
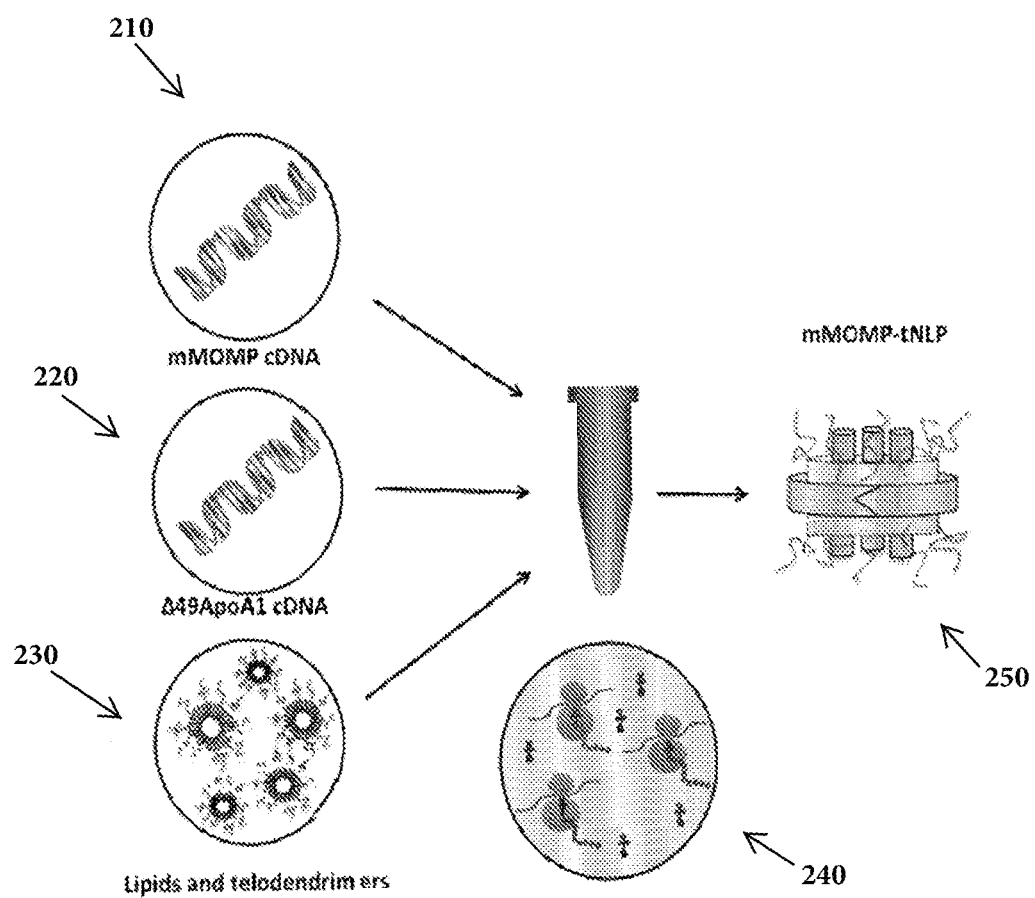
FIG. 2 shows a schematic of an exemplary method to prepare mMOMP-tNLP according to an embodiment herein described.

Codon optimization was used to alter sequences for mMOMP-tNLP expression in *E. coli* cell-free lysates (FIG. 2). Codon optimization of the Δ49ApoA1 and mMOMP sequences resulted in a ~20% change in the primary coding sequences for both proteins (FIGS. 3A-3B, 12C, 16 and 17). Co-translation reaction conditions using plasmids encoding Δ49ApoA1 and mMOMP were initially screened using a bodipy-lysine fluorescent amino acid to simplify visualization of protein expression and solubility screening.

The bodipy-lysine fluorescent amino acid is randomly inserted at lysine positions within the protein at a low insertion rate. The mMOMP protein is highly hydrophobic and is normally insoluble in the absence of a native lipid bilayer or detergents. Co-translation with both plasmids in the presence of DMPC lipid alone did not result in a soluble mMOMP expression product. Soluble mMOMP was observed only when the cell-free reactions were modified to include both DMPC lipid and telodendrimer PEG$^{5k}$-CA$_8$.

Figure 4A:
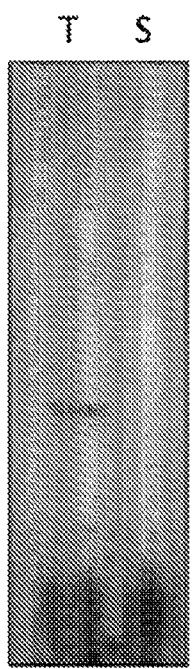
FIGS. 4A-4B shows images of SDS-PAGE gels with separated bands of bodipy (boron dipyrromethene)-labeled mMOMP visualized using a fluorescent imager. The gels show an example of soluble mMOMP production in presence of tNLPs, exemplified by bodipy-labeled mMOMP expressed in a cell-free system. Soluble protein was obtained by centrifuging at 14,100 rcf for 10 minutes and supernatant was collected. The total (T) and soluble (S) portions of the cell-free mixture were resolved by SDS-PAGE then imaged with fluorescent imager.
Figure 4B:
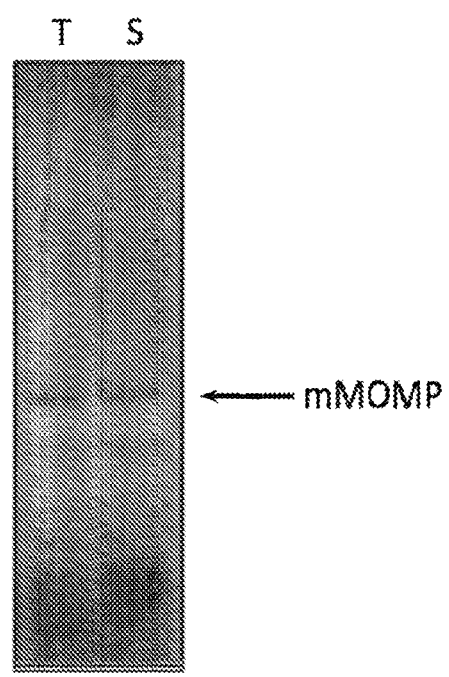

The solubility of mMOMP increased from 10% to 75% upon insertion into tNLP (FIGS. 4A-4B). The PEGylated tail of the telodendrimer may protect the mMOMP from interacting with surrounding mMOMP-tNLPs and thus increases its solubility.

After the cell-free reaction was completed, the total cell-free mixtures were centrifuged by a table centrifuge at max speed for 10 minutes. After centrifugation, the supernatant was collected. MOMP solubility is defined by the ratio of the amount MOMP protein in supernatant to the amount of MOMP protein in the total mixture.

In order to produce soluble mMOMP 0.1 to 0.5 mg/mL of telodendrimer were provided in the cell-free reaction.

By adding plasmids encoding mMOMP and scaffolding protein ApoA1 at different ratio, the expressed ratios of mMOMP:ApoA1 and the number of mMOMP per tNLP were controlled. Typically, the concentration of plasmid encoding mMOMP in the cell-free mixture is 15 ug/mL. Plasmid encoding ApoA1 is added at a mMOMP plasmid to ApoA1 plasmid ratio of 1:1, 2:1, 5:1, 10:1, 15:1, 20:1, 50:1, 100:1, or 200:1. The expressed ratios of mMOMP:ApoA1 is assessed by SDS-PAGE. The optimal expressed ratios of mMOMP:ApoA1 is expected to be from 1:1 to 3:1. The optimal expressed ratios of mMOMP:ApoA1 is achieved by using mMOMP plasmid to ApoA1 plasmid ratio from 10:1 to 25:1. At the optimal ration, the number of mMOMP per tNLP is expected to be from 1 to 3 mMOMP per tNLP.

Reactions were scaled up to 1 mL to produce sufficient quantities of mMOMP for subsequent nickel purification utilizing the HIS tag on the apolipoprotein scaffold component of the tNLP.

The purification provided a complex that was >95% pure based on SDS-PAGE analysis. On average, a 1 mL reaction yielded 1.5 mg of purified mMOMP-tNLP (FIG. 5A) based on gel densitometry. Distinct bands indicated that the two proteins, apolipoprotein and mMOMP, were co-purifying as a complex.

To further characterize the mMOMP-tNLP complex, individual affinity purification elution fractions were assessed by size exclusion chromatography (SEC) (FIG. 5B). SEC analysis confirmed that each mMOMP-tNLP fraction eluted at the appropriate time (retention time ($t_r$)~7 min) without un-incorporated protein or free lipid peaks ($t_r$~15 min and 4 min, respectively), indicating that the complex was a homogenous mixture of mMOMP-tNLPs.

Dot blots of SEC fractions demonstrated that both the apolipoprotein and mMOMP were co-localized within the peak fraction (FIG. 5C).

Example 3. mMOMP-tNLPs Form Disc Shaped Nanoparticles

Figure 6A:
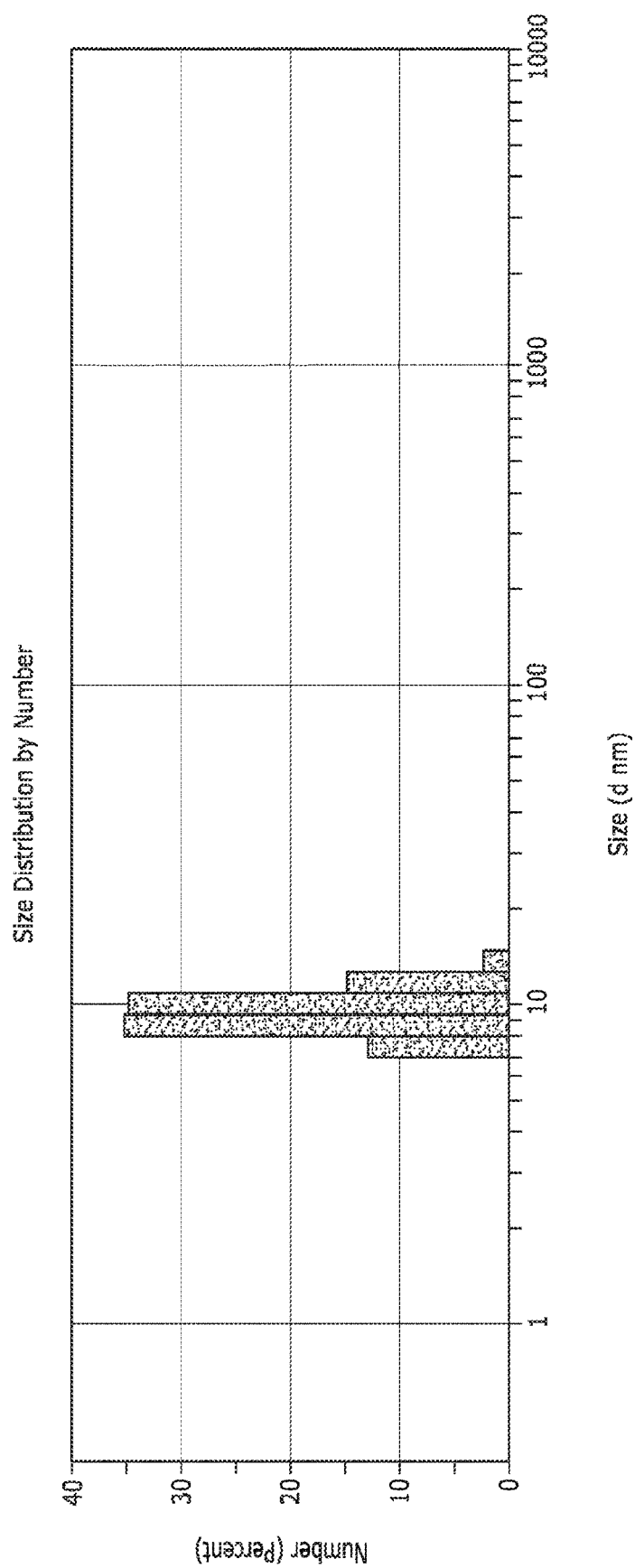
Figure 6B:
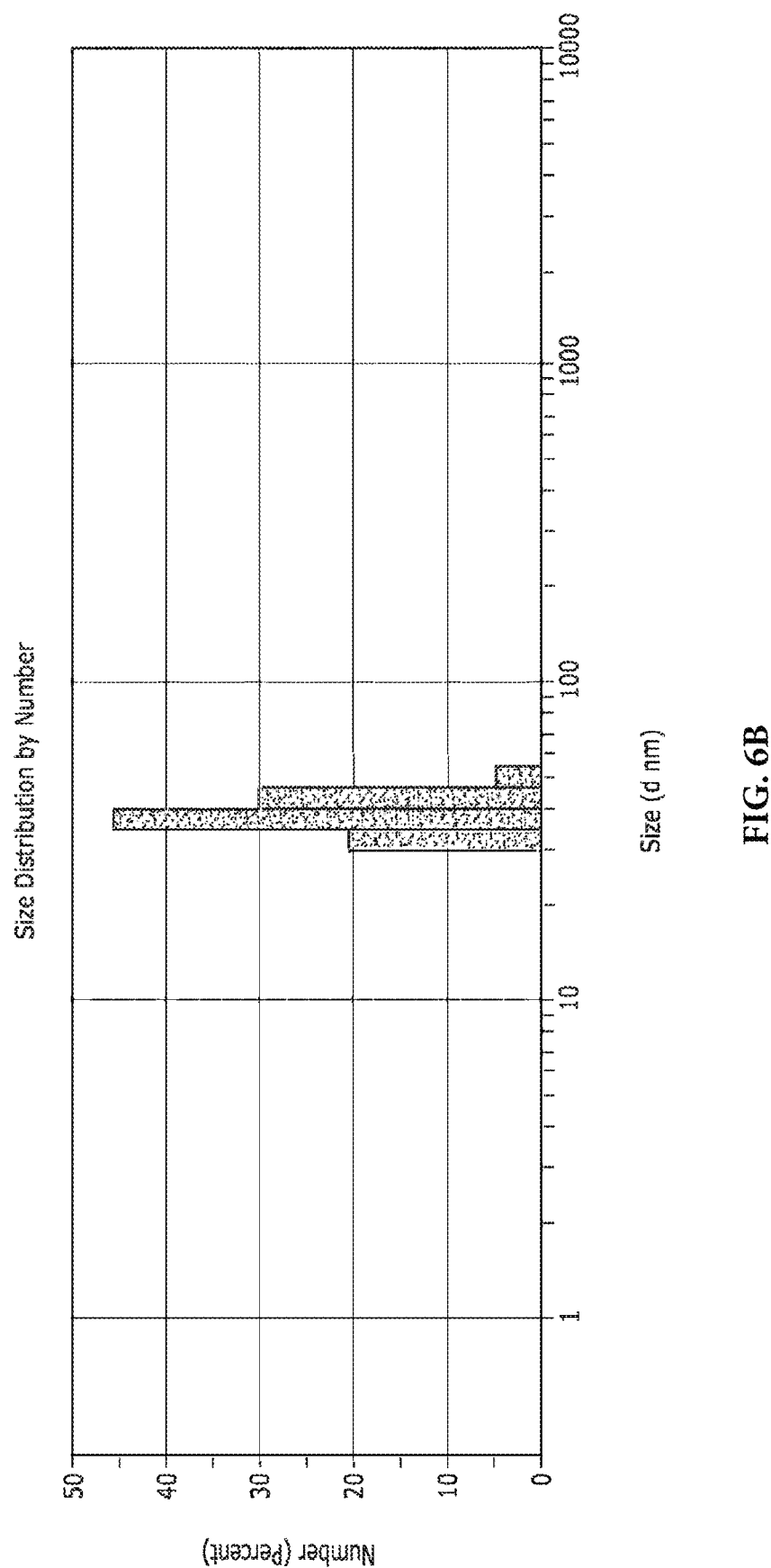
Figure 6C:
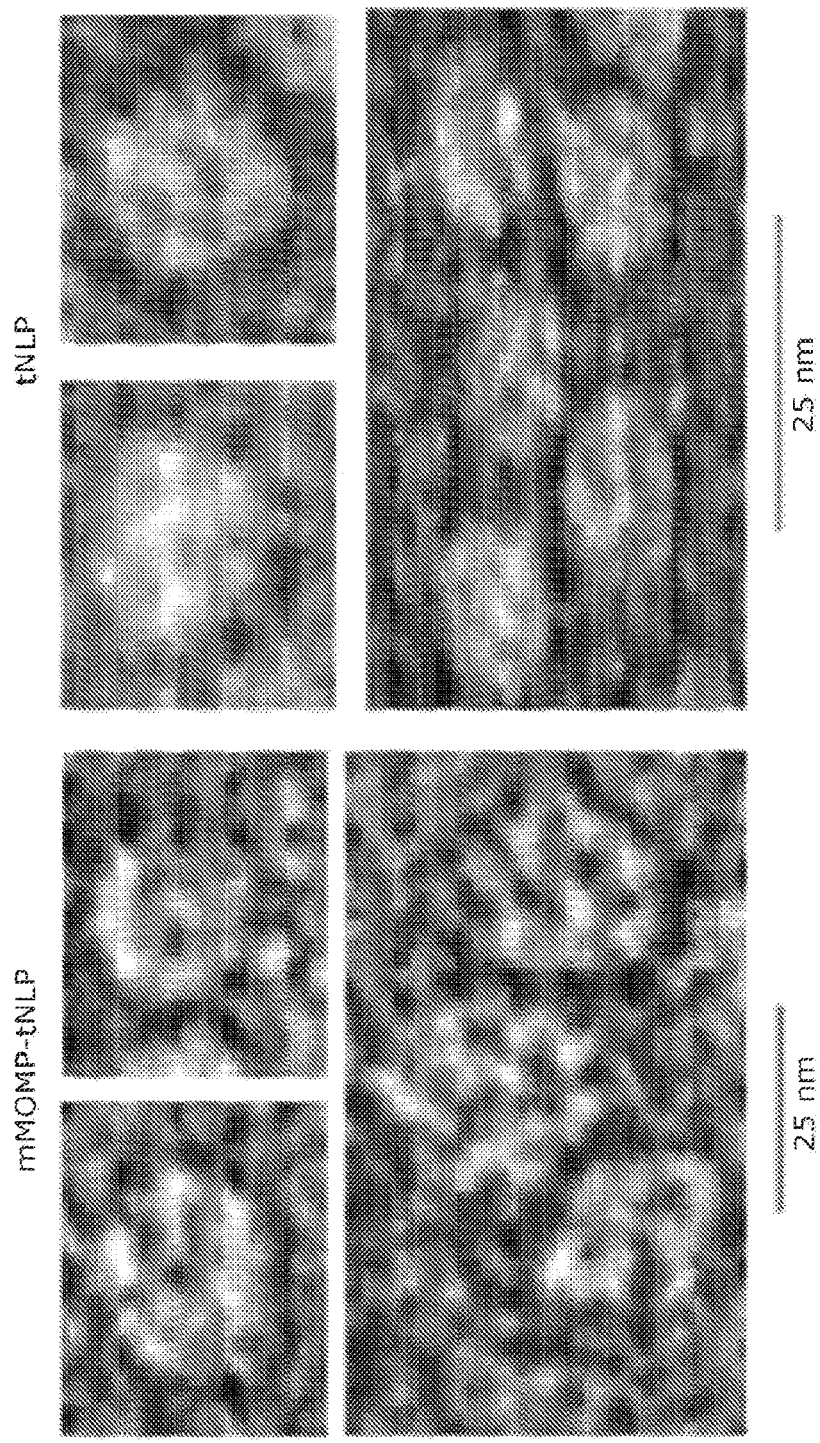

Dynamic light scattering (DLS) was used to visualize the overall size of the purified mMOMP-tNLP complex. The empty tNLPs were approximately 10 nm in diameter (FIG. 6A). The mMOMP-tNLP particle sizes showed an almost 4-fold increase in diameter to about 40 nm (FIG. 6B) wherein the term about when referred to length indicates ±0.5 the unit of length such as nm or Å. This large increase was unexpected, but plausible given that each mMOMP contains 16 transmembrane domains. In addition, image analysis using cryo-electron microscopy (cryoEM) indicated that mMOMP-tNLPs were disc-shaped (FIG. 6C).

A comparison between empty tNLPs and mMOMP-tNLPs via cryoEM also confirmed the larger particle size of mMOMP-tNLPs. The cryoEM images also revealed that mMOMP-tNLPs, not empty tNLPs, contained multiple regions of enhanced density of relatively uniform size with a diameter of about 20-30 Å. Since the samples were highly purified, these regions likely represent mMOMP proteins that form pores inside a tNLP. Interestingly, although the number of mMOMP pores per tNLP particle varied, the mMOMP-tNLP particles had an average of 3 mMOMP proteins inserted.

Example 4. mMOMP Associated with tNLPs Form Higher Order Structures

Figure 7B:
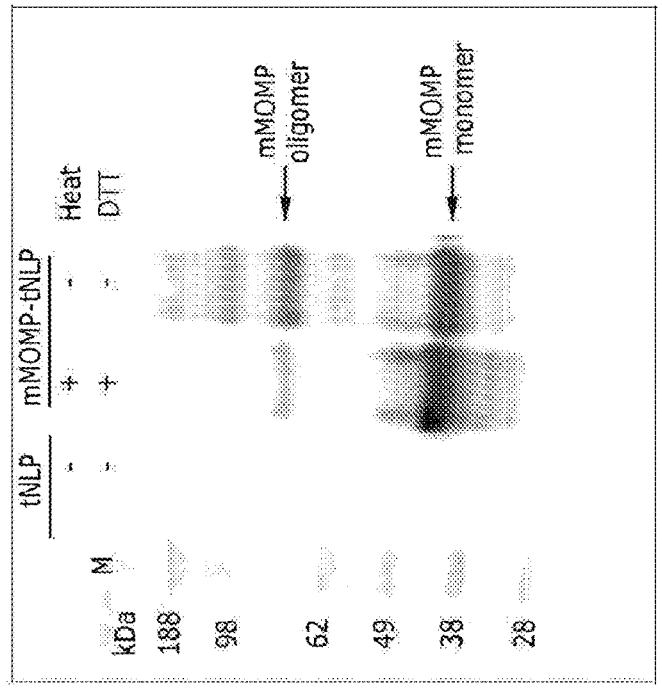
Figure 7A:
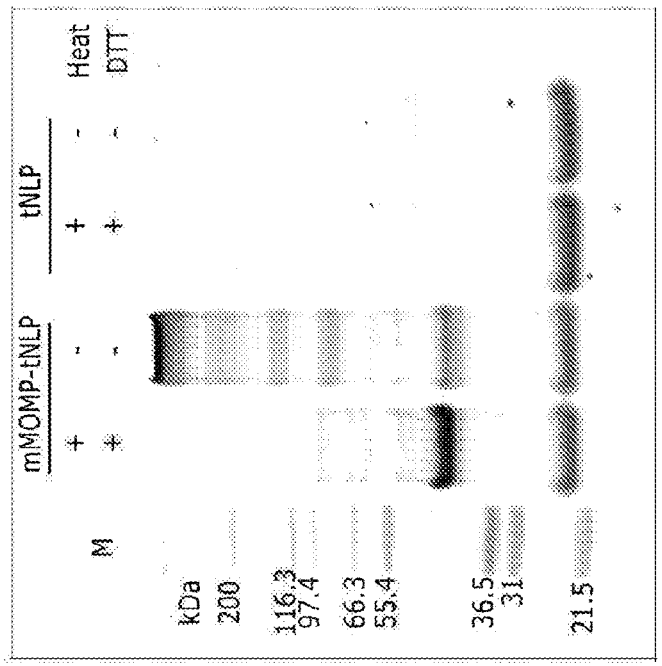

Membrane-bound porins are known to be resistant to denaturant, providing a means to probing the formation of oligomer species using SDS-polyacrylamide gels [25, 28]. By analyzing mMOMP-tNLP in the presence and absence of both heat and reducing agent, higher-order oligomers of mMOMP were identified. SDS-PAGE of heated samples in the presence of DTT showed primarily two distinct bands on the gel, corresponding to mMOMP and Δ49ApoA1 at approximately 40 kD and 22 kD, respectively. However, with heat and reducing agent (DTT) removed, distinct bands corresponding to mMOMP oligomers were observed on the gel that were absent in tNLP alone control, indicating that these oligomers are part of mMOMP and not oligomers of the apolipoprotein scaffold (FIG. 7A). These results closely resemble the gel banding pattern attributed to oligomer formation of native MOMP [28]. Western blot analysis probed with mAb40 also indicated the formation of the higher order structures of mMOMP (FIG. 7B). These multimeric structures are not evident in recombinant MOMP produced in traditional E. coli expression systems, suggesting that the confinement to the constrained lipid bilayer of the tNLP can promote native-like oligomerization [25].

Figure 8:
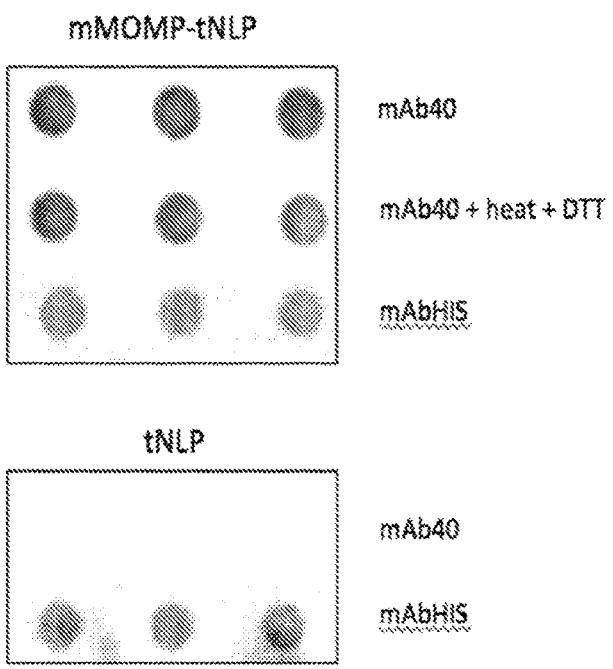

Dot blots were then tested to determine if adding both heat and reducing agent affect mMOMP antibody binding. Antibodies specific for mMOMP linear epitope detection (mAb40) with and without heat and reducing agent resulted in the same intensity of signal, indicating that the oligomers of mMOMP are broken down to monomers upon heat and DTT. Furthermore, heat and DTT do not affect the mAb40 binding to mMOMP. As a control, mAb-HIS was always able to detect the apolipoprotein supporting scaffold (FIG. 8).

Native MOMP forms dimers, trimers, and tetramers in an oxidized environment [15]. It has also been demonstrated that maintaining native MOMP structure is necessary to elicit a robust immune response [10, 19]. The results in this Example show that mMOMP supported by tNLP particles mimic native mMOMP oligomer structures. The mMOMP higher order oligomer resembles previously reported native MOMP trimers [19].

Example 5. tNLP Solubilized mMOMP Forms Functional Pores in Bilayers

Figure 9A:
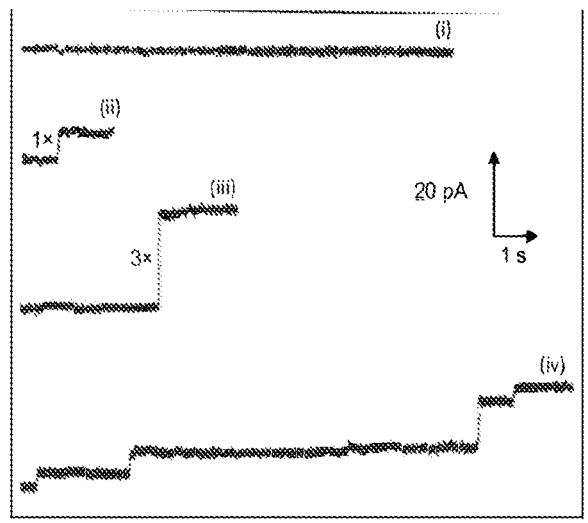
Figure 9B:
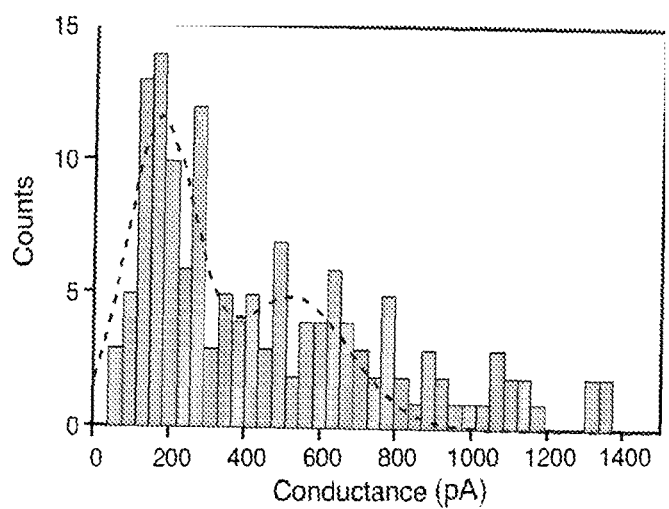

Previous studies have shown that the presence of mMOMP initiates pores in lipid bilayers [15]. Therefore, we used conductance analysis to test the function of mMOMP supported in the tNLP. The pore-forming activities of mMOMP-tNLP were tested in a typical black lipid membrane channel reconstitution experiment using the single-channel recording technique [29]. Control experiments with tNLP alone did not produce channel activity under a series of applied transmembrane voltages ranging from −100 to +100 mV (FIG. 9A, trace i). However, discrete increases in current were observed 3-5 seconds after the addition of 1-2 μL of mMOMP-tNLP solution to the cis-chamber. This current increase corresponded to the bilayer pore formation by the mMOMP proteins, indicating functional mMOMP insertion (FIG. 9B, traces ii-iv). All mMOMP channel incorporation events were permanent and did not show any gating or transient blockade patterns under the conditions studied. The mMOMP-tNLP conductance was predominantly ~172 pA at physiological condition.

The conductance change of a large number of incorporation events was plotted on a histogram (n=184, FIG. 9B) and is consistent with the presence of two gaussian peaks at 1× and 3× multiples of a single conductance value. Interestingly, attempts to fit the histogram to a sum of three peaks at 1×, 2×, and 3× did not produce a better fit, indicating that mMOMP channel may have a tendency to oligomerize within the membrane and form trimers (corresponding to three pores).

Thus, the results of the conductance assays suggest that a population of mMOMP in the mMOMP-tNLP sample is likely to be in a functional oligomeric state in the bilayer. Accordingly, cell-free produced mMOMP appears to adopt a functional conformation, which has never been previously reported for any recombinant MOMP. Importantly, cross-linking of the recombinant protein was not required to observe oligomerization. Cell-free expression followed by direct insertion into the tNLP appears to help maintain the functional conformation of membrane bound proteins [30, 31].

Example 6. The mMOMP-tNLP Complex Elicits an IgG Response in Mice

Figure 10A:
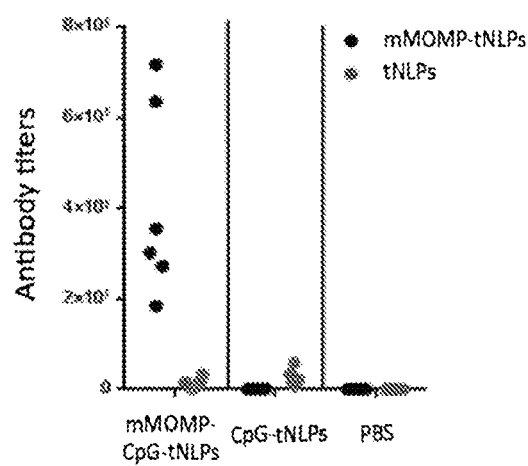
FIG. 10A shows results of ELISA analysis, revealing that mice administered with mMOMP-CpG-tNLPs displayed strong antibody titers compared to mice administered with tNLPs, CpG-tNLPs, or PBS. Sera from mice administered with mMOMP-CpG-tNLPs, CpG-tNLPs, or PBS were loaded on an ELISA plate pre-coated with mMOMP-tNLPs (black dots) or empty tNLPs (grey dots) and antibody titers were measured.

The tNLPs (negative control) or mMOMP-tNLPs were adjuvanted with CpG and injected intramuscularly (i.m.) into mice. Additional groups of mice were injected i.m. with PBS (negative control) or *Chlamydia* EB (positive control). It was found that mMOMP-tNLP supports the addition of CpG adjuvant and elicits significant levels of antigen-specific antibody titers compared to CpG:tNLP (no antigen) and PBS controls (FIG. 10A).

The formulation of mMOMP-tNLP plus CpG adjuvant results in the incorporation of the CpG adjuvant into the mMOMP-tNLP particle.

Pooled mouse sera from injected mice were then probed on a western blot to detect for specific mMOMP binding (FIG. 10B). The sera from mice injected with mMOMP-CpG-tNLP showed strong mMOMP binding. The lane from sera immunized with *Chlamydia* EB also detected some mMOMP binding. It is not surprising that EB sera showed less binding than mMOMP-CpG-tNLP sera because EB contains many other proteins other than mMOMP. Therefore, there were many antibodies generated against EB and only a portion of these antibodies was mMOMP-specific. Sera from PBS and CpG:tNLP control groups showed no mMOMP binding. This Example shows that immunogenic adjuvants such as CpG can be incorporated into mMOMP-tNLP formulation.

Example 7: MOMP-NLP Complexes are Immunogenic and Protective

The protective response of MOMP-NLPs formulated with CpG, a TLR-9 agonist that elicits Th1 responses, or CpG and $FSL_1$ was evaluated in a mouse intranasal challenge study. (FIGS. 18A-18C).

$FSL_1$ is a TLR-2/6 agonist that induces Th2 response. It is expected that when delivered together with antigens in the same NLP, the CpG and $FSL_1$ will elicit more robust protective responses than if antigens and adjuvants were simply injected simultaneously. CpG and $FSL_1$ can be administered to the mouse using systemic and/or mucosal routes for immunization.

Mice were inoculated intranasally with formulated controls or different formulations of MOMP-NLPs with CpG or CpG and $FSL_1$ adjuvants. With chlamydial challenges, the mice undergo weight loss and recovery. The recovery is an indication of protection for any formulation.

Figure 18A:
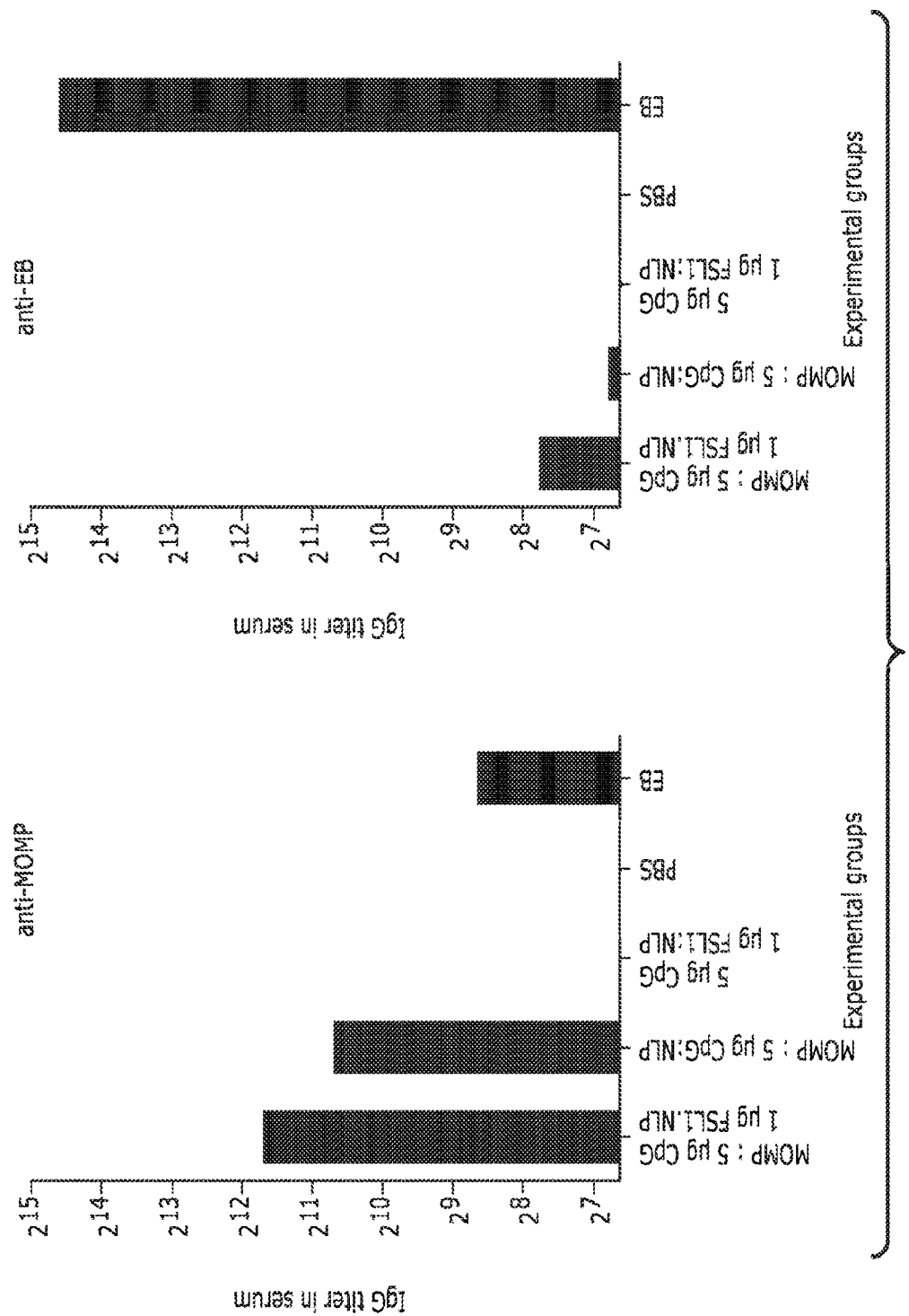
Figure 18B:
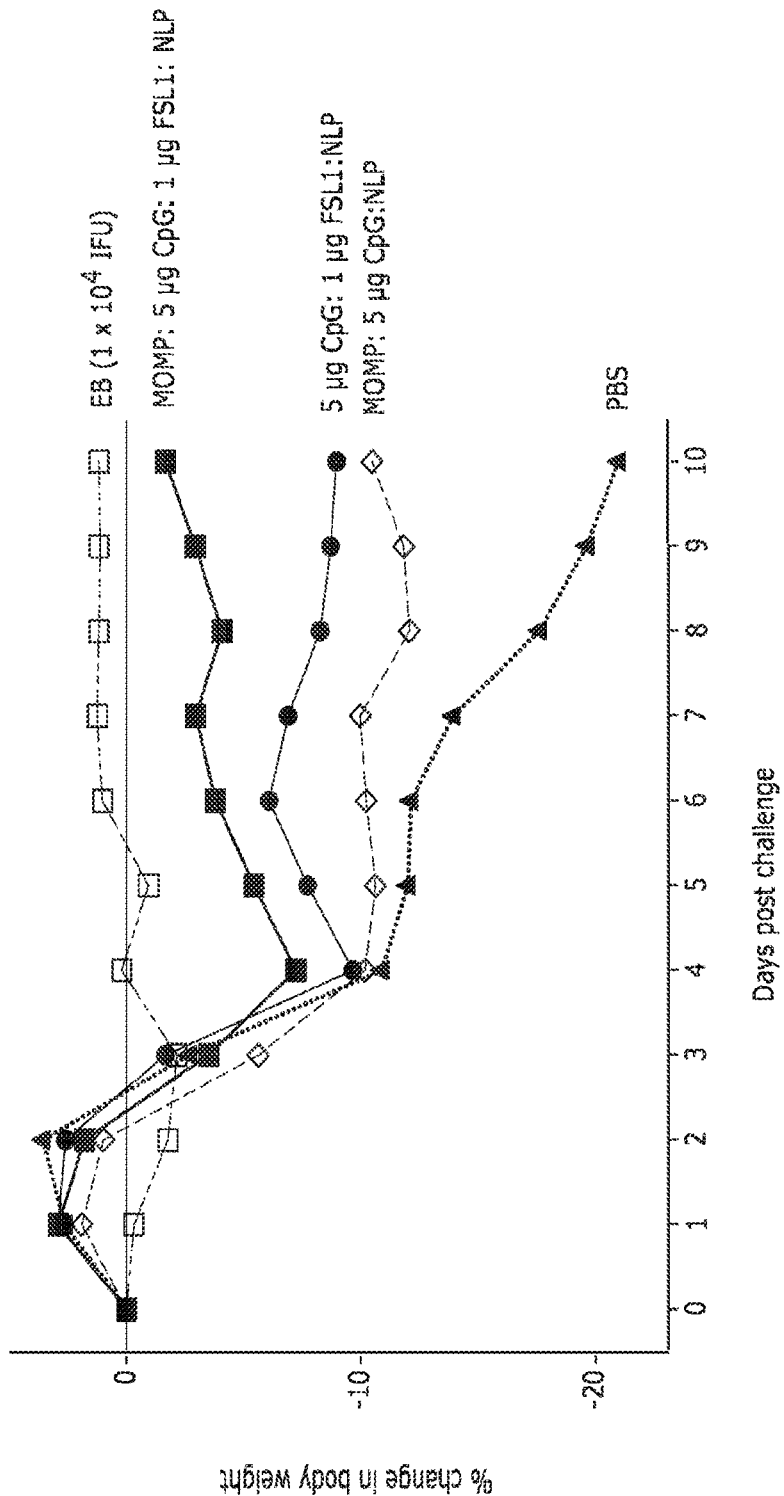
Figure 18C:
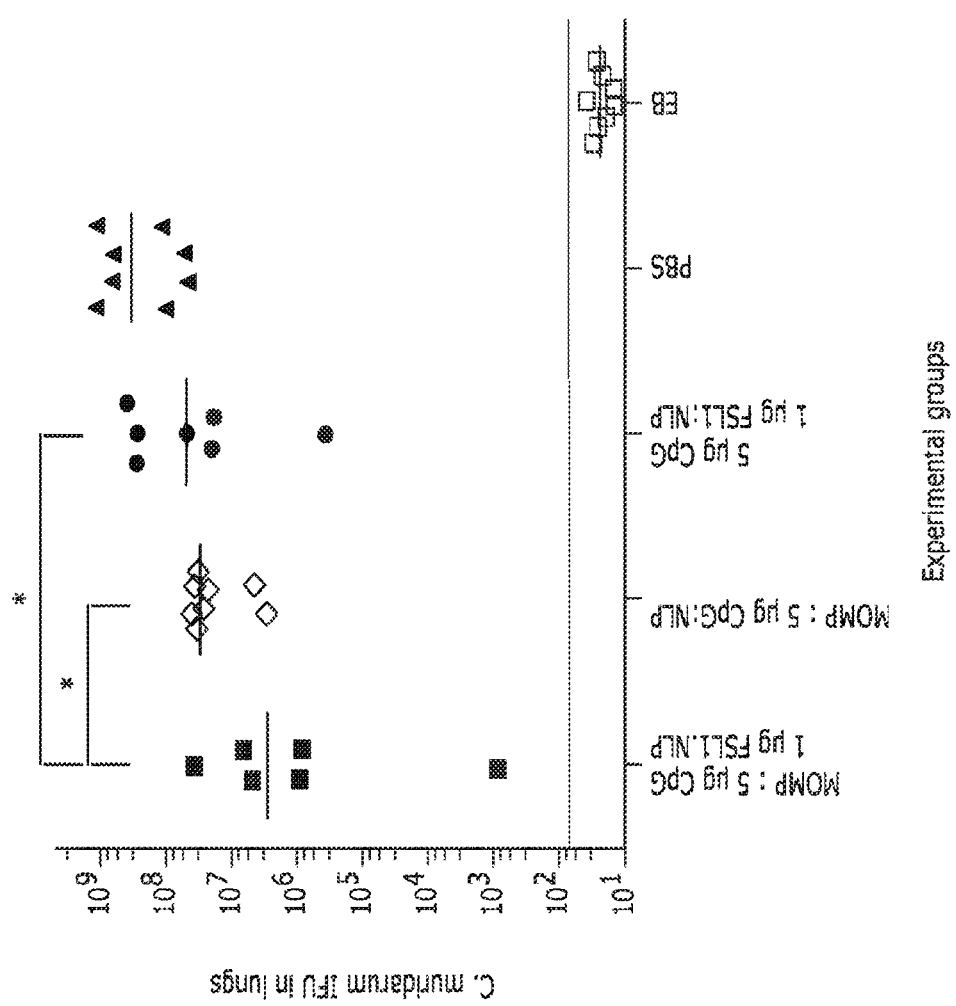

In FIG. 18A, the antibody tiers from immunized mice show antibody cross reactivity with *C. muridarum* MOMP (anti-MOMP) or EB (anti-EB). In FIG. 18B, weight loss over time following intranasal (i.n) challenge with *C. muridarum* was used as a measure of protection. Data was analyzed using RM two-way ANOVA with Sidak's multiple comparison analysis.

Mice immunized with MOMP:CpG:NLPs or MOMP:CpG:FSL1:NLPs generated antibodies that recognized both MOMP and EB (FIG. 18A). The MOMP:CpG:FSL1:NLP formulation with two adjuvants showed a substantial protective response in the intranasal model as compared to the other formulations (FIG. 18B). Lower MOMP-specific IgG titers in the EB sample is expected because there are other antigens, such as Pmps, presented on EB than just the MOMP protein. Additionally, mice immunized with MOMP:NLP lost significant body weight by 4 days post challenge (d.p.c.) but by 10 d.p.c. have recovered most of their weight (FIG. 18B).

FIG. 18C plots the number of Cm IFU recovered from mice vaccinated with different MOMP:NLPs formulations. Each dot represents a mouse. The horizontal line corresponds to the median. The number of Cm IFU recovered from mice vaccinated with MOMP:NLP was significantly less than from sham-vaccinated groups (p<0.05).

These combined preliminary results demonstrate the feasibility of extending NLP approach to the genital model for further vaccine development.

Additionally, since using systemic and/or mucosal routes for immunization, a better protection has been observed when using both routes[32, 33]. It is therefore expected that delivery of CpG-1826 and FSL-1 by both routes will result in enhancing systemic and mucosal humoral and cellular memory immune responses.

Example 8: Exemplary *Chlamydia* Vaccine Pipeline

NLPs provide a versatile platform for vaccine development. By combining the rapid production of functional membrane proteins with adjuvant addition and structural screening, a pipeline for vaccine generation is developed.

Figure 19:
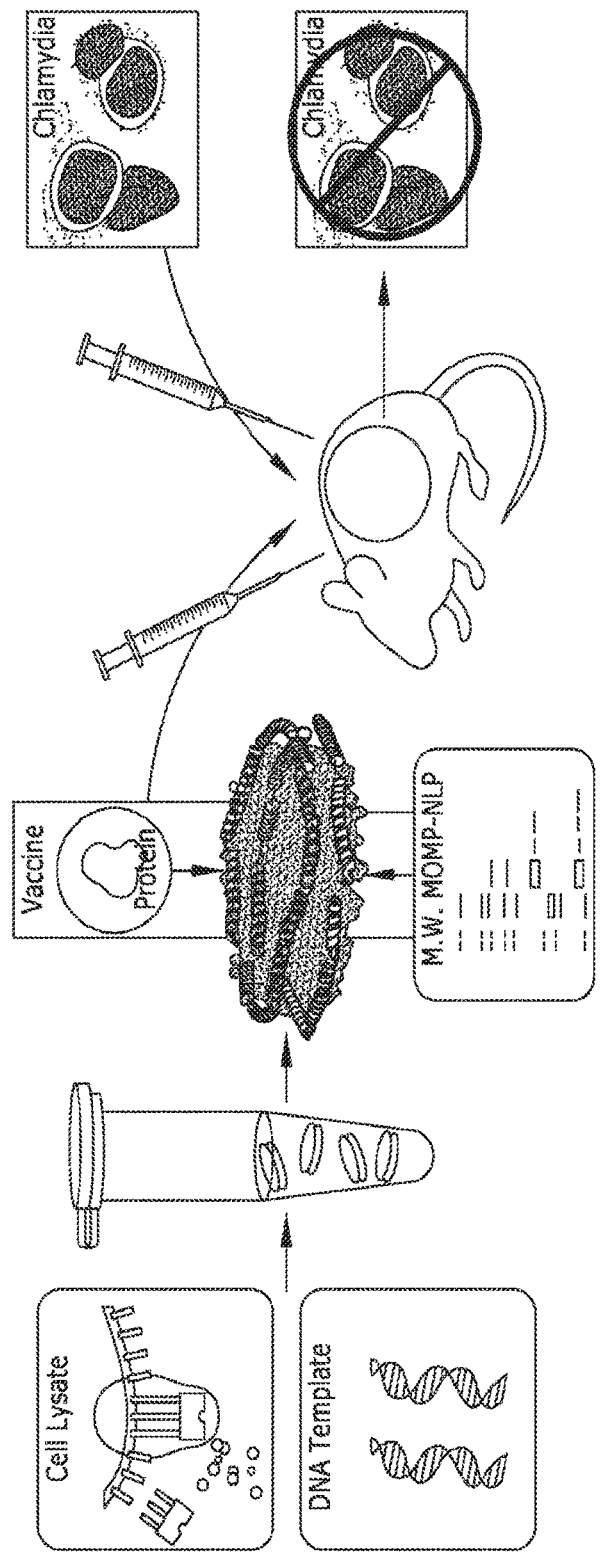

FIG. 19 illustrates a schematic of an exemplary *Chlamydia* vaccine pipeline. In particular, constituents such as DNA, lipids, cofactors and cell-free extracts are combined in a single reaction vial. The cell-free lysates utilize T7-coupled transcription and translation to produce nanoparticles complexed with the antigens and adjuvants of interest. The nanoparticles then can be characterized and administered to mice to protect them from a chlamydial infection.

Example 9: Generation of Optimal Vaccine Formulations

In this example, experiments were carrier out to optimize the ratio of MOMP to Apolipoprotein for high-level cell-free expression, purification, and formulation of functional complexes in NLPs.

Cell-free expression technologies have demonstrated to overcome bottlenecks associated with membrane protein expression. In this example, cell-free *C. muridarum* MOMP have been generated in which the plasmid ratio of pApo to pMOMP was provided at 1:1, 1:5, 1:10, 1:25, 1:50, and 1:100 as shown in FIG. 20A.

FIG. 20A shows results from the SDS-PAGE analysis following cell free synthesis of MOMP-NLPs using varying amounts of fluorescent labeled Apo and MOMP proteins. The plasmid ratio expression screening displays different levels of inserted MOMP embedded in the NLPS complex. The SDS-PAGE analysis results show that a higher ratio of MOMP to Apo leads to a higher amount of MOMP proteins incorporated in the NLPs.

Scanning electron microscopy was also used to determine average particle size of the MOMP-NLPs. FIG. 20B shows scanning electron microscopic images (SEM) of (A) empty NLP disc, (B) MOMP-NLP disc with 1-2 monomers of MOMP inserted, (C) MOMP-NLP disc with 1-2 trimers of MOMP inserted, and (D) MOMP-NLP disc with >3 trimers of MOMP inserted.

The images of FIG. 20B demonstrate that the MOMP-NLP particles are disc like in shape and there are size differences among MOMP-NLP particles with varying ratios of MOMP to Apo. The higher ratios of MOMP protein inserted in the disc correlate to particles with larger disc size.

Example 10: Cell-Free Production of Polymorphic Membrane Proteins Associated with MOMP Polymorphic membrane proteins (Pmps) are another group of surface exposed candidate antigens. C. trachomatis and C. muridarum have nine Pmp genes. Pmps are well conserved among all C. trachomatis serovars, as well as C. muridarum. Therefore, Pmps may help broaden the protective immune responses elicited by MOMP. This family of proteins is surface exposed and mediates the adhesion of Chlamydia EB to the eukaryotic host cells. The Pmp proteins are also immunogenic in humans and mice. Vaccination of mice with fragments derived from different Pmps elicits protection against both genital and respiratory challenges with C. muridarum. Based on these studies, PmpC, PmpE, PmpF, PmpG and PmpH were identified as potential protective antigens [34-38]. However, production of full-length recombinant Pmps has yet to be achieved.

In this example, experiments were carried out to engineer the expression plasmids and produce water soluble full-length and truncated C. muridarum Pmp C, E, F, G, and H using cell-free approaches described herein.

Exemplary PMP gene and protein sequences used in this study are listed in Table 3. The original sequences are retrieved from public databases such as Uniprot/SWISS-PROT or NCBI gene database as will be understood by a person of ordinary skill in the art

TABLE 3

Exemplary full-length and truncated PMP C, E, F, G, and H gene and protein sequences from C. muridarum

| Annotation | Sequences | SEQ ID NO |
|---|---|---|
| PmpC TC_RS03520-1246056 Original database sequence | ATGAAGTTTTTATCAGCTACCGCTGTATTTGCTGCAGCTCTTCCCTCTATCACAAGTGCTAGCTCCGTTGA ATCCCAAATAGAAACAAAAGATCTAAACTCTAGTAGAACAGGATCCTCATCATCGCAATCCTTCACTGAAA TAATTCCAGAAAATGGCGCAGAATATAGGGTATCTGGAGATGTTTCATTTTCTGATTTTTCAAATATACCA GAAGAAGCAGAGACTCTTGCTATATCGCACAAAGAACAGCCTAATAACGAAGTAGTACTCTCCGAAGAAAA CCACCAAGCATCCTTTCAAGATTCTGCACAAAACCAAACTGAAAATGCCTCTGAAGGAAACTCTCCTAATA GCGAGAATACTAACCAGTCATCTACCACAGAAACCGAGTCTATAACTACTGATGAACAAGTGCAGAATGAT AATGAATCTGCAGCTTCTGTACCTACTACTGTAGAAACAGCAACAGCTATGCGCCTCCCCTCTTACCATCT ACAAACAGAATCATTAGTAGAAGGGGCTACAGAAGAAGATCAAAATCAACCGAACTCTCAAAATACATCTA GTGGCGGCGGAGCATTTTATAACTCTCAACAAGGACCTTTATCCTTTATCAATGATCCCGATAAAGACAGT TCTCTCACCTTATCAAAAATTCGAGTAATAGGAGAGGGTGGTGCCATTTACTCGAAAGGACCATTAAGCAT AACAGGTCTTAAAAAATTAGCTTTAAAAGAAAACTTATCCCAAAAGGCTGGAGGAGCTATTTGTGCAGAAT CCACTATTTCAATAAGTAGTGTAGATTCTATCATTTTTTCTAAGAATACAGTCACTCCTCCAGCTGCCAAT AAACCTGAACTCCCTAACGATCCCTCTGGGAGTAATGGTAATGATGGTTCTGATGACAGTAACTCCTCAGG TAATACTGACTCAAATGAAAGCAACCCTAACAACAGCGCTTCTAATAACACTGGCTCTGAAAATGAGCTTT CTTCCAGTACCCCATCCGCACAACTTCCCAATCCCGCAACACCATTTTTATCATCTGTTTCTACAAACTCT CAACCTATAGACACAGAACCAGAAAATGCATGGCATGCTGAACTCAGGGTCTGGAGGAGCTATCTATTCTAA AGGCAAGCTTTCTATCGCAAGCTCTAAAGAAGTAGTCTTCGATCACAACTCGGCCACCAAAAATGGAGGAG CTATCTTCGGAGAGGAAGAAATTGCTCTCGAAAAAATAGCGTCTCTGAAATTCGATTCCAACACTACCGGT GAAAAAGGTGGGGCTATTCATGCGAAAACAGTTACACTATCTGATATCAAAAACACTTTGATTTTCGTTAA TAATACGGCTAAAACACCGGAAGAAAACTCTCTAAAATCTTCTCAACTAAACAACCAAAATCCTTCCGAAG AAGAGCACCAAGATACTAGTGAGGGTGAAGAAAGCCAGTCTCTTGAAACGTCACCTATAACTAATCAAGAC TCTGCATCCTCTCATGTAGCCATTTTCCGTTCTATAGCAGCATCCTCCTCTCAATCTAATAGCGAAAATAT CCCTAATGCAGATGGGTCTACATCTGCTGGGGGAGACGCAGGAAGCTCTTCACAACCATCGACACCAGGAT CCGATTCTTCGATAAATCATGTGATTGGAGGAGGAGCTATCTATGGAGAGGCAGTCAAAATCGAGAACCTC TCTGGATATGGAACATTCTCCAACAATAACGCTGTTGATCATCAAATTTCTGGATCTACATCCGATGTTTT AGGAGGAGCTATCTATGCTAAAACATCACTAACTATCGATAGCGGGAACTCTAGTGGAACCATTACATTCT CTGAAAATACCACTTCTTCCAAATCTACAACAGGACAGGTTGCTGGAGGAGCCATCTTCTCCCCTAGTGTA ACCATCACCACACCAGTGACCTTTTCTAAAAACTCTGCGATAAATGCCACAACCAGTTCTAAAAAGGATAC CTTTGGGGGAGCTATCGGTGCAATCTCTACAGTTTCTCTATCCAAAGGAGCTCGATTCTCAGAAAATATTG CCGATCTTGGATCTGCTATTGGATTAGTACCTACTACACAAGATGCAGAAACTGTTCAGCTAACAACAGGT TCTTACTATTTTGAAAAGAATAAAGCACTAAAACGAGCAACTGTTTACGCTCCTATCGTATCTATCAAAGC TCATACCGCAACATTCGATCAAAATATCTCTGCAGAAGAAGGAAGCGCGATTTATTTCACTAAAGAAGCCA CCATTGAGTCTTTGGGATCCGTTCTTTTTACAGGGAACTTGGTAACCCCAATACAAAGCACAACAGTGTTA ACTTCTGGAAACACCTCAAAATACGGGGCTGCTATTTTTGGACAAATAGCGAATGCAAGCGGATCTCAAAC TGATAACCTCCCCCTCAAACTGATCGCTTCTGGAGGGAATATCAGCTTCCGAAATAACGAATACCGTCCAG ATGCCACTAATACTGGACAATCTACTTTCTGTAGTATCGCTGGAGATATTAAATTAACCATGCAGGCTGCA GAAGGCAAAGTAATCAGTTTCTTTGATGCTATACGAACTTCCACTAAGAAAACAGGAACTCTGGCCTCTGC TTATGACACACTAGATATCAATAAATCGAATGATTCAGGGTCCATAAATTCAGCCTTTACAGGGACCATTA TGTTCTCCTCTGAATTACATGAGAACAAATCCTATATTCCACAAAACGTAGTCTTACACAGTGGCTCTCTC ATATTGAAAGCAAATACGGAACTTCATGTGCTTTCGTTTGATCAGAAAGAAGGCTCTTCTCTTATTATGGA ACCTGGATCTGTTCTTTCAAATCAAGATATTGCTGATGGTTCTTTAGTAGTAAATAGTCTTACCATTGATT TATCGAGTGTTGGAAGAAACAGTGCCTCTGGAGACAATATCTTCATGCCTCCAGAATTAAGAATCGTAGAT | 20 |

TABLE 3-continued

Exemplary full-length and truncated PMP C, E, F, G, and H gene and protein sequences from *C. muridarum*

| Annotation | Sequences | SEQ ID NO |
|---|---|---|
| | ACCTCTACAAATTCTGGAAACAGCTCTTCTACCCCGCCCTCATCGAATACACCACCAAACTCAACTCCGAC<br>AGCACAAGCTCCTATTTCCAAAAATTTTGCTGCCACAACCACGACACCAACAACACCTCCGACAACAGGGA<br>ACATCGTTTTCCTTAACGGAGTTATTAAACTGATTGATCCGAATGGGACATTTTTCCAAAACCCTGCATTA<br>GGATCTGACCAAAAAATCTCTCTACTAGTACTCCCTTCAGATCAAACAAAACTCCAAGCTCAGAAAGTTGT<br>GCTAACAGGAGACATCTCTCCTAAGAAAGGATACACAGGAACATTAACTCTTGATCCTCAACAATTACAAA<br>ATGGAGTAATCCAAGCTTTATGGACATTCAAATCCTACAGACAGTGGGCCTATATTCCTAGGGATAATCAC<br>TTTTATGCCAACTCGATTCTGGGATCCCAAATGTCTATGGCTACTGTCAAACAAGGATTAATCAATGATAA<br>ATTGAATCTTGCTCGCTTTGATGAGGTTGCTTACAATAATTTGTGGATATCAGGACTAGGAACCATGCTCT<br>CTCAAAGAGGAGGCCAGCGATCAGAGGAAATGACTTATTACAGTAGAGGAGCTTCTGTTGCTTTAGATGCG<br>AAACCTACCCAAGATTTGATCATTGGAGCAGCATTTAGTAAAATGATCGGAAGAAGCAAATCTTTGAAACT<br>AGAGCGTAACTACACCCACAAGGGATCGGAATATTCCTACCAAGCATCGGTTTATGGAGGTAGTCCTTTCT<br>ATCTTACAATTAACAAAGAAGCAGGCCGATCCCTCCCTCTCTTATTACAAGGGGTTATCTCCTACGGATAC<br>ATCAAACACGATACAGTTACCCACTATCCTACAATTCGTGAATTAAACAAAGGAGAGTGGGAAGACTTAGG<br>ATGGTTGACCGCTCTTCGAGTCTCTTCCATCTTAAAAACACCTAAACAAGGAGACTCCAAACGCATTACTG<br>TTTACGGAGAAGTTGAATATTCTAGCATCCGTCAAAAACAATTTACGGAAACGGAATATGATCCTCGTTAC<br>TTCAGTAACTGCACCTATAGAAACTTAGCAGTTCCTGTAGGATTAGCCTTAGAGGGAGAATTCAAAGGTAA<br>CGATATTTTGATGTACAACAGATTCTCTGTAGCTTACATGCCATCCATCTATCGAAACTCTCCAGTATGCA<br>AGTACCAAGTACTCTCATCTGGAGAAGGTGGAGAAATCGTCTGTGGTGTTCCCACCAGAAACTCCTCTCGA<br>GCAGAATATAGTACGCAGTTATACCTTGGTCCTCTATGGACTTTATATGGATCCTACACATTAGAAGCGGA<br>CGCTCACACGTTAGCCAATATGATTAACTGTGGGGCTCGCATGACATTCTAA | |
| PmpC<br>PMPC_CHLMU | *MKFLSATAVFAAALPSITSA*SSVESQIETKDLNSSRTGSSSSQSFTEIIPENGAEYRVSGDVSFSDFSNIP<br>EEAETLAISHKEQPNNEVVLSEENHQASFQDSAQNQTENASEGNSPNSENTNQSSTTETESITTDEQVQND<br>NESAASVPTTVETATAMRLPSYHLQTESLVEGATEEDQNQPNSQNTSSGGGAFYNSQQGPLSFINDPDKDS<br>SLTLSKIRVIGEGGAIYSKGPLSITGLKKLALKENLSQKAGGAICAESTISISSVDSIIFSKNTVTPPAAN<br>KPELPNDPSGSNGNDGSDDSNSSGNTDSNESNPNNSASNNTGSENELSSSTPSAQLPNPATPFLSSVSTNS<br>QPIDTEPENAWHAESGSGGAIYSKGKLSIASSKEVVFDHNSATKNGGAIFGEEEIALEKIASLKFDSNTTG<br>EKGGAIHAKTVTLSDIKNTLIFVNNTAKTPEENSLKSSQLNNQNPSEEEHQDTSEGEESQSLETSPITNQD<br>SASSHVAIFRSIAASSSQSNSENIPNADGSTSAGGDAGSSSQPSTPGSDSSINHVIGGGAIYGEAVKIENL<br>SGYGTFSNNNAVDHQISGSTSDVLGGAIYAKTSLTIDSGNSSGTITFSENTTSSKSTTGQVAGGAIFSPSV<br>TITTPVTFSKNSAINATTSSKKDTFGGAIGAISTVSLSKGARFSENIADLGSAIGLVPTTQDAETVQLTTG<br>SYYFEKNKALKRATVYAPIVSIKAHTATFDQNISAEEGSAIYFTKEATIESLGSVLFTGNLVTPIQSTTVL<br>TSGNTSKYGAAIFGQIANASGSQTDNLPLKLIASGGNISFRNNEYRPDATNTGQSTFCSIAGDIKLTMQAA<br>EGKVISFFDAIRTSTKKTGTLASAYDTLDINKSNDSGSINSAFTGTIMESSELHENKSYIPQNVVLHSGSL<br>ILKANTELHVLSFDQKEGSSLIMEPGSVLSNQDIADGSLVVNSLTIDLSSVGRNSASGDNIFMPPELRIVD<br>TSTNSGNSSSTPPSSNTPPNSTPTAQAPISKNFAATTTTPTTPPTTGNIVFLNGVIKLIDPNGTFFQNPAL<br>GSDQKISLLVLPSDQTKLQAQKVVLTGDISPKKGYTGTLTLDPQQLQNGVIQALWTFKSYRQWAYIPRDNH<br>FYANSILGSQMSMATVKQGLINDKLNLARFDEVAYNNLWISGLGTMLSQRGGQRSEEMTYYSRGASVALDA<br>KPTQDLIIGAAFSKMIGRSKSLKLERNYTHKGSEYSYQASVYGGSPFYLTINKEAGRSLPLLLQGVISYGY<br>IKHDTVTHYPTIRELNKGEWEDLGWLTALRVSSILKTPKQGDSKRITVYGEVEYSSIRQKQFTETEYDPRY<br>FSNCTYRNLAVPVGLALEGEFKGNDILMYNRFSVAYMPSIYRNSPVCKYQVLSSGEGGEIVCGVPTRNSSR<br>AEYSTQLYLGPLWTLYGSYTLEADAHTLANMINCGARMTF | 21 |
| PmpC<br>PmpC_EcOpt_dSig:<br>*E. coli* codon<br>optimized,<br>N-terminal<br>nuclear<br>localization<br>signal removed | CATATGAGCAGCGTTGAATCCCAAATAGAAACAAAAGATCTGAACTCTAGTCGCACAGGCTCCTCATCATC<br>GCAATCCTTCACTGAAATAATTCCAGAAAATGGCGCAGAATATCGCGTATCTGGAGATGTTTCATTTTCTG<br>ATTTTTCAAATATACCAGAAGAAGCAGAGACTCTTGCTATATCGCACAAAGAACAGCCTAATAACGAAGTA<br>GTACTCTCCGAAGAAAACCACCAAGCATCCTTTCAAGATTCTGCACAAAACCAAACTGAAAATGCCTCTGA<br>AGGAAACTCTCCTAATAGCGAGAATACTAACCAGTCATCTACCACAGAAACCGAGTCTATAACTACTGATG<br>AACAAGTGCAGAATGATAATGAATCTGCAGCTTCTGTACCTACTACTGTAGAAACAGCAACAGCTATGCGC<br>CTCCCCTCTTACCATCTGCAAACAGAATCATTAGTAGAAGGGGCTACAGAAGAAGATCAAAATCAACCGAA<br>CTCTCAAAATACATCTAGTGGCGGCGGAGCATTTTATAACTCTCAACAAGGACCTTTATCCTTTATCAATG<br>ATCCCGATAAAGACAGTTCTCTCACCTTATCAAAAATTCGAGTAATAGGAGAGGGTGGTGCCATTTACTCG<br>AAAGGACCATTAAGCATAACAGGTCTTAAAAAATTAGCTTTAAAAGAAAACTTATCCCAAAAGGCTGGAGG<br>AGCTATTTGTGCAGAATCCACTATTTCAATAAGTAGTGTAGATTCTATCATTTTTTCTAAGAATACAGTCA<br>CTCCTCCAGCTGCCAATAAACCTGAACTCCCTAACGATCCCTCTGGGAGTAATGGTAATGATGGTTCTGAT<br>GACAGTAACTCCTCAGGTAATACTGACTCAAATGAAAGCAACCCTAACAACAGCGCTTCTAATAACACTGG<br>CTCTGAAAATGAGCTTTCTTCCAGTACCCCATCCGCACAACTTCCCAATCCCGCAACACCATTTTTATCAT<br>CTGTTTCTACAAACTCTCAACCTATAGACACAGAACCAGAAAATGCATGGCATGCTGAATCAGGGTCTGGA<br>GGAGCTATCTATTCTAAAGGCAAACTTTCTATCGCAAGCTCTAAAGAAGTAGTCTTCGATCACAACTCGGC<br>CACCAAAAATGGAGGAGCTATCTTCGGAGAGGAAGAAATTGCTCTCGAAAAAATAGCGTCTCTGAAATTCG<br>ATTCCAACACTACCGGTGAAAAAGGTGGGGCTATTCATGCGAAAACAGTTACACTGTCTGACATCAAAAAC<br>ACTTTGATTTTCGTTAATAATACGGCTAAAACACCGGAAGAAAACTCTCTGAAATCTTCTCAACTGAACAA<br>CCAAAATCCTTCCGAAGAAGAGCACCAAGATACTAGTGAGGGTGAAGAAAGCCAGTCTCTTGAAACGTCAC<br>CTATAACTAATCAAGACTCTGCATCCTCTCATGTAGCCATTTTCCGTTCTATAGCAGCATCCTCCTCTCAA<br>TCTAATAGCGAAAATATCCCTAATGCAGATGGGTCTACATCTGCTGGGGGAGACGCAGGAAGCTCTTCACA<br>ACCATCGACACCAGGCTCCGATTCTTCGATAAATCATGTGATTGGAGGAGGAGCTATCTATGGAGAGGCAG<br>TCAAAATCGAGAACCTCTCTGGATATGGAACATTCTCCAACAATAACGCTGTTGATCATCAAATTTCTGGA<br>TCTACATCCGATGTTTTAGGAGGAGCTATCTATGCTAAAACATCACTGACTATCGATAGCGGGAACTCTAG<br>TGGAACCATTACATTCTCTGAAAATACCACTTCTTCCAAATCTACAACAGGACAGGTTGCTGGAGGAGCCA<br>TCTTCTCCCCTAGTGTAACCATCACCACACCAGTGACCTTTTCTAAAAACTCTGCGATAAATGCCACAACC<br>AGTTCTAAAAAGGATACCTTTGGGGGAGCTATCGGTGCAATCTCTACAGTTTCTCTGTCCAAAGGAGCCCG<br>ATTCTCAGAAAATATTGCCGATCTTGGATCTGCTATTGGATTAGTACCTACTACACAAGATGCAGAAACTG<br>TTCAGCTGACAACAGGTTCTTACTATTTTGAAAAGAATAAAGCACTGAAACGAGCAACTGTTTACGCTCCT<br>ATCGTATCTATCAAAGCTCATACCGCAACATTCGATCAAAATATCTCTGCAGAAGAAGGAAGCGCGATTTA | 22 |

TABLE 3-continued

Exemplary full-length and truncated PMP C, E, F, G, and H gene and protein sequences from *C. muridarum*

| Annotation | Sequences | SEQ ID NO |
|---|---|---|
| | TTTCACTAAAGAAGCCACCATTGAGTCTTTGGGTTCCGTTCTTTTTACAGGGAACTTGGTAACCCCAATAC<br>AAAGCACAACAGTGTTAACTTCTGGAAACACCTCAAAATACGGGGCTGCTATTTTTGGACAAATAGCGAAT<br>GCAAGCGGATCTCAAACTGATAACCTCCCCCTCAAACTGATCGCTTCTGGAGGGAATATCAGCTTCCGAAA<br>TAACGAATACCGTCCAGATGCCACTAATACTGGACAATCTACTTTCTGTAGTATCGCTGGAGATATTAAAT<br>TAACCATGCAGGCTGCAGAAGGCAAAGTAATCAGTTTCTTTGATGCTATACGAACTTCCACTAAGAAAACA<br>GGAACTCTGGCCTCTGCTTATGACACACTGGATATCAATAAATCGAATGATTCAGGGTCCATAAATTCAGC<br>CTTTACAGGGACCATTATGTTCTCCTCTGAGCTCCATGAGAACAAATCCTATATTCCACAAAACGTAGTCT<br>TACACAGTGGCTCTCTCATATTGAAAGCAAATACGGAACTTCATGTGCTTTCGTTTGATCAGAAAGAAGGC<br>TCTTCTCTTATTATGGAACCTGGATCTGTTCTTTCAAATCAAGATATTGCTGATGGTTCTTTAGTAGTAAA<br>TAGTCTTACCATTGATTTATCGAGTGTTGGACGCAACAGTGCCTCTGGAGACAATATCTTCATGCCTCCAG<br>AATTACGCATCGTAGATACCTCTACAAATTCTGGAAACAGCTCTTCTACCCCGCCCTCATCGAATACACCA<br>CCAAACTCAACTCCGACAGCACAAGCTCCTATTTCCAAAAATTTGCTGCCACAACCACGACACCAACAAC<br>ACCTCCGACAACAGGGAACATCGTTTTCCTTAACGGAGTTATTAAACTGATTGATCCGAATGGGACATTTT<br>TCCAAAACCCTGCATTAGGATCTGACCAAAAAATCTCTCTGCTGGTACTCCCTTCAGATCAAACAAAACTC<br>CAAGCTCAGAAAGTTGTGCTGACAGGAGACATCTCTCCTAAGAAAGGATACACAGGAACATTAACTCTTGA<br>TCCTCAACAATTACAAAATGGAGTAATCCAAGCCTTATGGACATTCAAATCCTACCGCCAGTGGGCCTATA<br>TTCCTCGCGATAATCACTTTTATGCCAACTCGATTCTGGGTTCCCAAATGTCCATGGCTACTGTCAAACAA<br>GGATTAATCAATGATAAATTGAATCTTGCTCGCTTTGATGAGGTTGCTTACAATAATTTGTGGATATCAGG<br>ACTGGGAACCATGCTCTCTCAACGCGGAGGCCAGCGATCAGAGGAAATGACTTATTACAGTCGCGGAGCTT<br>CTGTTGCTTTAGATGCGAAACCTACCCAAGATTTGATCATTGGAGCAGCATTTAGTAAAATGATCGGACGC<br>AGCAAATCTTTGAAACTGGAGCGTAACTACACCCACAAGGGATCGGAATATTCCTACCAAGCATCGGTTTA<br>TGGAGGTAGTCCTTTCTATCTTACAATTAACAAAGAAGCAGGCCGATCCCTCCCTCTCTTATTACAAGGGG<br>TTATCTCCTACGGATACATCAAACACGATACAGTTACCCACTATCCTACAATTCGTGAATTAAACAAAGGA<br>GAGTGGGAAGACTTAGGATGGTTGACCGCTCTTCGAGTCTCTTCCATCTTAAAAACACCTAAACAAGGAGA<br>CTCCAAACGCATTACTGTTTACGGAGAAGTTGAATATTCTAGCATCCGTCAAAAACAATTTACGGAAACGG<br>AATATGATCCTCGTTACTTCAGTAACTGCACCTATCGCAACTTAGCAGTTCCTGTAGGATTAGCCTTAGAG<br>GGAGAATTCAAAGGTAACGATATTTTGATGTACAACCGCTTCTCTGTAGCTTACATGCCATCCATCTATCG<br>AAACTCTCCAGTATGCAAGTACCAAGTACTCTCATCTGGAGAAGGTGGAGAAATCGTCTGTGGTGTTCCCA<br>CCCGCAACTCCTCCCGAGCAGAATATAGTACGCAGTTATACCTTGGTCCTCTGTGGACTTTATATGGCTCC<br>TACACATTAGAAGCGGACGCTCACACGTTAGCCAATATGATTAACTGTGGGGCTCGCATGACATTCtaaGG<br>ATCC | |
| PmpC<br>PmpC_EcOpt_dSig:<br>*E. coli* codon<br>optimized,<br>N-terminal<br>nuclear<br>localization<br>signal removed | MSSVESQIETKDLNSSRTGSSSSQSFTEIIPENGAEYRVSGDVSFSDFSNIPEEAETLAISHKEQPNNEVV<br>LSEENHQASFQDSAQNQTENASEGNSPNSENTNQSSTTETESITTDEQVQNDNESAASVPTTVETATAMRL<br>PSYHLQTESLVEGATEEDQNQPNSQNTSSGGGAFYNSQQGPLSFINDPDKDSSLTLSKIRVIGEGGAIYSK<br>GPLSITGLKKLALKENLSQKAGGAICAESTISISSVDSIIFSKNTVTPPAANKPELPNDPSGSNGNDGSDD<br>SNSSGNTDSNESNPNNSASNNTGSENELSSSTPSAQLPNPATPFLSSVSTNSQPIDTEPENAWHAESGSGG<br>AIYSKGKLSIASSKEVVEDHNSATKNGGAIFGEEEIALEKIASLKFDSNTTGEKGGAIHAKTVTLSDIKNT<br>LIFVNNTAKTPEENSLKSSQLNNQNPSEEEHQDTSEGEESQSLETSPITNQDSASSHVAIFRSIAASSSQS<br>NSENIPNADGSTSAGGDAGSSSQPSTPGSDSSINHVIGGGAIYGEAVKIENLSGYGTFSNNNAVDHQISGS<br>TSDVLGGAIYAKTSLTIDSGNSSGTITFSENTTSSKSTTGQVAGGAIFSPSVTITTPVTFSKNSAINATTS<br>SKKDTEGGAIGAISTVSLSKGARFSENIADLGSAIGLVPTTQDAETVQLTTGSYYFEKNKALKRATVYAPI<br>VSIKAHTATFDQNISAEEGSAIYFTKEATIESLGSVLFTGNLVTPIQSTTVLTSGNTSKYGAAIFGQTANA<br>SGSQTDNLPLKLIASGGNISFRNNEYRPDATNTGQSTFCSIAGDIKLTMQAAEGKVISFFDAIRTSTKKTG<br>TLASAYDTLDINKSNDSGSINSAFTGTIMESSELHENKSYIPQNVVLHSGSLILKANTELHVLSFDQKEGS<br>SLIMEPGSVLSNQDIADGSLVVNSLTIDLSSVGRNSASGDNIFMPPELRIVDTSTNSGNSSSTPPSSNTPP<br>NSTPTAQAPISKNFAATTTTPTTPPTTGNIVFLNGVIKLIDPNGTFFQNPALGSDQKISLLVLPSDQTKLQ<br>AQKVVLTGDISPKKGYTGTLTLDPQQLQNGVIQALWTFKSYRQWAYIPRDNHFYANSILGSQMSMATVKQG<br>LINDKLNLARFDEVAYNNLWISGLGTMLSQRGGQRSEEMTYYSRGASVALDAKPTQDLIIGAAFSKMIGRS<br>KSLKLERNYTHKGSEYSYQASVYGGSPFYLTINKEAGRSLPLLLQGVISYGYIKHDTVTHYPTIRELNKGE<br>WEDLGWLTALRVSSILKTPKQGDSKRITVYGEVEYSSIRQKQFTETEYDPRYFSNCTYRNLAVPVGLALEG<br>EFKGNDILMYNRFSVAYMPSIYRNSPVCKYQVLSSGEGGEIVCGVPTRNSSRAEYSTQLYLGPLWTLYGSY<br>TLEADAHTLANMINCGARMTF | 23 |
| PmpC<br>PmpC_EcOpt_dSig_<br>dPMP<br>*E. coli* codon<br>optimized,<br>N-terminal<br>nuclear<br>localization<br>signal removed,<br>adhesion domain<br>(ChlamPMP_M)<br>removed | CATATGAGCAGCGTTGAATCCCAAATAGAAACAAAAGATCTGAACTCTAGTCGCACAGGCTCCTCATCATC<br>GCAATCCTTCACTGAAATAATTCCAGAAAATGGCGCAGAATATCGCGTATCTGGAGATGTTTCATTTTCTG<br>ATTTTTCAAATATACCAGAAGAAGCAGAGACTCTTGCTATATCGCACAAAGAACAGCCTAATAACGAAGTA<br>GTACTCTCCGAAGAAAACCACCAAGCATCCTTTCAAGATTCTGCACAAAACCAAACTGAAAATGCCTCTGA<br>AGGAAACTCTCCTAATAGCGAGAATACTAACCAGTCATCTACCACAGAAACCGAGTCTATAACTACTGATG<br>AACAAGTGCAGAATGATAATGAATCTGCAGCTTCTGTACCTACTACTGTAGAAACAGCAACAGCTATGCGC<br>CTCCCCTCTTACCATCTGCAAACAGAATCATTAGTAGAAGGGGCTACAGAAGAAGATCAAAATCAACCGAA<br>CTCTCAAAATACATCTAGTGGCGGCGGAGCATTTTATAACTCTCAACAAGGACCTTTATCCTTTATCAATG<br>ATCCCGATAAAGACAGTTCTCTCACCTTATCAAAAATTCGAGTAATAGGAGAGGGTGGTGCCATTTACTCG<br>AAAGGACCATTAAGCATAACAGGTCTTAAAAAATTAGCTTTAAAAGAAAACTTATCCCAAAAGGCTGGAGG<br>AGCTATTTGTGCAGAATCCACTATTTCAATAAGTAGTGTAGATTCTATCATTTTTTCTAAGAATACAGTCA<br>CTCCTCCAGCTGCCAATAAACCTGAACTCCCTAACGATCCCTCTGGGAGTAATGGTAATGATGGTTCTGAT<br>GACAGTAACTCCTCAGGTAATACTGACTCAAATGAAAGCAACCCTAACAACAGCGCTTCTAATAACACTGG<br>CTCTGAAAATGAGCTTTCTTCCAGTACCCCATCCGCACAACTTCCCAATCCCGCAACACCATTTTTATCAT<br>CTGTTTCTACAAACTCTCAACCTATAGACACAGAACCAGAAAATGCATGGCATGCTGAATCAGGGTCTGGA<br>GGAGCTATCTATTCTAAAGGCAAACTTTCTATCGCAAGCTCTAAAGAAGTAGTCTTCGATCACAACTCGGC<br>CACCAAAAATGGAGGAGCTATCTTCGGAGAGGAAGAAATTGCTCTCGAAAAAATAGCGTCTCTGAAATTCG<br>ATTCCAACACTACCGGTGAAAAAGGTGGGGCTATTCATGCGAAAACAGTTACACTGTCTGACATCAAAAAC<br>ACTTTGATTTTCGTTAATAATACGGCTAAAACACCGGAAGAAAACTCTCTGAAATCTTCTCAACTGAACAA<br>CCAAAATCCTTCCGAAGAAGAGCACCAAGATACTAGTGAGGGTGAAGAAAGCCAGTCTCTTGAAACGTCAC | 24 |

TABLE 3-continued

Exemplary full-length and truncated PMP C, E, F, G, and H
gene and protein sequences from *C. muridarum*

| Ann

TABLE 3-continued

Exemplary full-length and truncated PMP C, E, F, G, and H
gene and protein sequences from *C. muridarum*

| Annotation | Sequences | SEQ ID NO |
|---|---|---|
| | AATATTGTGAAGACATTTGCCTCAAATGGAAAAATGTTGGGTGGAGGGGCAATTTTAGCTTCAGGAAATGT<br>TTTGATTAGCAAAAACTCTGGAGAGATTTCTTTTTGTAGGGAATGCTCGAGCTCCTCAGGCTATTCCGACTC<br>GTTCATCTGACGAATTGTCTTTTGGCGCACAATTAACTCAAACTACTTCAGGATGTTCTGGAGGAGGAGCT<br>CTTTTTGGTAAAGAGGTTGCCATTGTTCAAAATGCCACTGTTGTATTCGAGCAAAATCGCTTACAGTGTGG<br>CGAGCAGGAAACACATGGTGGAGGCGGTGCTGTTTATGGTATGGAGAGTGCCTCTATTATTGGAAACTCTT<br>TTGTGAGATTCGGAAATAATTACGCTGTAGGGAATCAGATTTCTGGAGGAGCTCTTTTATCCAAGAAGGTC<br>CGTTTAGCTGAAAATACAAGGGTAGATTTTTCTCGAAATATCGCTACTTTCTGCGGCGGGGCTGTTCAAGT<br>TTCTGATGGAAGTTGCGAATTGATCAACAATGGGTATGTGCTATTCAGAGATAACCGAGGGCAGACATTTG<br>GTGGGGCTATTTCTTGCTTGAAAGGAGATGTGATCATTTCCGGAAATAAAGATAGGGTTGAGTTTAGAGAT<br>AACATTGTGACGCGGCCTTATTTTGAAGAAAATGAAGAAAAAGTTGAGACAGCAGATATTAATTCAGATAA<br>GCAAGAAGCAGAAGAGCGCTCTTTATTAGAGAACATTGAGCAGAGCTTTATTACTGCAACTAATCAGACCT<br>TTTTCTTAGAGGAAGAGAAACTCCCCATCAGAAGCTTTTATCTCTGCTGAAGAACTTTCAAAGAAGAGAA<br>TGTGCTGGTGGGGCGATTTTTGCAAAACGGGTCTACATTACGGATAATAAAGAACCTATCTTGTTTTCGCA<br>TAATTTTTCTGATGTTTATGGGGGAGCTATTTTTACGGGTTCTCTACAGGAAACTGATAAACAAGATGTTG<br>TAACTCCTGAAGTTGTGATATCAGGCAACGATGGGGATGTCATTTTTTCTGGAAATGCAGCTAAACATGAT<br>AAGCATTTACCTGATACAGGTGGTGGAGCCATTTGTACACAGAATTTGACGATTTCCCAAAACAATGGGAA<br>TGTCTTGTTCTTGAACAATTTTGCTTGTTCTGGTGGAGCAGTTCGCATAGAGGATCATGGAGAAGTTCTTT<br>TAGAGGCTTTTGGGGGAGATATTATTTTCAATGGAAACTCTTCTTTCAGAGCTCAAGGATCGGATGCGATC<br>TATTTTGCTGGTAAGGACTCTAGAATTAAAGCTTTAAATGCTACTGAAGGACATGCGATTGTGTTCCAAGA<br>TGCATTGGTGTTTGAAAATATAGAAGAAAGAAAGTCTTCGGGACTATTGGTGATTAACTCTCAGGAAAATG<br>AGGGTTATACGGGATCCGTCCGATTTTTAGGATCTGAAAGTAAGGTTCCTCAATGGATTCATGTGCAACAG<br>GGAGGTCTTGAGTTGCTACATGGAGCTATTTTATGTAGTTATGGGGTTAAACAAGATCCTAGAGCTAAAAT<br>AGTATTATCTGCTGGATCTAAATTGAAGATTCTAGATTCAGAGCAAGAAAATAACGCAGAAATTGGAGATC<br>TTGAAGATTCTGTTAATTCAGAAAAAACACCATCTCTTTGGATTGGGAAGAACGCTCAAGCAAAAGTCCCT<br>CTGGTTGATATCCATACTATTTCTATTGATTTAGCATCATTTTCTTCTAAAGCTCAGGAAACCCCTGAGGA<br>AGCTCCACAAGTCATCGTCCCTAAGGGAAGTTGTGTCCACTCGGGAGAGTTAAGTTTGGAGTTGGTTAATA<br>CAACAGGAAAAGGTTATGAGAATCATGCGTTGTTAAAAAATGATACTCAGGTTTCTCTCATGTCTTTCAAA<br>GAGGAAAATGATGGATCTTTAGAAGATTTGAGTAAGTTGTCTGTTTCGGATTTACGCATTAAAGTTTCTAC<br>TCCAGATATTGTAGAAGAAACTTATGGCCATATGGGGGATTGGTCTGAAGCTACAATTCAAGATGGGGCTC<br>TTGTCATTAATTGGCATCCTACTGGATATAAATTAGATCCGCAAAAAGCTGGTTCTTTGGTATTCAATGCA<br>TTATGGGAGGAAGAGGCTGTATTGTCTACTCTAAAAAATGCTCGGATTGCCCATAACCTTACCATTCAGAG<br>AATGGAATTTGATTATTCTACAAATGCTTGGGGATTAGCTTTTAGTAGCTTTAGAGAGCTATCTTCAGAGA<br>AGCTTGTTTCTGTTGATGGATATAGAGGCTCTTATATAGGGGCTTCTGCAGGCATTGATACTCAGTTGATG<br>GAAGATTTTGTTTTGGGAATCAGCACGGCTTCCTTCTTCGGGAAAATGCATAGTCAGAATTTTGATGCAGA<br>GATTTCTCGACATGGTTTTGTTGGTTCGGTCTATACAGGCTTCCTAGCTGGGGCCTGGTTCTTCAAGGGGC<br>AGTACAGTCTTGGCGAAACACATAACGATATGACAACTCGTTACGGGGTTTTGGGAGAATGGTGTGCATGC<br>TGGAAGTCTCGAGGAGTACTAGCAGATGCTTTAGTTGAATATCGTAGTTTAGTCGGTCCAGCACGACCTAA<br>ATTTTATGCTTTGCATTTAATCCTTATGTCGAGGTATCTTATGCATCTGCGAAGTTCCCTAGTTTTGTAG<br>AACAAGGAGGAGAAGCTCGTGCTTTTGAAGAAACCTCTTTAACAAACATTACCGTTCCCTTTGGTATGAAA<br>TTTGAACTATCTTTTACAAAAGGACAGTTTTCAGAGACTAATTCTCTTGGAATAGGTTGTGCATGGGAAAT<br>GTATCGGAAAGTCGAAGGAAGATCTGTAGAGCTACTAGAAGCTGGTTTTGATTGGGAAGGATCTCCTATAG<br>ATCTCCCTAAACAAGAGCTGAGAGTGGCTTTAGAAAACAATACGGAATGGAGTTCGTATTTTAGTACAGCT<br>CTAGGAGTAACAGCATTTTGTGGAGGATTTTCTTCTATGGATAATAAACTAGGATACGAAGCGAATGCTGG<br>AATGCGTTTGATTTTCTAG | |
| PmpD<br>PmpD_CHLMU | MSSEKDKKNSCSKFSLSVVAAILASMSGLSNCSDLYAVGSSADHPAYLIPQAGLLLDHIKDIFIGPKDSQD<br>KGQYKLIIGEAGSFQDSNAETLPQKVEHSTLSFVTTPIIVQGIDQQDQVSSQGLVCNFSGDHSEEIFERES<br>FLGIAFLGNGSKDGITLTDIKSSLSGAALYSSDDLIFERIKGDIELSSCSSLERGGACSAQSILTHDCQGL<br>TVKHCAAGVNVEGVSASDHLGEGGGAFSTTSSLSGEKSLYMPAGDIVVATCDGPVCFEGNSAQLANGGAIA<br>ASGKVLFVANEKKISFTDNQALSGGAISASSSISFQNCAELVEKSNLAKGVKDKCSLGGGALASLESVVLK<br>DNLGITYEKNQSYSEGGAIFGKDCEIFENRGPVVERDNTAALGGGAILAQQTVAICGNKSGISFEGSKSSF<br>GGAIACGNESSENNSSALGSIDISNNLGDISFLRTLCTTSDLGQTDYQGGGALFAENISLSENAGAITFKD<br>NIVKTFASNGKMLGGGAILASGNVLISKNSGEISFVGNARAPQAIPTRSSDELSFGAQLTQTTSGCSGGGA<br>LFGKEVAIVQNATVVFEQNRLQCGEQETHGGGGAVYGMESASIIGNSFVREGNNYAVGNQISGGALLSKKV<br>RLAENTRVDFSRNIATFCGGAVQVSDGSCELINNGYVLFRDNRGQTFGGAISCLKGDVIISGNKDRVEFRD<br>NIVTRPYFEENEEKVETADINSDKQEAEERSLLENIEQSFITATNQTFFLEEEKLPSEAFISAEELSKRRE<br>CAGGAIFAKRVYITDNKEPILFSHNFSDVYGGAIFTGSLQETDKQDVVTPEVVISGNDGDVIFSGNAAKHD<br>KHLPDTGGGAICTQNLTISQNNGNVLFLNNFACSGGAVRIEDHGEVLLEAFGGDIIFNGNSSFRAQGSDAI<br>YFAGKDSRIKALNATEGHAIVFQDALVFENIEERKSSGLLVINSQENEGYTGSVRFLGSESKVPQWIHVQQ<br>GGLELLHGAILCSYGVKQDPRAKIVLSAGSKLKILDSEQENNAEIGDLEDSVNSEKTPSLWIGKNAQAKVP<br>LVDIHTISIDLASFSSKAQETPEEAPQVIVPKGSCVHSGELSLELVNTTGKGYENHALLKNDTQVSLMSFK<br>EENDGSLEDLSKLSVSDLRIKVSTPDIVEETYGHMGDWSEATIQDGALVINWHPTGYKLDPQKAGSLVFNA<br>LWEEEAVLSTLKNARIAHNLTIQRMEFDYSTNAWGLAFSSFRELSSEKLVSVDGYRGSYIGASAGIDTQLM<br>EDFVLGISTASFFGKMHSQNFDAEISRHGFVGSVYTGFLAGAWFFKGQYSLGETHNDMTTRYGVLGESNAT<br>WKSRGVLADALVEYRSLVGPARPKFYALHFNPYVEVSYASAKFPSFVEQGGEARAFEETSLTNIVPFGMK<br>FELSFTKGQFSETNSLGIGCAWEMYRKVEGRSVELLEAGFDWEGSPIDLPKQELRVALENNTEWSSYESTA<br>LGVTAFCGGFSSMDNKLGYEANAGMRLIF | 27 |
| PmpD<br>PmpD_EcOpt_dSig<br>*E. coli* codon<br>optimized,<br>N-terminal<br>nuclear | CATATGGCTATTCTGGCTTCTATGAGTGGTTTATCGAATTGTTCCGATCTGTATGCCGTAGGAAGTTCTGC<br>AGACCATCCTGCCTACTTGATTCCTCAAGCGGGGTTATTATTGGATCATATTAAGGATATTTTCATTGGCC<br>CTAAAGATAGTCAGGATAAGGGGCAGTATAAGTTGATTATTGGTGAGGCTGGCTCTTTCCAAGATAGTAAT<br>GCAGAGACTCTGCCTCAAAAGGTAGAGCACAGCACTTTGTTTTCAGTTACAACACCTATTATTGTGCAAGG<br>AATTGATCAACAAGATCAGGTCTCTTCGCAGGGATTGGTCTGTAATTTTTCAGGAGATCATTCAGAGGAGA<br>TTTTTGAGCGCGAATCCTTTTTAGGGATCGCTTTCCTGGGGAATGGTAGCAAGGATGGAATCACGTTAACA | 28 |

TABLE 3-continued

Exemplary full-length and truncated PMP C, E, F, G, and H gene and protein sequences from C. muridarum

| Annotation | Sequences | SEQ ID NO |
|---|---|---|
| localization signal removed, | GATATTAAATCTTCGTTATCTGGTGCTGC TABLE 3-continued Exemplary full-length and truncated PMP C, E, F, G, and H
gene and protein sequences from *C. muridarum*

| Annotation |

TABLE 3-continued

Exemplary full-length and truncated PMP C, E, F, G, and H
gene and protein sequences from C. muridarum

| Annotation

TABLE 3-continued

Exemplary full-length and truncated PMP C, E, F, G, and H
gene and protein sequences from C. muridarum

| Annotation | Sequences | SEQ

TABLE 3-continued

Exemplary full-length and truncated PMP C, E, F, G, and H
gene and protein sequences from *C. muridarum*

| Annotation | Sequences | SEQ ID NO |
|---|---|---|
| | TACAGGAAACAC

TABLE 3-continued

Exemplary full-length and truncated PMP C, E, F, G, and H
gene and protein sequences from *C. muridarum*

| Ann

TABLE 3-continued

Exemplary full-length and truncated PMP C, E, F, G, and H
gene and protein sequences from C. muridarum

| Ann

TABLE 3-continued

Exemplary full-length and truncated PMP C, E, F, G, and H gene and protein sequences from *C. muridarum*

| Annotation | S

TABLE 3-continued

Exemplary full-length and truncated PMP C, E, F, G, and H
gene and protein sequences from C. muridarum

| Annotation | Sequences | SEQ ID NO |
|---|---|---|
| PmpG PmpG_EcOpt_dSig_ dPMP E. coli codon optimized, TABLE 3-continued Exemplary full-length and truncated PMP C, E, F, G, and H
gene and protein sequences from C. muridarum

| Annotation | Sequences | SEQ ID NO |
|---|---|---|
| | TGGTGTTACTACAAGTGCCGTTACTCTGAATAATGCAGATACTGCG TABLE 3-continued Exemplary full-length and truncated PMP C, E, F, G, and H
gene and protein sequences from C. muridarum

| Annotation | Sequences | SEQ ID NO |
|---|---|---|
| PmpH PmpH_EcOpt_dSig total cell-free mixtures were resolved by SDS-PAGE and imaged by fluorescent imaging. The plasmids encoding Pmp and scaffolding protein ApoA1 or ApoE4 is at ratio of 50:1 (FIG. 21A).

Figure 21A:
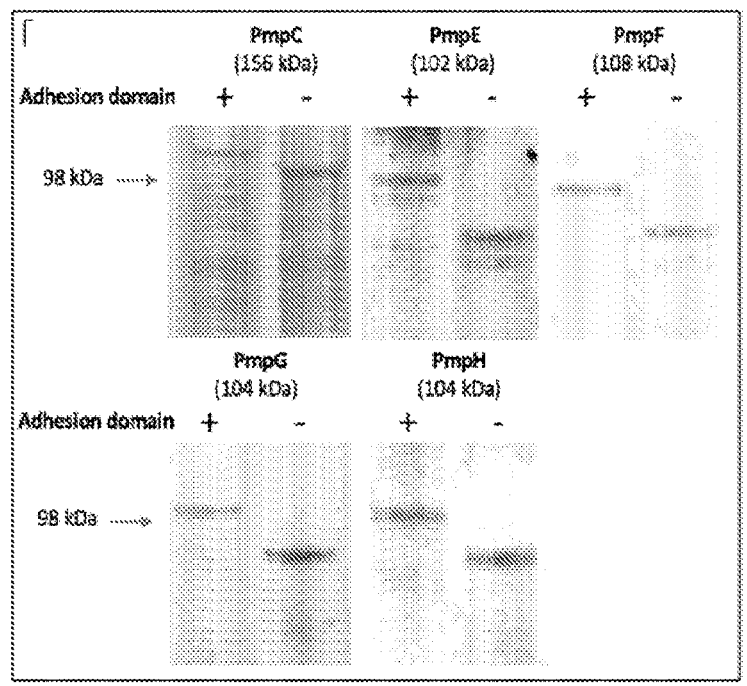
Figure 21:
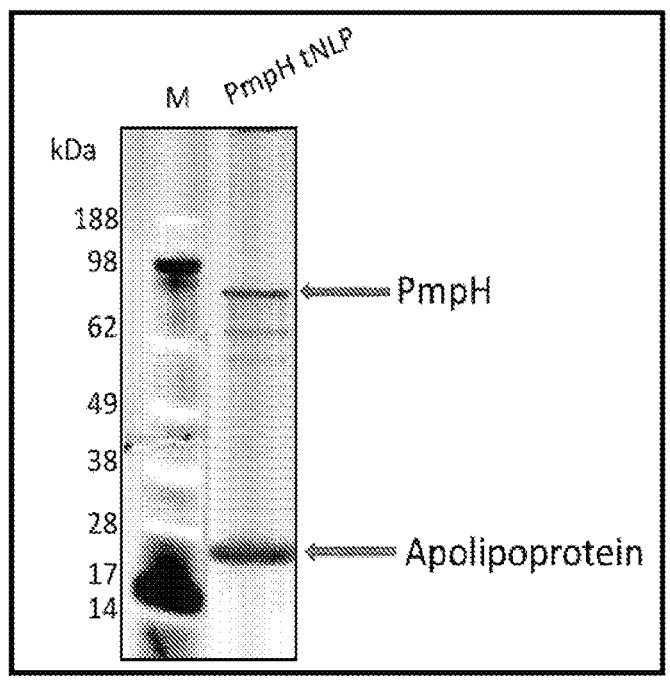

The results illustrated in FIG. 21A show SDS-PAGE images of codon-optimized fluorescent labeled Pmps (PmpC, PmpE, PmpF, PmpG, and PmpH) and truncated versions that lack the adhesion domain. These results show that full-length and truncation Pmp proteins can be cell-free expressed in the presence of lipid and telodendrimer as will be understood by a skilled person.

In a second set of experiments, co-translation reaction using plasmids encoding Δ49ApoA1 or ApoE4 and PmpH were set up in the presence of bodipy-lysine fluorescent amino acid, DMPC lipid and telodendrimer $PEG^{5k}$-$CA_8$. The plasmids encoding Pmp and scaffolding protein ApoA1 or ApoE4 is at ratio of 50:1. Reactions were scaled up to 1 mL to produce sufficient quantities of Pmp for subsequent nickel purification utilizing the HIS tag on the apolipoprotein scaffold component of the tNLP.

The purification provided a complex that was >95% pure based on SDS-PAGE analysis. On average, a 1 mL reaction produced ~200 μg of PmpH (FIG. 21B) based on gel densitometry. Distinct bands indicated that the two proteins, apolipoprotein and Pmp, were co-purifying as a complex.

The results are illustrated in FIG. 21B which shows SDS-PAGE images of cell-free expressed and nickel-purified PmpH and Δ49 $ApoA_1$, a truncated version of mouse ApoA1 in which the N-terminal 49 amino acids were removed. A 1 mL reaction produced ~200 μg of PmpH. Although in this set of experiments MOMP was not cotranslated with PmpH, MOMP can be translated with PmpH as will be understood by a skilled person upon reading of the present disclosure.

Example 11: Structural and Protective Assessment of Chlamydial Proteins

This example further demonstrates that NLPs are a vaccine delivery platform for membrane protein antigens. In addition, the example also confirms that *C. muridarum* MOMP is amenable to gene optimization, cell-free expression, and purification in the NLP complex.

The experiments were carried out using the approaches previously described in Examples 4 and 5. In particular, an *Escherichia coli*-based cell-free system was used to express a MOMP protein from the mouse-specific species *Chlamydia muridarum* (MoPn-MOMP or mMOMP). The codon-optimized mMOMP gene was co-translated with Δ49apolipoprotein A1 (Δ49ApoA1), a truncated version of mouse ApoA1 in which the N-terminal 49 amino acids were removed. This co-translation process produced mMOMP supported within a telodendrimer nanolipoprotein particle (mMOMP-tNLP). The cell-free expressed mMOMP-tNLPs contain mMOMP multimers similar to the native MOMP protein. This cell-free process produced on average 1.5 mg of purified, water-soluble mMOMP-tNLP complex in a 1-ml cell-free reaction.

Figures 22A, 22B:
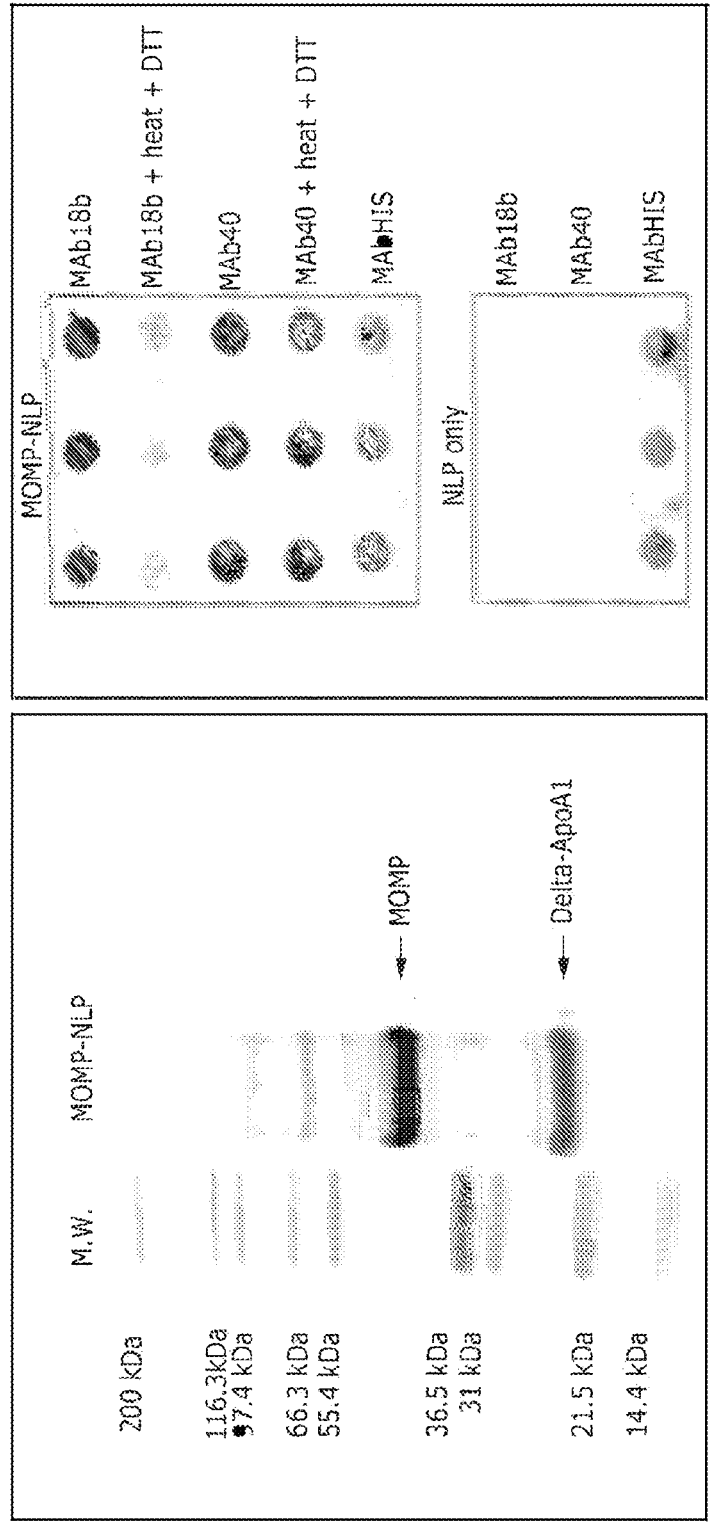
Figure 22C:
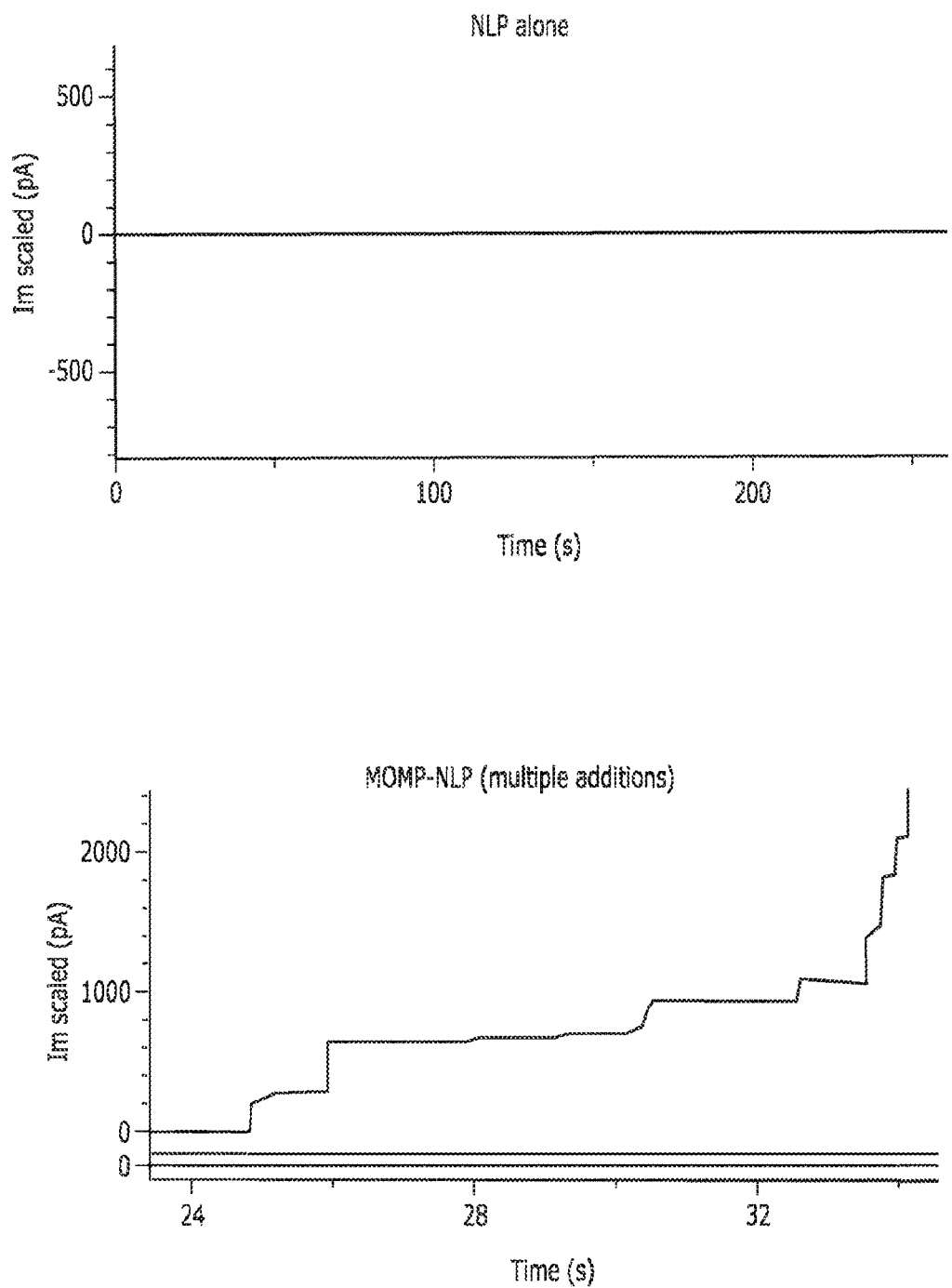

FIGS. 22A-22C demonstrates a cell-free production of MOMP co-translated with $ApoA_1$ $Δ49A_1$. FIG. 22A shows SDS-PAGE images of cell-free expressed and purified MOMP and ApoA1 Δ49A1.

FIG. 22B shows exemplary results of dot blot analysis MOMP-NLP and NLP assemblies treated with heat and reducing agent. The MOMP-NLP and NLP assemblies were blotted in triplicate and probed with mAb40, mAbHIS and mAb18b. The confirmation of the MOMP trimer was confirmed using the conformational monoclonal antibody mAb18b. Addition of heat and DTT results in a decrease in signal as detected by mAb18b, indicating a loss in trimer formation. mAb40 recognizes both MOMP monomer and trimer as it binds to a linear epitope. The mAbHIS recognizes the HIS tag on the Δ49A1 protein.

FIG. 22C shows conductance traces recorded at 50 mV applied voltage in physiological conditions after NLP alone and MOMP-NLP were added to the measurement chamber. Current increases observed after MOMP-NLP addition indicate the formation of bilayer pore formation by MOMP proteins, indicating functional MOMP insertion.

Using the mMOMP-tNLP formulation, a unique approach is demonstrated to solubilizing and administering membrane-bound proteins for future vaccine development. This method can also be applied to include other antigens such as Pmps while maintaining their full functionality and immunogenicity.

Example 12: Structural and Protective Assessment of Chlamydial Proteins

The experiments in this example were carried out using procedures described in Example 7.

In particular, the protective response of MOMP-NLP was evaluated in a mouse intranasal challenge study. Briefly, were inoculated intranasally with formulated controls (PBS or empty NLPs) or different formulations of MOMP-NLPs. With chlamydial challenges, the mice undergo weight loss and recovery. The recovery is an indication of protection for any formulation.

Figure 24:
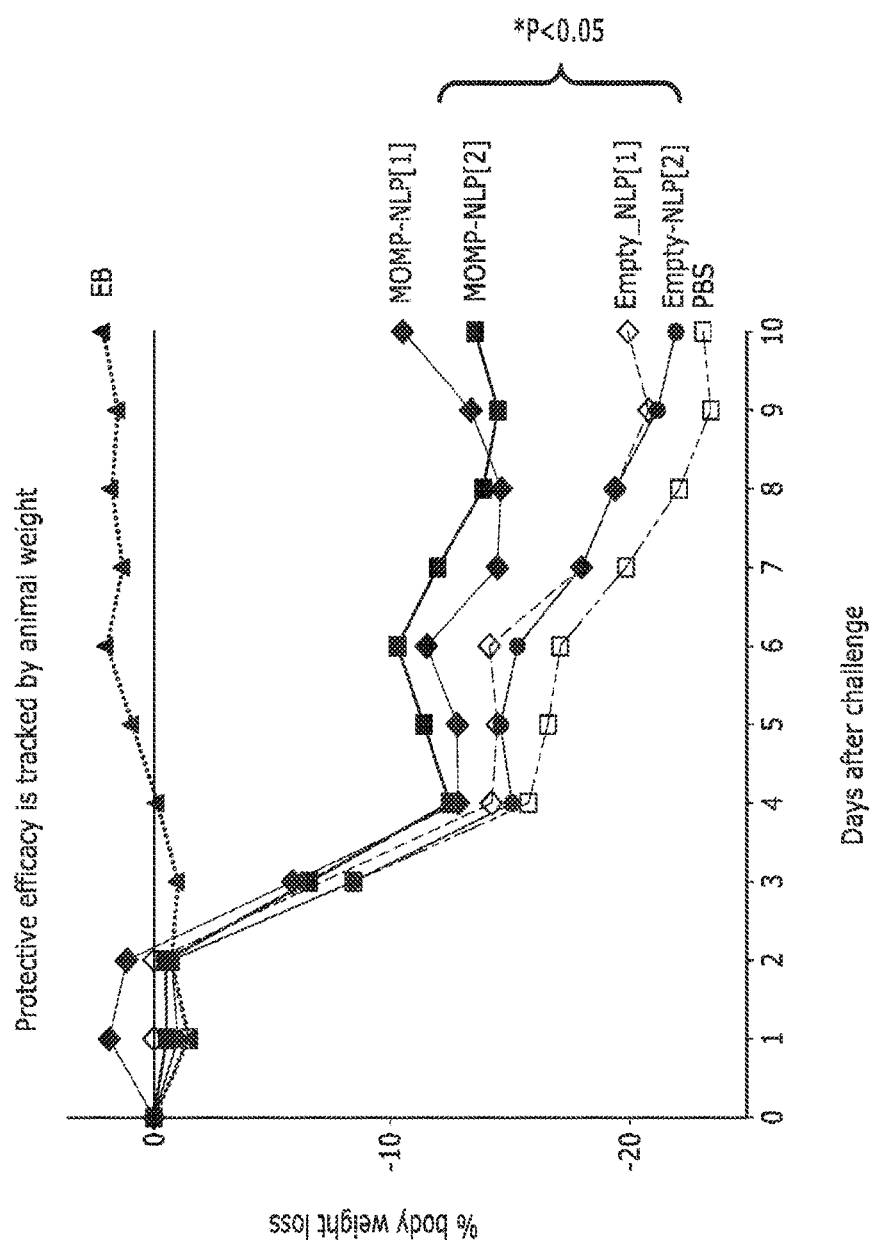

In FIG. 24, weight loss over time following intranasal (i.n) challenge with *C. muridarum* was used as a measure of protection. Data was analyzed using RM two-way ANOVA with Sidak's multiple comparison analysis.

In vivo vaccination with MOMP-NLPs displayed strong protection against *Chlamydia* challenge in mice compared to empty NLPs and PBS control. Additionally, mice immunized with MOMP:NLP lost significant body weight by 4 days post challenge (d.p.c.) but by 10 d.p.c. have recovered some of their weight (FIG. 24). The positive control, *Chlamydia* elementary body (EB), demonstrates complete protection.

These combined preliminary results demonstrate the feasibility of extending NLP approach to the genital model for further vaccine development.

Additionally, since using systemic and/or mucosal routes for immunization, a better protection has been observed when using both routes. It is therefore expected that delivery of MOMP-NLPs by both routes will result in enhancing systemic and mucosal humoral and cellular memory immune responses.

In summary, described herein is a telodendrimer-nanolipoprotein particle (t-NLP), comprising one or more membrane forming lipids, one or more telodendrimers, and a scaffold protein and a *Chlamydia* major outer membrane protein (MOMP) comprising a MOMP hydrophobic region, and related compositions methods and systems.

The examples set forth above are provided to give those of ordinary skill in the art a complete disclosure and description of how to make and use the embodiments of the materials, compositions, systems and methods of the disclosure, and are not intended to limit the scope of what the inventors regard as their disclosure. Those skilled in the art will recognize how to adapt the features of the exemplified NLPs and related uses to additional NLPs formed by other cationic lipids, membrane forming lipids, scaffold proteins, additives, and possibly functionalized amphipathic compounds and membrane proteins according to various embodiments and scope of the claims.

All patents and publications mentioned in the specification are indicative of the levels of skill of those skilled in the art to which the disclosure pertains.

The entire disclosure of each document cited (including patents, patent applications, journal articles, abstracts, laboratory manuals, books, or other disclosures) in the Background, Summary, Detailed Description, and Examples is hereby incorporated herein by reference. All references cited in this disclosure are incorporated by reference to the same extent as if each reference had been incorporated by reference in its entirety individually. However, if any inconsistency arises between a cited reference and the present disclosure, the present disclosure takes precedence. Further, the computer readable form of the sequence listing of the ASCII text file IL13105-PCT-Seq-List-ST25 is incorporated herein by reference in its entirety.

The terms and expressions which have been employed herein are used as terms of description and not of limitation, and there is no intention in the use of such terms and expressions of excluding any equivalents of the features shown and described or portions thereof, but it is recognized that various modifications are possible within the scope of the disclosure claimed. Thus, it should be understood that although the disclosure has been specifically disclosed by embodiments, exemplary embodiments and optional features, modification and variation of the concepts herein disclosed can be resorted to by those skilled in the art, and that such modifications and variations are considered to be within the scope of this disclosure as defined by the appended claims.

It is also to be understood that the terminology used herein is for the purpose of describing particular embodiments only, and is not intended to be limiting. As used in this specification and the appended claims, the singular forms "a," "an," and "the" include plural referents unless the content clearly dictates otherwise. The term "plurality" includes two or more referents unless the content clearly dictates otherwise. Unless defined otherwise, all technical and scientific terms used herein have the same meaning as commonly understood by one of ordinary skill in the art to which the disclosure pertains.

When a Markush group or other grouping is used herein, all individual members of the group and all combinations and possible subcombinations of the group are intended to be individually included in the disclosure. Every combination of components or materials described or exemplified herein can be used to practice the disclosure, unless otherwise stated. One of ordinary skill in the art will appreciate that methods, device elements, and materials other than those specifically exemplified may be employed in the practice of the disclosure without resort to undue experimentation. All art-known functional equivalents, of any such methods, device elements, and materials are intended to be included in this disclosure. Whenever a range is given in the specification, for example, a temperature range, a frequency range, a time range, or a composition range, all intermediate ranges and all subranges, as well as, all individual values included in the ranges given are intended to be included in the disclosure. Any one or more individual members of a range or group disclosed herein may be excluded from a claim of this disclosure. The disclosure illustratively described herein suitably may be practiced in the absence of any element or elements, limitation or limitations which is not specifically disclosed herein.

A number of embodiments of the disclosure have been described. The specific embodiments provided herein are examples of useful embodiments of the invention and it will be apparent to one skilled in the art that the disclosure can be carried out using a large number of variations of the devices, device components, methods steps set forth in the present description. As will be obvious to one of skill in the art, methods and devices useful for the present methods may include a large number of optional composition and processing elements and steps.

In particular, it will be understood that various modifications may be made without departing from the spirit and scope of the present disclosure. Accordingly, other embodiments are within the scope of the following claims.

REFERENCES

1. Feher, V. A., et al., *A 3-dimensional trimeric β-barrel model for Chlamydia MOMP contains conserved and novel elements of Gram-negative bacterial porins.* PloS one, 2013. 8(7): p. e68934.
2. Tu, J., et al., *A multi-epitope vaccine based on Chlamydia trachomatis major outer membrane protein induces specific immunity in mice.* Acta biochimica et biophysica Sinica, 2014. 46(5): p. 401-408.
3. Pal, S., et al., *Immunization with the Chlamydia trachomatis mouse pneumonitis major outer membrane protein can elicit a protective immune response against a genital challenge.* Infection and immunity, 2001. 69(10): p. 6240-6247.
4. Sperling, R. A. and W. J. Parak, *Surface modification, functionalization and bioconjugation of colloidal inorganic nanoparticles.* Philos Trans A Math Phys Eng Sci, 2010. 368(1915): p. 1333-83.
5. Cappuccio, J. A., et al., *Cell-free Co-expression of Functional Membrane Proteins and Apolipoprotein, Forming Soluble Nanolipoprotein Particles.* Molecular & Cellular Proteomics, 2008. 7(11): p. 2246-2253.
6. Gao, T. J., et al., *Characterizing diffusion dynamics of a membrane protein associated with nanolipoproteins using fluorescence correlation spectroscopy.* Protein Science, 2011. 20(2): p. 437-447.
7. Katzen, F., et al., *Insertion of membrane proteins into discoidal membranes using a cell-free protein expression approach.* Journal of Proteome Research, 2008. 7(8): p. 3535-3542.
8. Davidson, E. and B. J. Doranz, *A high-throughput shotgun mutagenesis approach to mapping B-cell antibody epitopes.* Immunology, 2014. 143(1): p. 13-20.
9. Koren, E., et al., *Clinical validation of the "in silico" prediction of immunogenicity of a human recombinant therapeutic protein.* Clinical Immunology, 2007. 124(1): p. 26-32.
10. Tifrea, D. F., et al., *Increased immunoaccessibility of MOMP epitopes in a vaccine formulated with amphipols may account for the very robust protection elicited against a vaginal challenge with Chlamydia muridarum*. The Journal of Immunology, 2014. 192(11): p. 5201-5213.
11. Badamchi-Zadeh, A., et al., *A multi-component prime-boost vaccination regimen with a consensus MOMP antigen enhances Chlamydia trachomatis clearance*. Frontiers in immunology, 2016. 7.
12. Baehr, W., et al., *Mapping antigenic domains expressed by Chlamydia trachomatis major outer membrane protein genes*. Proceedings of the National Academy of Sciences, 1988. 85(11): p. 4000-4004.

13. Conlan, J., et al., *Isolation of recombinant fragments of the major outer-membrane protein of Chlamydia trachomatis: their potential as subunit vaccines.* Microbiology, 1990. 136(10): p. 2013-2020.
14. Su, H. and H. D. Caldwell, *Immunogenicity of a chimeric peptide corresponding to T helper and B cell epitopes of the Chlamydia trachomatis major outer membrane protein.* Journal of Experimental Medicine, 1992. 175(1): p. 227-235.
15. Findlay, H. E., H. McClafferty, and R. H. Ashley, *Surface expression, single-channel analysis and membrane topology of recombinant Chlamydia trachomatis Major Outer Membrane Protein.* BMC Microbiol, 2005. 5: p. 5.
16. Rodriguez-Marañón, M. J., et al., *Prediction of the membrane-spanning β-strands of the major outer membrane protein of Chlamydia.* Protein science, 2002. 11(7): p. 1854-1861.
17. Wang, Y., et al., *Identification of surface-exposed components of MOMP of Chlamydia trachomatis serovar F.* Protein Science, 2006. 15(1): p. 122-134.
18. Manning, D. S. and S. J. Stewart, *Expression of the major outer membrane protein of Chlamydia trachomatis in Escherichia coli.* Infection and immunity, 1993. 61(10): p. 4093-4098.
19. Sun, G., et al., *Protection against an intranasal challenge by vaccines formulated with native and recombinant preparations of the Chlamydia trachomatis major outer membrane protein.* Vaccine, 2009. 27(36): p. 5020-5.
20. Farris, C. M., S. G. Morrison, and R. P. Morrison, *CD4+ T cells and antibody are required for optimal major outer membrane protein vaccine-induced immunity to Chlamydia muridarum genital infection.* Infection and immunity, 2010. 78(10): p. 4374-4383.
21. Pal, S., E. M. Peterson, and M. Luis, *Vaccination with the Chlamydia trachomatis major outer membrane protein can elicit an immune response as protective as that resulting from inoculation with live bacteria.* Infection and immunity, 2005. 73(12): p. 8153-8160.
22. Pal, S., et al., *Immunization with an acellular vaccine consisting of the outer membrane complex of Chlamydia trachomatis induces protection against a genital challenge.* Infection and immunity, 1997. 65(8): p. 3361-3369.
23. Cappuccio, J. A., et al., *Cell-free co-expression of functional membrane proteins and apolipoprotein, forming soluble nanolipoprotein particles.* Mol Cell Proteomics, 2008. 7(11): p. 2246-53.
24. Xiao, K., et al., *Telodendrimer-based nanocarriers for the treatment of ovarian cancer.* Ther Deliv, 2013. 4(10): p. 1279-92.
25. Tifrea, D. F., et al., *Amphipols stabilize the Chlamydia major outer membrane protein and enhance its protective ability as a vaccine.* Vaccine, 2011. 29(28): p. 4623-31.
26. Tang, G., et al., *EMAN2: an extensible image processing suite for electron microscopy.* J Struct Biol, 2007. 157(1): p. 38-46.
27. Ferrara, L. G. M., et al., *MOMP from Campylobacter jejuni Is a Trimer of 18-Stranded beta-Barrel Monomers with a Ca(2+) Ion Bound at the Constriction Zone.* J Mol Biol, 2016. 428(22): p. 4528-4543.
28. Sun, G., et al., *Structural and functional analyses of the major outer membrane protein of Chlamydia trachomatis.* J Bacteriol, 2007. 189(17): p. 6222-35.
29. Haque, F., et al., *Incorporation of a viral DNA-packaging motor channel in lipid bilayers for real-time, single-molecule sensing of chemicals and double-stranded DNA.* Nat Protoc, 2013. 8(2): p. 373-92.
30. Coleman, M. A., et al., *Expression and Association of the Yersinia pestis Translocon Proteins, YopB and YopD, Are Facilitated by Nanolipoprotein Particles.* PLoS One, 2016. 11(3): p. e0150166.
31. He, W., et al., *Cell-free expression of functional receptor tyrosine kinases.* Sci Rep, 2015. 5: p. 12896.
32. Ralli-Jain, P., et al., *Enhancement of the protective efficacy of a Chlamydia trachomatis recombinant vaccine by combining systemic and mucosal routes for immunization.* Vaccine, 2010. 28(48): p. 7659-66.
33. Carmichael, J. R., et al., *Induction of protection against vaginal shedding and infertility by a recombinant Chlamydia vaccine.* Vaccine, 2011. 29(32): p. 5276-83.
34. Inic-Kanada, A., et al., *A Probiotic Adjuvant Lactobacillus rhamnosus Enhances Specific Immune Responses after Ocular Mucosal Immunization with Chlamydial Polymorphic Membrane Protein C.* PLoS One, 2016. 11(9): p. e0157875.
35. Johnson, R. M., et al., *PmpG303-311, a protective vaccine epitope that elicits persistent cellular immune responses in Chlamydia muridarum-immune mice.* Infect Immun, 2012. 80(6): p. 2204-11.
36. Karunakaran, K. P., et al., *Immunoproteomic discovery of novel T cell antigens from the obligate intracellular pathogen Chlamydia.* J Immunol, 2008. 180(4): p. 2459-65.
37. Karunakaran, K. P., et al., *Outer membrane proteins preferentially load MHC class II peptides: implications for a Chlamydia trachomatis T cell vaccine.* Vaccine, 2015. 33(18): p. 2159-66.
38. Pal, S., et al., *Comparison of the nine polymorphic membrane proteins of Chlamydia trachomatis for their ability to induce protective immune responses in mice against a C. muridarum challenge.* Vaccine, 2017. 35(19): p. 2543-2549.

The invention claimed is:

1. A telodendrimer-nanolipoprotein particle (t-NLP), comprising
   one or more membrane forming lipids,
   one or more telodendrimers,
   one or more adjuvants, and
   a scaffold protein and a *Chlamydia* major outer membrane protein (MOMP) and/or a fragment thereof comprising a MOMP hydrophobic region,
wherein the one or more membrane forming lipids are arranged in a discoidal membrane lipid bilayer stabilized by the scaffold protein and the one or more telodendrimers, with the membrane lipid bilayer attaching
   the MOMP and/or the fragment thereof through interaction of the hydrophobic region with the membrane lipid bilayer and
   the one or more adjuvants through binding of the one or more adjuvants to the discoidal membrane bilayer or to a component thereof.

2. The telodendrimer-nanolipoprotein particle of claim 1, having a size between 5 nm to 100 nm in diameter and comprising a telodendrimer to lipid ratio of 1:10 to 1:1000 a ratio of scaffold protein to lipid of 1:30 to 1:100 and a ratio of MOMP to scaffold protein of 20:1 to 1:4.

3. The telodendrimer-nanolipoprotein particle of claim 1, wherein the telodendrimer is a compound of formula (I):

$$(T)_m\text{-}(A)_p\text{-L-D-}(R)_n \qquad (I)$$

wherein
   D is a dendrimer
   T is a tail group;
   A is a spacer moiety configured to be directly covalently connected to each T and to a linker moiety L, and comprises a polymer of 1 to m number of spacer A monomers, wherein the spacer A monomer comprises a substituted or unsubstituted linear $C_1$-$C_{15}$ alkyl; branched $C_3$-$C_{15}$ alkyl; cyclic $C_3$-$C_{15}$ alkyl; linear, cyclic, or branched $C_2$-$C_{15}$ alkenyl; linear, cyclic, or branched $C_2$-$C_{15}$ alkynyl; $C_6$-$C_{20}$ substituted or unsubstituted aryl; and $C_6$-$C_{20}$ substituted or unsubstituted heteroaryl,
   R can be a detergent moiety, a lipid and/or an amino acid
   m is 0-20 and p is 0-1, and
   wherein m is 0 or 1 when p is 0; or m is 2-20 when p is 1.

4. The telodendrimer-nanolipoprotein particle of claim 1, wherein the MOMP is a MOMP of *Chlamydia* species *Chlamydia trachomatis*, *Chlamydia pneumoniae*, and *Chlamydia psittaci* (human pathogens), *Chlamydia suis* (affects only swine), *Chlamydia pecorum* (affects cows/swine/koala) and *Chlamydia pneumonia* (affects koala) and *Chlamydia muridarum* (affects only mice and hamsters) or a variant thereof or a fragment thereof, and wherein the variant maintains a beta barrel structure with 18 transmembrane regions separated by loops of the MOMP.

5. The telodendrimer-nanolipoprotein particle of claim 1, wherein the MOMP is a MOMP immunogenic fragment.

6. The telodendrimer-nanolipoprotein particle of claim 1, wherein the membrane forming lipid comprises at least one phospholipid, selected from soy phosphatidylcholine, egg phosphatidylcholine, soy phosphatidylglycerol, egg phosphatidylglycerol, palmitoyl-oleoyl-phosphatidylcholine distearoylphosphatidylcholine, distearoylphosphatidylglycerol phosphatidylcholine, phosphatidylglycerol, sphingomyelin, phosphatidylserine, phosphatidic acid, phosphatidylethanolamine, lysolecithin, lysophosphatidylethanolamine, phosphatidylinositol, cephalin, cardiolipin, cerebrosides, dicetylphosphate, dioleoylphosphatidylcholine, dipalmitoylphosphatidylcholine, dipalmitoylphosphatidylglycerol, dioleoylphosphatidylglycerol, stearoyl-palmitoyl-phosphatidylcholine, di-palmitoyl-phosphatidylethanolamine, distearoyl-phosphatidylethanolamine, di-myrstoyl-phosphatidylserine, di-myrstoyl-phosphatidylcholine and dioleyl-phosphatidylcholine.

7. The telodendrimer-nanolipoprotein particle of claim 1, wherein the scaffold protein is one or more of a human derived apoE4, a truncated version of human derived apoE4, a human derived apoE3, a truncated version of human derived apoE3, a human derived apoE2, a truncated version of human derived apoE2, a human derived apoA1, a truncated version of human derived apoA1, a mouse derived apoE4, a truncated version of mouse derived apoE4, mouse derived apoE3, truncated versions of mouse derived apoE3, a mouse derived apoE2, a truncated version of mouse derived apoE2, a mouse derived apoA1, a truncated version of mouse derived apoA1, a rat derived apoE4, a truncated version of rat derived apoE4, a rat derived apoE3, a truncated version of rat derived apoE3, a rat derived apoE2, a truncated version of rat derived apoE2, a rat derived apoA1, a truncated version of rat derived apoA1, a lipophorin, a synthetic cyclic peptide mimicking an apolipoprotein function.

8. The telodendrimer-nanolipoprotein particle of claim 1, further comprising one or more polymorphic membrane proteins.

9. The telodendrimer-nanolipoprotein particle of claim 8, the one or more polymorphic membrane proteins are selected from Pmp A, PmpB, PmpC, PmpD, PmpE, PmpF, PmpG, PmpH, and PmpI from *Chlamydia muridarum* or *C. trachomatis*.

10. A method to provide a telodendrimer-nanolipoprotein particle presenting a *Chlamydia* major outer membrane proteins (MOMP), the method comprising
providing one or more membrane forming lipids, one or more telodendrimers, one or more adjuvants, a polynucleotide coding for the MOMP and a polynucleotide coding for a scaffold protein;
mixing the one or more membrane forming lipids and the one or more telodendrimers to provide a lipid-telodendrimer mixture;
mixing lipid-telodendrimer mixture with, the polynucleotide coding for the MOMP and the polynucleotide coding for the scaffold protein with an in vitro cell free translation system to provide a single reaction mixture;
translating the polynucleotide within the single reaction mixture via the in vitro cell free translation system, and
contacting the single reaction mixture with the one or more adjuvants
wherein the mixing the translating and the contacting are performed to allow self-assembly of the scaffold protein, the one or more membrane forming lipids and the one or more telodendrimers into a nanolipoprotein particle, the nanolipoprotein particle comprising the MOMP within a discoidal membrane lipid bilayer formed by the one or more membrane forming lipids and stabilized by the scaffold protein, the membrane lipid bilayer attaching the MOMP through interaction of a hydrophobic region of the MOMP with the membrane lipid bilayer the membrane lipid bilayer further attaching the one or more adjuvants through binding of the one or more adjuvants to the discoidal membrane bilayer or to a component thereof.

11. A system to provide a t-NLP comprising *Chlamydia* major outer membrane proteins (MOMP), the system comprising
one or more membrane forming lipids, one or more telodendrimers, one or more adjuvants, a polynucleotide coding for *Chlamydia* major outer membrane proteins (MOMP) and a polynucleotide coding for a scaffold protein for simultaneous combined or sequential use in the method to provide a t-NLP presenting a MOMP of claim 10.

12. A method to provide a telodendrimer-nanolipoprotein particle presenting a *Chlamydia* major outer membrane proteins (MOMP), the method comprising
providing one or more membrane forming lipids, one or more telodendrimers, one or more adjuvants, a scaffold protein and a polynucleotide coding for the MOMP;
mixing the one or more membrane forming lipids and the one or more telodendrimers to provide a lipid-telodendrimer mixture;
mixing lipid-telodendrimer mixture with the scaffold protein and the polynucleotide coding for the MOMP with an in vitro cell free translation system to provide a single reaction mixture;
translating the polynucleotide within the single reaction mixture via the in vitro cell free translation system, and
contacting the single reaction mixture with the one or more adjuvants
wherein the mixing the translating and the contacting are performed to allow self-assembly of the scaffold protein, the one or more membrane forming lipids and the one or more telodendrimers into a nanolipoprotein particle, the nanolipoprotein particle comprising the MOMP within a discoidal membrane lipid bilayer formed by the one or more membrane forming lipids and stabilized by the scaffold protein, the membrane lipid bilayer attaching the MOMP through interaction of a hydrophobic region of the MOMP with the membrane lipid bilayer, the membrane lipid bilayer further attaching the one or more adjuvants through binding of the one or more adjuvants to the membrane lipid bilayer and/or to a component thereof.

13. A system to provide a t-NLP comprising *Chlamydia* major outer membrane proteins (MOMP), the system comprising one or more membrane forming lipids, one or more telodendrimers, one or more adjuvants a polynucleotide coding for *Chlamydia* major outer membrane proteins (MOMP) and a polynucleotide coding for a scaffold protein for simultaneous combined or sequential use in the method to provide a t-NLP presenting a MOMP of claim 12.

14. A composition comprising one or more telodendrimer-nanolipoprotein particles of claim 1 (MOMP-t-NLPs) together with a suitable vehicle.

15. The composition of claim 14, wherein the composition is formulated for systemic administration, which includes parenteral administration and more particularly intravenous, intradermic, and intramuscular administration.

16. The composition of claim 14, wherein the composition is formulated for non-parenteral administration.

17. The composition of claim 14, wherein the composition is formulated for intranasal, intratracheal, vaginal, oral, and sublingual administration.

18. A method for immunizing an individual against *Chlamydia*, the method comprising
administering to the individual an effective amount one or more telodendrimer-nanolipoprotein particles (MOMP-t-NLPs) of claim 1 for a time and under conditions to allow contact of the MOMP-t-NLP with the immunitary system of the individual.

19. The method of claim 18, wherein the administering is performed via intranasal, intramuscular or a combination of intranasal and/or intramuscular route.

20. The method of claim 18, wherein effective amount of MOMP-t-NLP is from 1 to 20 ug.

21. A method for treating or preventing a *Chlamydia* infection or conditions associated thereto in an individual, the method comprising
administering to the individual a one or more telodendrimer-nanolipoprotein particle of claim 1 (MOMP-t-NLPs) in an effective amount to elicit an immunitary response to the MOMP-t-NLPs in the individual.

22. The method of claim 21, wherein the administering is performed via intranasal or intramuscular route or a combination of intranasal and intramuscular routes.

23. The method of claim 21, wherein the effective amount of MOMP-tNLP ranges from 1 to 20 ug.

24. A system for treating or preventing a *Chlamydia* infection or conditions associated thereto in an individual, the system comprising one or more telodendrimer-nanolipoprotein particles of claim 1 together with one or more adjuvant or adjuvant-NLPs for simultaneous, combined or sequential use a method for treating or preventing a *Chlamydia* infection or conditions associated thereto in an individual, the method comprising
administering to the individual a one or more telodendrimer-nanolipoprotein particle of claim 1 (MOMP-t-NLPs) in an effective amount to elicit an immunitary response to the MOMP-t-NLPs in the individual.

25. The telodendrimer-nanolipoprotein particle of claim 1, wherein at least one adjuvant of the one or more adjuvants comprises a hydrophobic region and the at least one adjuvant of the one or more adjuvants is attached to the membrane lipids bilayer through interaction of the hydrophobic region with the membrane lipid bilayer.

26. The telodendrimer-nanolipoprotein particle of claim 1,
wherein the telodendrimer nanolipoprotein particle further comprises a functionalized lipid having a hydrophobic portion and a hydrophilic portion in a configuration where the hydrophobic portion anchor is attached to the membrane lipid bilayer of the telodendrimer nanolipoprotein particle and the hydrophilic portion is presented on the membrane lipid bilayer, the hydrophilic portion comprising an anchor substrate functional group, and
wherein at least one adjuvant of the one or more adjuvants comprises an anchor functional group, the at least one adjuvant attached to the membrane lipid bilayer through binding of the at anchor functional group to the anchor substrate functional group of the functionalized lipid.

27. The telodendrimer-nanolipoprotein particle of claim 1, wherein the one or more adjuvants comprise CpG, FSL1, LPS and/or or MPLA.

28. The telodendrimer-nanolipoprotein particle of claim 1, wherein the telodendrimer-nanolipoprotein particle comprises two or more adjuvants.

29. The telodendrimer-nanolipoprotein particle of claim 1, wherein the one or more adjuvants are two or more adjuvants comprising CpG and FSL1.

30. The composition of claim 14, wherein the one or more telodendrimer-nanolipoprotein particles comprises a telodendrimer-nanolipoprotein particle comprising two or more adjuvants.

31. The method of claim 18, wherein the one or more telodendrimer-nanolipoprotein particles (MOMP-t-NLPs) comprises same or different two or more adjuvants.

* * * * *